United States Patent
Brill et al.

(10) Patent No.: US 12,414,952 B2
(45) Date of Patent: *Sep. 16, 2025

(54) SUBSTITUTED AMINO TRIAZOLOPYRIMIDINE AND AMINO TRIAZOLOPYRAZINE ADENOSINE RECEPTOR ANTAGONISTS, PHARMACEUTICAL COMPOSITIONS AND THEIR USE

(71) Applicant: Merck Sharp & Dohme LLC, Rahway, NJ (US)

(72) Inventors: Zachary G. Brill, Boston, MA (US); Amjad Ali, Freehold, NJ (US); Jared Cumming, Winchester, MA (US); Duane DeMong, Hanover, MA (US); Qiaolin Deng, Edison, NJ (US); Gioconda V. Gallo-Etienne, New Providence, NJ (US); Thomas H. Graham, Somerville, MA (US); Rongze Kuang, Green Brook, NJ (US); Matthew A. Larsen, Dedham, MA (US); Yeon-Hee Lim, South San Francisco, CA (US); Kun Liu, Needham, MA (US); Umar Faruk Mansoor, Hopkinton, MA (US); Jesus Moreno, Dorchester Center, MA (US); Brandon A. Vara, Boston, MA (US); Huijun Wang, Westfield, NJ (US); Yonglian Zhang, East Brunswick, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1065 days.

This patent is subject to a terminal disclaimer.

(21) Appl. No.: 17/292,571

(22) PCT Filed: Nov. 15, 2019

(86) PCT No.: PCT/US2019/061634
§ 371 (c)(1),
(2) Date: May 10, 2021

(87) PCT Pub. No.: WO2020/106560
PCT Pub. Date: May 28, 2020

(65) Prior Publication Data
US 2022/0040184 A1    Feb. 10, 2022

Related U.S. Application Data

(60) Provisional application No. 62/769,836, filed on Nov. 20, 2018.

(51) Int. Cl.
*A61K 31/519* (2006.01)
*A61K 31/4985* (2006.01)
(Continued)

(52) U.S. Cl.
CPC ........ *A61K 31/519* (2013.01); *A61K 31/4985* (2013.01); *A61K 31/506* (2013.01);
(Continued)

(58) Field of Classification Search
CPC .. C07D 487/04; C07D 519/00; A61K 31/519; A61K 31/4985; A61K 31/506; A61K 39/3955; A61K 45/06; A61P 35/00
See application file for complete search history.

(56) References Cited

U.S. PATENT DOCUMENTS

| 4,483,987 | A  |   | 11/1984 | Wagner  |            |
|-----------|----|---|---------|---------|------------|
| 7,041,666 | B2 | * | 5/2006  | Matasi  | A61P 25/00 |
|           |    |   |         |         | 544/263    |

(Continued)

FOREIGN PATENT DOCUMENTS

| WO | 2003032996 A1 | 4/2003 |
|----|---------------|--------|
| WO | 03048165 A1   | 6/2003 |

(Continued)

OTHER PUBLICATIONS

Ali et. al. (2014) Input of Isosteric and Bioisosteric Approach in Drug Design, J. Chem. Soc. Pak., 36, p. 150-169. (Year: 2014).*

(Continued)

*Primary Examiner* — Juliet C Switzer
*Assistant Examiner* — Dawanna Shar-Day White
(74) *Attorney, Agent, or Firm* — Sanjeev K. Mahanta; Andrew W. Custer

(57) ABSTRACT

In its many embodiments, the present invention provides certain substituted amino triazolopyrimidine and amino triazolopyrazine compounds of Formula (IA) and Formula (IB): and, and pharmaceutically acceptable salts thereof, wherein, $R^1$, n, $R^2$, and $R^3$ are as defined herein, pharmaceutical compositions comprising one or more such compounds (alone and in combination with one or more other therapeutically active agents), and methods for their preparation and use, alone and in combination with other therapeutic agents, as antagonists of A2a and/or A2b receptors, and their use in the treatment of a variety of diseases, conditions, or disorders that are mediated, at least in part, by the adenosine A2a receptor and/or the adenosine A2b receptor.

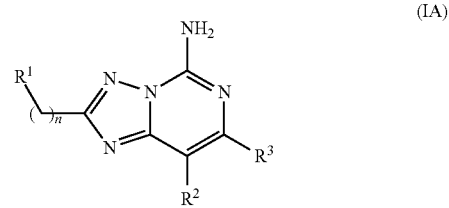

(IA)

(Continued)

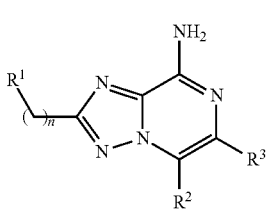

(IB)

10 Claims, No Drawings

(51) Int. Cl.
A61K 31/506 (2006.01)
A61K 39/395 (2006.01)
C07D 487/04 (2006.01)
C07D 519/00 (2006.01)

(52) U.S. Cl.
CPC ........ *A61K 39/3955* (2013.01); *C07D 487/04* (2013.01); *C07D 519/00* (2013.01)

(56) References Cited

U.S. PATENT DOCUMENTS

| 8,273,752 B2 | 9/2012 | Siegel et al. |
| 11,117,899 B2 | 9/2021 | Chen et al. |
| 2001/0016954 A1 | 8/2001 | Atkinson et al. |
| 2004/0012471 A1 | 1/2004 | Kojima et al. |
| 2006/0037003 A1 | 2/2006 | Long et al. |
| 2021/0094957 A1 | 4/2021 | Chen et al. |

FOREIGN PATENT DOCUMENTS

| WO | 2003048164 A2 | 6/2003 |
| WO | 2005044819 A1 | 5/2005 |
| WO | 2005103055 A1 | 11/2005 |
| WO | 2006068954 A2 | 6/2006 |
| WO | 2007035542 A1 | 3/2007 |
| WO | 2008002596 A2 | 1/2008 |
| WO | 2009077741 A2 | 6/2009 |
| WO | 2009111442 A1 | 9/2009 |
| WO | 2011060207 A1 | 5/2011 |
| WO | 2014101113 A1 | 7/2014 |
| WO | 2014101120 A1 | 7/2014 |
| WO | 2015027431 A1 | 3/2015 |
| WO | 2016081290 A1 | 5/2016 |
| WO | 2016089796 A1 | 6/2016 |
| WO | 2016126570 A1 | 8/2016 |
| WO | 2016/209787 A1 | 12/2016 |
| WO | 2016200717 A1 | 12/2016 |
| WO | 2017011214 A1 | 1/2017 |
| WO | 2018184590 A1 | 10/2018 |
| WO | 2019118313 A1 | 6/2019 |
| WO | 2019168847 A1 | 9/2019 |
| WO | 2019206336 A1 | 10/2019 |
| WO | 2019222677 A1 | 11/2019 |
| WO | 2020010197 A1 | 1/2020 |
| WO | 2020106558 A1 | 5/2020 |
| WO | 2020106560 A1 | 5/2020 |
| WO | 2020112700 A1 | 6/2020 |
| WO | 2020112706 A1 | 6/2020 |

OTHER PUBLICATIONS

Guillot, N. et al., A Mild and Regiospecific Synthesis of 3-MINO Substituted Triazolo-[4,3,c]-Pyrimidines by Cyclisation of 4-Hydrazinopyrimidines with Iminium Chlorides and With N-Aryl Phosgenemines, Tetrahedron, 1990, 3897-3908, 46(1).

Harris, Potent and selective adenosine A2A receptor antagonists [1,2,4]-triazole[4,3-c]pyrimidin-3-ones, Bioorganic Medical Chemistry Letters, 2011, 2497-2501, 21.

Matasi, Julius J. et al., 2-(2-Furanyl)-7-phenyl[1,2,4]triazolo[1,5-c]pyrimidin-5-amine analogs as adenosine A2A antagonists: The successful reduction of hERG activity. Part 2, Bioorganic & Medicinal Chemistry Letters, 2005, 3675-3678, 15.

Matasi, Julius J. et al., 2-(2-Furanyl)-7-phenyl[1,2,4]triazolo[1,5-c]pyrimidin-5-amine analogs: Highly potent, orally active, adenosine A2A antagonists. Part 1, Bioorganic & Medicinal Chemistry Letters, 2005, 3670-3674, 15.

Pubchem. Compound Summary for SID 236343793, Available Date: Feb. 13, 2015 [retrieved on Dec. 18, 2019]. Retrieved from the Internet: URL: https://pubchem.ncbi.nlm.nih.gov/substance/236343793 entire document (7 pages).

* cited by examiner

SUBSTITUTED AMINO TRIAZOLOPYRIMIDINE AND AMINO TRIAZOLOPYRAZINE ADENOSINE RECEPTOR ANTAGONISTS, PHARMACEUTICAL COMPOSITIONS AND THEIR USE

CROSS REFERENCE TO RELATED APPLICATIONS

This application is a U.S. National Phase application under 35 U.S.C. § 371 of PCT Application No. PCT/US19/061634, filed Nov. 15, 2019, which published as WO 2020/106560 A1 on May 28, 2020 which claims priority under 35 U.S.C. § 365(b) from U.S. provisional patent application No. 62/769,836, filed Nov. 20, 2018.

FIELD OF THE INVENTION

The present invention relates to novel compounds that inhibit at least one of the A2a and A2b adenosine receptors, and pharmaceutically acceptable salts thereof, and compositions comprising such compound(s) and salts, methods for the synthesis of such compounds, and their use in the treatment of a variety of diseases, conditions, or disorders that are mediated, at least in part, by the adenosine A2a receptor and/or the adenosine A2b receptor. Such diseases, conditions, and disorders include but are not limited to cancer and immune-related disorders. The invention further relates to combination therapies, including but not limited to a combination comprising a compound of the invention and a PD-1 antagonist.

BACKGROUND OF THE INVENTION

Adenosine is a purine nucleoside compound comprised of adenine and ribofuranose, a ribose sugar molecule. Adenosine occurs naturally in mammals and plays important roles in various biochemical processes, including energy transfer (as adenosine triphosphate and adenosine monophosphate) and signal transduction (as cyclic adenosine monophosphate). Adenosine also plays a causative role in processes associated with vasodilation, including cardiac vasodilation. It also acts as a neuromodulator (e.g., it is thought to be involved in promoting sleep). In addition to its involvement in these biochemical processes, adenosine is used as a therapeutic antiarrhythmic agent to treat supraventricular tachycardia and other indications.

The adenosine receptors are a class of purinergic G protein-coupled receptors with adenosine as the endogenous ligand. The four types of adenosine receptors in humans are referred to as A1, A2a A2b, and A3. Modulation of A1 has been proposed for the management and treatment of neurological disorders, asthma, and heart and renal failure, among others. Modulation of A3 has been proposed for the management and treatment of asthma and chronic obstructive pulmonary diseases, glaucoma, cancer, stroke, and other indications. Modulation of the A2a and A2b receptors are also believed to be of potential therapeutic use.

In the central nervous system, A2a antagonists are believed to exhibit antidepressant properties and to stimulate cognitive functions. A2a receptors are present in high density in the basal ganglia, known to be important in the control of movement. Hence, A2a receptor antagonists are believed to be useful in the treatment of depression and to improve motor impairment due to neurodegenerative diseases such as Parkinson's disease, senile dementia (as in Alzheimer's disease), and in various psychoses of organic origin.

In the immune system, adenosine signaling through A2a receptors and A2b receptors, expressed on a variety of immune cells and endothelial cells, has been established as having an important role in protecting tissues during inflammatory responses. In this way (and others), tumors have been shown to evade host responses by inhibiting immune function and promoting tolerance. (See, e.g., Fishman, P., et al., Handb. Exp. Pharmacol. (2009) 193:399-441). Moreover, A2a and A2b cell surface adenosine receptors have been found to be upregulated in various tumor cells. Thus, antagonists of the A2a and/or A2b adenosine receptors represent a new class of promising oncology therapeutics. For example, activation of A2a adenosine receptors results in the inhibition of the immune response to tumors by a variety of cell types, including but not limited to: the inhibition of natural killer cell cytotoxicity, the inhibition of tumor-specific CD4+/CD8+ activity, promoting the generation of LAG-3 and Foxp3+ regulatory T-cells, and mediating the inhibition of regulatory T-cells. Adenosine A2a receptor inhibition has also been shown to increase the efficacy of PD-1 inhibitors through enhanced anti-tumor T cell responses. As each of these immunosuppressive pathways has been identified as a mechanism by which tumors evade host responses, a cancer immunotherapeutic regimen that includes an antagonist of the A2a and/or A2b receptors, alone or together with one or more other therapeutic agents designed to mitigate immune suppression, may result in enhanced tumor immunotherapy. (See, e.g., P. Beavis, et al., Cancer Immunol. Res. DOI: 10.1158/2326-6066. CIR-14-0211, Feb. 11, 2015; Willingham, S B., et al., Cancer Immunol. Res., 6(10), 1136-49; and Leone R D, et al., Cancer Immunol. Immunother., August 2018, Vol. 67, Issue 8, 1271-1284).

Cancer cells release ATP into the tumor microenvironment when treated with chemotherapy and radiation therapy, which is subsequently converted to adenosine. (See Martins, I., et al., Cell Cycle, vol. 8, issue 22, pp. 3723 to 3728.) The adenosine can then bind to A2a receptors and blunt the anti-tumor immune response through mechanisms such as those described above. The administration of A2a receptor antagonists during chemotherapy or radiation therapy has been proposed to lead to the expansion of the tumor-specific T-cells while simultaneously preventing the induction of tumor-specific regulatory T-cells. (Young, A., et al., Cancer Discovery (2014) 4:879-888).

The combination of an A2a receptor antagonist with anti-tumor vaccines is believed to provide at least an additive therapeutic effect in view of their different mechanisms of action. Further, A2a receptor antagonists may be useful in combination with checkpoint blockers. By way of example, the combination of a PD-1 inhibitor and an adenosine A2a receptor inhibitor is thought to mitigate the ability of tumors to inhibit the activity of tumor-specific effector T-cells. (See, e.g., Willingham, S B., et al., Cancer Immunol. Res.; 6(10), 1136-49; Leone, R D., et al., Cancer Immunol. Immunother., August 2018, Vol. 67, Issue 8, pp. 1271-1284; Fishman, P., et al., Handb. Exp. Pharmacol. (2009) 193:399-441; and Sitkovsky, M V., et al., (2014) Cancer Immunol. Res 2:598-605.)

The A2b receptor is a G protein-coupled receptor found in various cell types. A2b receptors require higher concentrations of adenosine for activation than the other adenosine receptor subtypes, including A2a. (Fredholm, B B., et al., Biochem. Pharmacol. (2001) 61:443-448). Conditions which activate A2b have been seen, for example, in tumors where hypoxia is observed. The A2b receptor may thus play an important role in pathophysiological conditions associated with massive adenosine release. While the pathway(s) associated with A2b receptor-mediated inhibition are not well understood, it is believed that the inhibition of A2b receptors (alone or together with A2a receptors) may block pro-tumorigenic functions of adenosine in the tumor microenvironment, including suppression of T-cell function and angiogenesis, and thus expand the types of cancers treatable by the inhibition of these receptors.

A2b receptors are expressed primarily on myeloid cells. The engagement of A2b receptors on myeloid derived suppressor cells (MDSCs) results in their expansion in vitro (Ryzhov, S. et al., J. Immunol. 2011, 187:6120-6129). MDSCs suppress T-cell proliferation and anti-tumor immune responses. Selective inhibitors of A2b receptors and A2b receptor knockouts have been shown to inhibit tumor growth in mouse models by increasing MDSCs in the tumor microenvironment (Iannone, R., et al., Neoplasia Vol. 13 No. 12, (2013) pp. 1400-1409; Ryzhov, S., et al., Neoplasia (2008) 10: 987-995). Thus, A2b receptor inhibition has become an attractive biological target for the treatment of a variety of cancers involving myeloid cells. Examples of cancers that express A2b receptors can be readily obtained through analysis of the publicly available TCGA database. Such cancers include lung, colorectal, head and neck, and cervical cancer, among others, and are discussed in further detail below.

Angiogenesis plays an important role in tumor growth. The angiogenesis process is highly regulated by a variety of factors and is triggered by adenosine under particular circumstances that are associated with hypoxia. The A2b receptor is expressed in human microvascular endothelial cells, where it plays an important role in the regulation of the expression of angiogenic factors such as the vascular endothelial growth factor (VEGF). In certain tumor types, hypoxia has been observed to cause an upregulation of the A2b receptors, suggesting that inhibition of A2b receptors may limit tumor growth by limiting the oxygen supply to the tumor cells. Furthermore, experiments involving adenylate cyclase activation indicate that A2b receptors are the sole adenosine receptor subtype in certain tumor cells, suggesting that A2b receptor antagonists may exhibit effects on particular tumor types. (See, e.g., Feoktistov, I., et al., (2003) Circ. Res. 92:485-492; and P. Fishman, P., et al., Handb. Exp. Pharmacol. (2009) 193:399-441).

A2a/A2b inhibitors are known in the art, e.g. WO2019/168847. In view of their promising and varied therapeutic potential, there remains a need in the art for potent and selective inhibitors of the A2a and/or A2b adenosine receptors, for use alone or in combination with other therapeutic agents. The present invention addresses this and other needs.

SUMMARY OF THE INVENTION

In one aspect, the present invention provides compounds (hereinafter referred to as compounds of the invention) which, surprisingly and advantageously, have been found to be inhibitors of the adenosine A2a receptor and/or the adenosine A2b receptor. The compounds of the invention have a structure in accordance with Formula (IA) or Formula (IB):

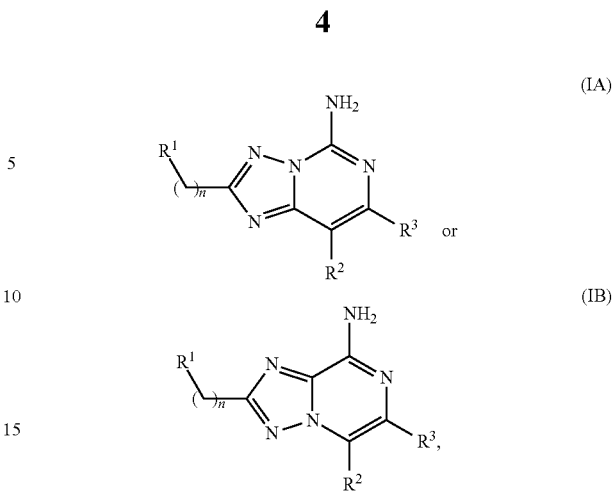

or a pharmaceutically acceptable salt thereof, wherein $R^1$, n, $R^2$, and $R^3$ are as defined below.

In another aspect, the present invention provides pharmaceutical compositions comprising at least one compound of the invention, or a pharmaceutically acceptable salt thereof, in a pharmaceutically acceptable carrier or diluent. Such compositions according to the invention may optionally further include one or more additional therapeutic agents as described herein.

In another aspect, the present invention provides a method for treating or preventing a disease, condition, or disorder that is mediated, at least in part, by the adenosine A2a receptor and/or the adenosine A2b receptor in a subject (e.g., an animal or human) in need thereof, said method comprising administering to the subject a therapeutically effective amount of at least one compound of the invention, or a pharmaceutically acceptable salt thereof, alone or in combination with one or more additional therapeutic agents. These and other aspects and embodiments of the invention are described more fully below.

DETAILED DESCRIPTION OF THE INVENTION

For each of the following embodiments, any variable not explicitly defined in the embodiment is as defined in Formula (IA) or (IB). In each of the embodiments described herein, each variable is selected independently of the other.

In one aspect, the present invention provides compounds (hereinafter referred to as compounds of the invention) which have, surprisingly and advantageously, been found to be inhibitors of the adenosine A2a receptor and/or the adenosine A2b receptor.

In one embodiment, the compounds of the invention have the structural Formula (IA) or Formula (IB):

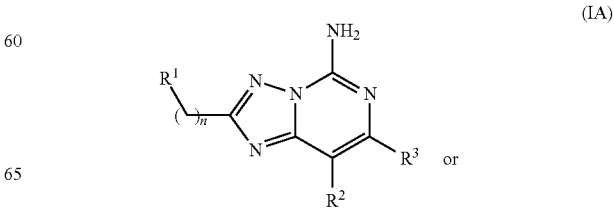

-continued

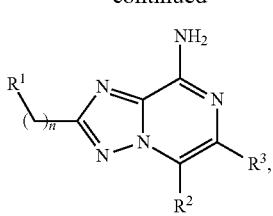

(IB)

or a pharmaceutically acceptable salt thereof, wherein:
n is 1 or 2;
$R^1$ is selected from:
H,
OH,
$S(O)_2R^{1C}$, wherein $R^{1C}$ is selected from $(C_1-C_6)$alkyl and $(C_3-C_5)$cycloalkyl;
phenyl, wherein said phenyl is unsubstituted or substituted with 1, 2, or 3 $R^{1AB}$ groups,
phenyl fused to a 5 or 6 membered partially or fully unsaturated ring comprising 1, 2, or 3 ring heteroatoms independently selected from N, O, and S, wherein said fused phenyl is unsubstituted or substituted with 1, 2, or 3 $R^{1AB}$ groups,
heteroaryl, wherein said heteroaryl is a 4, 5 or 6 membered monocyclic ring comprising 1, 2, or 3 ring heteroatoms selected from N, O, and S, wherein said heteroaryl is unsubstituted or substituted with 1, 2, or 3 $R^{1AB}$ groups,
$N(R^{1A})(R^{1B})$, and
$C(O)N(R^{1A})(R^{1B})$, wherein:
$R^{1A}$ is selected from H, $(C_1-C_6)$alkyl, and $(C_1-C_6)$haloalkyl;
$R^{1B}$ is selected from —$CH_2$phenyl and —$CH_2$heteroaryl, wherein said —$CH_2$phenyl, and said —$CH_2$heteroaryl are unsubstituted or substituted with 1, 2 or 3 groups independently selected from $(C_1-C_6)$alkyl, $(C_1-C_6)$haloalkyl, and $(C_1-C_6)$alkyl-OH;
or, alternatively, $R^{1A}$ and $R^{1B}$ in each of said $N(R^{1A})(R^{1B})$ and said $C(O)N(R^{1A})(R^{1B})$ of $R^1$ are taken together with the nitrogen atom to which they are shown attached to form a 4, 5, or 6 membered monocyclic heterocycloalkyl ring comprising 1 or 2 ring nitrogen atoms (including the nitrogen atom of $N(R^{1A})(R^{1B})$ and of $C(O)N(R^{1A})(R^{1B})$), wherein said monocyclic heterocycloalkyl ring is optionally fused to a 5 or 6 membered ring, which fused ring is partially or fully unsaturated and comprises 1, 2, or 3 additional ring heteroatoms independently selected from N, O, and S, and wherein said optionally fused heterocycloalkyl ring is unsubstituted or substituted with 1, 2, or 3 $R^{1AB}$ groups,
each $R^{1AB}$ group is independently selected from:
F, Cl, OH, CN, oxo, $(C_1-C_6)$alkyl, $O(C_1-C_6)$alkyl, $(C_1-C_6)$alkyl-OH, $(C_1-C_6)$haloalkyl, $O(C_1-C_6)$haloalkyl, $C(O)O(C_1-C_6)$alkyl, $(C_3-C_6)$cycloalkyl, $(C_1-C_4)$alkyl, $(C_3-C_6)$cycloalkyl, $C(O)(C_3-C_6)$cycloalkyl, and heteroaryl,
wherein said cycloalkyl and said heteroaryl portions of $R^{1AB}$ are unsubstituted or further substituted with 1, 2, or 3 $R^{ab}$ groups independently selected from F, OH, $(C_1-C_4)$alkyl, and $O(C_1-C_6)$alkyl;
$R^2$ is selected from H, $(C_1-C_6)$alkyl, and $(C_3-C_4)$cycloalkyl,
wherein each said $(C_1-C_6)$alkyl, and $(C_3-C_6)$cycloalkyl of $R^2$ is unsubstituted or substituted with 1, 2, or 3 $R^{2A}$ groups, wherein each $R^{2A}$ group is independently selected from F, Cl, OH, oxo, $(C_1-C_6)$alkyl, $O(C_1-C_6)$alkyl, $(C_1-C_6)$alkyl-OH, and $(C_1-C_6)$haloalkyl, and
$R^3$ is selected from phenyl and heteroaryl, wherein said heteroaryl is a 4, 5 or 6 membered monocyclic ring comprising 1, 2, or 3 ring heteroatoms selected from N, O, and S,
wherein said phenyl and said heteroaryl of $R^3$ are each unsubstituted or substituted with 1, 2, or 3 $R^{3A}$ groups, and
wherein each $R^{3A}$ group is independently selected from the group consisting of F, Cl, OH, CN, $(C_1-C_6)$alkyl, $(C_1-C_6)$haloalkyl, $O(C_1-C_6)$alkyl, and $O(C_1-C_6)$haloalkyl;
provided that, in Formula (IA), when $R^1$ is:
OH,
phenyl, wherein said phenyl is unsubstituted or substituted with 1, 2, or 3 $R^{1AB}$ groups, or
heteroaryl, wherein said heteroaryl is a 4, 5 or 6 membered monocyclic ring comprising 1, 2, or 3 ring heteroatoms selected from N, O, and S, wherein said heteroaryl is unsubstituted or substituted with 1, 2, or 3 $R^{1AB}$ groups,
then each $R^{3A}$ group is independently selected from the group consisting of F, Cl, OH, $(C_1-C_6)$alkyl, $(C_1-C_6)$haloalkyl, $O(C_1-C_6)$alkyl, and $O(C_1-C_6)$haloalkyl, and
further provided that, in Formula (IA), $R^2$ is selected from H and $(C_1-C_6)$alkyl,
wherein said $(C_1-C_6)$alkyl, of $R^2$ is unsubstituted or substituted with 1, 2, or 3 $R^{2A}$ groups,
wherein each $R^{2A}$ group is independently selected from F, Cl, OH, oxo, $(C_1-C_6)$alkyl, $O(C_1-C_6)$alkyl, $(C_1-C_6)$alkyl-OH, and $(C_1-C_6)$haloalkyl.

In another embodiment, in each of Formulas (IA) and (IB):
$R^1$ is selected from H and OH. In one such embodiment, $R^1$ is H; and nisi. In another such embodiment, $R^1$ is OH; and n is 2.

In another embodiment, in each of Formulas (IA) and (IB):
n is 2; and
$R^1$ is $S(O)_2R^{1C}$, wherein $R^{1C}$ is selected from $(C_1-C_6)$alkyl and $(C_3C_5)$cycloalkyl.

In another embodiment, in each of Formulas (IA) and (IB):
n is 2; and
$R^1$ is $S(O)_2R^{1C}$, wherein $R^{1C}$ is selected from methyl, ethyl, n-propyl, isopropyl, n-butyl, i-butyl, i-butyl, cyclopropyl, and cyclobutyl.

In another embodiment, in each of Formulas (IA) and (IB):
n is 2; and
$R^1$ is $S(O)_2R^{1C}$, wherein $R^{1C}$ is selected from cyclopropyl and cyclobutyl.

In another embodiment, in each of Formulas (IA) and (IB):
n is 2; and
$R^1$ is $S(O)_2R^{1C}$, wherein $R^{1C}$ is cyclopropyl.

In another embodiment, in each of Formulas (IA) and (IB):
n is 1 or 2; and
$R^1$ is phenyl, wherein said phenyl is unsubstituted or substituted with 1, 2, or 3 $R^{1AB}$ groups.

In another embodiment, in each of Formulas (IA) and (IB):
n is 1 or 2; and
$R^1$ is phenyl.

In another embodiment, in each of Formulas (IA) and (IB):
n is 1 or 2; and
R¹ is phenyl, wherein said phenyl is substituted with 1, 2, or 3 $R^{1AB}$ groups.

In another embodiment, in each of Formulas (IA) and (IB):
n is 1 or 2; and
R¹ is phenyl, wherein said phenyl is substituted with 1, 2, or 3 $R^{1AB}$ groups, wherein each
$R^{1AB}$ group is independently selected from:
F, Cl, OH, CN,
CH₃, CH₂CH₃, CH₂CH₂CH₃, CH(CH₃)CH₃, CH₂CH₂CH₂CH₃, CH(CH₃)CH₂CH₃, CH₂CH(CH₃) CH₃, C(CH₃)₃,
OCH₃, OCH₂CH₃, OCH₂CH₂CH₃, OCH(CH₃)CH₃, OCH₂CH₂CH₂CH₃, OCH(CH₃)CH₂CH₃, OCH₂CH (CH₃)CH₃, OC(CH₃)₃,
CH₂OH, CH₂CH₂OH, CH₂CH₂CH₂OH, CH(CH₃) CH₂OH, CH₂CH₂CH₂CH₂OH, CH₂C(CH₃)₂OH, CH(CH₃)CH₂CH₂OH, CH₂CH(CH₃)CH₂OH, C(CH₃)₂ OH,
CF₃, CH₂CF₃, CH₂CHF₂, CF₂CF₃, CH₂CH₂CF₃, CH(CF₃)CF₃, CH₂CH₂CH₂CF₃, CH(CH₃)CH₂CF₃, CH₂CH(CH₃)CF₃, C(CF₃)₃,
OCF₃, OCH₂CF₃, OCH₂CHF₂, OCF₂CF₃, OCH₂CH₂CF₃, OCH(CF₃)CF₃, OCH₂CH₂CH₂CF₃, OCH(CH₃)CH₂CF₃, OCH₂CH(CH₃)CF₃, OC(CF₃)₃,
C(O)OCH₃, C(O)OCH₂CH₃, C(O)OCH₂CH₂CH₃, C(O) OCH(CH₃)CH₃, C(O)OCH₂CH₂CH₂CH₃, C(O)OCH (CH₃)CH₂CH₃, C(O)OCH₂CH(CH₃)CH₃, C(O)OC (CH₃)₃,

[structures with $(R^{ab})_p$ and $q$ substituents shown]

wherein p is 0, 1, or 2;
q is 0, 1, or 2; and wherein
each $R^{ab}$ is independently selected from H, F, OH, CH₃, CH₂CH₃, —OCH₃, and —OCH₂CH₃.

In another embodiment, in each of Formulas (IA) and (IB):
n is 1 or 2; and
R¹ is phenyl, wherein said phenyl is substituted with 1, 2, or 3 $R^{1AB}$ groups, wherein each $R^{1AB}$ group is independently selected from:
F, Cl, OH, CN, CH₃, CH₂CH₃, CH(CH₃)₂, CH₂CH(CH₃)₂, C(CH₃)₃, C(CH₃)₂OH, CH₂C(CH₃)₂OH,
OCH₃, OCH₂CH₃, OCH(CH₃)₂, OCH₂CH(CH₃)₂, OC(CH₃)₃,
CF₃, CH(CF₃)₂, CH₂CHF₂, CH₂CF₃, CH₂CH(CF₃)₂, C(CF₃)₃,
OCF₃, OCH(CF₃)₂, OCH₂CHF₂, OCH₂CH(CF₃)₂, OC(CF₃)₃, and

[structure with $(R^{ab})_p$ and $q$ substituent shown]

wherein p is 0, 1, or 2;
q is 0, 1, or 2; and wherein
each $R^{ab}$ is independently selected from H, F, OH, CH₃, CH₂CH₃, —OCH₃, and —OCH₂CH₃.

In another embodiment, in each of Formulas (IA) and (IB):
n is 1 or 2; and
R¹ is phenyl fused to a 5 or 6 membered partially or fully unsaturated ring comprising 1, 2, or 3 ring heteroatoms independently selected from N, O, and S, wherein said fused phenyl is unsubstituted or substituted with 1, 2, or 3 $R^{1AB}$ groups.

In another embodiment, in each of Formulas (IA) and (IB):
n is 1 or 2; and
R¹ is phenyl fused to a 5 or 6 membered partially or fully unsaturated ring comprising 1, 2, or 3 ring nitrogen atoms, wherein said fused phenyl is unsubstituted or substituted with 1, 2, or 3 $R^{1AB}$ groups.

In another embodiment, in each of Formulas (IA) and (IB):
n is 1 or 2; and
R¹ is phenyl fused to a 5 or 6 membered partially or fully unsaturated ring comprising 1, 2, or 3 ring nitrogen atoms, wherein said fused phenyl is unsubstituted or substituted with 1, 2, or 3 $R^{1AB}$ groups, wherein each $R^{1AB}$ group is independently selected from:
F, Cl, OH, CN,
CH₃, CH₂CH₃, CH₂CH₂CH₃, CH(CH₃)CH₃, CH₂CH₂CH₂CH₃, CH(CH₃)CH₂CH₃, CH₂CH(CH₃) CH₃, C(CH₃)₃,
OCH₃, OCH₂CH₃, OCH₂CH₂CH₃, OCH(CH₃)CH₃, OCH₂CH₂CH₂CH₃, OCH(CH₃)CH₂CH₃, OCH₂CH (CH₃)CH₃, OC(CH₃)₃,
CH₂OH, CH₂CH₂OH, CH₂CH₂CH₂OH, CH(CH₃) CH₂OH, CH₂CH₂CH₂CH₂OH, CH₂C(CH₃)₂OH, CH(CH₃)CH₂CH₂OH, CH₂CH(CH₃)CH₂OH, C(CH₃)₂ OH,
CF₃, CH₂CF₃, CH₂CHF₂, CF₂CF₃, CH₂CH₂CF₃, CH(CF₃)CF₃, CH₂CH₂CH₂CF₃, CH(CH₃)CH₂CF₃, CH₂CH(CH₃)CF₃, C(CF₃)₃,
OCF₃, OCH₂CF₃, OCH₂CHF₂, OCF₂CF₃, OCH₂CH₂CF₃, OCH(CF₃)CF₃, OCH₂CH₂CH₂CF₃, OCH(CH₃)CH₂CF₃, OCH₂CH(CH₃)CF₃, OC(CF₃)₃,
C(O)OCH₃, C(O)OCH₂CH₃, C(O)OCH₂CH₂CH₃, C(O) OCH(CH₃)CH₃, C(O)OCH₂CH₂CH₂CH₃, C(O)OCH (CH₃)CH₂CH₃, C(O)OCH₂CH(CH₃)CH₃, C(O)OC (CH₃)₃,

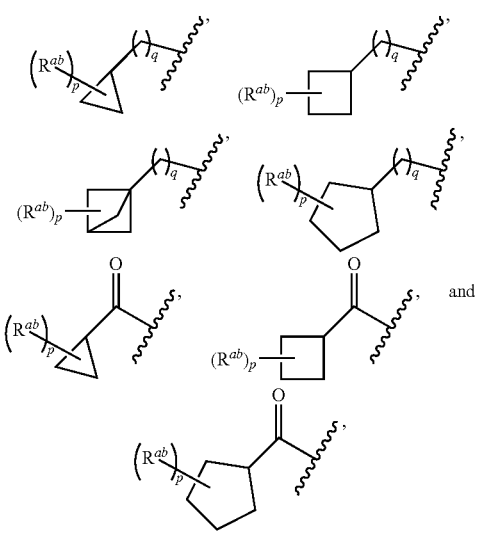

wherein p is 0, 1, or 2;
q is 0, 1, or 2; and wherein
each $R^{ab}$ is independently selected from H, F, OH, $CH_3$, $CH_2CH_3$, $OCH_3$, and $OCH_2CH_3$.

In another embodiment, in each of Formulas (IA) and (IB):
n is 1 or 2; and
$R^1$ is selected from

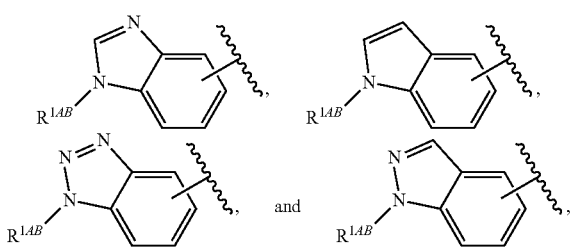

In another embodiment, in each of Formulas (IA) and (IB):
n is 1 or 2; and
$R^1$ is a moiety selected from:

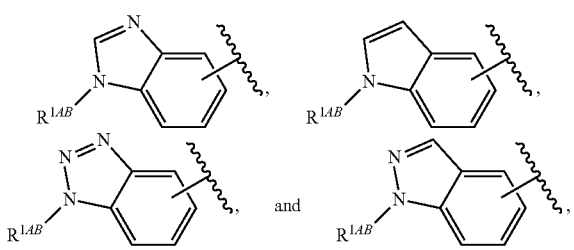

wherein:
$R^{1AB}$ is selected from:
$CH_3$, $CH_2CH_3$, $CH(CH_3)_2$, $CH_2CH(CH_3)_2$, $C(CH_3)_3$, $C(CH_3)_2OH$, $CH_2C(CH_3)_2OH$,

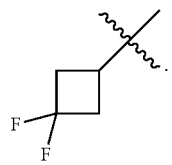

$CF_3$, $CH(CF_3)_2$, $CH_2CHF_2$, $CH_2CH(CF_3)_2$, $C(CF_3)_3$, and F

In another embodiment, in each of Formulas (IA) and (IB):
$R^1$ is heteroaryl, wherein said heteroaryl is a 5 or 6 membered monocyclic ring comprising 1, 2, 3, or 4 ring heteroatoms selected from N, O, and S, wherein said heteroaryl is unsubstituted or substituted with 1, 2, or 3 $R^{1AB}$ groups. In one such embodiment, n is 1. In another such embodiment, n is 2.

In another embodiment, in each of Formulas (IA) and (IB):
n is 1 or 2;
$R^1$ is heteroaryl, wherein said heteroaryl is a 5 or 6 membered monocyclic ring comprising 1, 2, 3, or 4 ring heteroatoms selected from N, O, and S, wherein said heteroaryl is unsubstituted or substituted with 1, 2, or 3 $R^{1AB}$ groups, wherein:
each $R^{1AB}$ group is independently selected from:
F, Cl, OH, CN,
$CH_3$, $CH_2CH_3$, $CH_2CH_2CH_3$, $CH(CH_3)CH_3$, $CH_2CH_2CH_2CH_3$, $CH(CH_3)CH_2CH_3$, $CH_2CH(CH_3)CH_3$, $C(CH_3)_3$,
$OCH_3$, $OCH_2CH_3$, $OCH_2CH_2CH_3$, $OCH(CH_3)CH_3$, $OCH_2CH_2CH_2CH_3$, $OCH(CH_3)CH_2CH_3$, $OCH_2CH(CH_3)CH_3$, $OC(CH_3)_3$,
$CH_2OH$, $CH_2CH_2OH$, $CH_2CH_2CH_2OH$, $CH(CH_3)CH_2OH$, $CH_2CH_2CH_2CH_2OH$, $CH_2C(CH_3)_2OH$, $CH_2CH_2C(CH_3)_2OH$, $CH(CH_3)CH_2CH_2OH$, $CH_2CH(CH_3)CH_2OH$, $C(CH_3)_2OH$,
$CF_3$, $CH_2CF_3$, $CH_2CHF_2$, $CF_2CF_3$, $CH_2CH_2CF_3$, $CH(CF_3)CF_3$, $CH_2CH_2CH_2CF_3$, $CH(CH_3)CH_2CF_3$, $CH_2CH(CH_3)CF_3$, $C(CF_3)_3$,
$OCF_3$, $OCH_2CF_3$, $OCH_2CHF_2$, $OCF_2CF_3$, $OCH_2CH_2CF_3$, $OCH(CF_3)CF_3$, $OCH_2CH_2CH_2CF_3$, $OCH(CH_3)CH_2CF_3$, $OCH_2CH(CH_3)CF_3$, $OC(CF_3)_3$,
$C(O)OCH_3$, $C(O)OCH_2CH_3$, $C(O)OCH_2CH_2CH_3$, $C(O)OCH(CH_3)CH_3$, $C(O)OCH_2CH_2CH_2CH_3$, $C(O)OCH(CH_3)CH_2CH_3$, $C(O)OCH_2CH(CH_3)CH_3$, $C(O)OC(CH_3)_3$,

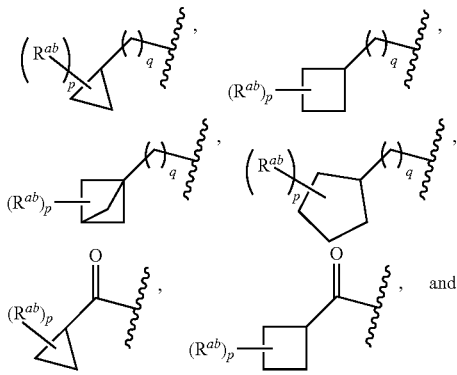

-continued

[Structure: cyclopentanone with $(R^{ab})_p$ substituent]

wherein p is 0, 1, or 2;
q is 0, 1, or 2; and wherein
each $R^{ab}$ is independently selected from H, F, OH, $CH_3$, $CH_2CH_3$, $OCH_3$, and $OCH_2CH_3$.

In another embodiment, in each of Formulas (IA) and (IB):
n is 1 or 2;
$R^1$ is selected from pyridyl and pyrazolyl, wherein said pyridyl and pyrazolyl are unsubstituted or substituted with 1, 2, or 3 $R^{1AB}$ groups, wherein each $R^{1AB}$ group is independently selected from:
F, Cl, OH, CN,
$CH_3$, $CH_2CH_3$, $CH(CH_3)_2$, $CH_2CH(CH_3)_2$, $C(CH_3)_3$, $C(CH_3)_2OH$, $CH_2C(CH_3)_2OH$, $CH_2CH_2CH_2C(CH_3)_2OH$,
$OCH_3$, $OCH_2CH_3$, $OCH(CH_3)_2$, $OCH_2CH(CH_3)_2$, $OC(CH_3)_3$,
$CF_3$, $CH(CF_3)_2$, $CH_2CHF_2$, $CH_2CF_3$, $CH_2CH(CF_3)_2$, $C(CF_3)_3$,
$OCF_3$, $OCH(CF_3)_2$, $OCH_2CHF_2$, $OCH_2CH(CF_3)_2$, $OC(CF_3)_3$,
$C(O)OCH_3$, $C(O)OCH_2CH_3$, $C(O)OCH_2CH_2CH_3$, and

[Structure: cyclobutane with $(R^{ab})_p$ substituent]

wherein p is 0, 1, or 2;
q is 0, 1, or 2; and wherein
each $R^{ab}$ is independently selected from H, F, OH, $CH_3$, $CH_2CH_3$, —$OCH_3$, and —$OCH_2CH_3$.

In another embodiment, in each of Formulas (IA) and (IB):
n is 1;
$R^1$ is selected from $N(R^{1A})(R^{1B})$ and $C(O)N(R^{1A})(R^{1B})$, wherein:
$R^{1A}$ is selected from H, $(C_1-C_6)$alkyl, and $(C_1-C_6)$haloalkyl;
$R^{1B}$ is selected from —$CH_2$-phenyl and —$CH_2$-heteroaryl, wherein said —$CH_2$-phenyl, and said —$CH_2$-heteroaryl are unsubstituted or substituted with 1 or 2 groups independently selected from $(C_1-C_6)$alkyl, $(C_1-C_6)$haloalkyl, and $(C_1-C_6)$alkyl-OH.

In another embodiment, in each of Formulas (IA) and (IB):
n is 1 or 2;
$R^1$ is $N(R^{1A})(R^{1B})$, wherein:
$R^{1A}$ is selected from H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)CH_3$, $C(CH_3)_3$, $CF_3$, $CH_2CF_3$, $CH_2CHF_2$, $CF_2CH_3$, $CHFCFH_2$, $CF_2CF_3$, $CH_2CH_2CF_3$, $CH(CF_3)CF_3$, $CH_2CH_2CH_2CF_3$, $CH(CH_3)CH_2CF_3$, $CH_2CH(CH_3)CF_3$, and $C(CF_3)_3$;
$R^{1B}$ is selected from $CH_2$phenyl, $CH_2$pyridyl, and $CH_2$pyrazolyl, wherein said $CH_2$phenyl, said —$CH_2$pyridyl, and said —$CH_2$pyrazolyl are unsubstituted or substituted with 1 or 2 groups independently selected from:
$CH_3$, $CH_2CH_3$, $CH_2CH_2CH_3$, $CH(CH_3)CH_3$, $CH_2CH_2CH_2CH_3$, $CH(CH_3)CH_2CH_3$, $CH_2CH(CH_3)CH_3$, $C(CH_3)_3$,
$CF_3$, $CH_2CF_3$, $CH_2CHF_2$, $CF_2CF_3$, $CH_2CH_2CF_3$, $CH(CF_3)CF_3$, $CH_2CH_2CH_2CF_3$, $CH(CH_3)CH_2CF_3$, $CH_2CH(CH_3)CF_3$, $C(CF_3)_3$,
$CH_2OH$, $CH_2CH_2OH$, $CH_2CH_2CH_2OH$, $CH(CH_3)CH_2OH$, $CH_2CH_2CH_2CH_2OH$, $CH(CH_3)CH_2CH_2OH$, $CH_2CH(CH_3)CH_2OH$, $CH(CH_3)_2OH$, $CH_2C(CH_3)_2OH$, and $C(CH_3)_2OH$.

In one such embodiment, n is 1. In another such embodiment, n is 2.

In another embodiment, in each of Formulas (IA) and (IB):
n is 1 or 2;
$R^1$ is selected from $N(R^{1A})(R^{1B})$ and $C(O)N(R^{1A})(R^{1B})$, wherein:
$R^{1A}$ and $R^{1B}$ in each of said $N(R^{1A})(R^{1B})$ and said $C(O)N(R^{1A})(R^{1B})$ of $R^1$ are taken together with the nitrogen atom to which they are shown attached to form a 4, 5, or 6 membered monocyclic heterocycloalkyl ring comprising 1 or 2 ring nitrogen atoms (including the nitrogen atom of $N(R^{1A})(R^{1B})$ and of $C(O)N(R^{1A})(R^{1B})$), wherein said monocyclic heterocycloalkyl ring is optionally fused to a 5 or 6 membered ring, which fused ring is partially or fully unsaturated and comprises 1, 2, or 3 additional ring heteroatoms independently selected from N, O, and S, and wherein said optionally fused heterocycloalkyl ring is unsubstituted or substituted with 1, 2, or 3 $R^{1AB}$ groups. In one such embodiment, n is 1. In another such embodiment, n is 2.

In another embodiment, in each of Formulas (IA) and (IB):
n is 1 or 2;
$R^1$ is selected from $N(R^{1A})(R^{1B})$ and $C(O)N(R^{1A})(R^{1B})$, wherein:
$R^{1A}$ and $R^{1B}$ in each of said $N(R^{1A})(R^{1B})$ and said $C(O)N(R^{1A})(R^{1B})$ of $R^1$ are taken together with the nitrogen atom to which they are shown attached to form a 4, 5, or 6 membered monocyclic heterocycloalkyl ring comprising 1 or 2 ring nitrogen atoms (including the nitrogen atom of $N(R^{1A})(R^{1B})$ and of $C(O)N(R^{1A})(R^{1B})$), wherein said monocyclic heterocycloalkyl ring is optionally fused to a 5 or 6 membered ring, which fused ring is partially or fully unsaturated and comprises 1, 2, or 3 additional ring heteroatoms independently selected from N, O, and S, and wherein said optionally fused heterocycloalkyl ring is unsubstituted or substituted with 1, 2, or 3 $R^{1AB}$ groups, wherein each $R^{1AB}$ group is independently selected from:
F, Cl, OH, CN, oxo,
$CH_3$, $CH_2CH_3$, $CH_2CH_2CH_3$, $CH(CH_3)CH_3$, $CH_2CH_2CH_2CH_3$, $CH(CH_3)CH_2CH_3$, $CH_2CH(CH_3)CH_3$, $C(CH_3)_3$,
$OCH_3$, $OCH_2CH_3$, $OCH_2CH_2CH_3$, $OCH(CH_3)CH_3$, $OCH_2CH_2CH_2CH_3$, $OCH(CH_3)CH_2CH_3$, $OCH_2CH(CH_3)CH_3$, $OC(CH_3)_3$,
$CH_2OH$, $CH_2CH_2OH$, $CH_2CH_2CH_2OH$, $CH(CH_3)CH_2OH$, $CH_2CH_2CH_2CH_2OH$, $CH_2C(CH_3)_2OH$, $CH(CH_3)CH_2CH_2OH$, $CH_2CH(CH_3)CH_2OH$, $C(CH3)_2OH$, CF₃, CH₂CF₃, CH₂CHF₂, CF₂CF₃, CH₂CH₂CF₃, CH(CF₃)CF₃, CH₂CH₂CH₂CF₃, CH(CH₃)CH₂CF₃, CH₂CH(CH₃)CF₃, C(CF₃)₃, OCF₃, OCH₂CF₃, OCH₂CHF₂, OCF₂CF₃, OCH₂CH₂CF₃, OCH(CF₃)CF₃, OCH₂CH₂CH₂CF₃, OCH(CH₃)CH₂CF₃, OCH₂CH(CH₃)CF₃, OC(CF₃)₃, C(O)OCH₃, C(O)OCH₂CH₃, C(O)OCH₂CH₂CH₃, C(O)OCH(CH₃)CH₃, C(O)OCH₂CH₂CH₂CH₃, C(O)OCH(CH₃)CH₂CH₃, C(O)OCH₂CH(CH₃)CH₃, C(O)OC(CH₃)₃,

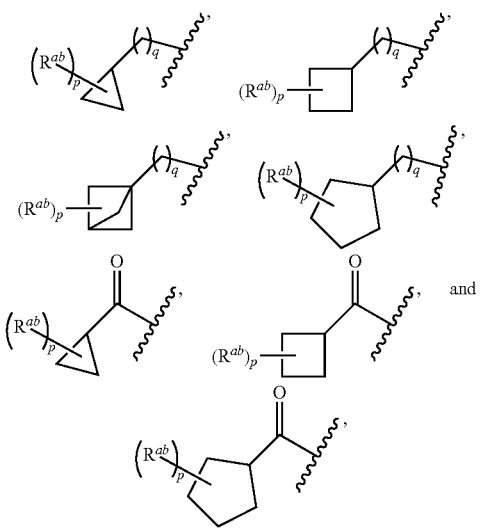

wherein p is 0, 1, or 2;
q is 0, 1, or 2; and wherein
each $R^{ab}$ is independently selected from H, F, OH, CH₃, CH₂CH₃, OCH₃, and OCH₂CH₃.

In another embodiment, in each of Formulas (IA) and (IB):
n is 1 or 2;
$R^1$ is $N(R^{1A})(R^{1B})$, wherein $R^{1A}$ and $R^{1B}$ are taken together with the nitrogen atom to which they are shown attached to form a 4, 5, or 6 membered monocyclic heterocycloalkyl ring comprising 1 or 2 ring nitrogen atoms (including the nitrogen atom of $N(R^{1A})(R^{1B})$ and of $C(O)N(R^{1A})(R^{1B})$), wherein said heterocycloalkyl ring is unsubstituted or substituted with 1, 2, or 3 $R^{1AB}$ groups.

In another embodiment, in each of Formulas (IA) and (IB):
n is 1 or 2;
$R^1$ is $N(R^{1A})(R^{1B})$, wherein $R^{1A}$ and $R^{1B}$ are taken together with the nitrogen atom to which they are shown attached to form a 4, 5, or 6 membered monocyclic heterocycloalkyl ring comprising 1 or 2 ring nitrogen atoms (including the nitrogen atom of $N(R^{1A})(R^{1B})$ and of $C(O)N(R^{1A})(R^{1B})$), wherein said heterocycloalkyl ring is unsubstituted or substituted with 1, 2, or 3 $R^{1AB}$ groups, wherein each $R^{1AB}$ group is independently selected from:
F, Cl, OH, CN,
CH₃, CH₂CH₃, CH₂CH₂CH₃, CH(CH₃)CH₃, CH₂CH₂CH₂CH₃, CH(CH₃)CH₂CH₃, CH₂CH(CH₃)CH₃, C(CH₃)₃,
OCH₃, OCH₂CH₃, OCH₂CH₂CH₃, OCH(CH₃)CH₃, OCH₂CH₂CH₂CH₃, OCH(CH₃)CH₂CH₃, OCH₂CH(CH₃)CH₃, OC(CH₃)₃,
CH₂OH, CH₂CH₂OH, CH₂CH₂CH₂OH, CH(CH₃)CH₂OH, CH₂CH₂CH₂CH₂OH, CH₂C(CH₃)₂OH, CH(CH₃)CH₂CH₂OH, CH₂CH(CH₃)CH₂OH, C(CH3)₂OH,
CF₃, CH₂CF₃, CH₂CHF₂, CF₂CF₃, CH₂CH₂CF₃, CH(CF₃)CF₃, CH₂CH₂CH₂CF₃, CH(CH₃)CH₂CF₃, CH₂CH(CH₃)CF₃, C(CF₃)₃,
OCF₃, OCH₂CF₃, OCH₂CHF₂, OCF₂CF₃, OCH₂CH₂CF₃, OCH(CF₃)CF₃, OCH₂CH₂CH₂CF₃, OCH(CH₃)CH₂CF₃, OCH₂CH(CH₃)CF₃, OC(CF₃)₃,
C(O)OCH₃, C(O)OCH₂CH₃, C(O)OCH₂CH₂CH₃, C(O)OCH(CH₃)CH₃, C(O)OCH₂CH₂CH₂CH₃, C(O)OCH(CH₃)CH₂CH₃, C(O)OCH₂CH(CH₃)CH₃, C(O)OC(CH₃)₃,

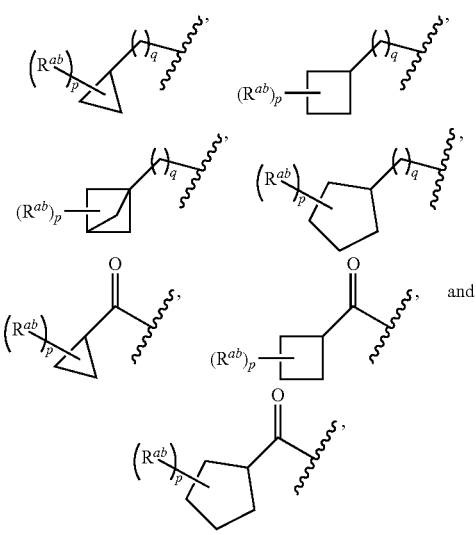

wherein p is 0, 1, or 2;
q is 0, 1, or 2; and wherein
each $R^{ab}$ is independently selected from H, F, OH, CH₃, CH₂CH₃, OCH₃, and OCH₂CH₃.

In another embodiment, in each of Formulas (IA) and (IB):
n is 2;
$R^1$ is $N(R^{1A})(R^{1B})$, wherein $R^{1A}$ and $R^{1B}$ are taken together with the nitrogen atom to which they are shown attached to form a moiety selected from:

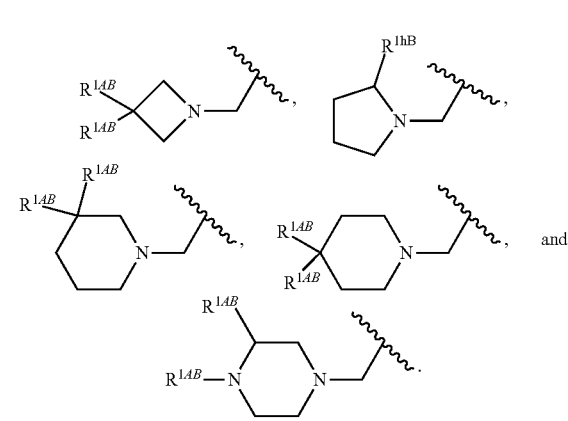

In another embodiment, in each of Formulas (IA) and (IB):

n is 2;

$R^1$ is $N(R^{1A})(R^{1B})$, wherein $R^{1A}$ and $R^{1B}$ are taken together with the nitrogen atom to which they are shown attached to form a moiety selected from:

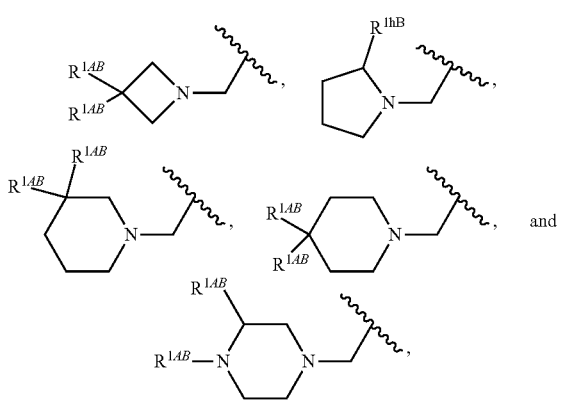

wherein each $R^{1AB}$ is independently selected from:

F, Cl, OH, CN, oxo, $CH_3$, $CH_2CH_3$, $CH(CH_3)_2$, $CH_2CH(CH_3)_2$, $C(CH_3)_3$, $OCH_3$, $OCH_2CH_3$, $OCH(CH_3)_2$, $OCH_2CH(CH_3)_2$, $OC(CH_3)_3$, $CH_2C(CH_3)_2OH$, $C(CH_3)_2OH$, $C(O)OCH_3$, $C(O)OCH_2CH_3$, $C(O)OCH(CH_3)_2$, $C(O)OCH_2CH(CH_3)_2$, $C(O)OC(CH_3)_3$, $CF_3$, $CH(CF_3)_2$, $CH_2CHF_2$, $CH_2CF_3$, $CH_2CH(CF_3)_2$, $C(CF_3)_3$, $OCF_3$, $OCH(CF_3)_2$, $OCH_2CHF_2$, $OCH_2CH(CF_3)_2$, $OC(CF_3)_3$, cyclopropyl, $CH_2$cyclopropyl,

wherein p is 0, 1, or 2; and q is 0, 1, or 2 and wherein each $R^{ab}$ is independently selected from H, F, OH, $CH_3$, $CH_2CH_3$, $OCH_3$, and $OCH_2CH_3$.

In another embodiment, in each of Formulas (IA) and (IB):

n is 1; and $R^1$ is

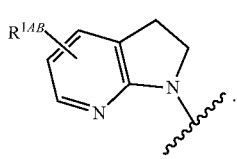

In another embodiment, in each of Formulas (IA) and (IB):

n is 2;

$R^1$ is a moiety selected from:

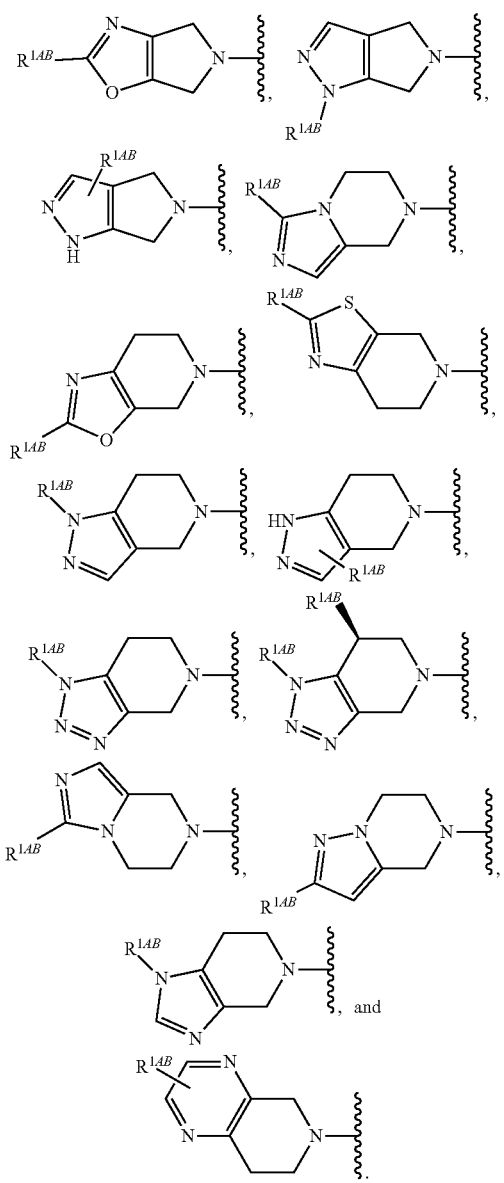

In another embodiment, in each of Formulas (IA) and (IB):

n is 1;

$R^1$ is

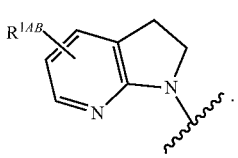

wherein $R^{1AB}$ is selected from:

F, Cl, OH, CN, $CH_3$, $CH_2CH_3$, $CH(CH_3)_2$, $CH_2CH(CH_3)_2$, $C(CH_3)_3$, $OCH_3$, $OCH_2CH_3$, $OCH(CH_3)_2$, $OCH_2CH(CH_3)_2$, $OC(CH_3)_3$, $CH_2C(CH_3)_2OH$, $C(CH_3)_2OH$, $C(O)OCH_3$, $C(O)OCH_2CH_3$, $C(O)OCH(CH_3)_2$, $C(O)OCH_2CH(CH_3)_2$, $C(O)OC(CH_3)_3$, $CF_3$, $CH(CF_3)_2$, $CH_2CHF_2$, $CH_2CF_3$, $CH_2CH(CF_3)_2$, $C(CF_3)_3$, $OCF_3$, $OCH(CF_3)_2$, $OCH_2CHF_2$, $OCH_2CH(CF_3)_2$, $OC(CF_3)_3$, cyclopropyl, —$CH_2$-cyclopropyl,

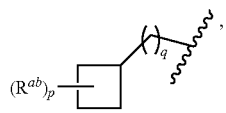

wherein p is 0, 1, or 2; and q is 0, 1, or 2 and wherein each $R^{ab}$ is independently selected from H, F, OH, $CH_3$, $CH_2CH_3$, $OCH_3$, and $OCH_2CH_3$.

In another embodiment, in each of Formulas (IA) and (IB):

n is 2;

$R^1$ is a moiety selected from:

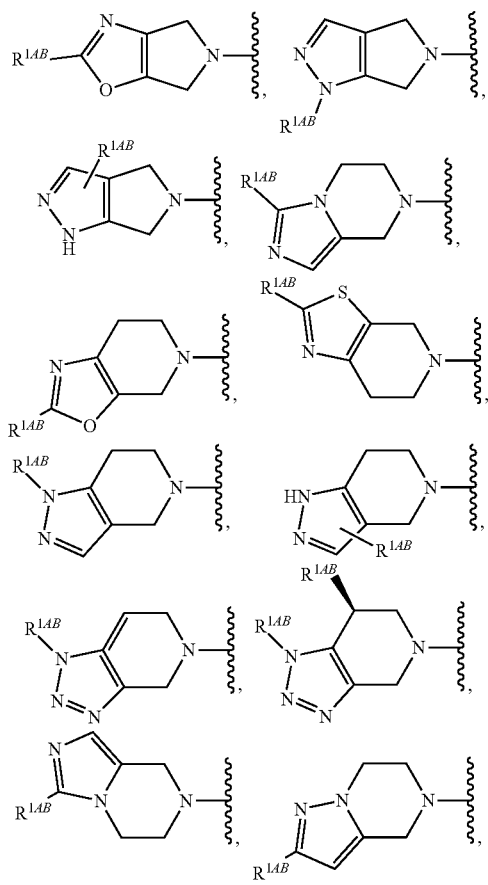

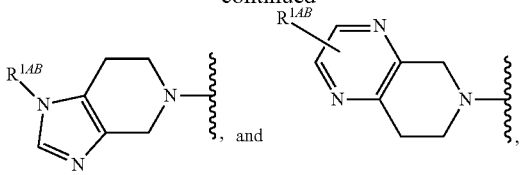

wherein each $R^{1AB}$ is independently selected from:

F, Cl, OH, CN, $CH_3$, $CH_2CH_3$, $CH(CH_3)_2$, $CH_2CH(CH_3)_2$, $C(CH_3)_3$, $OCH_3$, $OCH_2CH_3$, $OCH(CH_3)_2$, $OCH_2CH(CH_3)_2$, $OC(CH_3)_3$, $CH_2C(CH_3)_2OH$, $C(CH_3)_2OH$, $C(O)OCH_3$, $C(O)OCH_2CH_3$, $C(O)OCH(CH_3)_2$, $C(O)OCH_2CH(CH_3)_2$, $C(O)OC(CH_3)_3$, $CF_3$, $CH(CF_3)_2$, $CH_2CHF_2$, $CH_2CF_3$, $CH_2CH(CF_3)_2$, $C(CF_3)_3$, $OCF_3$, $OCH(CF_3)_2$, $OCH_2CHF_2$, $OCH_2CH(CF_3)_2$, $OC(CF_3)_3$, cyclopropyl, —$CH_2$-cyclopropyl,

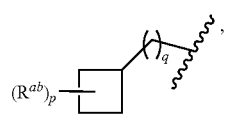

wherein p is 0, 1, or 2; and q is 0, 1, or 2 and wherein each $R^{ab}$ is independently selected from H, F, OH, $CH_3$, $CH_2CH_3$, $OCH_3$, and $OCH_2CH_3$.

In another embodiment, in Formula (IA), and in each of the additional embodiments of $R^1$ described above:

$R^2$ is selected from H, methyl, and propyl, wherein said methyl and said propyl are unsubstituted or substituted with 1, 2, or 3 $R^{2A}$ groups, wherein $R^{2A}$ is as defined in Formulas (IA) and (IB).

In another embodiment, in Formula (IB), and in each of the additional embodiments of $R^1$ described above:

$R^2$ is selected from H, methyl, propyl, and cyclopropyl, wherein said methyl, propyl, and cyclopropyl are unsubstituted or substituted with 1, 2, or 3 $R^{2A}$ groups, wherein $R^{2A}$ is as defined in Formulas (IA) and (IB).

In another embodiment, in each of Formulas (IA) and (IB), and in each of the alternative embodiments of Formulas (IA) and (IB) and of $R^1$ described above, each $R^{2A}$ is independently selected from:

F, Cl, OH, oxo, ($C_1$-$C_6$)alkyl, O($C_1$-$C_6$)alkyl, ($C_1$-$C_6$) haloalkyl, O($C_1$-$C_6$)haloalkyl, and ($C_1$-$C_6$)alkyl-OH.

In another embodiment, in Formula (IA), and in each of the additional embodiments of $R^1$ described above:

$R^2$ is selected from H, methyl, ethyl, and propyl, wherein said methyl, ethyl, and said propyl are unsubstituted or substituted with 1, 2, or 3 $R^{2A}$ groups, wherein each $R^{2A}$ group is independently selected from F, Cl, OH, oxo, $CH_3$, $CF_3$, $OCH_3$ $OCHF_2$, and $C(CH_3)_2OH$.

In another embodiment, in Formula (IB), and in each of the additional embodiments of $R^1$ described above:

$R^2$ is selected from H, methyl, ethyl, propyl, and cyclopropyl wherein said methyl, ethyl, propyl, and cyclopropyl are unsubstituted or substituted with 1, 2, or 3 $R^{2A}$ groups, wherein each $R^{2A}$ group is independently selected from F, Cl, OH, oxo, $CH_3$, $CF_3$. $OCH_3$ $OCHF_2$, and $C(CH_3)_2OH$.

In another embodiment, in Formula (IA), and in each of the additional embodiments of $R^1$ described above:
$R^2$ is selected from H, methyl, $CH_2F$, $CHF_2$, $CF_3$, and $C(CH_3)_2OH$.

In another embodiment, in Formula (IB), and in each of the additional embodiments of $R^1$ described above:
$R^2$ is selected from H, methyl, $CH_2F$, $CHF_2$, $CF_3$, $C(CH_3)_2OH$, and cyclopropyl.

In another embodiment, in Formula (IA), and in each of the additional embodiments of $R^1$ and of $R^2$, alone and in combination, described above:
$R^3$ is selected from phenyl, oxazolyl, pyrimidinyl, pyrazolyl, pyridinyl, and thiazoyl, wherein said phenyl, oxazolyl, pyrazolyl, pyridinyl, and thiazoyl are unsubstituted or substituted with 1, 2, or 3 $R^{3A}$ groups, wherein each $R^{3A}$ group is independently selected from the group consisting of F, Cl, OH, CN, $(C_1$-$C_6)$alkyl, $(C_1$-$C_6)$haloalkyl, $O(C_1$-$C_6)$alkyl, and $O(C_1$-$C_6)$haloalkyl.

In another embodiment, in Formula (IB), and in each of the additional embodiments of $R^1$ and of $R^2$, alone and in combination, described above:
$R^3$ is selected from phenyl, oxazolyl, pyrimidinyl, pyrazolyl, pyridinyl, and thiazoyl, wherein said phenyl, oxazolyl, pyrazolyl, pyridinyl, and thiazoyl are unsubstituted or substituted with 1, 2, or 3 $R^{3A}$ groups, wherein each $R^{3A}$ group is independently selected from the group consisting of F, Cl, OH, $(C_1$-$C_6)$alkyl, $(C_1$-$C_6)$haloalkyl, $O(C_1$-$C_6)$alkyl, and $O(C_1$-$C_6)$haloalkyl.

In another embodiment, in Formula (IA), and in each of the additional embodiments of $R^1$ and of $R^2$ described above:
$R^3$ is selected from phenyl, oxazolyl, pyrimidinyl, pyrazolyl, thiazoyl, and pyridinyl,
phenyl substituted with 1, 2, or 3 substituents independently selected from F, Cl, OH, CN, $CH_3$, $OCH_3$, and $OCHF_2$,
oxazolyl substituted with 1, 2, or 3 substituents independently selected from $CH_3$, $CF_3$, and $OCH_3$,
pyrimidinyl substituted with 1, 2, or 3 substituents independently selected from F, Cl, $CH_3$, $CF_3$, and $OCH_3$,
pyrazolyl substituted with 1 or 2 substituents independently selected from $CH_3$, $CF_3$, and
thiazoyl substituted with 1 or 2 substituents independently selected $CH_3$, $CF_3$, and $OCH_3$, and
pyridinyl substituted with 1, 2, or 3 substituents independently selected from F, Cl, $CH_3$, $CF_3$, and $OCH_3$.

In another embodiment, in Formula (IB), and in each of the additional embodiments of $R^1$ and of $R^2$ described above:
$R^3$ is selected from phenyl, oxazolyl, pyrimidinyl, pyrazolyl, thiazoyl, and pyridinyl,
phenyl substituted with 1, 2, or 3 substituents independently selected from F, Cl, OH, $CH_3$, $OCH_3$, and $OCHF_2$,
oxazolyl substituted with 1, 2, or 3 substituents independently selected from $CH_3$, $CF_3$, and $OCH_3$,
pyrimidinyl substituted with 1, 2, or 3 substituents independently selected from F, Cl, $CH_3$, $CF_3$, and $OCH_3$,
pyrazolyl substituted with 1 or 2 substituents independently selected from $CH_3$, and $CF_3$, and
thiazoyl substituted with 1 or 2 substituents independently selected $CH_3$, $CF_3$, and $OCH_3$, and
pyridinyl substituted with 1, 2, or 3 substituents independently selected from F, Cl, $CH_3$, $CF_3$, and $OCH_3$.

In another embodiment, in Formula (IA), and in each of the additional embodiments of $R^1$ and $R^2$ described above:
each $R^{3A}$ group is independently selected from F, Cl, OH, CN, $CH_3$, $CF_3$, $OCH_3$, and $OCHF_2$.

In another embodiment, in Formula (IB), and in each of the additional embodiments of $R^1$ and $R^2$ described above:
each $R^{3A}$ group is independently selected from F, Cl, OH, CN, $CH_3$, $CF_3$, $OCH_3$, and $OCHF_2$.

In another embodiment, in Formula (IA), and in each of the additional embodiments of $R^1$ and $R^2$ described above:
each $R^{3A}$ group is independently selected from F, Cl, OH, $CH_3$, $CF_3$, $OCH_3$, and $OCHF_2$.

In another embodiment, the compounds of the invention comprise those compounds identified herein as examples in the tables below, and pharmaceutically acceptable salts thereof.

In another aspect, the present invention provides pharmaceutical compositions comprising a pharmaceutically acceptable carrier and a compound of the invention or a pharmaceutically acceptable salt thereof. Such compositions according to the invention may optionally further include one or more additional therapeutic agents as described herein.

In another aspect, the present invention provides a method for the manufacture of a medicament or a composition which may be useful for treating diseases, conditions, or disorders that are mediated, at least in part, by the adenosine A2a receptor and/or the adenosine A2b receptor, comprising combining a compound of the invention with one or more pharmaceutically acceptable carriers.

In another aspect, the present invention provides a method for treating or preventing a disease, condition, or disorder that is mediated, at least in part, by the adenosine A2a receptor and/or the adenosine A2b receptor in a subject (e.g., an animal or human) in need thereof, said method comprising administering to the subject in need thereof a therapeutically effective amount of at least one compound of the invention, or a pharmaceutically acceptable salt thereof, alone or in combination with one or more additional therapeutic agents. Specific non-limiting examples of such diseases, conditions, and disorders are described herein.

Oncology

In some embodiments, the disease, condition or disorder is a cancer. Any cancer for which a PD-1 antagonist and/or an A2a and/or A2b inhibitor are thought to be useful by those of ordinary skill in the art are contemplated as cancers treatable by this embodiment, either as a monotherapy or in combination with other therapeutic agents discussed below. Cancers that express high levels of A2a receptors or A2b receptors are among those cancers contemplated as treatable by the compounds of the invention. Examples of cancers that express high levels of A2a and/or A2b receptors may be discerned by those of ordinary skill in the art by reference to The Cancer Genome Atlas (TCGA) database. Non-limiting examples of cancers that express high levels of A2a receptors include cancers of the kidney, breast, lung, and liver. Non-limiting examples of cancers that express high levels of the A2b receptor include lung, colorectal, head & neck cancer, and cervical cancer.

Thus, one embodiment provides a method of treating cancer comprising administering an effective amount of a compound of the invention, or a pharmaceutically acceptable salt thereof, to a subject in need of such treatment, wherein said cancer is a cancer that expresses a high level of A2a receptor. A related embodiment provides a method of treating cancer comprising administering an effective amount of a compound of the invention, or a pharmaceutically acceptable salt thereof, to a subject in need of such treatment, wherein said cancer is selected from kidney (or renal) cancer, breast cancer, lung cancer, and liver cancer.

Another embodiment provides a method of treating cancer comprising administering an effective amount of a compound of the invention, or a pharmaceutically acceptable salt thereof, to a subject in need of such treatment, wherein said cancer is a cancer that expresses a high level of A2b receptor. A related embodiment provides a method of treating cancer comprising administering an effective amount of a compound of the invention, or a pharmaceutically acceptable salt thereof, to a subject in need of such treatment, wherein said cancer is selected from lung cancer, colorectal cancer, head & neck cancer, and cervical cancer.

Additional non-limiting examples of cancers which may be treatable by administration of a compound of the invention (alone or in combination with one or more additional agents described below) include cancers of the prostate, colon, rectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small cell lung cancer and non-small cell lung cancer), adrenal gland, thyroid, kidney, or bone. Additional cancers treatable by a compound of the invention include glioblastoma, mesothelioma, renal cell carcinoma, gastric carcinoma, sarcoma, choriocarcinoma, cutaneous basocellular carcinoma, and testicular seminoma, and Kaposi's sarcoma.

CNS and Neurological Disorders

In other embodiments, the disease, condition or disorder is a central nervous system or a neurological disorder. Non-limiting examples of such diseases, conditions or disorders include movement disorders such as tremors, bradykinesias, gait disorders, dystonias, dyskinesias, tardive dyskinesias, other extrapyramidal syndromes, Parkinson's disease, and disorders associated with Parkinson's disease. The compounds of the invention also have the potential, or are believed to have the potential, for use in preventing or reducing the effect of drugs that cause or worsen such movement disorders.

Infections

In other embodiments, the disease, condition or disorder is an infective disorder. Non-limiting examples of such diseases, conditions or disorders include an acute or chronic viral infection, a bacterial infection, a fungal infection, or a parasitic infection. In one embodiment, the viral infection is human immunodeficiency virus. In another embodiment, the viral infection is cytomegalovirus.

Immune Disease

In other embodiments, the disease, condition or disorder is an immune-related disease, condition or disorder. Non-limiting examples of immune-related diseases, conditions, or disorders include multiple sclerosis and bacterial infections. (See, e.g., Safarzadeh, E. et al., Inflamm Res 2016 65(7):511-20; and Antonioli, L., et al., Immunol Lett S0165-2478(18)30172-X 2018).

Additional Indications

Other diseases, conditions, and disorders that have the potential to be treated or prevented, in whole or in part, by the inhibition of the A2a and/or A2b adenosine receptor(s) are also candidate indications for the compounds of the invention and salts thereof. Non-limiting examples of other diseases, conditions or disorders in which a compound of the invention, or a pharmaceutically acceptable salt thereof, may be useful include the treatment of hypersensitivity reaction to a tumor antigen and the amelioration of one or more complications related to bone marrow transplant or to a peripheral blood stem cell transplant. Thus, in another embodiment, the present invention provides a method for treating a subject receiving a bone marrow transplant or a peripheral blood stem cell transplant by administering to said subject a therapeutically effective amount of a compound of the invention, or a pharmaceutically acceptable salt thereof, sufficient to increase the delayed-type hypersensitivity reaction to tumor antigen, to delay the time-to-relapse of post-transplant malignancy, to increase relapse-free survival time post-transplant, and/or to increase long-term post-transplant survival.

Combination Therapy

In another aspect, the present invention provides methods for the use of a compound of the invention, or a pharmaceutically acceptable salt thereof, (or a pharmaceutically acceptable composition comprising a compound of the invention or pharmaceutically acceptable salt thereof) in combination with one or more additional agents. Such additional agents may have some adenosine A2a and/or A2b receptor activity, or, alternatively, they may function through distinct mechanisms of action. The compounds of the invention may be used in combination with one or more other drugs in the treatment, prevention, suppression or amelioration of diseases or conditions for which the compounds of the invention or the other drugs described herein may have utility, where the combination of the drugs together are safer or more effective than either drug alone. The combination therapy may have an additive or synergistic effect. Such other drug(s) may be administered in an amount commonly used therefore, contemporaneously or sequentially with a compound of the invention or a pharmaceutically acceptable salt thereof. When a compound of the invention is used contemporaneously with one or more other drugs, the pharmaceutical composition may in specific embodiments contain such other drugs and the compound of the invention or its pharmaceutically acceptable salt in separate doses or in unit dosage form. However, the combination therapy may also include therapies in which the compound of the invention or its pharmaceutically acceptable salt and one or more other drugs are administered sequentially, on different or overlapping schedules. It is also contemplated that when used in combination with one or more other active ingredients, the compounds of the invention and the other active ingredients may be used in lower doses than when each is used singly. Accordingly, the pharmaceutical compositions comprising the compounds of the invention include those that contain one or more other active ingredients, in addition to a compound of the invention or a pharmaceutically acceptable salt thereof.

The weight ratio of the compound of the present invention to the second active ingredient may be varied and will depend upon the effective dose of each ingredient. Generally, an effective dose of each will be used. Thus, for example, when a compound of the invention is used in combination with another agent, the weight ratio of the compound of the present invention to the other agent may generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should generally be used.

Given the immunosuppressive role of adenosine, the administration of an A2a receptor antagonist, an A2b receptor antagonist, and/or an A2a/A2b receptor dual antagonist according to the invention may enhance the efficacy of immunotherapies such as PD-1 antagonists. Thus, in one embodiment, the additional therapeutic agent comprises an anti-PD-1 antibody. In another embodiment, the additional therapeutic agent is an anti-PD-L1 antibody.

As noted above, PD-1 is recognized as having an important role in immune regulation and the maintenance of peripheral tolerance. PD-1 is moderately expressed on naive T-cells, B-cells and NKT-cells and up-regulated by T-cell and B-cell receptor signaling on lymphocytes, monocytes and myeloid cells (Sharpe et al., Nature Immunology (2007); 8:239-245).

Two known ligands for PD-1, PD-L1 (B7-H1) and PD-L2 (B7-DC) are expressed in human cancers arising in various tissues. In large sample sets of, for example, ovarian, renal, colorectal, pancreatic, and liver cancers, and in melanoma, it was shown that PD-L1 expression correlated with poor prognosis and reduced overall survival irrespective of subsequent treatment. (Dong et al., Nat Med. 8(8):793-800 (2002); Yang et al., Invest Ophthamol Vis Sci. 49: 2518-2525 (2008); Ghebeh et al., Neoplasia 8:190-198 (2006); Hamanishi et al., Proc. Natl. Acad. Sci. USA 104: 3360-3365 (2007); Thompson et al., Cancer 5: 206-211 (2006); Nomi et al., Clin. Cancer Research 13:2151-2157 (2007); Ohigashi et al., Clin. Cancer Research 11: 2947-2953; Inman et al., Cancer 109: 1499-1505 (2007); Shimauchi et al., Int. J. Cancer 121:2585-2590 (2007); Gao et al., Clin. Cancer Research 15: 971-979 (2009); Nakanishi J., Cancer Immunol Immunother. 56: 1173-1182 (2007); and Hino et al., Cancer 00: 1-9 (2010)).

Similarly, PD-1 expression on tumor infiltrating lymphocytes was found to mark dysfunctional T-cells in breast cancer and melanoma (Ghebeh et al., BMC Cancer. 2008 8:5714-(2008); and Ahmadzadeh et al., Blood 114: 1537-1544 (2009)) and to correlate with poor prognosis in renal cancer (Thompson et al., Clinical Cancer Research 15: 1757-1761(2007)). Thus, it has been proposed that PD-L1 expressing tumor cells interact with PD-1 expressing T-cells to attenuate T-cell activation and to evade immune surveillance, thereby contributing to an impaired immune response against the tumor.

Immune checkpoint therapies targeting the PD-1 axis have resulted in groundbreaking improvements in clinical response in multiple human cancers (Brahmer, et al., N Engl J Med 2012, 366: 2455-65; Garon et al., N Engl J Med 2015, 372: 2018-28; Hamid et al., N Engl J Med 2013, 369: 134-44; Robert et al., Lancet 2014, 384: 1109-17; Robert et al., N Engl J Med 2015, 372: 2521-32; Robert et al., N Engl J Med 2015, 372: 320-30; Topalian et al., N Engl J Med 2012, 366: 2443-54; Topalian et al., J Clin Oncol 2014, 32: 1020-30; and Wolchok et al, N Engl J Med 2013, 369: 122-33).

"PD-1 antagonist" means any chemical compound or biological molecule that blocks binding of PD-L1 expressed on a cancer cell to PD-1 expressed on an immune cell (T-cell, B-cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment methods, medicaments and uses of the present invention in which a human individual is being treated, the PD-1 antagonist blocks binding of human PD-L1 to human PD-1, and preferably blocks binding of both human PD-L1 and PD-L2 to human PD-E Human PD-1 amino acid sequences can be found in NCBI Locus No.: NP 005009. Human PD-L1 and PD-L2 amino acid sequences can be found in NCBI Locus No.: NP_054862 and NP_079515, respectively.

PD-1 antagonists useful in any of the treatment methods, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments. Examples of PD-1 antagonists include, but are not limited to, pembrolizumab (KEYTRUDA®, Merck and Co., Inc., Kenilworth, NJ, USA). "Pembrolizumab" (formerly known as MK-3475, SCH 900475 and lambrolizumab and sometimes referred to as "pembro") is a humanized IgG4 mAb with the structure described in WHO Drug Information, Vol. 27, No. 2, pages 161-162 (2013). Additional examples of PD-1 antagonists include nivolumab (OPDIVO®, Bristol-Myers Squibb Company, Princeton, NJ, USA), atezolizumab (MPDL3280A; TECENTRIQ®, Genentech, San Francisco, CA, USA), durvalumab (IMFINZI®, Astra Zeneca Pharmaceuticals, LP, Wilmington, DE, and avelumab (BAVENCIO®, Merck KGaA, Darmstadt, Germany and Pfizer, Inc., New York, NY).

Examples of monoclonal antibodies (mAbs) that bind to human PD-1, and useful in the treatment methods, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment methods, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment methods, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment methods, medicaments and uses of the present invention include AMP-224 (also known as B7-DCIg), which is a PD-L2-FC fusion protein that binds to human PD-1.

Thus, one embodiment provides for a method of treating cancer comprising administering an effective amount of a compound of the invention, or a pharmaceutically acceptable salt thereof, in combination with a PD-1 antagonist to a subject in need thereof. In such embodiments, the compounds of the invention, or a pharmaceutically acceptable salt thereof, and PD-1 antagonist are administered concurrently or sequentially.

Specific non-limiting examples of such cancers in accordance with this embodiment include melanoma (including unresectable or metastatic melanoma), head & neck cancer (including recurrent or metastatic head and neck squamous cell cancer (HNSCC)), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, and salivary cancer.

In one embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma. In one such embodiment, the agent is a PD-1 antagonist. In one such embodiment, the agent is pembrolizumab. In another such embodiment, the agent is nivolumab. In another such embodiment, the agent is atezolizumab.

Pembrolizumab is approved by the U.S. FDA for the treatment of patients with unresectable or metastatic melanoma and for the treatment of certain patients with recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma, as described in the Prescribing Information for KEYTRUDA™ (Merck & Co., Inc., Whitehouse Station, NJ USA; initial U.S. approval 2014, updated November 2018). In another embodiment, there is provided a method of treating cancer comprising administering an effective amount of a compound of the invention, or a pharmaceutically acceptable salt thereof, to a person in need thereof, in combination with pembrolizumab, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, head and neck squamous cell cancer (HNSCC), Hodgkin lymphoma, primary mediastinal large B-cell lymphoma, urothelial carcinoma, microsatellite instability-high cancer, gastric cancer, Merkel cell carcinoma, hepatocellular carcinoma, esophageal cancer and cervical cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, small cell lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab.

In one embodiment, there is provided a method of treating unresectable or metastatic melanoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating recurrent or metastatic head and neck squamous cell cancer (HNSCC) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating classical Hodgkin lymphoma (cHL) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating urothelial carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating gastric cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating cervical cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating primary mediastinal large-B-cell lymphoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating microsatellite instability-high (MSI-H) cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating non-small cell lung cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating hepatocellular carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In another embodiment, the additional therapeutic agent is at least one immunomodulator other than an A2a or A2b receptor inhibitor. Non-limiting examples of immunomodulators include CD40L, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, anti-IL-10 and indolamine 2,3-dioxygenase 1 (IDO1) inhibitors.

In another embodiment, the additional therapeutic agent comprises radiation. Such radiation includes localized radiation therapy and total body radiation therapy.

In another embodiment, the additional therapeutic agent is at least one chemotherapeutic agent. Non-limiting examples of chemotherapeutic agents contemplated for use in combination with the compounds of the invention include: pemetrexed, alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethynyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); luteinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide).

In another embodiment, the additional therapeutic agent is at least one signal transduction inhibitor (STI). Non-limiting examples of signal transduction inhibitors include BCR/ABL kinase inhibitors, epidermal growth factor (EGF) receptor inhibitors, HER-2/neu receptor inhibitors, and farnesyl transferase inhibitors (FTIs).

In another embodiment, the additional therapeutic agent is at least one anti-infective agent. Non-limiting examples of anti-infective agents include cytokines, non-limiting examples of which include granulocyte-macrophage colony stimulating factor (GM-CSF) and an flt3-ligand.

In another embodiment, the present invention provides a method for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackievirus, and human immunodeficiency virus (HIV).

In another embodiment, the present invention provides a method for the treatment of an infective disorder, said method comprising administering to a subject in need thereof an effective amount of a compound of the invention, or a pharmaceutically acceptable salt thereof, in combination with a vaccine. In some embodiments, the vaccine is an anti-viral vaccine, including, for example, an anti-HTV vaccine. Other antiviral agents contemplated for use include an anti-HIV, anti-HPV, anti HCV, anti HSV agents and the like. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In another embodiment, the vaccine includes one or more immunogenic peptides and/or dendritic cells.

In another embodiment, the present invention provides for the treatment of an infection by administering a compound of the invention, or a pharmaceutically acceptable salt thereof, and at least one additional therapeutic agent, wherein a symptom of the infection observed after administering both the compound of the invention (or a pharmaceutically acceptable salt thereof) and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

Definitions

As used herein, unless otherwise specified, the following terms have the following meanings.

Unsatisfied valences in the text, schemes, examples, structural formulae, and any Tables herein are assumed to have a hydrogen atom or atoms of sufficient number to satisfy the valences.

When a variable appears more than once in any moiety or in any compound of the invention (e.g., aryl, heterocycle, $N(R)_2$), the selection of moieties defining that variable for each occurrence is independent of its definition at every other occurrence unless specified otherwise in the local variable definition.

As used herein, unless otherwise specified, the term "A2a receptor antagonist" (equivalently, A2a antagonist) and/or "A2b receptor antagonist" (equivalently, A2b antagonist) means a compound exhibiting a potency ($IC_{50}$) of less than about 1 μM with respect to the A2a and/or A2b receptors, respectively, when assayed in accordance with the procedures described herein. Preferred compounds exhibit at least 10-fold selectivity for antagonizing the A2a receptor and/or the A2b receptor over any other adenosine receptor (e.g., A1 or A3).

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administrations.

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

Whether used in reference to a substituent on a compound or a component of a pharmaceutical composition the phrase "one or more", means the same as "at least one".

"Concurrently" and "contemporaneously" both include in their meaning (1) simultaneously in time (e.g., at the same time); and (2) at different times but within the course of a common treatment schedule.

"Consecutively" means one following the other.

"Sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component.

"Effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating a cancer as described herein with one or more of the compounds of the invention optionally in combination with one or more additional agents, "effective amount" (or "therapeutically effective amount") means, for example, providing the amount of at least one compound of the invention that results in a therapeutic response in a patient afflicted with the disease, condition, or disorder, including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition.

"Patient" and "subject" means an animal, such as a mammal (e.g., a human being) and is preferably a human being.

"Prodrug" means compounds that are rapidly transformed, for example, by hydrolysis in blood, in vivo to the parent compound, e.g., conversion of a prodrug of a compound of the invention to a compound of the invention, or to a salt thereof. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention.

The term "substituted" means that one or more of the moieties enumerated as substituents (or, where a list of substituents are not specifically enumerated, the substituents specified elsewhere in this application) for the particular type of substrate to which said substituent is appended, provided that such substitution does not exceed the normal valence rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution by a moiety is described (e.g. "optionally substituted") the term means that if substituents are present, one or more of the enumerated (or default) moieties listed as optional substituents for the specified substrate can be present on the substrate in a bonding position normally occupied by the default substituent, for example, a hydrogen atom on an alkyl chain can be substituted by one of the optional substituents, in accordance with the definition of "substituted" presented herein.

"Alkyl" means an aliphatic hydrocarbon group, which may be straight or branched, comprising 1 to 10 carbon atoms. "($C_1$-$C_6$)alkyl" means an aliphatic hydrocarbon group, which may be straight or branched, comprising 1 to 6 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl (up to and including each available hydrogen group) is replaced by a halogen atom. As appreciated by those of skill in the art, "halo" or "halogen" as used herein is intended to include chloro (Cl), fluoro (F), bromo (Br) and iodo (I). Chloro (Cl) and fluoro (F) halogens are generally preferred.

"Aryl" means an aromatic monocyclic or multi cyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridinyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic fully saturated monocyclic or multi cyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyl groups contain 4, 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

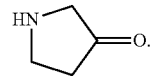

As used herein, the term "monocyclic heterocycloalkyl" refers to monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

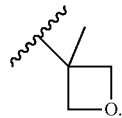

It is noted that in hetero-atom containing ring systems of this invention, there are no hydroxyl groups on carbon atoms adjacent to a N, O or S, as well as there are no N or S groups on carbon adjacent to another heteroatom.

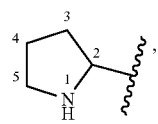

there is no —OH attached directly to carbons marked 2 and 5.

The line ——— as a bond generally indicates a mixture of, or either of, the possible isomers, e.g., containing (R)— and (S)— stereochemistry. For example:

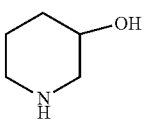

means containing both

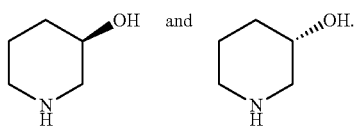

The wavy line ∼∼∼, as used herein, indicates a point of attachment to the rest of the compound. Lines drawn into the ring systems, such as, for example:

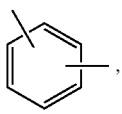

indicate that the indicated line (bond) may be attached to any of the substitutable ring atoms.

"Oxo" is defined as an oxygen atom that is double bonded to a ring carbon in a cycloalkyl, cycloalkenyl, heterocyclyl, heterocyclenyl, or other ring described herein, e.g.,

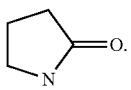

As well known in the art, a bond drawn from a particular atom wherein no moiety is depicted at the terminal end of the bond indicates a methyl group bound through that bond to the atom, unless stated otherwise. For example:

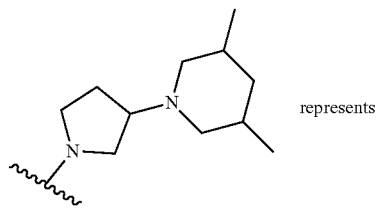 represents

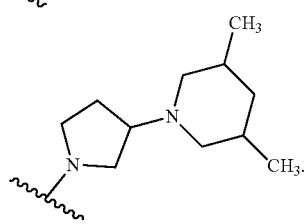

One or more compounds of the invention may also exist as, or optionally be converted to, a solvate. Preparation of solvates is generally known. Thus, for example, M. Caira et al., J. Pharmaceutical Sci., 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al., AAPS PharmSciTech., 5(1), article 12 (2004); and A. L. Bingham et al., Chem. Commun., 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

This invention also includes the compounds of the invention in isolated and purified form obtained by routine techniques. Polymorphic forms of the compounds of the invention, and of the salts, solvates and prodrugs of the thereof, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In similar manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

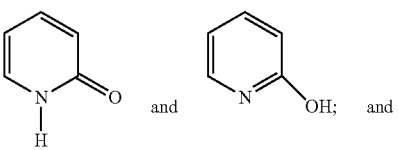 and

-continued

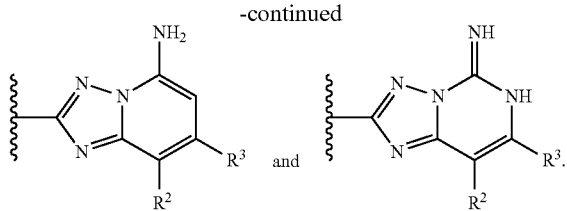

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al., The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quartemized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), arylalkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the scope of the invention.

A functional group in a compound termed "protected" means that the group is in modified form to preclude undesired side reactions at the protected site when the protected compound is subjected to particular reaction conditions aimed at modifying another region of the molecule. Suitable protecting groups are known, for example, as by reference to standard textbooks, for example, T. W. Greene et al., Protective Groups in organic Synthesis (1991), Wiley, New York.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the Schemes and Examples herein using appropriate isotopically-enriched reagents and/or intermediates.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes also may be incorporated by known means.

Certain isotopically-labeled compounds of the invention (e.g., those labeled with $^{3}H$, $^{11}C$ and $^{14}C$) are recognized as being particularly useful in compound and/or substrate tissue distribution assays using a variety of known techniques. Tritiated (i.e., $^{3}H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

The term "composition" is intended to encompass a product comprising the specified ingredients in the specified amounts, and any product which results, directly or indirectly, from combination of the specified ingredients in the specified amounts.

The term "pharmaceutical composition" as used herein encompasses both the bulk composition and individual dosage units comprised of one, or more than one (e.g., two), pharmaceutically active agents such as, for example, a compound of the present invention (optionally together with an additional agent as described herein), along with any pharmaceutically inactive excipients. As will be appreciated by those of ordinary skill in the art, excipients are any constituent which adapts the composition to a particular route of administration or aids the processing of a composition into a dosage form without itself exerting an active pharmaceutical effect. The bulk composition and each individual dosage unit can contain fixed amounts of the aforesaid one, or more than one, pharmaceutically active agents. The bulk composition is material that has not yet been formed into individual dosage units.

It will be appreciated that pharmaceutical formulations of the invention may comprise more than one compound of the invention (or a pharmaceutically acceptable salt thereof), for example, the combination of two or three compounds of the invention, each present in such a composition by adding to the formulation the desired amount of the compound in a pharmaceutically acceptably pure form. It will be appreciated also that in formulating compositions of the invention, a composition may comprise, in addition to one or more of compounds of the invention, one or more other agents which also have pharmacological activity, as described herein.

While formulations of the invention may be employed in bulk form, it will be appreciated that for most applications the inventive formulations will be incorporated into a dosage form suitable for administration to a patient, each dosage form comprising an amount of the selected formulation which contains an effective amount of one or more compounds of the invention. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions comprising compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, minitablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, MD.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In accordance with the present invention, antagonism of adenosine A2a and/or A2b receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, or a salt thereof, and at least one pharmaceutically acceptable carrier (described herein). It will be appreciated that pharmaceutically formulations of the invention may comprise more than one compound of the invention, or a salt thereof, for example, the combination of two or three compounds of the invention, or, additionally or alternatively, another therapeutic agent such as those described herein, each present by adding to the formulation the desired amount of the compound or a salt thereof (or agent, where applicable) which has been isolated in a pharmaceutically acceptably pure form.

As mentioned above, administration of a compound of the invention to effect antagonism of A2a and/or A2b receptors is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, NJ 07645-1742, USA), the Physician's Desk Reference, 56$^{th}$ Edition, 2002 (published by Medical Economics company, Inc. Montvale, NJ 07645-1742), or the Physician's Desk Reference, 57$^{th}$ Edition, 2003 (published by Thompson PDR, Montvale, NJ 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As those of ordinary skill in the art will appreciate, an appropriate dosage level for a compound (or compounds) of the invention will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during a treatment cycle.

In general, in whatever form administered, the dosage form administered will contain an amount of at least one compound of the invention, or a salt thereof, which will provide a therapeutically effective serum level of the compound in some form for a suitable period of time such as at least 2 h, more preferably at least four h or longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active agents as may be additionally needed or desired in the course of providing treatment. As will be appreciated, the dosage form administered may also be in a form providing an extended release period for the pharmaceutically active compound which will provide a therapeutic serum level for a longer period, necessitating less frequent dosage intervals.

Biological Assays

The $IC_{50}$ values reported for each of the compounds of the invention shown in the tables below were measured in accordance with the methods described below. Method (A) describes the procedure used to measure A2a binding affinity using radioligand binding. Method (B) describes the procedure used to measure A2a binding affinity using SPA technology. Method (C) describes an alternative procedure used to measure A2a binding affinity using radioligand binding. The method used to measure A2b binding affinity is also described below. The method used to determine the A2a $IC_{50}$ value reported for each compound in the table is indicated next to the reported value. The A2b $IC_{50}$ value measured using the A2b binding affinity assay is shown in the table next to the compound under the corresponding A2a value. An asterisk (*) indicates that the $IC_{50}$ value was not available.

The A2a receptor affinity binding assay measured the amount of binding of a tritiated ligand with high affinity for the A2a adenosine receptor to membranes made from HEK293 or CHO cells recombinantly expressing the human A2a adenosine receptor, in the presence of varying concentrations of a compound of the invention. The data were generated using either filtration binding or a homogenous scintillation proximity assay (SPA). In both assay formats, the tested compounds of the invention were solubilized in 100% DMSO and further diluted in 100% DMSO to generate, typically, a 10-point titration at half-log intervals such that the final assay concentrations did not exceed 10 µM of compound or 1% DMSO.

Method (A): Measurement of A2a Binding Affinity Using Radioligand Binding

148 µL (5 µg/mL) membranes (Perkin Elmer, Cat. No. RBHA2aM400UA) and 2 µL compounds of the invention to be tested (test compound) were transferred to individual wells of a 96-well polypropylene assay plate and incubated for 15 to 30 min at room temperature. [$^3$H] SCH58261 ((7-(2-phenylethyl)-5-amino-2-(2-furyl)-pyrazolo-[4,3-e]-1,2,4-triazolo[1,5-c]pyrimidine)) was diluted in assay buffer (50 mM Tris pH 7.4, 10 mM $MgCl_2$, 0.005% Tween20) to a concentration of 4 nM and 50 µL transferred to each well of the assay plate. To define total and non-specific binding, wells containing 1% DMSO and 1 µM ZM241385 (Tocris Bioscience, Cat. No. 1036) respectively, were also included. The assay plate was incubated at room temperature for 60 min with agitation. Using a FilterMate Harvester® (Perkin Elmer), the contents of the assay plate were filtered through a UniFilter-96® PEI coated plate (Perkin Elmer Cat. No. 6005274 or 6005277). Filtering was achieved by aspirating the contents of the assay plate for 5 sec, then washing and aspirating the contents three times with ice-cooled wash buffer (50 mM Tris-HCl pH 7.4, 150 mM NaCl) and allowing the vacuum manifold to dry the plate for sec. The filter plate was incubated for at least 1 h at 55° C. and allowed to dry. The bottom of the filter plate was sealed with backing tape. 40 µL Ultima Gold™ (Perkin Elmer, Cat. No. 6013329) was added to each well of the filter plate and the top of the plate was sealed with TopSeal-A PLUS® clear plate seal (Perkin Elmer, Cat. No. 6050185). The plate was incubated for at least 20 min, and then the amount of radioactivity remaining in each well was determined using a TopCount® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

Method (B): Measurement of A2a Binding Affinity Using SPA

Binding affinity using SPA was conducted as follows. Test compounds (50 nL) were dispensed into individual wells of a 384-well OptiPlate™ well (Perkin Elmer) by Echo® acoustic liquid transfer (Labcyte). 20 µL of 1.25 nM [$^3$H] SCH58261 ((7-(2-phenylethyl)-5-amino-2-(2-furyl)-pyrazolo-[4,3-e]-1,2,4-triazolo[1,5-c]pyrimidine)) in DPBS assay buffer (Dulbecco's phosphate buffered saline without calcium and magnesium, ThermoFisher Scientific, Cat. No. A1285601) supplemented with 10 mM $MgCl_2$ was added. A2a receptor-expressing membranes were incubated with 20 µg/mL adenosine deaminase (Roche, Cat. No. 10 102 105 001) for 15 min at room temperature. The receptor-expressing membranes were then combined with wheat germ agglutinin-coated yttrium silicate SPA beads (GE Healthcare, Cat. No. RPNQ0023) in a ratio of 1:1000 (w/w) and incubated for 30 min at room temperature. 30 µL of the membrane/bead mixture (0.25 µg and 25 µg per well respectively) were added to the 384-well OptiPlate™ well. To define total and non-specific binding, wells containing 1% DMSO or 1 µM CGS15943 (Tocris Bioscience, Cat. No. 1699) respectively were also included in the experiment. The plate was incubated for one h at room temperature with agitation. The assay plate was then incubated for an h to allow the beads to settle before data were collected using a TopCount® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

Method (C): Measurement of A2a Binding Affinity Using an Alternative Radioligand Binding Assay Membranes used in this procedure were made by washing cell cultures twice with DPBS buffer (Dulbecco's phosphate buffered saline without calcium and magnesium, ThermoFisher Scientific, Cat. No. A1285601), and harvesting the cell cultures by mechanical scraping. The cells were collected by centrifugation and re-suspended in 10 mM HEPES, pH 7.4 containing 0.1 mM benzamidine (Sigma, Cat. No. B6506) and 0.1 mM PMSF (phenylmethylsulfonyl fluoride, Sigma, Cat. No. 10837091001). Cells were freeze-thawed twice in a dry ice/ethanol bath and homogenized with 25 to 30 strokes in a glass dounce homogenizer (Wheaton, Cat. No. 357546). Membranes were pelleted at 40,000×g for 20 min at 4° C. and re-suspended in assay buffer (5 mM HEPES, pH 7.4, 5 mM $MgCl_2$; supplemented with 0.1 mM benzamidine) at a protein concentration of 2.6 mg/mL. Protein concentration was determined by the Bio-Rad method (Bio-Rad, Cat. No. 5000002). Membranes were then incubated with adenosine deaminase (final concentration 2U/mL) for 20 min at 37° C. before use in the binding assay.

To perform the binding assay, 50 µg CHO.A2a membranes, 5 nM [$^3$H]CGS21680 (Perkin Elmer, Cat. No.

NET1021), and 1 µL of test compound were combined in individual tubes to a volume of 100 µL. To define total and non-specific binding, wells containing 1% DMSO and 20 µM N-ethylcarboxamidoadenosine (Tocris Bioscience, Cat. No. 1691) respectively, were also included. The samples were incubated for 2 h at 37° C. The samples were filtered rapidly through a glass fiber filter using a cell harvester and washed with cold buffer (10 mM Tris, pH7.4, 5 mM $MgCl_2$). The filter was allowed to dry and individual filters were placed into vials together with liquid scintillant and subjected to scintillation counting. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

Measurement of A2b Binding Affinity

The reported affinity of the compounds of the invention for the human A2b adenosine receptor was determined experimentally using a radioligand filtration binding assay. This assay measures the amount of binding of a tritiated proprietary A2b receptor antagonist, in the presence and absence of a compound of the invention, to membranes made from HEK293 cells recombinantly expressing the human A2b adenosine receptor (Perkin Elmer, Cat. No. ES-013-C).

To perform the assay, compounds of the invention to be tested were first solubilized in 100% DMSO and further diluted in 100% DMSO to generate, typically, a 10-point titration at half-log intervals such that the final assay concentrations did not exceed 10 µM of compound or 1% DMSO. 148 µL (135 µg/mL) membranes and 2 µL test compounds were transferred to individual wells of a 96-well polypropylene assay plate and incubated for 15 to 30 min at room temperature with agitation. Tritiated radioligand was diluted to a concentration of 14 nM in assay buffer (phosphate buffered saline without Magnesium and Calcium, pH 7.4; GE Healthcare Life Sciences, Cat. No. SH30256.01) and then 50 µL of the solution were transferred to each well of the assay plate. To define total and non-specific binding, wells containing 1% DMSO and 20 µM N-ethylcarboxamidoadenosine (Tocris Bioscience, Cat. No. 1691) respectively, were also included. The wells of the assay plate were incubated at room temperature for 60 min with agitation, then filtered using a FilterMate Harvester® (Perkin Elmer) or similar equipment through a UniFilter-96® PEI coated plate (Perkin Elmer Cat. No. 6005274 or 6005277). Filtering was achieved by aspirating the contents of the assay plate for 5 sec, then washing and aspirating the contents three times with ice-cooled wash buffer (assay buffer supplemented with 0.0025% Brij58) and allowing the vacuum manifold to dry the plate for 30 sec. The filter plate was incubated for at least 1 h at 55° C. and allowed to dry. The bottom of the filter plate was then sealed with backing tape. 40 µL Ultima Gold™ (Perkin Elmer, Cat. No. 6013329) was added to each well of the filter plate and the top of the plate was sealed with TopSeal-A PLUS® clear plate seal (Perkin Elmer, Cat. No. 6050185). The plates were then incubated for at least 20 min, and then the amount of radioactivity remaining in each well was determined using a TopCount® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

PREPARATIVE EXAMPLES

The compounds of the present invention can be prepared readily according to the following schemes and specific examples, or modifications thereof, using readily available starting materials, reagents and conventional synthetic procedures. In these reactions, it is also possible to make use of variants which are themselves known to those of ordinary skill in this art but are not mentioned in detail. The general procedures for making the compounds claimed in this invention can be readily understood and appreciated by one skilled in the art from viewing the following Schemes and descriptions.

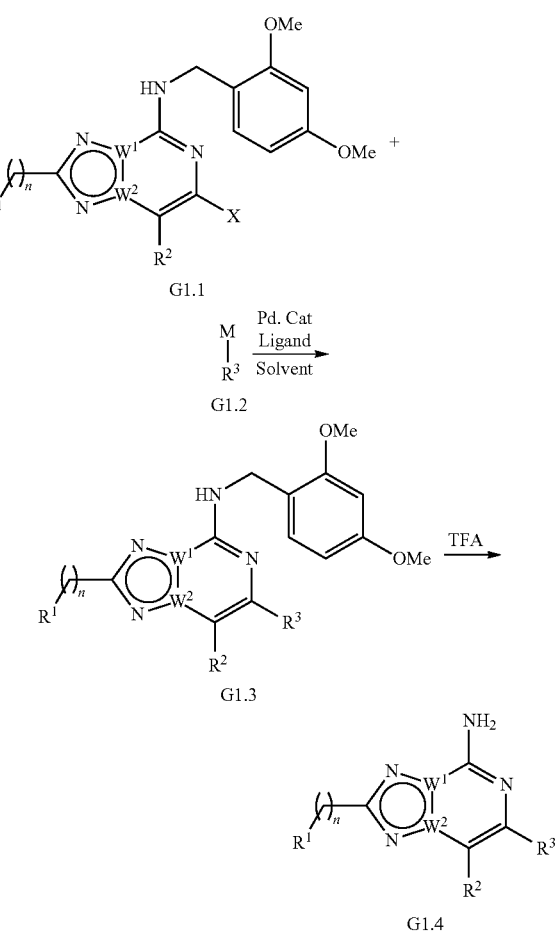

One general strategy for the synthesis of compounds of type G1.4 is via a two-step procedure shown in General Scheme 1, wherein one, but not both, of $W^1$ and $W^2$ are nitrogen, and the other is carbon, X is a halogen, M is either a boronic acid or ester or a trialkyl stannane, and $R^1$, $R^2$, and $R^3$ are as defined in Formula (IA) or (IB), and n is 1 or 2. Heteroaryl halides G1.1 can be combined with coupling partners G1.2 under deoxygenated conditions with the appropriate palladium catalyst, solvent and base (when necessary) to form intermediates of type G1.3. Bases such as cesium carbonate and tripotassium phosphate, catalysts such as XPhos Pd G2, (dppf)PdCl$_2$—CH$_2$C$_{1-2}$, Pd(PPh$_3$)$_4$, (2-dicyclohexylphosphino-2',4',6'-triisopropyl-1,1'-biphenyl)[2-(2-aminoethyl)phenyl]palladium(II) chloride, and SiliaCat DPP-Pd Resin, and solvents such as dioxane, THF and combinations thereof with water can be used. In the second step, intermediates of type G1.3 can be treated with TFA in the absence of solvent or in DCM, heating at 40-50° C., to provide products of type G1.4. Products of type G1.4 can be purified by silica gel chromatography or preparative reversed-phase HPLC.

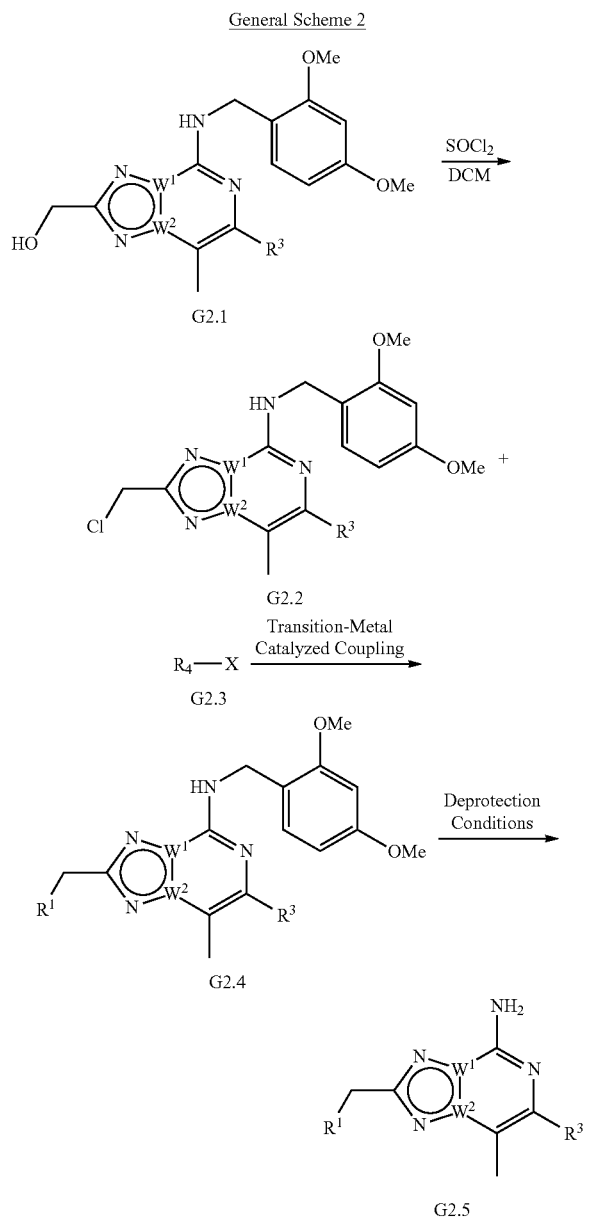

G2.1

G2.2

G2.3

G2.4

G2.5

One general strategy for the synthesis of compounds of type G2.5 is via a three-step procedure shown in General Scheme 2, wherein one, but not both, of W$^1$ and W$^2$ are nitrogen, and the other is carbon, X is either a halogen, a boronic acid or ester thereof, or a trialkyl stannane, R$_3$ is as defined in Formula (IA) or (IB), and R$^1$ is an aryl or heteroaryl group. In the first step, primary alcohols G2.1 can be converted to chloride intermediates G2.2 under the action of thionyl chloride in dichloromethane as solvent at room temperature. In the second step, intermediates of type G2.2 can be converted into intermediates of type G2.4 through a transition-metal catalyzed cross coupling reaction with a coupling partner G2.3. In cases where X is a halogen, the reaction is performed under deoxygenated conditions with catalytic quantities of [Ni(dtbbpy)(H$_2$O)$_4$]C$_{1-2}$ and (Ir[dF(CF$_3$)ppy]$_2$(dtbbpy))PF$_6$, a reductant such as (TMS)$_3$SiH, and a base such as lithium hydroxide in a solvent such as dimethoxyethane, under irradiation with blue LED light. In cases where X is a boronic acid or ester thereof, the reaction is performed under deoxygenated conditions with catalytic quantities of (dppf) PdCl$_2$·CH$_2$Cl$_2$, bases such as tripotassium phosphate, and solvents such as a mixture of dioxane and water at the appropriate temperature. In cases where X is a trialkyl stannane, the reaction is performed under deoxygenated conditions with catalytic quantities of XPhos Pd G2 in a solvent such as dioxane. In the third step, intermediates of type G2.4 can be converted into products of type G2.5 via either an oxidative or acidic cleavage of the dimethoxybenzyl amine linkage. Intermediates G2.4 are either treated with TFA in the absence of solvent, by heating at 50° C., or with DDQ in dichloromethane, at ambient temperature, to provide products of type G2.5. Products of type G2.5 can be purified by silica gel chromatography or preparative reversed-phase HPLC.

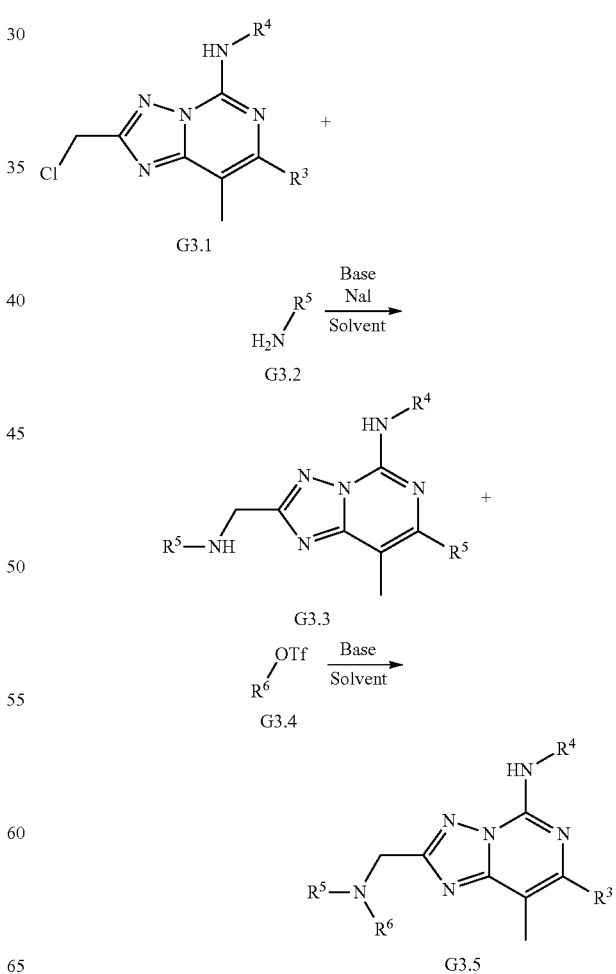

G3.1

G3.2

G3.3

G3.4

G3.5

One general strategy for the synthesis of compounds of type G3.5 is via a two-step procedure outlined in General Scheme 3, wherein $R^3$ is defined in Formula (IA) or (IB), $R^4$ is either hydrogen or a dimethoxybenzyl group, and $R^5$ and $R^6$ are both optionally substituted alkyl substituents. Benzylic chlorides G3.1, which are a subset of intermediates G2.2 in General Scheme 2, can be converted in situ to the corresponding iodides with sodium iodide and combined with primary amines G3.2 in the presence of bases such as DIPEA and in solvents such as DMF. After heating to the appropriate temperature for the appropriate time, intermediates G3.3 are formed. In the second step, intermediates of type G3.3 can be combined with alkyl triflates G3.4 in the presence of bases such as DIPEA and in solvents such as DCE or DMF to provide products G3.5. Products of type G3.5 can be purified by silica gel chromatography or preparative reversed-phase HPLC, or can be taken forward without additional purification. In many cases only step 1 is performed and not step 2.

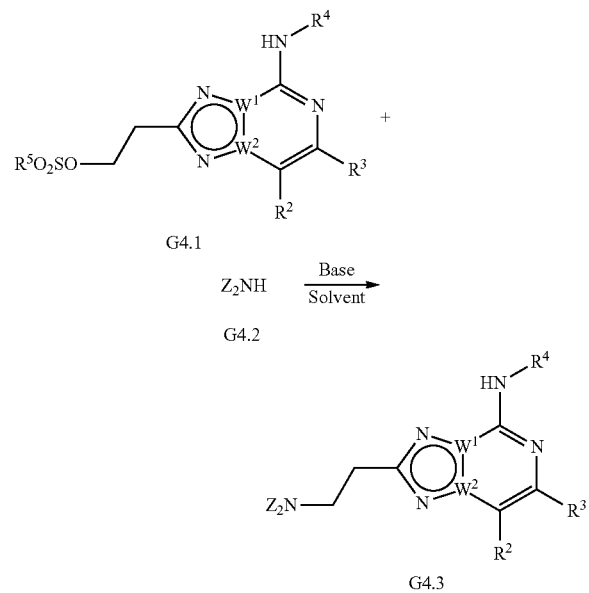

General Scheme 4

G4.1

Z₂NH / Base / Solvent

G4.2

G4.3

One general strategy for the synthesis of compounds of type G4.3 is outlined in General Scheme 4, wherein one, but not both, of $W^1$ and $W^2$ are nitrogen, and the other is carbon, $Z_2N$ is a partially or fully saturated monocyclic or bicyclic secondary amine, $R^2$ and $R^3$ are defined in Formula (IA) or (IB), $R^4$ is either hydrogen or a dimethoxybenzyl group, and $R^5$ is a substituted aryl group. Alkyl aryl sulfonates G4.1 can be combined with secondary amines G4.2 in the presence of bases such as sodium carbonate, DIPEA, or CsF in solvents such as acetonitrile or dioxane. After heating to the appropriate temperature for the appropriate time, products G4.3 are formed. Products of type G4.3 can be purified by silica gel chromatography, SFC, or preparative reversed-phase HPLC, or can be taken forward without additional purification.

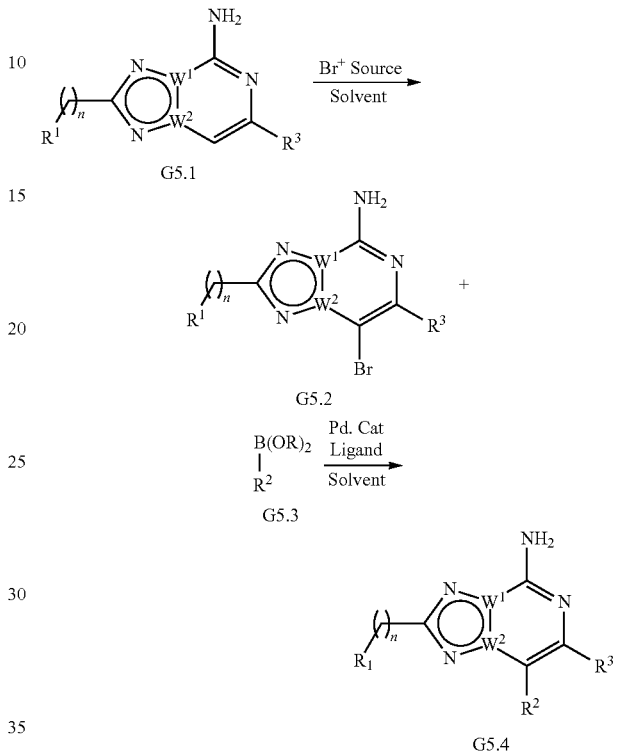

General Scheme 5

One general strategy for the synthesis of compounds of type G5.4 is via a two-step procedure outlined in General Scheme 5, wherein one, but not both, of $W^1$ and $W^2$ are nitrogen, and the other is carbon, and $R^1$, $R^2$ and $R^3$ are defined in Formula (IA) or (IB). Amino heterocycles G5.1 can be converted into brominated intermediates G5.2 in the presence of brominating agents such as NBS or 1,3-dibromo-5,5-dimethylimidazolidine-2,4-dione, and in solvents such as DCM or acetonitrile, at ambient temperature. In the second step, intermediates of type G5.2 can be combined with boronic acids or their respective esters G5.3 under deoxygenated conditions in the presence of the appropriate palladium catalyst, base, and solvent to provide products of type G5.4 after heating at the appropriate temperature. Palladium catalysts such as (dppf) PdCl₂—CH₂Cl₂, bases such as potassium carbonate and cesium carbonate, and solvents such as dioxane, or a mixture of dioxane and water, can be used. The products G5.4 can be purified by silica gel chromatography or preparative reversed-phase HPLC.

Abbreviations used herein have the following meaning:

| | |
|---|---|
| °C. | Degrees Celsius |
| µL | Microliter |
| µmol | Micromolar |
| AcOH | Acetic acid |
| aq. | Aqueous |
| Boc | Tert-butoxycarbonyl |
| Boc₂O | Di-tert-butyl dicarbonate |

-continued

| | |
|---|---|
| °C. | Degrees Celsius |
| BSA | N,O-Bis(trimethylsilyl)acetamide |
| DAST | Diethylaminosulfur trifluoride |
| DBU | 1,8-Diazabicyclo[5.4.0]undec-7-ene |
| DCE | Dichloroethane |
| DCM | Dichloromethane |
| DDQ | 2,3-Dichloro-5,6-dicyano-1,4-benzoquinone |
| DIPEA | N,N-Diisopropylethylamine |
| DMAP | 4-Dimethylaminopyridine |
| DME | Dimethoxyethane |
| DMF | Dimethylformamide |
| DMF-DMA | N,N-dimethylformamide dimethyl acetal |
| DMSO | Dimethyl sulfoxide |
| DMSO-$d_6$ | Deuterated dimethyl sulfoxide |
| DPP | Diphenylphosphine |
| dppf | Bis(diphenylphosphino)ferrocene |
| dtbbpy | 4,4'-Di-tert-butyl-2,2'-dipyridyl |
| dtbpf | (Di-tert-butylphosphino)ferrocene |
| EDCI | 1-Ethyl-3-(3-dimethylaminopropyl)carbodiimide |
| ESI | Electrospray Ionization |
| $Et_3N$ | Triethylamine |
| EtOAc | Ethyl acetate |
| EtOH | Ethanol |
| g | Grams |
| h | Hour/Hours |
| HATU | 1-[Bis(dimethylamino)methylene]-1H-1,2,3-triazolo[4,5-b]pyridinium 3-oxidhexafluorophosphate |
| HEPES | (4-(2-hydroxyethyl)-1-piperazineethanesulfonic acid) |
| HFIP | Hexafluoroisopropanol |
| HOAt | 1-Hydroxy-7-azabenzotriazole |
| HPLC | High Performance Liquid Chromatography |

(Ir[dF($CF_3$)ppy]$_2$(dtbbpy))$PF_6$
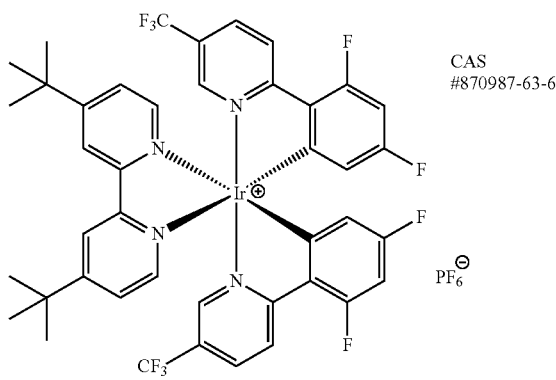
CAS #870987-63-6

| | |
|---|---|
| LED | Light-emitting diode |
| M | Molar |
| mCPBA | meta-Chloroperoxybenzoic acid |
| MeCN | Acetonitrile |
| MeMgBr | Methylmagnesium bromide |
| MeOD-$d_4$ | Deuterated methanol-d4 |
| MeOH | Methanol |
| Mes | Mesityl = 2,4,5-trimethylphenyl |
| mg | Milligrams |
| MHz | Megahertz |
| min | Minutes/Minutes |
| mL | Milliliters |
| mmol | Millimoles |
| MS | Mass Spectroscopy |
| NBS | N-Bromosuccinimide |
| nM | Nanomolar |
| nm | Nanometers |
| NMP | N-methyl-2-pyrrolidinone |
| NMR | Nuclear magnetic resonance |
| Pd/C | Palladium on carbon |
| Pd($PPh_3$)$_4$ | Tetrakis(triphenylphosphine)palladium(0) |
| PIFA | [Bist(trifluoroacetoxy)iodo]benzene |
| ppy | 2-phenylpyridinato |
| Prep SFC | Preparative Super Critical fluid ($CO_2$) Chromatography |

-continued

| | |
|---|---|
| °C. | Degrees Celsius |
| psi | Pounds per square inch |
| P(t-Bu)₃ Pd G2 | Chloro(tri-tert-butylphosphino)[2-(2'-amino-1,1'-biphenyl)]palladium(II) |
| RT | Retention Time |
| Ru(phen)₃Cl₂ | Dichlorotris(1,10-phenanthroline)ruthenium(II) |
| sat. | Saturated |
| t-BuOH | Tert-butanol |
| TBAF | Tetra-n-butylammonium fluoride |
| t-BuXPhos Pd G3 | 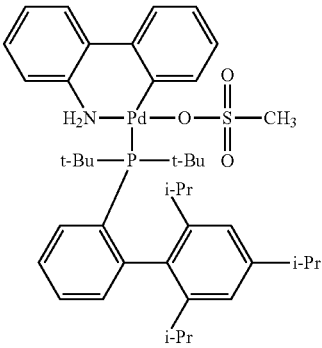<br>[(2-Di-tert-butylphosphino-2',4',6'-triisopropyl-1,1'-biphenyl)-2-(2'-amino-1,1'-biphenyl)] palladium(II) methanesulfonate<br>CAS #1447963-75-8 |
| t-BuXPhos | 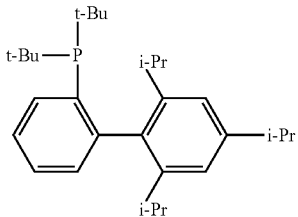<br>2-Di-tert-butylphosphino-2',4',6'-triisopropylbiphenyl<br>CAS #564483-19-8 |
| TFA | Trifluoroacetic acid |
| TfCl | Trifluoromethanesulfonyl chloride |
| THF | Tetrahydrofuran |
| TLC | Thin Layer Chromatography |
| TMS | Trimethylsilyl |
| XPhos Pd G2 | 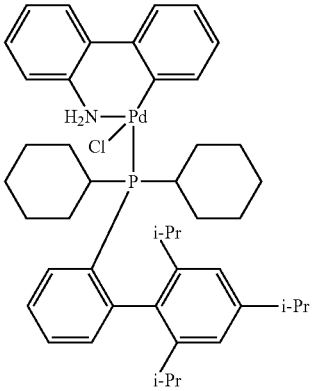<br>Chloro(2-dicyclohexylphosphino-2',4',6'-triisopropyl-1,1'-biphenyl)[2-(2'-amino-1,1'-biphenyl)]palladium(II)<br>CAS #1310584-14-5 |

General Experimental Information:
Unless otherwise noted, all reactions were magnetically stirred and performed under an inert atmosphere such as nitrogen or argon.
Unless otherwise noted, diethyl ether used in the experiments described below was Fisher ACS certified material and stabilized with BHT.
Unless otherwise noted, "concentrated" means evaporating the solvent from a solution or mixture using a rotary evaporator or vacuum pump.
Unless otherwise noted, flash chromatography was carried out on an ISCO®, Analogix®, or Biotage® automated chromatography system using a commercially available cartridge as the column. Columns were usually filled with silica gel as the stationary phase. Reversed-phase preparative HPLC conditions can be found at the end of the experimental section ("Method A" and "Method B". Aqueous solutions were concentrated on a Genevac® evaporator or were lyophilized.
Unless otherwise noted, "degassed" refers to a solvent from which oxygen has been removed, generally by bubbling an inert gas such as nitrogen or argon through the solution for 10 to 15 minutes with an outlet needle to normalize pressure. When indicated, "Method C" for degassing refers to bubbling argon through a solution for 15 minutes while the solution is submerged in an ultrasonic bath.
Unless otherwise noted, proton nuclear magnetic resonance ($^1$H NMR) spectra and proton-decoupled carbon nuclear magnetic resonance ($^{13}$C {$^1$H} NMR) spectra were recorded on 400, 500, or 600 MHz Bruker or Varian NMR spectrometers at ambient temperature. All chemical shifts (δ) were reported in parts per million (ppm). Proton resonances were referenced to residual protium in the NMR solvent, which can include, but is not limited to, CDCl$_3$, DMSO-d$_6$, and MeOD-d$_4$. Carbon resonances are referenced to the carbon resonances of the NMR solvent. Data are represented as follows: chemical shift, multiplicity (br=broad, br s=broad singlet, s=singlet, d=doublet, dd=doublet of doublets, ddd=doublet of doublet of doublets, t=triplet,q=quartet, m=multiplet), coupling constants (J) in Hertz (Hz), integration.

Preparation of Intermediate A.3,
N-(3,5-dibromopyrazin-2-yl)-2-phenylacetimidamide

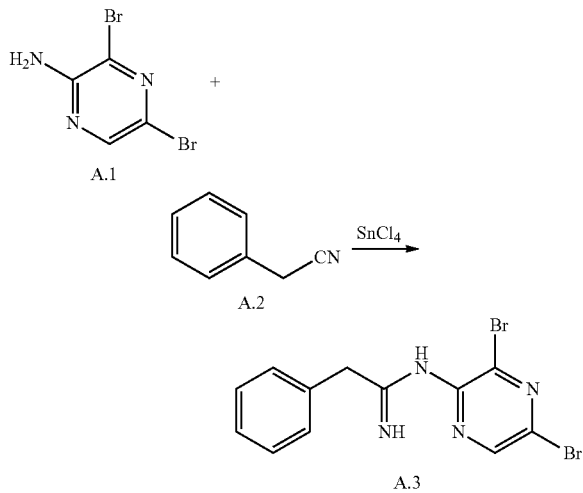

A 100 mL round bottom flask was charged with 3,5-dibromopyrazin-2-amine (10.0 g, 39.5 mmol) and 2-phenylacetonitrile (4.56 mL, 39.5 mmol), then heated to 90° C. and stirred for 30 min. Perchloro stannane (5.54 mL, 47.5 mmol) was then added, and the reaction mixture was heated to 120° C. and stirred for 3.5 h. Soon after the addition of perchloro stannane, the entire reaction mixture became a solid block. After cooling to 25° C., a spatula was used to grind up the solid into a free-flowing powder. The solid powder was transferred into a 1 L flask containing 500 mL DCM, 200 mL 1 M NaOH, and 300 mL water, then stirred at 25° C. overnight. The biphasic mixture was then filtered to remove any undissolved solids, and the filtrate was transferred into a separatory funnel and the layers were separated. The aq. layer was extracted with DCM (2×300 mL), and the combined organic layers were dried over anhydrous MgSO$_4$ filtered, and concentrated. The resulting crude material was recrystallized from hot MeOH to provide N-(3,5-dibromopyrazin-2-yl)-2-phenylacetimidamide. MS (ESI) m/z calc'd for C$_{12}$H$_{11}$Br$_2$N$_4$ [M+H]$^+$ 368.9, found 368.9, 370.9, 372.9.

Preparation of Intermediate B.2, N-(3,5-dibromo-6-methylpyrazin-2-yl)-2-phenylacetimidamide

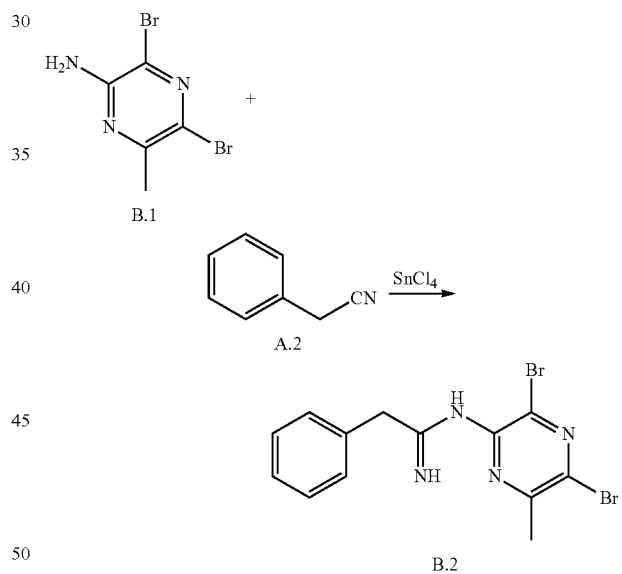

A 40 mL scintillation vial was charged with 3,5-dibromo-6-methylpyrazin-2-amine (5 g, 18.7 mmol) and 2-phenylacetonitrile (2.16 mL, 18.7 mmol), then heated to 90° C. and stirred for 30 min. The reaction was then heated to 120° C. and stirred for 20 min, then perchloro stannane (2.63 mL, 22.5 mmol) was added and the reaction mixture and then stirred at 120° C. for 3 h. Soon after the addition of perchloro stannane, the entire reaction mixture became a solid block. After cooling to 25° C., the reaction was uncapped, and the entire vial was placed in a 300 mL beaker that was filled with 250 mL DCM. The beaker was allowed to sit overnight, during which point material slowly dissolved in the solvent. The contents of the beaker were transferred into a 1 L flask containing 200 mL 1 M NaOH and 200 mL water, and the biphasic mixture was stirred for 1 h. The mixture was filtered to remove any undissolved solids, and the filtrate was transferred into a separatory funnel and the layers were separated. The aq. layer was extracted with DCM (2×250 mL), and the combined organic layers were dried over anhydrous MgSO$_4$, filtered, and concentrated. The resulting crude residue was purified by silica gel chromatography (gradient elution: 0-100% EtOAc/Hexanes) to provide A-(3, 5-dibromo-6-methylpyrazin-2-yl)-2-phenylacetimidamide. MS (ESI) m/z calc'd for C$_{13}$H$_{13}$Br$_2$N$_4$ [M+H]$^+$ 382.9, found 382.9, 384.9, 386.0.

Preparation of Intermediate C.1,2-benzyl-6,8-dibromo-[1,2,4]triazolo[1,5-a]pyrazine

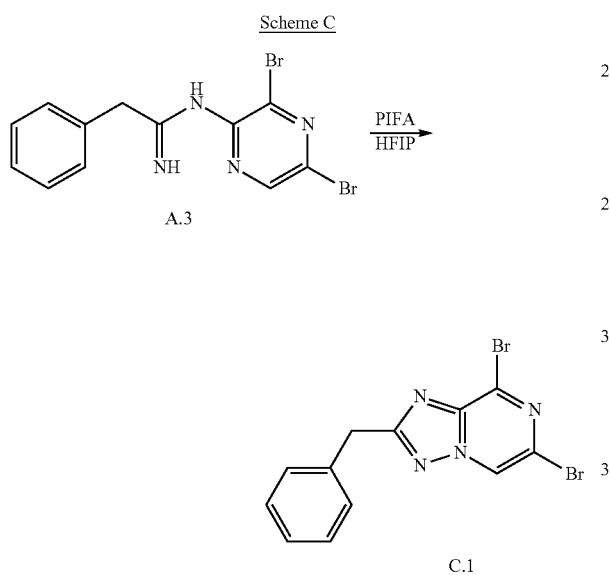

A 250 mL round bottom flask was charged with A-(3,5-dibromopyrazin-2-yl)-2-phenylacetimidamide (4.20 g, 11.4 mmol). HFIP (57 mL) and PIFA (5.86 g, 13.62 mmol) were then added, and the reaction mixture was heated to 65° C. and stirred for 20 min. After cooling, the reaction was quenched with sat. aq. NaHCO$_3$ (100 mL) and extracted with DCM (3×200 mL). The combined organic layers were washed with brine (150 mL), dried over anhydrous MgSO$_4$, filtered, and concentrated. The resulting crude residue was purified by silica gel chromatography (gradient elution: 0-100% EtOAc/Hexanes) to provide 2-benzyl-6,8-dibromo-[1,2,4]triazolo[1,5-a]pyrazine. MS (ESI) m/z calc'd for C$_{12}$H$_9$Br$_2$N$_4$ [M+H]$^+$ 366.9, found 366.5, 368.5, 370.5.

Scheme D

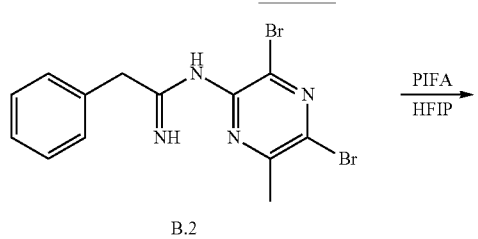

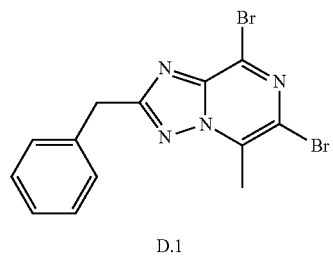

Intermediate D.1 was also synthesized according to the method shown in Scheme C, but starting with B.2. MS (ESI) m/z calc'd for C$_{13}$H$_{11}$Br$_2$N$_4$ [M+H]$^+$ 380.9, found 380.9, 382.9, 385.0.

Preparation of Intermediate E.2, O-(mesitylsulfonyl) hydroxylamine

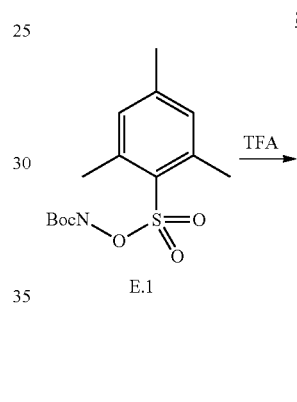

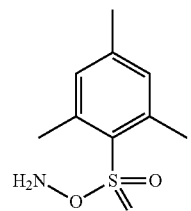

A 250 mL round bottom flask was charged with TFA (11.2 mL) and cooled to 0° C. Tert-butyl ((mesitylsulfonyl)oxy)-λ2-azanecarboxylate (3.00 g, 9.51 mmol) was then added, and the resulting solution was stirred for 15 min. The reaction was then quenched with water (80 mL) and stirred at 0° C. for 15 min. The solid precipitate that formed during the quench was then filtered, and the precipitate rinsed with 10 mL water. The solid was transferred to a 250 mL round bottom flask and DCM (40 mL) was added, followed by enough MgSO$_4$ to dry the resulting solution. The resulting mixture was stirred for 10 min. The mixture was then filtered, and the filtrate was used directly for the reactions described in Scheme F and Scheme G.

Preparation of Intermediate F.1, 1,2-diamino-3,5-dibromo-6-methylpyrazin-1-ium 2,4,6-trimethylbenzenesulfonate Scheme F

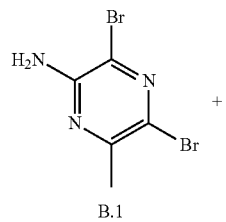

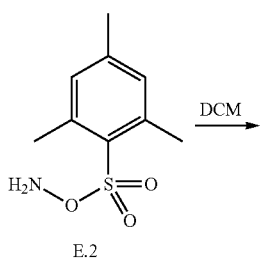

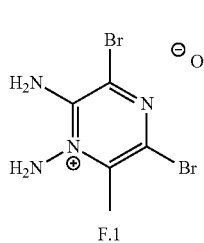

A 100 mL round bottom flask was charged with 3,5-dibromo-6-methylpyrazin-2-amine (1.27 g, 4.77 mmol). A solution of O-(mesitylsulfonyl)hydroxylamine (2.05 g, 9.54 mmol) in DCM (50 mL), freshly prepared from the procedure in Scheme E, was then added, and the resulting mixture was stirred at 25° C. overnight. The solid precipitate that formed during the reaction was then filtered, and the precipitate rinsed with 25 mL DCM. The solid was dried on high vacuum for 2 h to provide 1,2-diamino-3,5-dibromo-6-methylpyrazin-1-ium 2,4,6-trimethylbenzenesulfonate. MS (ESI) m/z calc'd for $C_5H_7Br_2N_4$ $[M]^+$ 280.9, found 281.0, 283.0, 285.0.

Scheme G

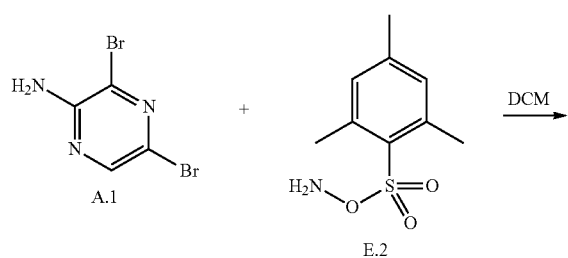

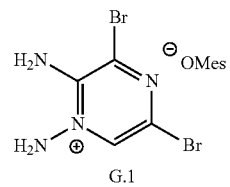

Intermediate G.1 was also synthesized according to the method shown in Scheme F, but stargint with A.1. MS (ESI) m/z calc'd for $C_4H_5Br_2N_4$ $[M]^+$ 266.9, found 266.9, 268.9, 270.9.

Preparation of Intermediate H.2, 6,8-dibromo-2-(((tert-butyldimethylsilyl)oxy)methyl)-5-methyl-[1,2,4]triazolo[1,5-a]pyrazine Scheme H

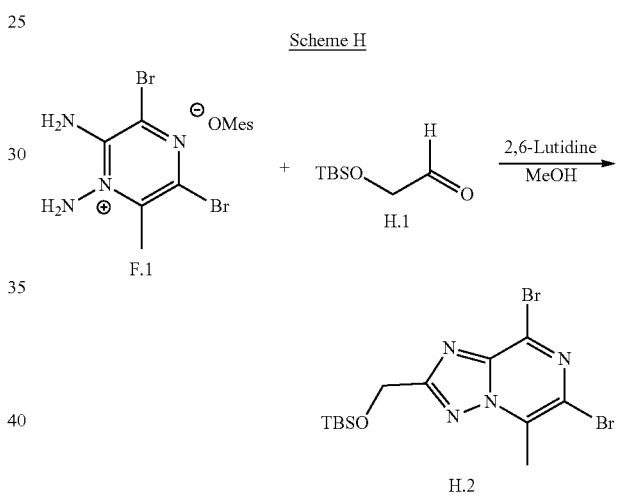

A 250 mL round bottom flask was charged with 1,2-diamino-3,5-dibromo-6-methylpyrazin-1-ium 2,4,6-trimethylbenzenesulfonate (2.70 g, 5.60 mmol) and 2-((tert-butyldimethylsilyl)oxy)acetaldehyde (7.43 mL, 39.2 mmol). MeOH (56 mL) and 2,6-lutidine (1.30 mL, 11.2 mmol) were then added, and the resulting solution was stirred at 25° C. under an atmosphere of air for 2.5 days. DCM (60 mL) and water (60 mL) were added and the phases were separated. The aq. phase was further extracted with DCM (2×60 mL), and the combined organic layers were dried over anhydrous MgSO$_4$, filtered, and concentrated. The resulting crude residue was then purified by silica gel chromatography (gradient elution: 0-100% EtOAc/Hexanes) to provide 6,8-dibromo-2-(((tert-butyldimethylsilyl)oxy)methyl)-5-methyl-[1,2,4]triazolo[1,5-a]pyrazine. MS (ESI) m/z calc'd for $C_{13}H_{21}Br_2N_4OSi$ $[M+H]^+$ 435.0, found 435.1, 437.1, 439.1.

Preparation of Intermediate I.2, 6,8-dibromo-2-(2-((tert-butyldimethylsilyl)oxy)ethyl)-5-methyl-[1,2,4]triazolo[1,5-a]pyrazine

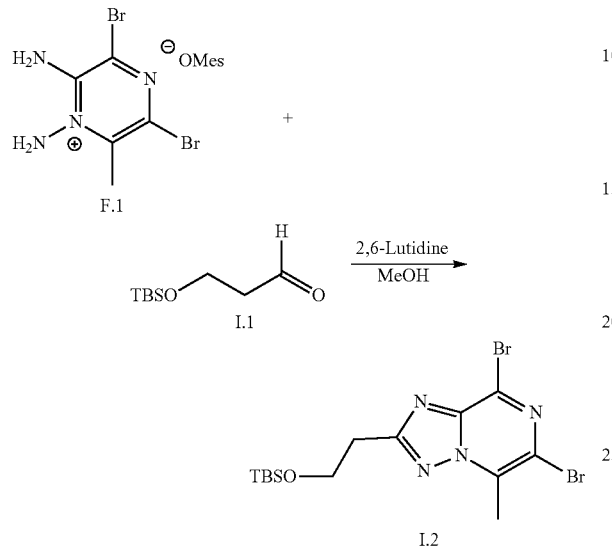

Intermediate I.2 was also synthesized according to the method shown in Scheme H, but starting with I.1 in place of H.1. MS (ESI) m/z calc'd for $C_{14}H_{23}Br_2N_4OSi$ [M+H]$^+$ 449.0, found 449.0, 451.0, 453.0.

Preparation of Intermediate J.1, 6,8-dibromo-2-(2-((tert-butyldimethylsilyl)oxy)ethyl)-[1,2,4]triazolo[1,5-a]pyrazine

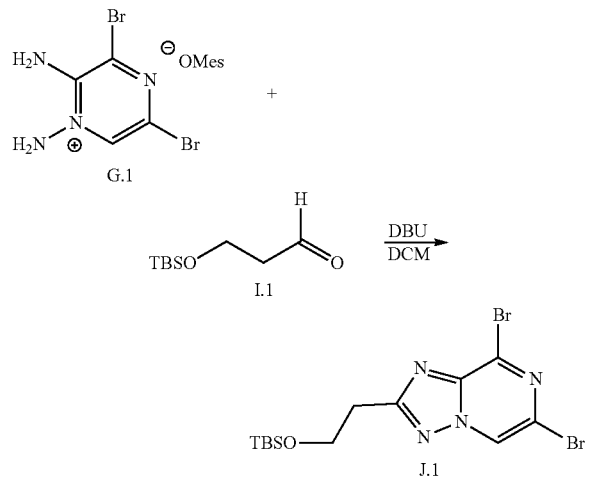

DBU (2.30 mL, 15.26 mmol) was added to a stirred solution of 3-((tert-butyldimethylsilyl)oxy) propanal (9.63 g, 51.2 mmol) and 1,2-diamino-3,5-dibromopyrazin-1-ium 2,4,6-trimethylbenzenesulfonate (2.40 g, 5.12 mmol) in DCM (100 mL). The resulting mixture was stirred at 25° C. for 5 h. After completion, the reaction mixture was concentrated. The resulting crude residue was purified by silica gel chromatography (elution: 17% EtOAc/petroleum ether) to provide 6,8-dibromo-2-(2-((tert-butyldimethylsilyl)oxy)ethyl)-[1,2,4]triazolo[1,5-a]pyrazine. MS (ESI) calc'd for $C_{13}H_{21}Br_2N_4OSi$ [M+H]$^+$ 435.0, found 434.8, 436.8, 439.8.

Preparation of Intermediate K.2, 6-bromo-2-(((tert-butyldimethylsilyl)oxy)methyl)-N-(2,4-dimethoxybenzyl)-5-methyl-[1,2,4]triazolo[1,5-a]pyrazin-8-amine

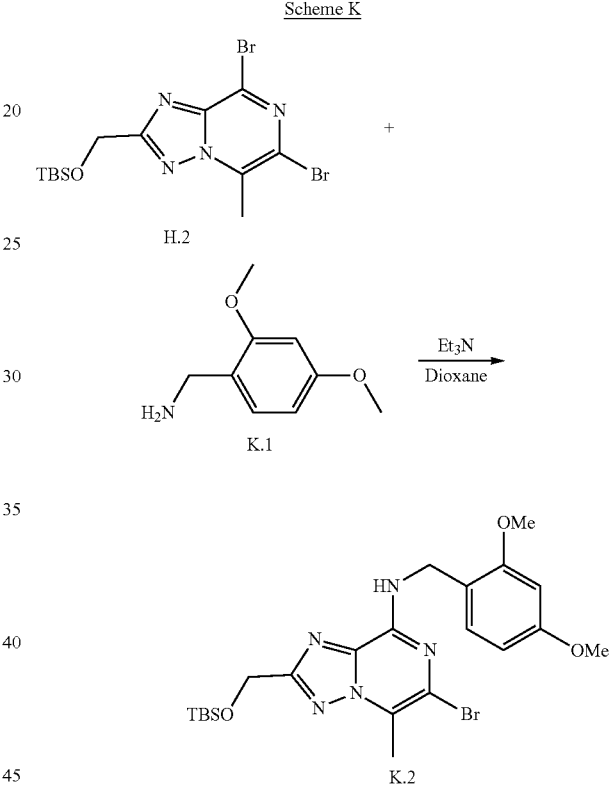

A 100 mL round bottom flask was charged with 6,8-dibromo-2-(((tert-butyldimethylsilyl)oxy)methyl)-5-methyl-[1,2,4]triazolo[1,5-a]pyrazine (1.70 g, 3.90 mmol) and dioxane (39 mL). Et$_3$N (1.09 mL, 7.79 mmol) and (2,4-dimethoxyphenyl)methanamine (0.878 mL, 5.85 mmol) were then added sequentially, and the resulting solution was stirred at 90° C. for 2 h. After cooling, the reaction mixture was concentrated. The residue was taken up in 75 mL of DCM and washed with sat. aq. NaHCO$_3$ (25 mL) and brine (25 mL), dried over anhydrous MgSO$_4$, filtered, and concentrated. The resulting crude residue was then purified by silica gel chromatography (gradient elution: 0-100% EtOAc/Hexanes) to provide 6-bromo-2-(((tert-butyldimethylsilyl)oxy)methyl)-N-(2,4-dimethoxybenzyl)-5-methyl-[1,2,4]triazolo[1,5-a]pyrazin-8-amine. MS (ESI) m/z calc'd for $C_{22}H_{33}BrN_5O_3Si$ [M+H]$^+$ 522.2, found 522.1, 524.1. Compounds in Table 1 were prepared according to Scheme K, either starting from commercially available intermediates or from intermediates I.2, B.2, A.3, or J.1.

TABLE 1

Intermediate Compounds Prepared According to Scheme K

| Entry | Structure Name | Observed m/z [M + H]+ |
|---|---|---|
| K.3 | 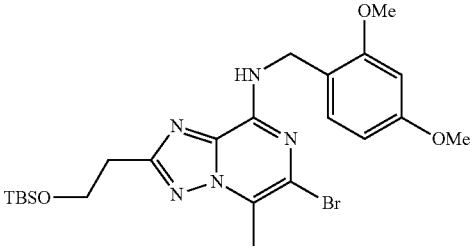 [SMILES: COc1ccc(CNc2nc(Br)c(C)n3nc(CCO[Si](C)(C)C(C)(C)C)nc23)c(OC)c1]<br>6-bromo-2-(2-((tert-butyldimethylsilyl)oxy)ethyl)-N-(2,4-dimethoxybenzyl)-5-methyl-[1,2,4]triazolo[1,5-a]pyrazin-8-amine | 536.1, 538.1 |
| K.4 | 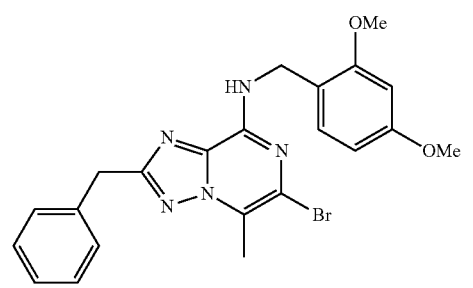 [SMILES: COc1ccc(CNc2nc(Br)c(C)n3nc(Cc4ccccc4)nc23)c(OC)c1]<br>2-benzyl-6-bromo-N-(2,4-dimethoxybenzyl)-5-methyl-[1,2,4]-triazolo[1,5-a]pyrazin-8-amine | 468.0, 470.0 |
| K.5 | 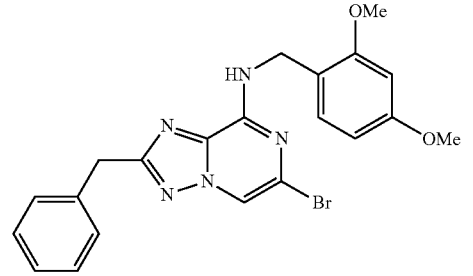 [SMILES: COc1ccc(CNc2nc(Br)cn3nc(Cc4ccccc4)nc23)c(OC)c1]<br>2-benzyl-6-bromo-N-(2,4-dimethoxybenzyl)-[1,2,4]triazolo[1,5-a]pyrazin-8-amine | 454.1, 456.1 |
| K.6 | 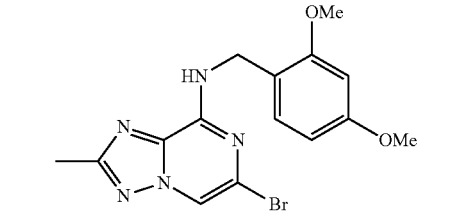 [SMILES: COc1ccc(CNc2nc(Br)cn3nc(C)nc23)c(OC)c1]<br>6-bromo-N-(2,4-dimethoxybenzyl)-2-methyl-[1,2,4]triazolo[1,5-a]pyrazin-8-amine | 378.0, 380.0 |
| K.7 | 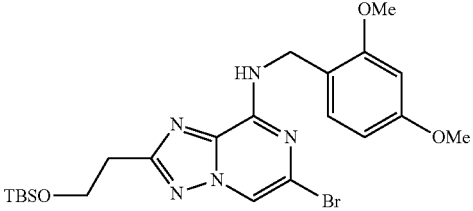 [SMILES: COc1ccc(CNc2nc(Br)cn3nc(CCO[Si](C)(C)C(C)(C)C)nc23)c(OC)c1] | 521.9, 523.9 |

TABLE 1-continued

Intermediate Compounds Prepared According to Scheme K

| Entry | Structure Name | Observed m/z [M + H]⁺ |
|---|---|---|
| K.8 | 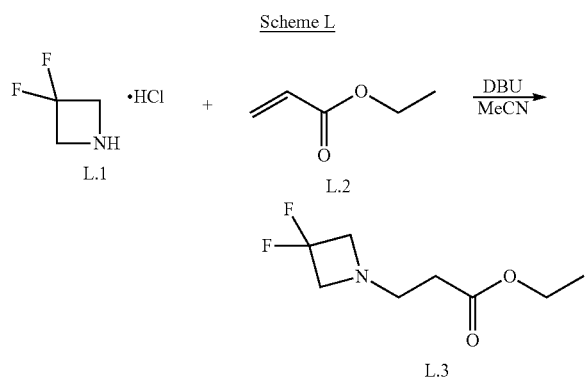<br>7-chloro-N-(2,4-dimethoxybenzyl)-2-methyl-[1,2,4]triazolo[1,5-c]pyrimidin-5-amine | 334.1 |

6-bromo-2-(2-((tert-butyldimethylsilyl)oxy)ethyl)-N-(2,4-dimethoxybenzyl)-[1,2,4]triazolo [1,5-a]pyrazin-8-amine

Preparation of Intermediate L.3, ethyl 3-(3,3-difluoroazetidin-1-yl)propanoate Scheme L A solution of 3,3-difluoroazetidine hydrochloride (1.56 g, 7.75 mmol) in MeCN (8 mL) was treated with DBU (2.25 mL, 9.80 mmol). The resulting mixture was stirred at 25° C. for 30 min. Ethyl acrylate (1.75 mL, 10.1 mmol) was then added, and the reaction mixture was stirred at 30° C. overnight. The mixture was then concentrated, and the resulting crude residue was purified by silica gel chromatography (elution: 4% EtOAc/petroleum ether) to provide ethyl 3-(3,3-difluoroazetidin-1-yl)propanoate. MS (ESI) in m/z calc'd for $C_8H_{14}F_2NO_2$ [M+H]⁺ 194, found 194.

Preparation of Intermediate M.2, 3-hydroxypropanehydrazide

Scheme M

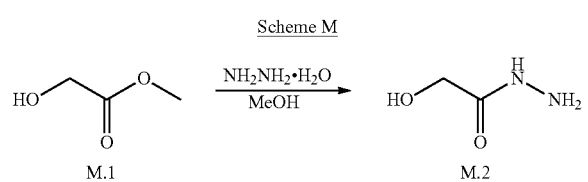

Hydrazine hydrate (16.5 mL, 271 mmol) was added to a solution of methyl glycolate (12.2 g, 135 mmol) in MeOH (102 mL). The clear reaction mixture was heated at 60° C. and stirred over 4 days. After cooling, the reaction was concentrated to remove solvent and hydrazine. DCM was added (50 mL), then the mixture was concentrated to provide 2-hydroxyacetohydrazide, which was used directly without further purification.

Compounds in Table 2 were prepared according to Scheme M, starting from the commercial methyl ester or from Intermediate L.3.

TABLE 2

Intermediate Compounds Prepared According to Scheme M

| Entry | Structure Name | Observed m/z [M + H]⁺ |
|---|---|---|
| M.3 | ![structure]<br>2-phenylacetohydrazide | 151.0 |
| M.4 | ![structure]<br>3-(3,3-difluoroazetidin-1-yl)propanehydrazide | 180 |

Preparation of Intermediate N.2, 3-hydroxypropanehydrazide

Scheme N

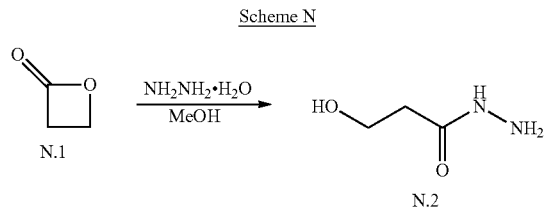

Hydrazine hydrate (1.19 g, 20.2 mmol) was added to a stirred mixture of oxetan-2-one (2.00 g, 19.2 mmol) MeOH (20 mL) at 20° C. and the mixture was stirred at 20° C. for 4 h. The mixture was concentrated to give 3-hydroxypropanehydrazide, which was used without further purification. $^1$H NMR (600 MHz, DMSO-d$_6$) δ 8.94 (br s, 1H), 4.55 (br s, 1H), 4.15 (br s, 2H), 3.59 (t, J=6.60 Hz, 2H), 2.17 (t, J=6.60 Hz, 2H).

Preparation of Intermediate O.4, 2-(7-chloro-5-((2,4-dimethoxybenzyl)amino)-8-methyl-[1,2,4]triazolo[1,5-c]pyrimidin-2-yl)ethanol

Scheme O

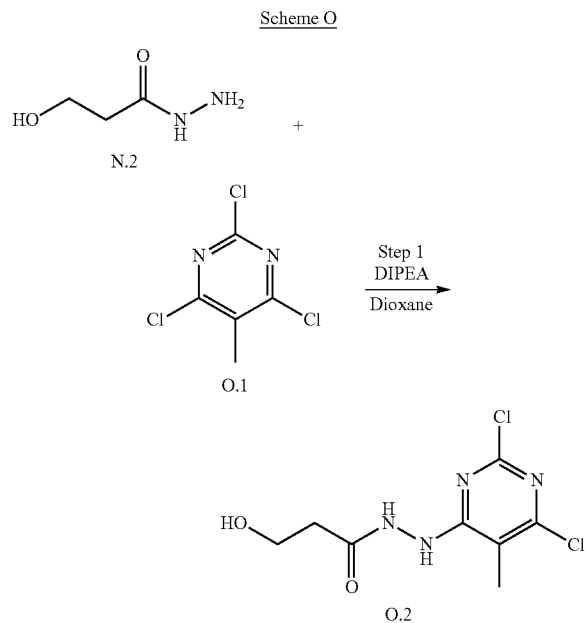

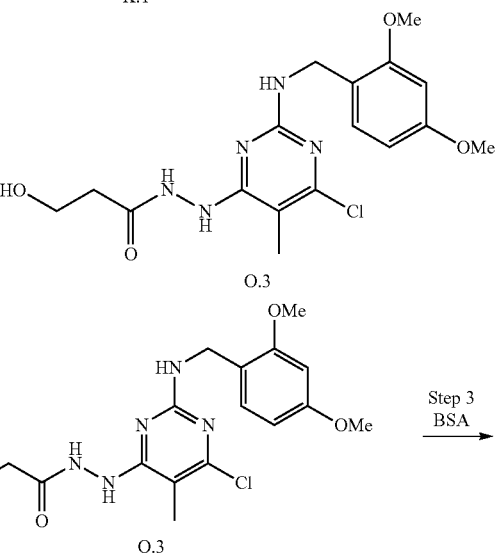

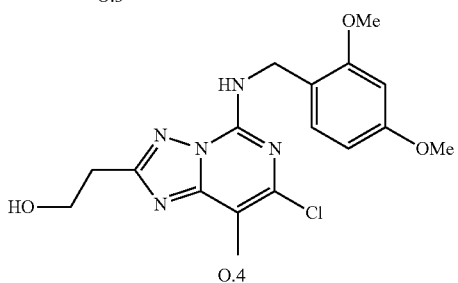

Step 1—Synthesis of Intermediate O.2, N'-(2,6-dichloro-5-methylpyrimidin-4-yl)-3-hydroxypropane-hydrazide DIPEA (2.70 mL, 15.5 mmol) was added to a stirred mixture of 2,4,6-trichloro-5-methylpyrimidine (1.50 g, 7.60 mmol) and 3-hydroxypropanehydrazide (0.870 g, 8.36 mmol) in dioxane (20 mL), and the reaction mixture was stirred at 70° C. for 12 h. After cooling, the mixture was concentrated to provide N'-(2,6-dichloro-5-methylpyrimidin-4-yl)-3-hydroxypropane-hydrazide, which was used without further purification. MS (ESI) calc'd for C$_8$H$_{11}$Cl$_2$N$_4$O$_2$ [M+H]$^+$ 265.0, found 264.8.

Step 2—Synthesis of Intermediate O.3, N'-(6-chloro-2-((2,4-dimethoxybenzyl)amino)-5-methylpyrimidin-4-yl)-3-hydroxy propanehydrazide (2,4-dimethoxyphenyl)methanamine (1.80 g, 10.8 mmol) was added to a stirred mixture of DIPEA (2.60 mL, 14.9 mmol) and N'-(2,6-dichloro-5-methylpyrimidin-4-yl)-3-hydroxypropane hydrazide (2.00 g, 7.54 mmol) in dioxane (20 mL), and the reaction mixture was stirred at 95° C. for 12 h. After cooling, the mixture was concentrated to provide N'-(6-chloro-2-((2,4-dimethoxybenzyl)amino)-5-methylpyrimidin-4-yl)-3-hydroxy propanehydrazide, which was used without further purification. MS (ESI) calc'd for $C_{17}H_{23}ClN_5O_4$ [M+H]$^+$ 396.1, found 396.2.

Step 3—Synthesis of Intermediate O.4, 2-(7-chloro-5-((2,4-dimethoxybenzyl)amino)-8-methyl-[1,2,4]triazolo [1,5-c]pyrimidin-2-yl)ethanol BSA (10.0 mL, 40.9 mmol) was added to a stirred mixture of N'-(6-chloro-2-((2,4-dimethoxybenzyl)amino)-5-methylpyrimidin-4-yl)-3-hydroxypropanehydrazide (1.00 g, 2.53 mmol), and the reaction mixture was stirred at 120° C. for 6 h. After cooling, the reaction mixture was concentrated to remove BSA. The resulting crude product was diluted with DCM (50 mL) and the organic layer was washed with aq. NaHCO$_3$ (10 mL), dried over anhydrous MgSO$_4$, filtered, and concentrated. The resulting crude material was dissolved in MeOH (10 mL), and HCl (1 mL, 4 M) was added. The resulting mixture was stirred at 25° C. for 30 min. Sat. aq. NaHCO$_3$ (10 mL) was then added, and the mixture was extracted with DCM (3×20 mL). The combined organic layers were dried over anhydrous MgSO$_4$, filtered, and concentrated. The resulting crude residue was purified by silica gel chromatography (gradient elution: 0-50% EtOAc/petroleum ether) to provide 2-(7-chloro-5-((2,4-dimethoxybenzyl)amino)-8-methyl-[1,2,4]triazolo[1,5-c]pyrimidin-2-yl)ethanol. MS (ESI) calc'd for $C_{17}H_{21}ClN_5O_3$ [M+H]$^+$ 378.1, found: 377.9.

Compounds in Table 3 were prepared according to Scheme O, starting from intermediates N.2, M.2, or M.4.

TABLE 3

Intermediate Compounds Prepared According to Scheme O

| Entry | Structure Name | Observed m/z [M + H]$^+$ |
|---|---|---|
| O.5 | 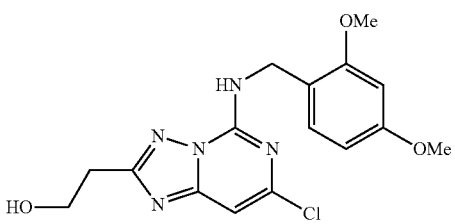 [SMILES: COc1ccc(CNc2nc(Cl)cc3nc(CCO)nn23)c(OC)c1] 2-(7-chloro-5-((2,4-dimethoxybenzyl)amino)-[1,2,4]triazolo[1,5-c]pyrimidin-2-yl)ethan-1-ol | 364.1 |
| O.6 | 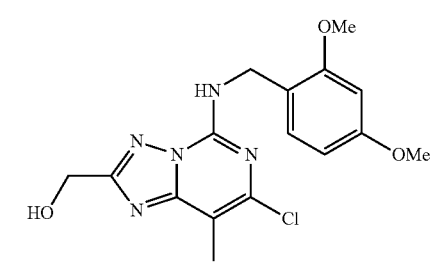 [SMILES: COc1ccc(CNc2nc(Cl)c(C)c3nc(CO)nn23)c(OC)c1] (7-chloro-5-((2,4-dimethoxybenzyl)amino)-8-methyl-[1,2,4]triazolo[1,5-c]pyrimidin-2-yl)methanol | 364.1 |
| O.7 | 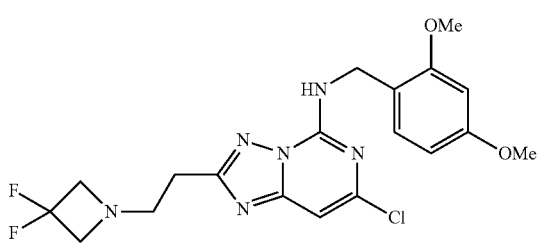 [SMILES: COc1ccc(CNc2nc(Cl)cc3nc(CCN4CC(F)(F)C4)nn23)c(OC)c1] 7-chloro-2-(2-(3,3-difluoroazetidin-1-yl)ethyl)-N-(2,4-dimethoxybenzyl)-[1,2,4]triazolo[1,5-c]pyrimidin-5-amine | 439 |

Preparation of Intermediate P.5, 2-benzyl-7-chloro-N-(2,4-dimethoxybenzyl)-[1,2,4]triazolo[1,5-c]pyrimidin-5-amine

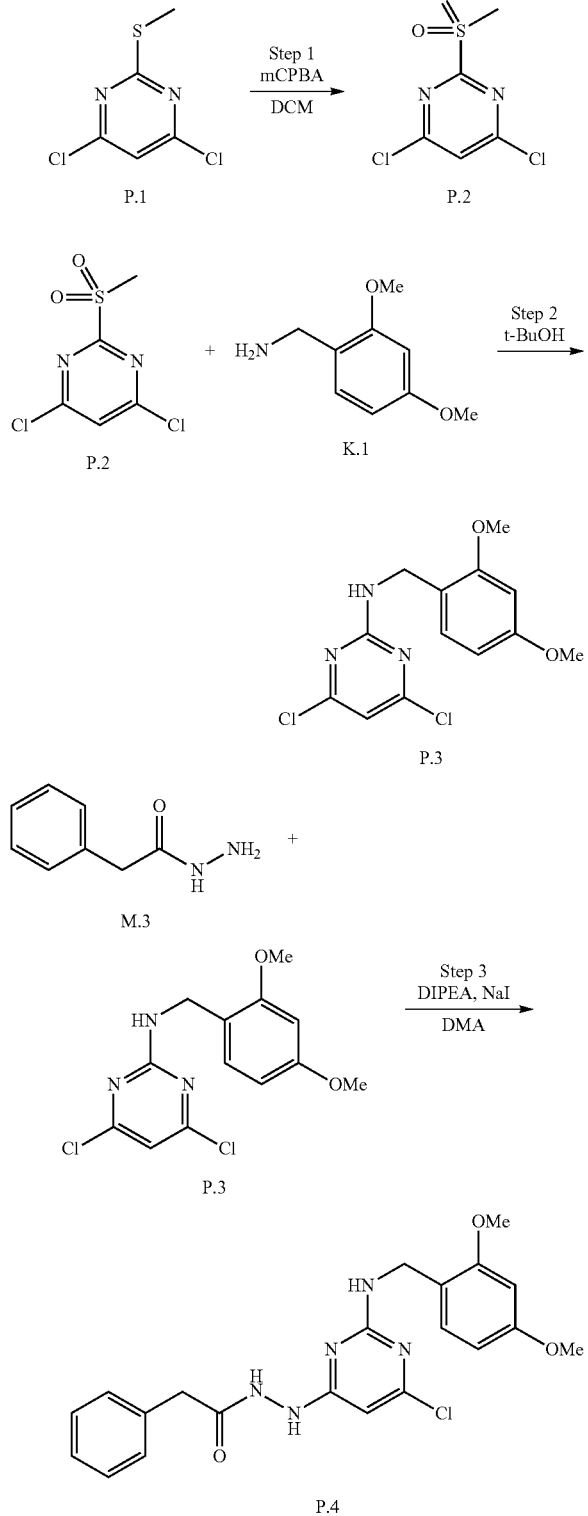

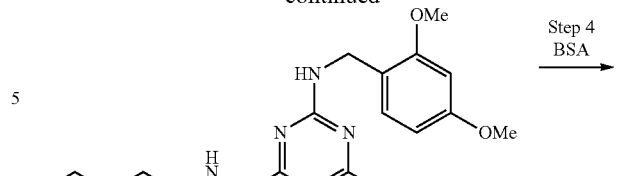

Step 1—Synthesis of Intermediate P.2, 4,6-dichloro-2-(methylsulfonyl) pyrimidine mCPBA (52.0 g, 256 mmol) was added to a stirred mixture of 4,6-dichloro-2-(methylthio) pyrimidine (20.0 g, 103 mmol) in DCM (200 mL) at 0° C. The resulting mixture was warmed to 25° C. and stirred at that temperature for 4 h. Upon completion, the reaction mixture was diluted with DCM (300 mL) and washed with 50% $Na_2S_2O_3$/$NaHCO_3$ (20% w/w in water, 100 mL). The organic layer was dried over anhydrous $Mg_2SO_4$, filtered, and concentrated. The resulting crude residue was purified by silica gel chromatography (gradient elution: 10-30% EtOAc/petroleum ether) to provide 4,6-dichloro-2-(methylsulfonyl) pyrimidine. MS (ESI) m/z calc'd for $C_5H_5Cl_2N_2O_2S$ [M+H]$^+$ 226.9, found 226.8.

Step 2—Synthesis of Intermediate P.3, 4,6-dichloro-N'-(2,4-dimethoxybenzyl)pyrimidin-2-amine (2,4-dimethoxyphenyl)methanamine (6.63 g, 39.6 mmol) was added to a stirred mixture of 4,6-dichloro-2-(methylsulfonyl)pyrimidine (9.00 g, 39.6 mmol) in t-BuOH (90 mL). The resulting mixture was stirred at 90° C. for 4 h. After cooling, sat. aq. $NaHCO_3$ (10 mL) was added and the mixture was extracted with EtOAc (2×50 mL). The combined organic layers were washed with brine (15 mL), dried over anhydrous $Mg_2SO_4$, filtered, and concentrated. The resulting crude residue was purified by silica gel chromatography (gradient elution: 20-40% EtOAc/petroleum ether) to provide 4,6-dichloro-N-(2,4-dimethoxybenzyl)pyrimidin-2-amine. MS (ESI) calc'd for $C_{13}H_{14}Cl_2N_3O_2$ [M+H]$^+$ 314.0, found 314.0.

Step 3—Synthesis of Intermediate P.4, N'-(6-chloro-2-((2,4-dimethoxybenzyl)amino)pyrimidin-4-yl)-2-phenylacetohydrazide 2-phenylacetohydrazide (1.67 g, 11.1 mmol) was added to a stirred mixture of 4,6-dichloro-N-(2,4-dimethoxybenzyl)pyrimidin-2-amine (3.50 g, 11.1 mmol), DIPEA (2.34 mL, 13.4 mmol), and NaI (2.00 g, 13.4 mmol) in dioxane (40 mL). The resulting mixture was then stirred at 100° C. for 24 h. After cooling, water (40 mL) was added and the reaction mixture was extracted with EtOAc (2×40 mL). The combined organic layers were washed with brine (20 mL), dried over anhydrous Mg$_2$SO$_4$, filtered, and concentrated. The resulting crude residue was purified by silica gel chromatography (elution: 50% EtOAc/petroleum ether) to provide N'-(6-chloro-2-((2,4-dimethoxybenzyl)amino)pyrimidin-4-yl)-2-phenylacetohydrazide. MS (ESI) calc'd for C$_{21}$H$_{23}$ClN$_5$O$_3$ [M+H]$^+$ 428.1, found 428.1.

Step 4—Synthesis of Intermediate P.5, 2-benzyl-7-chloro-N-(2,4-dimethoxybenzyl)-[1,2,4]triazolo[1,5-c]pyrimidin-5-amine A mixture of N'-(6-chloro-2-((2,4-dimethoxybenzyl)amino) pyrimidin-4-yl)-2-phenylacetohydrazide (2.10 g, 4.91 mmol) in BSA (20 mL) was stirred at 140° C. for 18 h. After cooling, the reaction mixture was concentrated. The residue was purified by silica gel chromatography, (elution: 17% EtOAc/petroleum ether) to provide 2-benzyl-7-chloro-A-(2,4-dimethoxybenzyl)-[1,2,4]triazolo[1,5-c]pyrimidin-5-amine. MS (ESI) calc'd for C$_{21}$H$_{21}$ClN$_5$O$_2$ [M+H]$^+$ 410.1, found 410.1.

Preparation of Intermediate Q.2, 2-(((tert-butyldimethylsilyl)oxy)methyl)-N-(2,4-dimethoxybenzyl)-5-methyl-6-(oxazol-2-yl)-[1,2,4]triazolo[1,5-a]pyrazin-8-amine Scheme Q

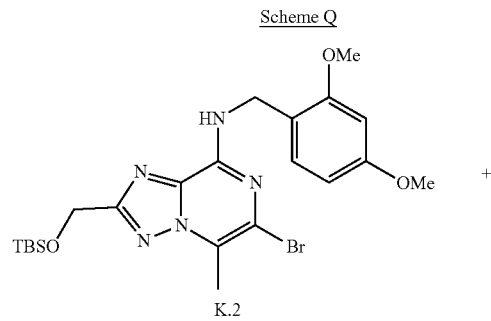

K.2

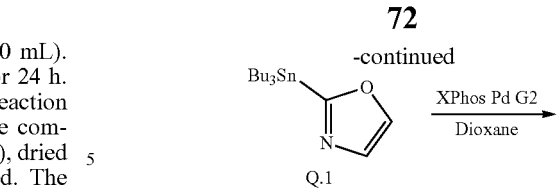

Q.1

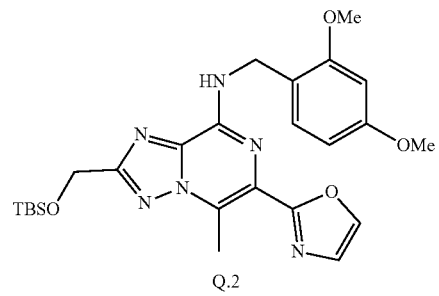

Q.2

A 40 mL vial was charged with 6-bromo-2-(((tert-butyldimethylsilyl)oxy)methyl)-N-(2,4-dimethoxybenzyl)-5-methyl-[1,2,4]triazolo[1,5-a]pyrazin-8-amine (1.00 g, 1.91 mmol) and XPhos Pd G2 (151 mg, 0.191 mmol), and the vial was evacuated and backfilled with nitrogen (3×). A degassed [Method C]solution of 2-(tributylstannyl) oxazole (1.17 mL, 3.83 mmol) in dioxane (13 mL) was added and the reaction was heated to 80° C. overnight. The reaction was then cooled to 25° C. and concentrated. The resulting crude residue was then purified by silica gel chromatography (gradient elution: 0-100% EtOAc/Hexanes) to provide 2-(((tert-butyldimethylsilyl)oxy)methyl)-N-(2,4-dimethoxybenzyl)-5-methyl-6-(oxazol-2-yl)-[1,2,4]triazolo[1,5-a]pyrazin-8-amine. MS (ESI) m/z calc'd for C$_{25}$H$_{35}$N$_6$O$_4$Si [M+H]$^+$ 511.2, found 511.2.

Compounds in Table 4 were prepared according to Scheme Q and General Scheme 1, starting from intermediates K.7, 0.6 or P.5.

TABLE 4

Intermediate Compounds Prepared According to General Scheme 1 and Scheme Q

| Entry | Structure Name | Observed m/z [M + H]$^+$ |
|---|---|---|
| Q.3 | 2-(2-((tert-butyldimethylsilyl)oxy)ethyl)-N-(2,4-dimethoxybenzyl)-6-(oxazol-2-yl)-[1,2,4]triazolo[1,5-a]pyrazin-8-amine | 511.0 |

TABLE 4-continued

Intermediate Compounds Prepared According to General Scheme 1 and Scheme Q

| Entry | Structure Name | Observed m/z [M + H]+ |
|---|---|---|
| Q.4 | (5-((2,4-dimethoxybenzyl)amino)-8-methyl-7-(oxazol-2-yl)-[1,2,4]triazolo[1,5-c]pyrimidin-2-yl)methanol | 397.1 |
| Q.5 | 2-benzyl-N-(2,4-dimethoxybenzyl)-7-(oxazol-2-yl)-[1,2,4]triazolo[1,5-c]pyrimidin-5-amine | 443.1 |

Preparation of Intermediate R.2, 2-(((tert-butyldimethylsilyl)oxy)methyl)-6-(2,5-difluorophenyl)-N-(2,4-dimethoxybenzyl)-5-methyl-[1,2,4]triazolo[1,5-a]pyrazin-8-amine Scheme R

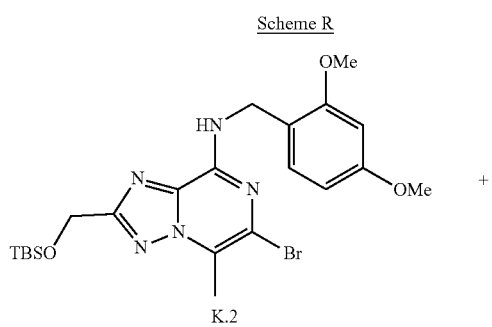

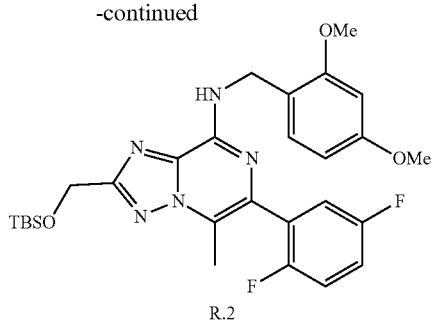

A 20 mL Biotage® microwave vial was charged with 6-bromo-2-(((tert-butyldimethylsilyl)oxy)methyl)-N-(2,4-dimethoxybenzyl)-5-methyl-[1,2,4]triazolo[1,5-a]pyrazin-8-amine (1.23 g, 2.35 mmol), cesium carbonate (0.767 g, 2.35 mmol), (2,5-difluorophenyl)boronic acid (0.558 g, 3.53 mmol), and 1,1'-bis(diphenylphosphino)ferrocene-palladium(II)dichloride dichloromethane complex (0.192 g, 0.235 mmol) and the vial was evacuated and backfilled with nitrogen (3×). A degassed 4:1 mixture of dioxane (9.4 mL) and water (2.3 mL) was added and the reaction was heated at 130° C. for 2.5 h. The reaction was cooled to 25° C., and then DCM (20 mL) and water (10 mL) were added. The organic phase was separated, and the aq. phase extracted with DCM (2×20 mL). The organic extracts were combined, dried over anhydrous $MgSO_4$, filtered, and concentrated. The resulting crude residue was then purified by silica gel chromatography (gradient elution: 0-100% EtOAc/Hexanes) to provide 2-(((tert-butyldimethylsilyl)oxy)methyl)-6-(2,5-difluorophenyl)-N-(2,4-dimethoxybenzyl)-5-methyl-[1,2,4]triazolo[1,5-a]pyrazin-8-amine. MS (ESI) m/z calc'd for $C_{28}H_{36}F_2N_5O_3Si$ [M+H]+ 556.3, found 556.3.

Compounds in Table 5 were prepared according to Scheme R and General Scheme 1, starting from intermediates O.6, K.7, or O.4 and the appropriate commercial boronic acid.

TABLE 5

Intermediate Compounds Prepared According to General Scheme 1 and Scheme R

| Entry | Structure<br>Name | Observed m/z<br>[M + H]$^+$ |
|---|---|---|
| R.3 | 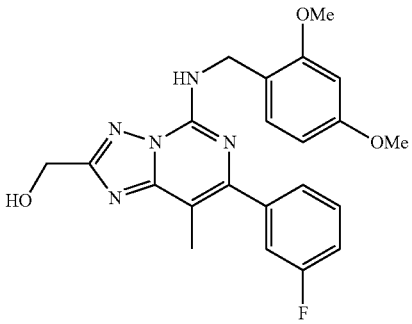<br>(5-((2,4-dimethoxybenzyl)amino)-7-(3-fluorophenyl)-8-methyl-[1,2,4]triazolo[1,5-c]pyrimidin-2-yl)methanol | 424.2 |
| R.4 | 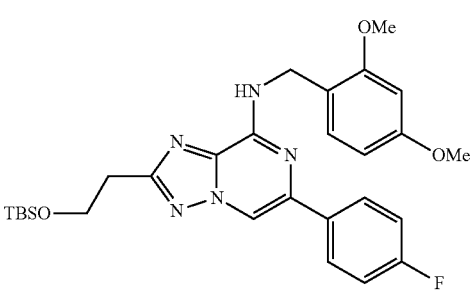<br>2-(2-((tert-butyldimethylsilyl)oxy)ethyl)-N-(2,4-dimethoxybenzyl)-6-(4-fluorophenyl)-[1,2,4]triazolo[1,5-a]pyrazin-8-amine | 538.3 |
| R.5 | 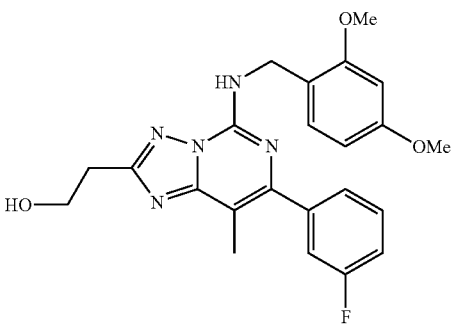<br>2-(5-((2,4-dimethoxybenzyl)amino)-7-(3-fluorophenyl)-8-methyl-[1,2,4]triazolo[1,5-c]pyrimidin-2-yl)ethan-1-ol | 438.3 |

Preparation of Intermediate S.1, (6-(2,5-difluorophenyl)-8-((2,4-dimethoxybenzyl)amino)-5-methyl-[1,2,4]triazolo[1,5-a]pyrazin-2-yl)methanol Scheme S

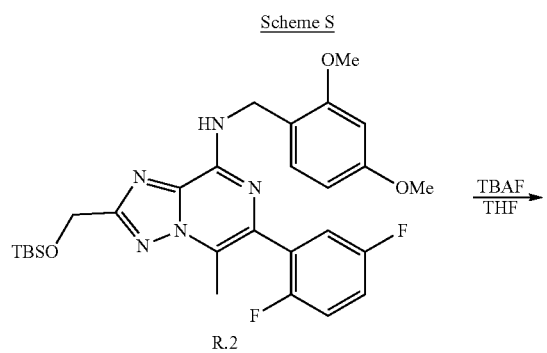

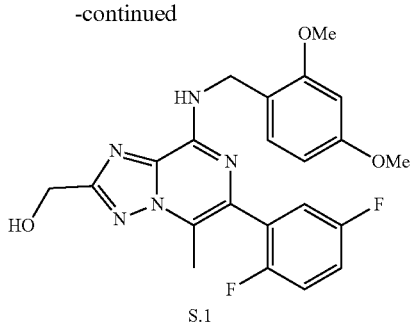

S.1

A 40 mL scintillation vial was charged with to 2-(((tert-butyldimethylsilyl)oxy)methyl)-6-(2,5-difluorophenyl)-N'-(2,4-dimethoxybenzyl)-5-methyl-[1,2,4]triazolo[1,5-a]pyrazin-8-amine. THF (17.1 mL) was added, followed by drop wise addition of TBAF (1 M in THF, 2.06 mL, 2.06 mmol), and the resulting reaction mixture was stirred at 25° C. for 2 h. The reaction was quenched with sat. aq. NH$_4$Cl and extracted with DCM (3×20 mL), dried over anhydrous MgSO$_4$, filtered, and concentrated. The resulting crude residue was triturated with DCM to provide (6-(2,5-difluorophenyl)-8-((2,4-dimethoxybenzyl)amino)-5-methyl-[1,2,4]triazolo[1,5-a]pyrazin-2-yl)methanol. MS (ESI) m/z calc'd for C$_{22}$H$_{22}$F$_2$N$_5$O$_3$ [M+H]$^+$ 442.2, found 442.1. Compounds in Table 6 were prepared according to Scheme S, starting from intermediates K.3, Q.2, or Q.3.

TABLE 6

Intermediate Compounds Prepared According to Scheme S

| Entry | Structure Name | Observed m/z [M + H]$^+$ |
|---|---|---|
| S.2 | 2-(6-bromo-8-((2,4-dimethoxybenzyl)amino)-5-methyl-[1,2,4]triazolo[1,5-a]pyrazin-2-yl)ethan-1-ol | 422.0, 424.0 |
| S.3 | (8-((2,4-dimethoxybenzyl)amino)-5-methyl-6-(oxazol-2-yl)-[1,2,4]-triazolo[1,5-a]pyrazin-2-yl)methanol | 397 |

TABLE 6-continued

Intermediate Compounds Prepared According to Scheme S

| Entry | Structure Name | Observed m/z [M + H]+ |
|---|---|---|
| S.4 | 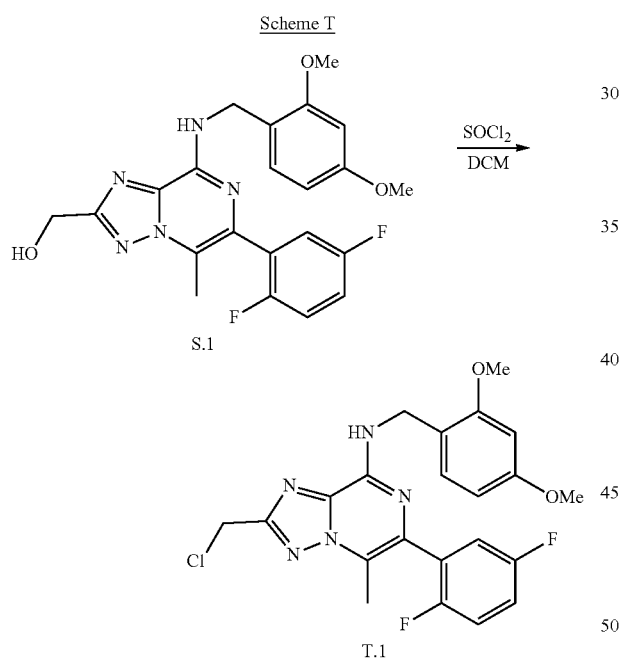<br>2-(8-((2,4-dimethoxybenzyl)amino)-6-(oxazol-2-yl)-[1,2,4]-triazolo[1,5-a]pyrazin-2-yl)ethanol | 397.1 |

Preparation of Intermediate T.1, 2-(chloromethyl)-6-(2,5-difluorophenyl)-N-(2,4-dimethoxybenzyl)-5-methyl-[1,2,4]triazolo[1, 5-a]pyrazin-8-amine A 20 mL scintillation vial was charged with (6-(2,5-difluorophenyl)-8-((2,4-dimethoxybenzyl)amino)-5-methyl-[1,2,4]triazolo[1,5-a]pyrazin-2-yl)methanol (188 mg, 0.426 mmol). DCM (4.3 mL) was added, followed by thionyl chloride (47 µL, 0.639 mmol), and the reaction was stirred at 25° C. for 4 h. The reaction was quenched with sat. aq. NaHCO₃ (5 mL) and DCM (3 mL) and stirred at 25° C. for 30 min. The organic phase was then separated and the aq. phase extracted with DCM (2×10 mL). The combined organic layers were dried over anhydrous MgSO₄, filtered, and concentrated to provide 2-(chloromethyl)-6-(2,5-difluorophenyl)-N'-(2,4-dimethoxybenzyl)-5-methyl-[1,2,4]triazolo[1,5-a]pyrazin-8-amine. MS (ESI) m/z calc'd for $C_{22}H_{21}ClF_2N_5O_2$ [M+H]⁺ 460.1, found 460.1.

Compounds in Table 7 were prepared according to Scheme T and General Scheme 2, starting from intermediates S.3, Q.4 or R.3.

TABLE 7

Intermediate Compounds Prepared According to General Scheme 2 and Scheme T

| Entry | Structure Name | Observed m/z [M + H]⁺ |
|---|---|---|
| T.2 | 2-(chloromethyl)-N-(2,4-dimethoxybenzyl)-5-methyl-6-(oxazol-2-yl)-[1,2,4]triazolo[1,5-a]pyrazin-8-amine | 415.0 |
| T.3 | 2-(chloromethyl)-N-(2,4-dimethoxybenzyl)-8-methyl-7-(oxazol-2-yl)-[1,2,4]triazolo[1,5-c]pyrimidin-5-amine | 415.1 |
| T.4 | 2-(chloromethyl)-N-(2,4-dimethoxybenzyl)-7-(3-fluorophenyl)-8-methyl-[1,2,4]triazolo[1,5-c]pyrimidin-5-amine | 442.1 |

Preparation of Intermediate U.1, 2-benzyl-7-(oxazol-2-yl)-[1,2,4]triazolo[1,5-c]pyrimidin-5-amine Preparation of Intermediate W.1, 2-(7-chloro-5-((2,4-dimethoxybenzyl)amino)-8-methyl-[1,2,4]triazolo[1,5-c]pyrimidin-2-yl)ethyl 4-methylbenzenesulfonate

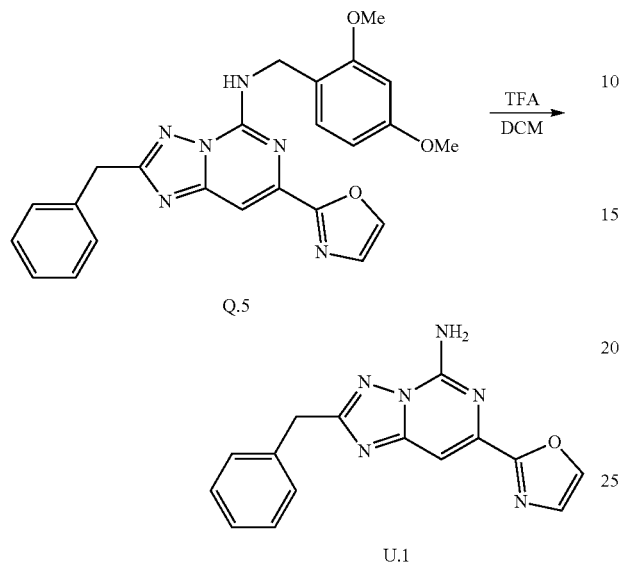

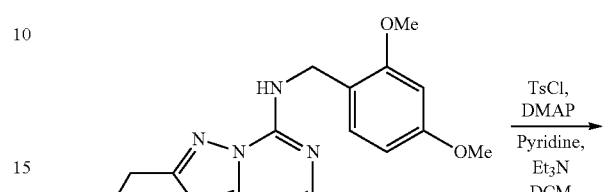

TFA (2 mL) was added to a stirred mixture of 2-benzyl-N-(2,4-dimethoxybenzyl)-7-(oxazol-2-yl)-[1,2,4]triazolo[1,5-c]pyrimidin-5-amine (180 mg, 0.407 mmol) in DCM (2 mL). The resulting mixture was stirred at 40° C. for 18 h. After cooling, the reaction mixture was concentrated to provide 2-benzyl-7-(oxazol-2-yl)-[1,2,4]triazolo[1,5-c]pyrimidin-5-amine, which was used in the next step without further purification. MS (ESI) calc'd for $C_{15}H_{13}N_6O$ $[M+H]^+$ 293.1, found 293.1.

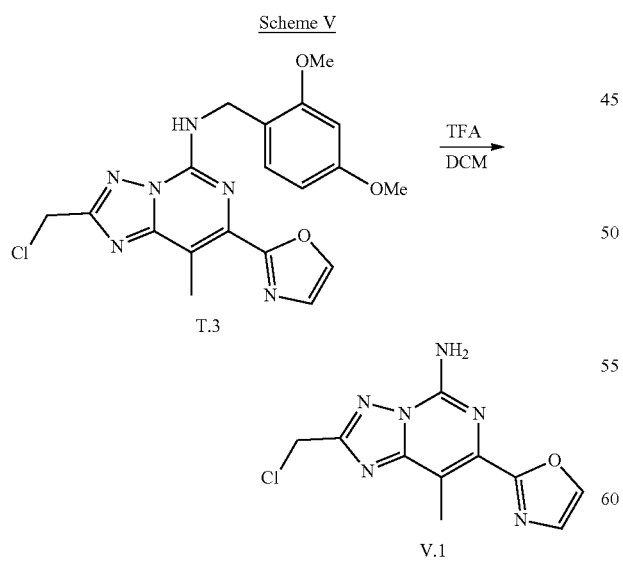

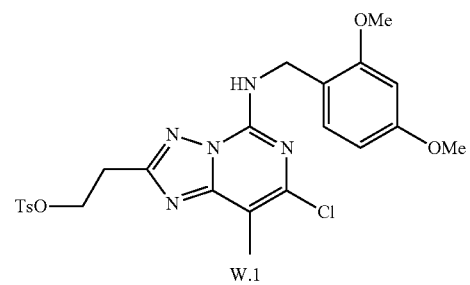

Intermediate V.1 was also synthesized according to the method shown in Scheme U, but starting with T.3. MS (ESI) m/z calc'd for $C_{10}H_{10}ClN_6O$ $[M+H]^+$ 265.1, found 265.1.

A 500 mL round bottom flask was charged with 2-(7-chloro-5-((2,4-dimethoxybenzyl)amino)-8-methyl-[1,2,4]triazolo[1,5-c]pyrimidin-2-yl)ethanol (7.50 g, 19.85 mmol) and DCM (200 mL). DMAP (1.21 g, 9.93 mmol), Et$_3$N (8.30 mL, 59.6 mmol), pyridine (3.21 mL, 39.7 mmol), and TsCl (6.43 g, 33.7 mmol) were added sequentially, and the reaction mixture was stirred at 25° C. for 2 h. The reaction was quenched with brine (150 mL) and the organic layer was separated. The aq. layer was extracted with DCM (2×150 mL), and the combined organic layers were dried over anhydrous MgSO$_4$, filtered, and concentrated. The resulting crude residue was purified by silica gel chromatography (gradient elution: 0-100% EtOAc/Hexanes) to provide 2-(7-chloro-5-((2,4-dimethoxybenzyl)amino)-8-methyl-[1,2,4]triazolo[1,5-c]pyrimidin-2-yl)ethyl 4-methylbenzenesulfonate. MS (ESI) m/z calc'd for $C_{24}H_{27}ClN_5O_5S$ $[M+H]^+$ 532.1, found 532.0. Compounds in Table 8 were prepared according to Scheme W, starting from intermediates O.5, S.2 or S.4 and the appropriate sulfonyl chloride, either TsCl or 4-trifluoromethylphenylsulfonyl chloride.

TABLE 8

Intermediate Compounds Prepared According to Scheme W

| Entry | Structure / Name | Observed m/z [M + H]+ |
|---|---|---|
| W.2 | 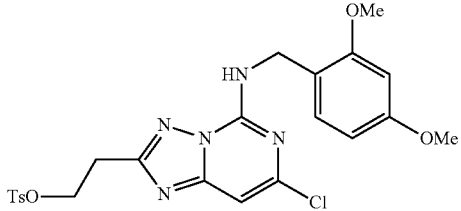 [SMILES: COc1ccc(CNc2nc(Cl)cc3nc(CCOS(=O)(=O)c4ccc(C)cc4)nn23)c(OC)c1]<br>2-(7-chloro-5-((2,4-dimethoxybenzyl)amino)-[1,2,4]triazolo[1,5-c]pyrimidin-2-yl)ethyl 4-methylbenzenesulfonate | 518.1, 520.0 |
| W.3 | 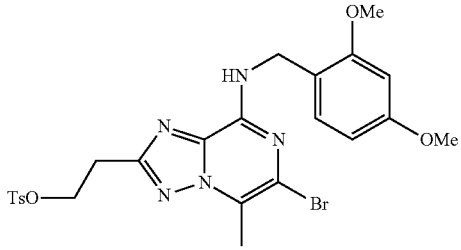 [SMILES: COc1ccc(CNc2nc(Br)c(C)n3nc(CCOS(=O)(=O)c4ccc(C)cc4)nc23)c(OC)c1]<br>2-(6-bromo-8-((2,4-dimethoxybenzyl)amino)-5-methyl-[1,2,4]triazolo[1,5-a]pyrazin-2-yl)ethyl 4-methylbenzenesulfonate | 576.1, 578.1 |
| W.4 | 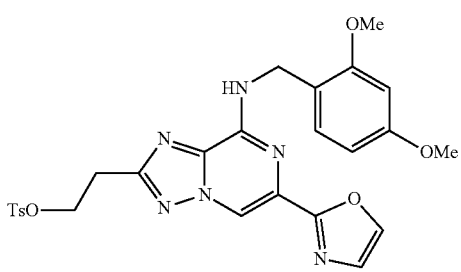 [SMILES: COc1ccc(CNc2nc(-c3ncco3)cn3nc(CCOS(=O)(=O)c4ccc(C)cc4)nc23)c(OC)c1]<br>2-(8-((2,4-dimethoxybenzyl) amino)-6-(oxazol-2-yl)-[1,2,4]triazolo[1,5-a]pyrazin-2-yl)ethyl 4-methylbenzene-sulfonate | 551.1 |
| W.5 | 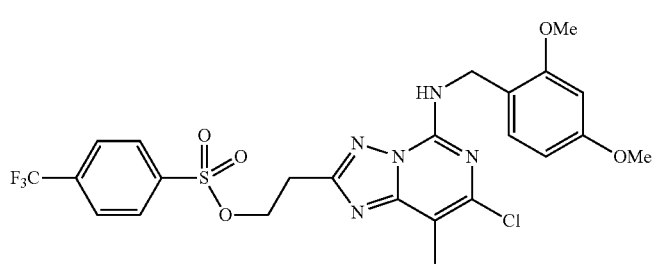 [SMILES: COc1ccc(CNc2nc(Cl)c(C)c3nc(CCOS(=O)(=O)c4ccc(C(F)(F)F)cc4)nn23)c(OC)c1]<br>2-(7-chloro-5-((2,4-dimethoxybenzyl)amino)-8-methyl-[1,2,4]triazolo[1,5-c]pyrimidin-2-yl)ethyl 4-(trifluoromethyl)benzenesulfonate | 585.8 |

TABLE 8-continued

Intermediate Compounds Prepared According to Scheme W

| Entry | Structure Name | Observed m/z [M + H]+ |
|---|---|---|
| W.6 | 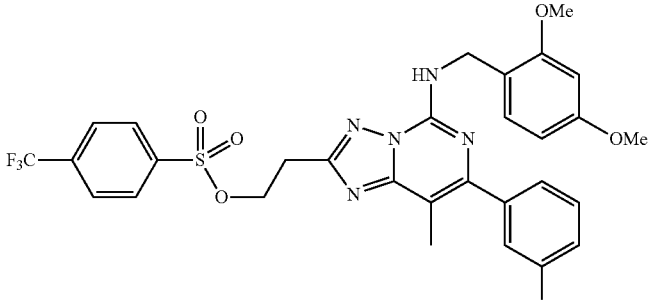  2-(5-((2,4-dimethoxybenzyl)amino)-7-(3-fluorophenyl)-8-methyl-[1,2,4]triazolo[1,5-c]pyrimidin-2-yl)ethyl 4-(trifluoromethyl)benzenesulfonate | 646.3 |

Preparation of Intermediate X.1, 2-(5-((2,4-dimethoxybenzyl)amino)-8-methyl-7-(oxazol-2-yl)-[1,2,4]triazolo[1,5-c]pyrimidin-2-yl)ethyl 4-methylbenzenesulfonate Scheme X

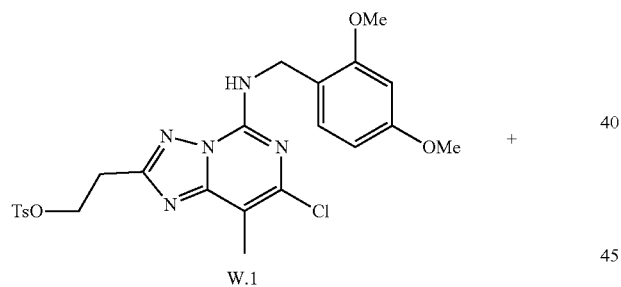

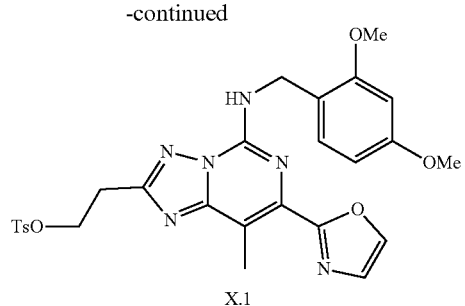

A 40 mL scintillation vial was charged with 2-(7-chloro-5-((2,4-dimethoxybenzyl)amino)-8-methyl-[1,2,4]triazolo[1,5-c]pyrimidin-2-yl)ethyl 4-methylbenzenesulfonate (1.50 g, 2.82 mmol) and XPhos Pd G2 (0.222 g, 0.282 mmol), and the vial was evacuated and backfilled with nitrogen (3×). A degassed [Method C] solution of 2-(tributylstannyl)oxazole (1.29 mL, 4.23 mmol) in dioxane (11.3 mL) was added and the reaction was heated to 80° C. overnight. The reaction was then cooled to 25° C. and concentrated. The resulting crude residue was then purified by silica gel chromatography (gradient elution: 0-100% EtOAc/Hexanes) to provide 2-(5-((2,4-dimethoxybenzyl)amino)-8-methyl-7-(oxazol-2-yl)-[1,2,4]triazolo[1,5-c]pyrimidin-2-yl)ethyl 4-methylbenzenesulfonate. MS (ESI) m/z calc'd for $C_{27}H_{29}N_6O_6S$ [M+H]+ 565.2, found 565.4.

Compounds in Table 9 were prepared according to Scheme X, starting from intermediates W.2, W.1, or W.5, and the appropriate commercial tributylstannane.

TABLE 9

Intermediate Compounds Prepared According to Scheme X

| Entry | Structure Name | Observed m/z [M + H]⁺ |
|---|---|---|
| X.2 | 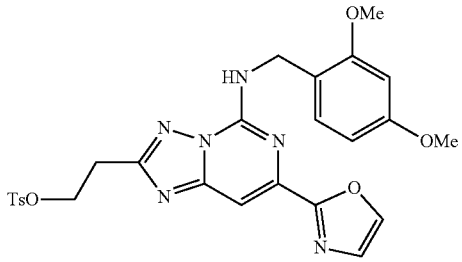 [SMILES: COc1ccc(CNc2nc(-c3ncco3)cc3nc(CCOS(=O)(=O)c4ccc(C)cc4)nn23)c(OC)c1] 2-(5-((2,4-dimethoxybenzyl)amino)-7-(oxazol-2-yl)-[1,2,4]triazolo[1,5-c]pyrimidin-2-yl)ethyl 4-methylbenzenesulfonate | 551.3 |
| X.3 | 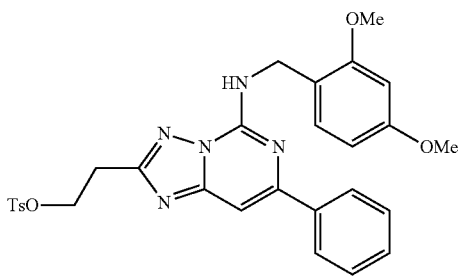 [SMILES: COc1ccc(CNc2nc(-c3ccccc3)cc3nc(CCOS(=O)(=O)c4ccc(C)cc4)nn23)c(OC)c1] 2-(5-((2,4-dimethoxybenzyl)amino)-7-phenyl-[1,2,4]triazolo[1,5-c]pyrimidin-2-yl)ethyl 4-methylbenzenesulfonate | 560.0 |
| X.4 | 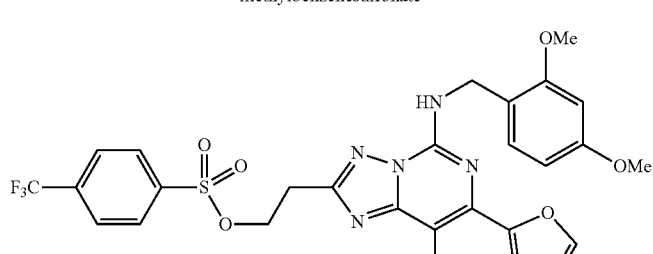 2-(5-((2,4-dimethoxybenzyl)amino)-8-methyl-7-(oxazol-2-yl)-[1,2,4]triazolo[1,5-c]pyrimidin-2-yl)ethyl 4-(trifluoromethyl)benzenesulfonate | 619.2 |

Preparation of Intermediate Y.5, 3-cyclobutylimidazo[1,5-a]pyrazine

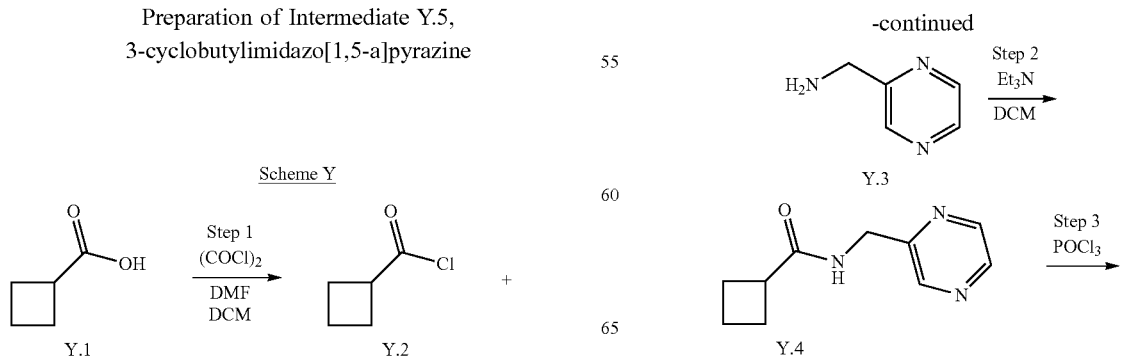

91

-continued

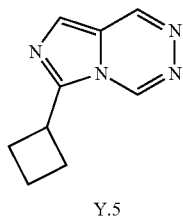

Y.5

Step 1—Synthesis of Intermediate Y.2, cyclobutanecarbonyl chloride

A solution of cyclobutanecarboxylic acid (2.00 g, 20.0 mmol) in DCM (40 mL) was cooled to 0° C. and $(COCl)_2$ (3.50 mL, 40.0 mmol) was added dropwise. After the addition was complete, DMF (0.2 mL) was added, and the resulting mixture was stirred at 0° C. for 2 h. The reaction mixture was then concentrated to afford cyclobutanecarbonyl chloride, which was used directly in the next reaction without further purification.

Step 2—Synthesis of Intermediate Y.4, N'-(pyrazin-2-ylmethyl)cyclobutanecarboxamide A solution of pyrazin-2-ylmethanamine (2.00 g, 18.3 mmol) in DCM (20 mL) was treated with $Et_3N$ (5.11 mL, 36.7 mmol), then the mixture was cooled to 0° C. and a solution of cyclobutanecarbonyl chloride (2.28 g, 19.2 mmol) in DCM (10 mL) was slowly added. After the addition was complete, the reaction mixture was warmed to 10° C. and stirred at that temperature for 16 h. The reaction mixture was then washed with water (30 mL), and the layers were separated. The organic layer was dried over anhydrous $Mg_2SO_4$, filtered, and concentrated. The resulting crude residue was purified by silica gel chromatography (gradient elution: 25-50% EtOAc/petroleum ether) to provide N-(pyrazin-2-ylmethyl)cyclobutanecarboxamide. MS (ESI) m/z calc'd for $C_{10}H_{14}N_3O$ $[M+H]^+$ 192.1, found 191.9.

Step 3—Preparation of Intermediate Y.5, 3-cyclobutylimidazo[1,5-a]pyrazine

A solution of N-(pyrazin-2-ylmethyl)cyclobutanecarboxamide (500 mg, 2.61 mmol) in $POCl_3$ (5.05 mL, 54.1 mmol) was stirred at 70° C. for 16 h. The reaction mixture was then concentrated, and the residue was quenched with ice water (50 mL). Aq. $NH_4OH$ was used to bring the pH to around 10, and then the mixture was extracted with DCM (3×50 mL). The combined organic layers were washed with brine (20 mL) and $H_2O$ (20 mL), dried over anhydrous $Mg_2SO_4$, filtered, and concentrated to provide 3-cyclobutylimidazo[1,5-a]pyrazine, which was used in the subsequent reaction without further purification. MS (ESI) m/z calc'd for $C_{10}H_{12}N_3$ $[M+H]^+$: 174.1, found 174.0.

92

Compounds in Table 10 were prepared according to Scheme Y, starting from commercial carboxylic acids.

TABLE 10

Intermediate Compounds Prepared According to Scheme Y

| Entry | Structure Name | Observed m/z $[M + H]^+$ |
|---|---|---|
| Y.6 | 3-cyclopropylimidazo[1,5-a]pyrazine | 160.1 |
| Y.7 | 3-(3,3-difluorocyclobutyl)imidazo[1,5-a]pyrazine | 210.1 |
| Y.8 | 3-cyclopentylimidazo[1,5-a]pyrazine | 188.2 |
| Y.9 | 3-(bicyclo[1.1.1]pentan-1-yl)imidazo[1,5-a]pyrazine | 186.2 |

Preparation of Intermediate Z.1, 3-cyclobutyl-5,6,7,8-tetrahydroimidazo[1,5-a]pyrazine Scheme Z

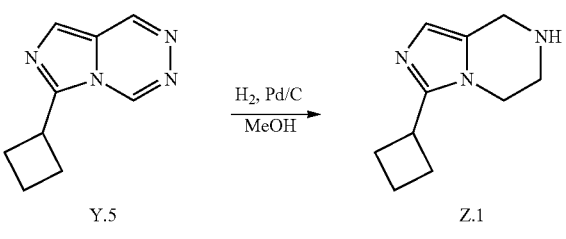

Y.5 → Z.1

$H_2$, Pd/C
MeOH

A solution of 3-cyclobutylimidazo[1,5-a]pyrazine (200 mg, 1.155 mmol) in MeOH (20 mL) was treated with Pd/C (10%, 123 mg, 0.115 mmol). The resulting mixture was stirred under an atmosphere of hydrogen (15 psi) at 10° C. for 16 h. The reaction mixture was then filtered through Celite™ (diatomaceous earth) and concentrated to provide 3-cyclobutyl-5,6,7,8-tetrahydroimidazo[1,5-a]pyrazine, which was used in the subsequent reaction without further purification. MS (ESI) m/z calc'd for $C_{10}H_{16}N_3$ $[M+H]^+$ 178.1, found 178.1.

Compounds in Table 11 were prepared according to Scheme Z, starting from intermediates Y.7 or Y.8.

TABLE 11

Intermediate Compounds Prepared According to Scheme Z

| Entry | Structure Name | Observed m/z $[M + H]^+$ |
|---|---|---|
| Z.2 | 3-(3,3-difluorocyclobutyl)-5,6,7,8-tetrahydroimidazo[1,5-a]pyrazine | 214.1 |
| Z.3 | 3-cyclopentyl-5,6,7,8-tetrahydroimidazo[1,5-a]pyrazine | 192.1 |

Preparation of Intermediate AA.1, 3-(bicyclo[1.1.1]pentan-1-yl)-5,6,7,8-tetrahydroimidazo[1,5-a]pyrazine

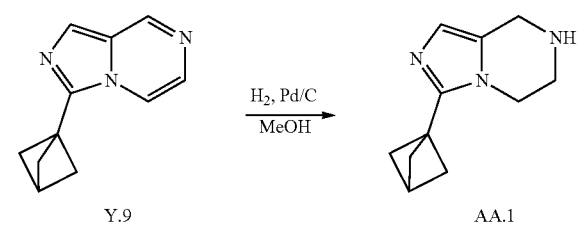

A solution of 3-(bicyclo[1.1.1]pentan-1-yl)imidazo[1,5-a]pyrazine (410 mg, 2.214 mmol) in MeOH (44 mL) was recycled through a H-cube mini (1 mL/min flow rate) at 75° C. and 50 bar system pressure using a Pd/C cartridge for 3.5 h. After completion of the reaction, the mixture was concentrated to provide 3-(bicyclo[1.1.1]pentan-1-yl)-5,6,7,8-tetrahydroimidazo[1,5-a]pyrazine. MS (ESI) m/z calc'd for $C_{11}H_{16}N_3$ $[M+H]^+$ 190.1, found 190.1.

Preparation of Intermediate AB.1, 3-cyclopropyl-5,6,7,8-tetrahydroimidazo[1,5-a]pyrazine

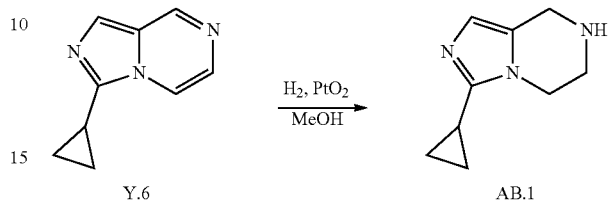

PtO₂ (114 mg, 0.503 mmol) was added to a solution of 3-cyclopropylimidazo[1,5-a]pyrazine (80 mg, 0.503 mmol) in MeOH (5 mL). The resulting mixture was stirred at 15° C. under hydrogen atmosphere (50 psi) for 3 h. The reaction mixture was filtered through Celite™ (diatomaceous earth) and concentrated to provide 3-cyclopropyl-5,6,7,8-tetrahydroimidazo[1,5-a]pyrazine, which was used in the subsequent reaction without further purification. MS (ESI) m/z calc'd for $C_9H_{14}N_3$ $[M+H]^+$ 164.1, found 164.1.

Preparation of Intermediate AC.6, 1-isopropyl-4,5,6,7-tetrahydro-1H-[1,2,3]triazolo [4,5-c]pyridine

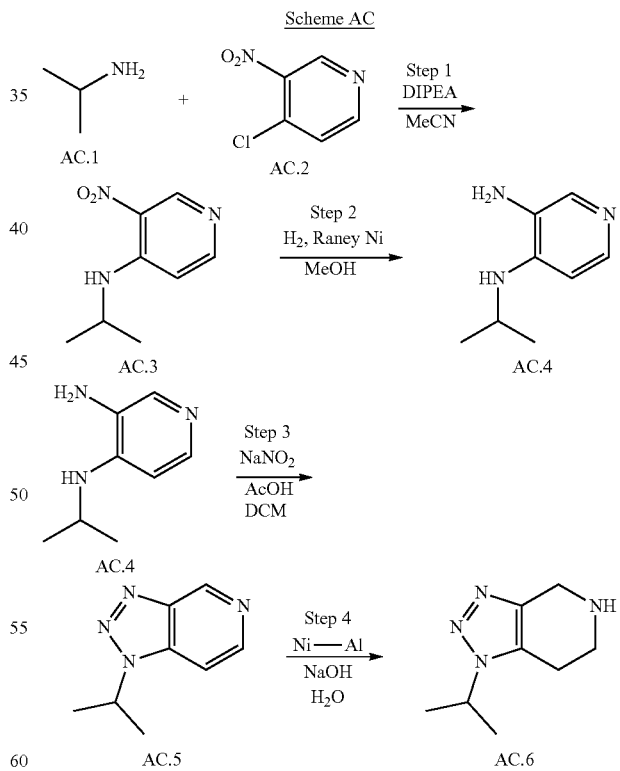

Step 1—Synthesis of Intermediate AC.3, N-isopropyl-3-nitropyridin-4-amine

Propan-2-amine (0.373 g, 6.31 mmol) was added to a stirred mixture of DIPEA (1.40 mL, 8.02 mmol) and 4-chloro-3- nitropyridine (1.00 g, 6.31 mmol) in MeCN (20 mL). The resulting mixture was heated to 70° C. and stirred at this temperature for 8 h. After cooling, the reaction mixture was diluted with EtOAc (20 mL), washed with brine (3×10 mL), dried over anhydrous Mg$_2$SO$_4$, filtered, and concentrated. The resulting crude residue was purified by silica gel chromatography (gradient elution: 0-60% EtOAc/petroleum ether) to provide N-isopropyl-3-nitropyridin-4-amine. $^1$H NMR (400 MHz, CDCl$_3$) δ 9.21 (s, 1H), 8.24-8.30 (m, 1H), 8.09 (br s, 1H), 6.71 (d, J=6.11 Hz, 1H), 3.87 (qd, J=6.51, 13.24 Hz, 1H), 1.36 (d, J=6.36 Hz, 6H).

Step 2—Synthesis of Intermediate AC.4, N$^4$-isopropylpyridine-3,4-diamine

Raney-Ni (65 mg, 1.11 mmol) was carefully added to a mixture of N-isopropyl-3-nitropyridin-4-amine (950 mg, 5.24 mmol) in MeOH (10 mL). The reaction mixture was degassed and then stirred under an atmosphere of hydrogen (15 psi) at 20° C. for 6 h. The reaction mixture then was diluted with MeOH (20 mL), filtered, and concentrated. The resulting crude residue was purified by silica gel chromatography (gradient elution: 0-20% MeOH/DCM) to provide N$^4$-isopropylpyridine-3,4-diamine. MS (ESI) m/z calc'd for C$_8$H$_{14}$N$_3$[M+H]$^+$ 152.1, found 151.9.

Step 3—Synthesis of Intermediate AC.5, 1-isopropyl-1H-[1,2,3]triazolo[4,5-c]pyridine A mixture of N$^4$-isopropylpyridine-3,4-diamine (350 mg, 2.32 mmol) in DCM (7 mL) and AcOH (7.00 mL, 61.10 mmol) was cooled to 0° C. and sodium nitrite (287 mg, 4.17 mmol) was added. The reaction mixture was then stirred at 0° C. for 30 min, warmed to 20° C., and stirred at 20° C. for 1 h. The mixture was then cooled to 0° C. and sat. aq. NaHCO$_3$ was added until the pH reached 9. The mixture was then extracted with DCM (3×10 mL), and the combined organic layers were washed with brine (10 mL), dried over anhydrous Mg$_2$SO$_4$, filtered, and concentrated. The resulting crude residue was purified by silica gel chromatography (gradient elution: 50-100% EtOAc/petroleum ether) to provide 1-isopropyl-1H-[1,2,3]triazolo[4,5-c]pyridine. MS (ESI) m/z calc'd for C$_8$H$_{11}$N$_4$[M+H]$^+$ 163.1, found 162.9.

Step 4—Preparation of Intermediate AC.6, 1-isopropyl-4,5,6,7-tetrahydro-1H-[1,2,3]triazolo [4,5-c]pyridine Aluminum-nickel alloy (740 mg, 8.63 mmol) was added to a stirred mixture of 1-isopropyl-1H-[1,2,3]triazolo[4,5-c]pyridine (350 mg, 2.16 mmol) in NaOH (1 M in H$_2$O, 16.0 mL, 16.0 mmol). The resulting mixture was stirred at 20° C. for 12 h. The reaction mixture was then filtered and concentrated. The resulting crude solid was suspended in DCM (10 mL), filtered, and concentrated to provide 1-isopropyl-4,5,6,7-tetrahydro-1H-[1,2,3]triazolo[4,5-c]pyridine, which was used the subsequent reaction without further purification. MS (ESI) m/z calc'd for C$_8$H$_{15}$N$_4$[M+H]$^+$ 167.1, found 167.1.

Compounds in Table 12 were prepared according to Scheme AC, starting from commercial carboxylic acids.

TABLE 12

Intermediate Compounds Prepared According to Scheme AC

| Entry | Structure Name | Observed m/z [M + H]$^+$ |
|---|---|---|
| AC.7 | 1-cyclopropyl-4,5,6,7-tetrahydro-1H-[1,2,3]triazolo[4,5-c]pyridine | 165.1 |
| AC.8 | 1-(bicyclo[1.1.1]pentan-1-yl)-4,5,6,7-tetrahydro-1H-[1,2,3]triazolo[4,5-c]pyridine | 191.1 |
| AC.9 | 1-(3,3-difluorocyclobutyl)-4,5,6,7-tetrahydro-1H-[1,2,3]triazolo[4,5-c]pyridine | 215.1 |
| AC.10 | 1-cyclopentyl-4,5,6,7-tetrahydro-1H-[1,2,3]triazolo[4,5-c]pyridine | 193.1 |
| AC.11 | 2-methyl-1-(4,5,6,7-tetrahydro-1H-[1,2,3]triazolo[4,5-c]pyridin-1-yl)propan-2-ol | 197.0 |

TABLE 12-continued

Intermediate Compounds Prepared According to Scheme AC

| Entry | Structure Name | Observed m/z [M + H]+ |
|---|---|---|
| AC.12 | 1-(2,2,2-trifluoroethyl)-4,5,6,7-tetrahydro-1H-[1,2,3]triazolo[4,5-c]pyridine | 207.1 |

Preparation of Intermediate AD.7, 1-isopropyl-7-methyl-4,5,6,7-tetrahydro-1H-[1,2,3]triazolo[4,5-c]pyridine

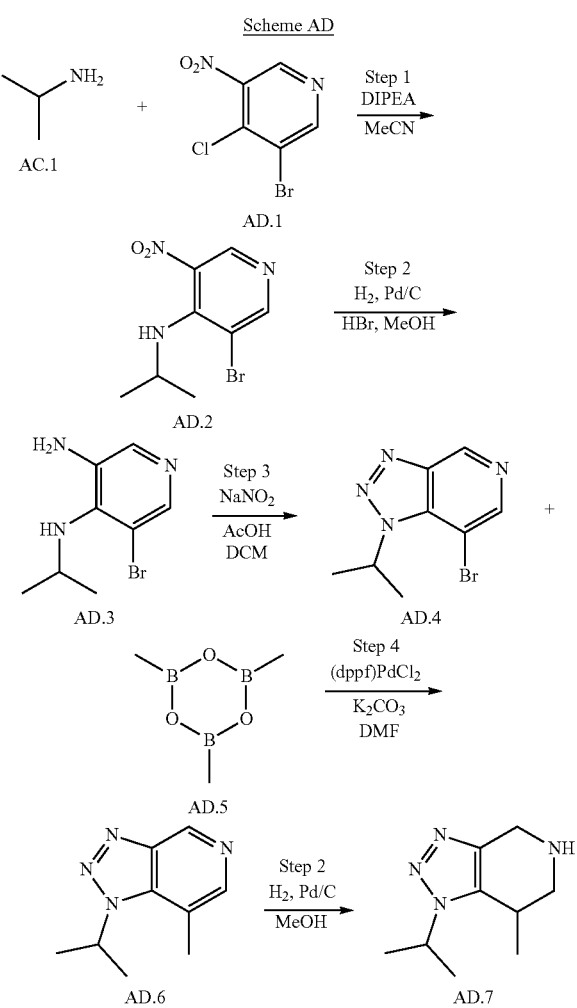

Scheme AD

Step 1—Synthesis of Intermediate AD.2, 3-bromo-N-isopropyl-5-nitropyridin-4-amine A solution of 3-bromo-4-chloro-5-nitropyridine (5.00 g, 21.1 mmol) in MeCN (50 mL) was treated with DIPEA (12.0 mL, 68.7 mmol) and propan-2-amine (1.37 g, 23.2 mmol). The resulting mixture was stirred at 80° C. for 16 h. After cooling, the reaction mixture was concentrated. The resulting crude residue was purified by silica gel chromatography (Gradient Elution: 0-17% EtOAc/petroleum ether) to provide 3-bromo-N-isopropyl-5-nitropyridin-4-amine. MS (ESI) m/z calc'd for $C_8H_{11}BrN_3O_2[M+H^+]$ 260.0, found 260.0, 262.0.

Step 2—Synthesis of Intermediate AD.3, 5-bromo-$N^4$-isopropylpyridine-3,4-diamine A stirred solution of 3-bromo-N-isopropyl-5-nitropyridin-4-amine (1.00 g, 3.84 mmol) in MeOH (30 mL) was treated with Pd/C (10%, 0.409 g, 0.384 mmol) and HBr (0.50 mL, 4.42 mmol). The resulting mixture was then stirred at 20° C. for 1 h under an atmosphere of hydrogen. The reaction mixture was then filtered through Celite™ (diatomaceous earth) and concentrated to provide 5-bromo-Na-isopropylpyridine-3,4-diamine, which was used in the subsequent reaction without further purification. MS (ESI) m/z calc'd for $C_8H_{13}BrN_3$ [M+H+] 230.0, found 230.0, 232.0.

Step 3—Synthesis of Intermediate AD.4, 7-bromo-1-isopropyl-1H-[1,2,3]triazolo[4,5-c]pyridine A mixture of $N^4$-isopropylpyridine-3,4-diamine (350 mg, 2.32 mmol) in DCM (10 mL) and AcOH (10 mL, 87 mmol) was cooled to 0° C. and sodium nitrite (0.525 g, 7.61 mmol) was added. The reaction mixture was then stirred at 0° C. for 30 min, warmed to 20° C., and stirred at 20° C. for 2 h. The reaction mixture was then concentrated, and the resulting crude residue was diluted with DCM (20 mL). Sat. aq. NaHCO$_3$ (20 mL) was added to adjust the pH to 8-10. The reaction mixture was extracted with DCM (2×20 mL), and the combined organic layers were concentrated. The residue was purified by silica gel chromatography (gradient elution: 0-25% EtOAc/petroleum ether) to provide 7-bromo-1-isopropyl-1H-[1,2,3]triazolo[4,5-c]pyridine. MS (ESI) m/z calc'd for $C_8H_{10}BrN_4$ [M+H+] 241.0, found 241.0, 243.0.

Step 4—Synthesis of Intermediate AD.6, 1-isopropyl-7-methyl-1H-[1,2,3]triazolo[4,5-c]pyridine A stirred solution of 7-bromo-1-isopropyl-1H-[1,2,3]triazolo[4,5-c]pyridine (432 mg, 1.792 mmol) in DMF (10 mL) was treated with potassium carbonate (1.24 g, 8.96 mmol), 2,4,6-trimethyl-1,3,5,2,4,6-trioxatriborinane (1.80 g, 7.17 mmol) and (dppf)PdCl$_2$ (131 mg, 0.179 mmol). The resulting reaction mixture was stirred at 110° C. for 16 h. After cooling, the mixture was concentrated. The resulting crude residue was diluted with water (20 mL) and extracted with DCM (2×15 mL), and the combined organic layers were concentrated. The resulting residue was purified by silica gel chromatography (gradient elution: 0-35% EtOAc/petroleum ether) to provide 1-isopropyl-7-methyl-1H-[1,2,3]triazolo[4,5-c]pyridine. MS (ESI) m/z calc'd for $C_9H_{13}N_4$ [M+H+] 177.1, found 177.1.

Step 5—Preparation of Intermediate AD.7, 1-isopropyl-7-methyl-4,5,6,7-tetrahydro-1H-[1,2,3]triazolo[4,5-c]pyridine A stirred solution of 1-isopropyl-7-methyl-1H-[1,2,3]triazolo[4,5-c]pyridine (346 mg, 1.96 mmol) in MeOH (20 mL) was treated with Pd/C (10% 209 mg, 0.196 mmol). The resulting mixture was then stirred at 25° C. for 16 h under an atmosphere of hydrogen. The reaction mixture was then filtered through Celite™ (diatomaceous earth) and concentrated to provide 1-isopropyl-7-methyl-4,5,6,7-tetrahydro-1H-[1,2,3]triazolo[4,5-c]pyridine, which was used in the subsequent reaction without additional purification. $^1$H NMR (400 MHz, MeOD-$d_4$) δ 4.63-4.74 (m, 1H), 3.78-3.95 (m, 2H), 2.98-3.09 (m, 2H), 2.83-2.89 (m, 1H), 1.60 (d, J=6.6 Hz, 3H), 1.55 (d, J=6.6 Hz, 3H), 1.30 (d, J=7.0 Hz, 3H).

Preparation of Intermediates AE.5 and AE.6, 1-cyclopentyl-4,5,6,7-tetrahydro-1H-pyrazolo [4,3-c] pyridine and 2-cyclopentyl-4,5,6,7-tetrahydro-2H-pyrazolo[4,3-c]pyridine

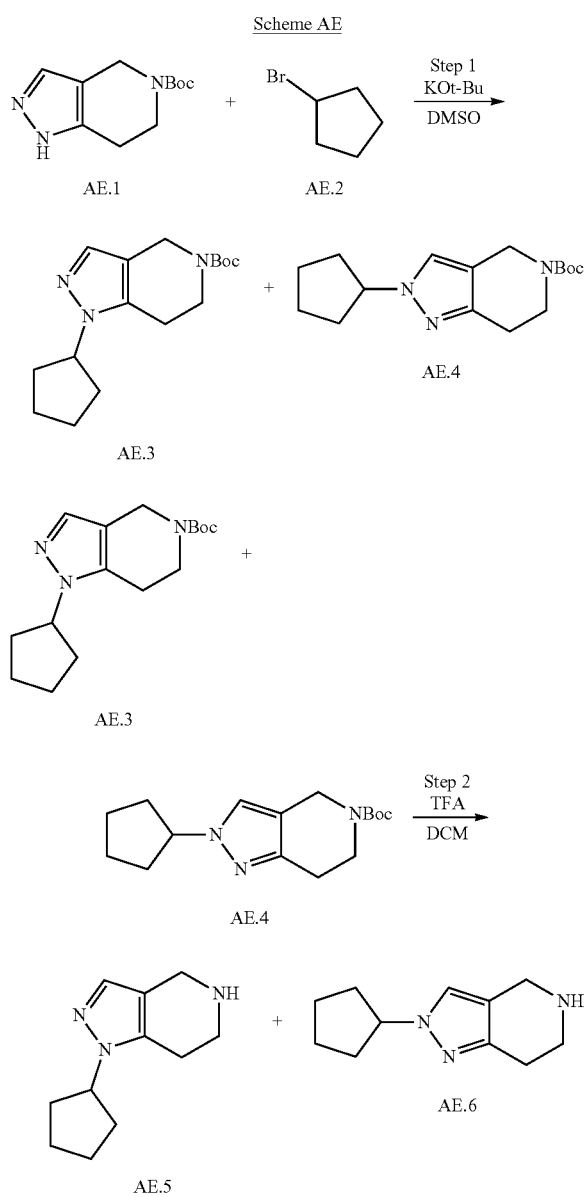

Step 1—Synthesis of Intermediates AE.3 and AE.4, tert-butyl 1-cyclopentyl-6,7-dihydro-1H-pyrazolo[4,3-c]pyridine-5(4H)-carboxylate and tert-butyl 2-cyclopentyl-6,7-dihydro-2H-pyrazolo[4,3-c]pyridine-5 (4H)-carboxylate A solution of tert-butyl 6,7-dihydro-1H-pyrazolo[4,3-c]pyridine-5(4H)-carboxylate (500 mg, 2.24 mmol) in DMSO (8 mL) was treated with potassium tert-butoxide (503 mg, 4.48 mmol). The resulting mixture was stirred for 5 min at 25° C., and then bromocyclopentane (1.00 g, 6.72 mmol) was added. The reaction mixture was then heated to 120° C. under microwave irradiation and stirred for 1 h. After cooling, the reaction mixture was diluted with EtOAc (50 mL) and water (200 mL) and extracted with EtOAc (3×50 mL). The combined organic layers were dried over anhydrous $Mg_2SO_4$, filtered, and concentrated. The resulting crude residue was purified by silica gel chromatography (gradient elution: 0-27% EtOAc/petroleum ether) to provide a mixture of tert-butyl 1-cyclopentyl-6,7-dihydro-1H-pyrazolo[4,3-c]pyridine-5(4H)-carboxylate and tert-butyl 2-cyclopentyl-6,7-dihydro-2H-pyrazolo[4,3-c]pyridine-5(4H)-carboxylate. MS (ESI) m/z calc'd for $C_{16}H_{26}N_3O_2$ [M+H$^+$] 292.2, found 292.2.

Step 2—Preparation of Intermediates AE.5 and AE.6, 1-cyclopentyl-4,5,6,7-tetrahydro-1H-pyrazolo [4,3-c]pyridine and 2-cyclopentyl-4,5,6,7-tetrahydro-2H-pyrazolo[4,3-c]pyridine A solution of tert-butyl 1-cyclopentyl-6,7-dihydro-1H-pyrazolo[4,3-c]pyridine-5(4H)-carboxylate (45 mg, 0.154 mmol) and tert-butyl 2-cyclopentyl-6,7-dihydro-2H-pyrazolo[4,3-c]pyridine-5(4H)-carboxylate (135 mg, 0.463 mmol) in DCM (1.0 mL) was treated with TFA (1.0 mL, 13.0 mmol). The resulting mixture was stirred at 20° C. for 1 h. The reaction mixture was then concentrated to provide a mixture of 1-cyclopentyl-4,5,6,7-tetrahydro-1H-pyrazolo[4,3-c]pyridine and 2-cyclopentyl-4,5,6,7-tetrahydro-2H-pyrazolo[4,3-c]pyridine, which were used as a mixture in the next step without further purification. MS (ESI) m/z calc'd $C_{11}H_{18}N_3$ [M+H$^+$]192.1, found 192.1.

Compounds in Table 13 were prepared according to Scheme AE, starting from commercial alkyl bromides.

TABLE 13

Intermediate Compounds Prepared According to Scheme AE

| Entry | Structure Name | Observed m/z [M + H]$^+$ |
|---|---|---|
| AE.7 | 1-cyclobutyl-4,5,6,7-tetrahydro-1H-pyrazolo[4,3-c]pyridine | 178.1 |
| AE.8 | 2-cyclobutyl-4,5,6,7-tetrahydro-2H-pyrazolo[4,3-c]pyridine | 178.1 |

Preparation of Intermediates AF.2 and AF.3, tert-butyl 1-(3-oxocyclobutyl)-6,7-dihydro-1H-pyrazolo[4,3-c]pyridine-5(4H)-carboxylate and tert-butyl 2-(3,3-difluorocyclobutyl)-6,7-dihydro-2H-pyrazolo[4,3-c]pyridine-5(4H)-carboxylate

Scheme AF

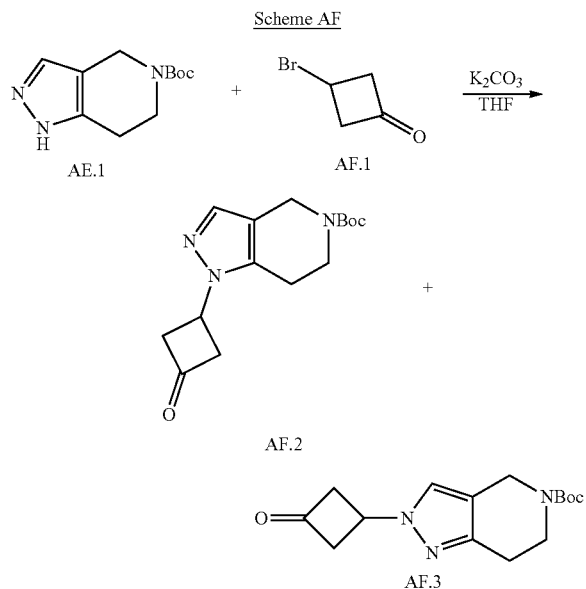

Potassium carbonate (930 mg, 6.72 mmol) was added to a stirred mixture of tert-butyl 6,7-dihydro-1H-pyrazolo[4,3-c]pyridine-5(4H)-carboxylate (1.0 g, 4.48 mmol) and 3-bromocyclobutanone (0.934 g, 6.27 mmol) in THF (10 mL). The resulting mixture was stirred at 20° C. for 5 h. The reaction mixture was then filtered and concentrated, and the resulting crude residue was purified by preparative TLC (silica gel, elution: 50% EtOAc/petroleum ether) to provide tert-butyl 1-(3-oxocyclobutyl)-6,7-dihydro-1H-pyrazolo[4,3-c]pyridine-5(4H)-carboxylate (AF.2) and tert-butyl 2-(3,3-difluoro cyclobutyl)-6,7-dihydro-2H-pyrazolo[4,3-c]pyridine-5(4H)-carboxylate (AF.3). MS (ESI) m/z calc'd for $C_{15}H_{22}N_3O_3$ [M+H]$^+$ 292.2, found 292.1.

Preparation of Intermediate AG.2, 1-(3,3-difluorocyclobutyl)-4,5,6,7-tetrahydro-1H-pyrazolo[4,3-c]pyridine

Scheme AG

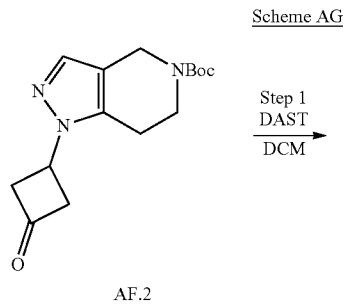

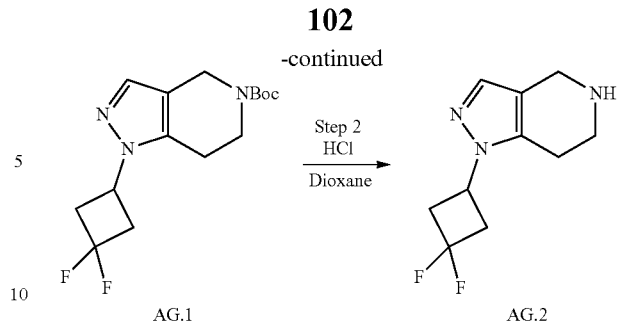

Step 1—Synthesis of Intermediate AG.1, tert-butyl 1-(3,3-difluorocyclobutyl)-6,7-dihydro-1H-pyrazolo[4,3-c]pyridine-5(4H)-carboxylate A mixture of tert-butyl 1-(3-oxocyclobutyl)-6,7-dihydro-1H-pyrazolo[4,3-c]pyridine-5(4H)-carboxylate (340 mg, 1.167 mmol) in DCM (4 mL) was cooled to 0° C. and then treated with DAST (0.771 mL, 5.83 mmol). The reaction mixture was then stirred at 25° C. for 5 h. The mixture was then diluted with DCM (40 mL), washed with sat. aq. NaHCO$_3$ (2×15 mL), dried over anhydrous Mg$_2$SO$_4$, filtered, and concentrated. The resulting crude residue was purified by silica gel chromatography (gradient elution: 5-10% EtOAc/petroleum ether) to provide tert-butyl 1-(3,3-difluorocyclobutyl)-6,7-dihydro-1H-pyrazolo[4,3-c]pyridine-5(4H)-carboxylate. MS (ESI) m/z calc'd for $C_{15}H_{22}F_2N_3O_2$[M+H]$^+$ 314.1, found 314.1.

Step 2—Preparation of Intermediate AG.2, 1-(3,3-difluorocyclobutyl)-4,5,6,7-tetrahydro-1H-pyrazolo[4,3-c]pyridine Tert-butyl 1-(3,3-difluorocyclobutyl)-6,7-dihydro-1H-pyrazolo[4,3-c]pyridine-5(4H)-carboxylate (120 mg, 0.383 mmol) was treated with HCl (4 M in dioxane, 3.0 mL, 12.0 mmol) and the resulting mixture was stirred at 20° C. for 2 h. The reaction mixture was concentrated to provide 1-(3,3-difluorocyclobutyl)-4,5,6,7-tetrahydro-1H-pyrazolo[4,3-c]pyridine, which was used in the subsequent reaction without additional purification. MS (ESI) m/z calc'd for $C_{10}H_{14}F_2N_3$ [M+H]$^+$: 214.1, found 214.3.

Scheme AH

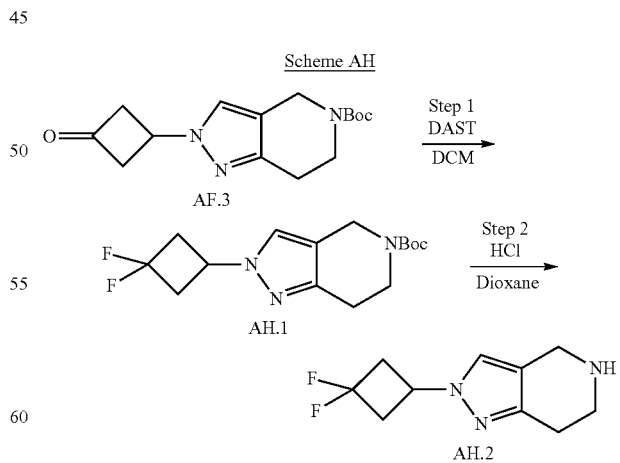

Intermediate AH.2 was also synthesized according to the method shown in Scheme AG, but starting with AF.3. MS (ESI) m/z calc'd for $C_{10}H_{14}F_2N_3$ [M+H]$^+$: 214.1, found 214.3.

Preparation of Intermediate AI.2, 7-chloro-N-(2,4-dimethoxybenzyl)-2-(2-(3-isopropyl-5,6-dihydroimidazo[1,5-a]pyrazin-7(8H)-yl)ethyl)-8-methyl-[1,2,4]triazolo[1,5-c]pyrimidin-5-amine

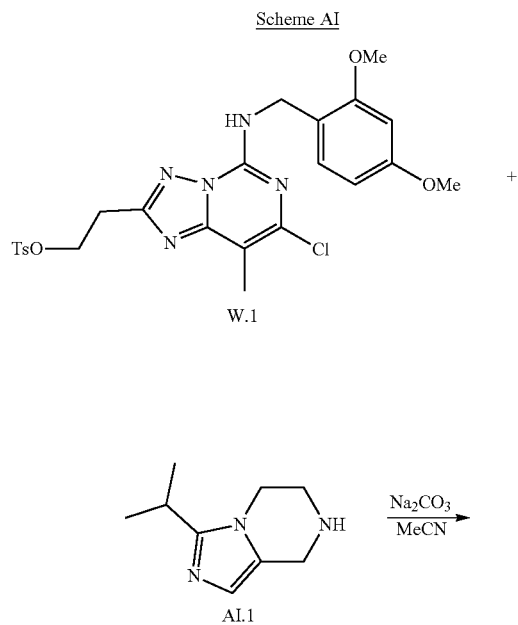

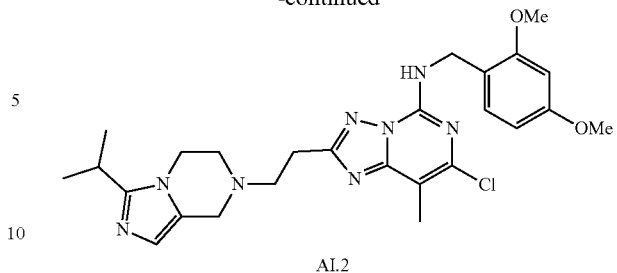

AI.2

A 250 mL round bottom flask was charged with 2-(7-chloro-5-((2,4-dimethoxybenzyl)amino)-8-methyl-[1,2,4]triazolo[1,5-c]pyrimidin-2-yl)ethyl 4-methylbenzenesulfonate (6.00 g, 11.3 mmol), sodium carbonate (2.99 g, 28.2 mmol) and 3-isopropyl-5,6,7,8-tetrahydroimidazo[1,5-a]pyrazine (2.24 g, 13.5 mmol). MeCN (100 mL) was then added and the reaction mixture was stirred overnight at 85° C. After cooling to 25° C., DCM (100 mL) was added and the mixture was filtered through Celite™ (diatomaceous earth) and concentrated. The resulting crude residue was purified by silica gel chromatography (gradient elution: 0-10% MeOH/DCM) to provide 7-chloro-N-(2,4-dimethoxybenzyl)-2-(2-(3-isopropyl-5,6-dihydroimidazo[1,5-a]pyrazin-7(8H)-yl)ethyl)-8-methyl-[1,2,4]triazolo[1,5-c]pyrimidin-5-amine. MS (ESI) m/z calc'd for $C_{26}H_{34}ClN_8O_2[M+H]^+$ 525.2, found 525.2.

Compounds in Table 14 were prepared according to Scheme AI and General Scheme 4, starting from intermediate arylsulfonates W.2, W.3, W.1, W.5 or W.6, and amine or thiol coupling partners comprising either commercially available materials or intermediates AC.6, Z.1, AB.1, AH7, AH.8, AC.7, AC.12, or AC.11.

TABLE 14

Intermediate Compounds Prepared According to General Scheme 4 and Scheme AI

| Entry | Structure Name | Observed m/z [M + H]+ |
|---|---|---|
| AI.3 | 7-chloro-N-(2,4-dimethoxybenzyl)-2-(2-(3-isopropyl-5,6-dihydroimidazo[1,5-a]pyrazin-7(8H)-yl)ethyl)-[1,2,4]triazolo[1,5-c]pyrimidin-5-amine | 511.2 |
| AI.4 | 6-bromo-N-(2,4-dimethoxybenzyl)-2-(2-(3-isopropyl-5,6-dihydroimidazo[1,5-a]pyrazin-7(8H)-yl)ethyl)-5-methyl-[1,2,4]triazolo[1,5-a]pyrazin-8-amine | 569.2, 571.2 |

TABLE 14-continued

Intermediate Compounds Prepared According to General Scheme 4 and Scheme AI

| Entry | Structure Name | Observed m/z [M + H]+ |
|---|---|---|
| AI.5 | 7-chloro-N-(2,4-dimethoxybenzyl)-8-methyl-2-(2-(2-methyl-4,6-dihydro-5H-pyrrolo[3,4-d]oxazol-5-yl)ethyl)-[1,2,4]triazolo[1,5-c]pyrimidin-5-amine | 484.3 |
| AI.6 | 7-chloro-N-(2,4-dimethoxybenzyl)-8-methyl-2-(2-(2-methyl-6,7-dihydrothiazolo[5,4-c]pyridin-5(4H)-yl)ethyl)-[1,2,4]triazolo[1,5-c]pyrimidin-5-amine | 514.3 |
| AI.7 | 7-chloro-N-(2,4-dimethoxybenzyl)-2-(2-(1-isopropyl-1,4,6,7-tetrahydro-5H-[1,2,3]triazolo[4,5-c]pyridin-5-yl)ethyl)-8-methyl-[1,2,4]triazolo[1,5-c]pyrimidin-5-amine | 526.4 |
| AI.8 | 7-chloro-2-(2-(3-cyclobutyl-5,6-dihydroimidazo[1,5-a]pyrazin-7(8H)-yl)ethyl)-N-(2,4-dimethoxybenzyl)-8-methyl-[1,2,4]triazolo[1,5-c]pyrimidin-5-amine | 537.3 |

TABLE 14-continued

Intermediate Compounds Prepared According to General Scheme 4 and Scheme AI

| Entry | Structure Name | Observed m/z [M + H]⁺ |
|---|---|---|
| AI.9 | 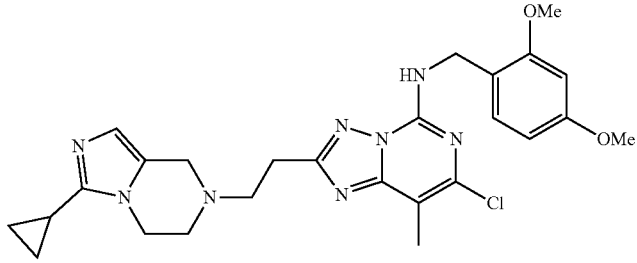 [SMILES: COc1ccc(CNc2nc(Cl)c(C)c3nc(CCN4CCn5c(cnc5C5CC5)C4)nn23)c(OC)c1]<br>7-chloro-2-(2-(3-cyclopropyl-5,6-dihydroimidazo[1,5-a]pyrazin-7(8H)-yl)ethyl)-N-(2,4-dimethoxybenzyl)-8-methyl-[1,2,4]triazolo[1,5-c]pyrimidin-5-amine | 523.3 |
| AI.10 | 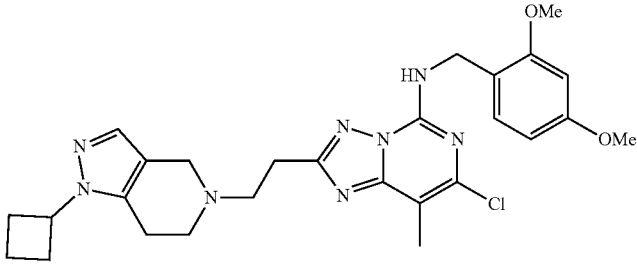 [SMILES: COc1ccc(CNc2nc(Cl)c(C)c3nc(CCN4CCc5c(cnn5C5CCC5)C4)nn23)c(OC)c1]<br>7-chloro-2-(2-(1-cyclobutyl-1,4,6,7-tetrahydro-5H-pyrazolo[4,3-c]pyridin-5-yl)ethyl)-N-(2,4-dimethoxybenzyl)-8-methyl-[1,2,4]triazolo[1,5-c]pyrimidin-5-amine | 537.3 |
| AI.11 | 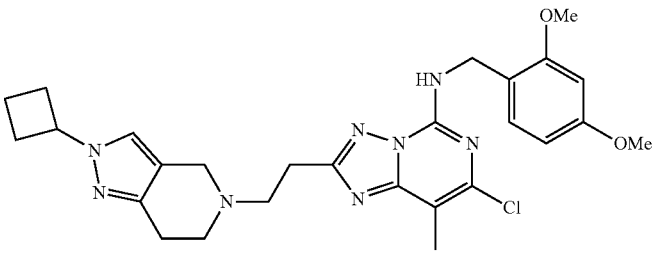 [SMILES: COc1ccc(CNc2nc(Cl)c(C)c3nc(CCN4CCc5nn(C6CCC6)cc5C4)nn23)c(OC)c1]<br>7-chloro-2-(2-(2-cyclobutyl-2,4,6,7-tetrahydro-5H-pyrazolo[4,3-c]pyridin-5-yl)ethyl)-N-(2,4-dimethoxybenzyl)-8-methyl-[1,2,4]triazolo[1,5-c]pyrimidin-5-amine | 537.3 |
| AI.12 | 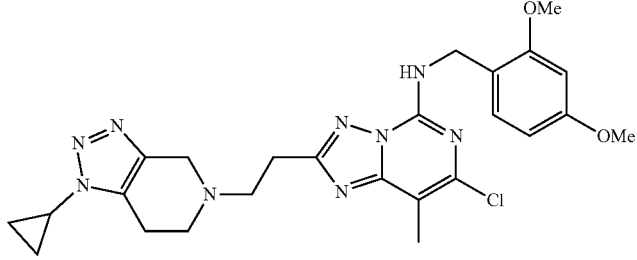 [SMILES: COc1ccc(CNc2nc(Cl)c(C)c3nc(CCN4CCc5c(nnn5C5CC5)C4)nn23)c(OC)c1]<br>7-chloro-2-(2-(1-cyclopropyl-1,4,6,7-tetrahydro-5H-[1,2,3]triazolo[4,5-c]pyridin-5-yl)ethyl)-N-(2,4-dimethoxybenzyl)-8-methyl-[1,2,4]triazolo[1,5-c]pyrimidin-5-amine | 524.0 |

TABLE 14-continued

Intermediate Compounds Prepared According to General Scheme 4 and Scheme AI

| Entry | Structure Name | Observed m/z [M + H]+ |
|---|---|---|
| AI.13 | 7-chloro-N-(2,4-dimethoxybenzyl)-8-methyl-2-(2-(1-(2,2,2-trifluoroethyl)-1,4,6,7-tetrahydro-5H-[1,2,3]triazolo[4,5-c]pyridin-5-yl)ethyl)-[1,2,4]triazolo[1,5-c]pyrimidin-5-amine | 566.2 |
| AI.14 | 1-(5-(2-(7-chloro-5-((2,4-dimethoxybenzyl)amino)-8-methyl-[1,2,4]triazolo[1,5-c]pyrimidin-2-yl)ethyl)-4,5,6,7-tetrahydro-1H-[1,2,3]triazolo[4,5-c]pyridin-1-yl)-2-methylpropan-2-ol | 556.3 |
| AI.15 | 2-(2-(cyclopropylthio)ethyl)-N-(2,4-dimethoxybenzyl)-7-(3-fluorophenyl)-8-methyl-[1,2,4]triazolo[1,5-c]pyrimidin-5-amine | 494.2 |
| AI.16 | 7-chloro-N-(2,4-dimethoxybenzyl)-2-(2-(1-isopropyl-1,4,6,7-tetrahydro-5H-[1,2,3]triazolo[4,5-c]pyridin-5-yl)ethyl)-[1,2,4]triazolo[1,5-c]pyrimidin-5-amine | 512.3 |

Preparation of Intermediate AJ.2, 2-(6-bromopyridin-3-yl)propan-2-ol

Scheme AJ

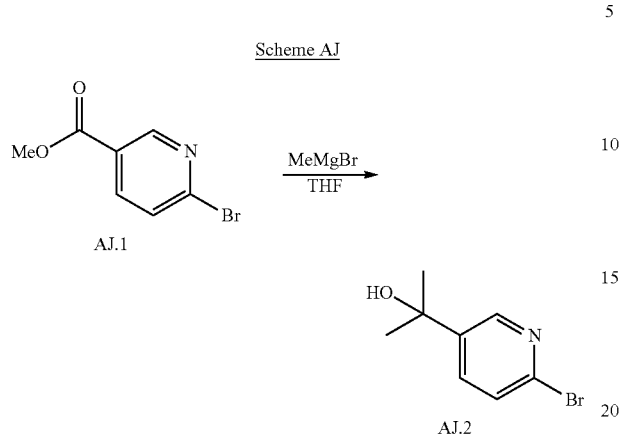

A 50 mL round bottom flask was charged with methyl 6-bromonicotinate (1.50 g, 6.94 mmol). THF (15 mL) was added and the mixture was cooled to −30° C. Methylmagnesium bromide (3 M in Et$_2$O, 5.10 mL, 15.3 mmol) was then added over 5 min, and the reaction mixture was warmed to 25° C. over 15 min and stirred at that temperature for 30 min. The reaction was quenched with sat. NH$_4$Cl (10 mL). DCM (15 mL) was added and the biphasic mixture was stirred for 5 min. The layers were separated, and the aq. layer was extracted with DCM (2×15 mL). The combined organic layers were then dried over anhydrous MgSO$_4$, filtered, and concentrated. The resulting crude material was purified by silica gel chromatography (gradient elution: 0-100% EtOAc/Hexanes) to provide 2-(6-bromopyridin-3-yl)propan-2-ol. MS (ESI) m/z calc'd for C$_8$H$_{11}$BrNO [M+H]$^+$ 216.0, found 216.1, 218.1.

Compounds in Table 15 were prepared according to Scheme AJ, starting from the appropriate commercially available esters or methyl ketones.

TABLE 15

Intermediate Compounds Prepared According to Scheme AJ

| Entry | Structure Name | Observed m/z [M + H]$^+$ |
|---|---|---|
| AJ.3 | 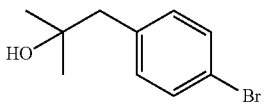 1-(4-bromophenyl)-2-methylpropan-2-ol | 211.1, 213.1 |
| AJ.4 | 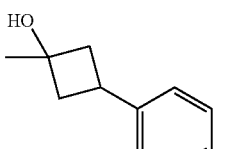 3-(4-bromophenyl)-1-methylcyclobutan-1-ol | 223.1, 225.1 |

Preparation of Intermediate AK.3, 4-bromo-1-(2,2-difluoroethyl)-1H-benzo[d]imidazole Scheme AK

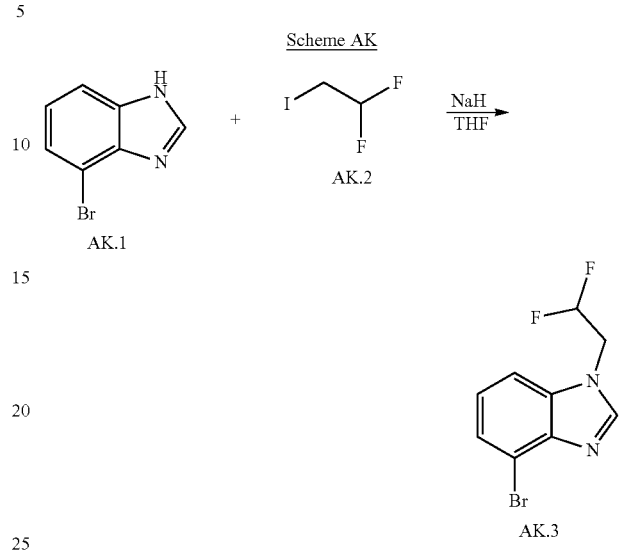

A 100 mL round bottom flask was charged with 4-bromo-1H-benzo[d]imidazole (1 g, 5.08 mmol). THF (50.8 mL) was added, then the reaction mixture was cooled to 0° C. and sodium hydride (60% in mineral oil, 0.203 g, 5.08 mmol) was added. The reaction mixture was stirred at 0° C. for 30 min, followed by the addition of 1,1-difluoro-2-iodoethane (0.447 mL, 5.08 mmol). The reaction was then heated to 65° C. and stirred overnight. Water (25 mL) and DCM (50 mL) were added, and the layers were separated. The aq. layer was extracted with DCM (2×40 mL), and the combined organic layers were dried over anhydrous MgSO$_4$, filtered, and concentrated. The resulting crude material was purified by silica gel chromatography (gradient elution: 0-10% MeOH/DCM) to provide 4-bromo-1-(2,2-difluoroethyl)-1H-benzo[d]imidazole. MS (ESI) m/z calc'd for C$_9$H$_8$BrF$_2$N$_2$ [M+H]$^+$ 261.0, found 261.0, 263.0.

Scheme AL

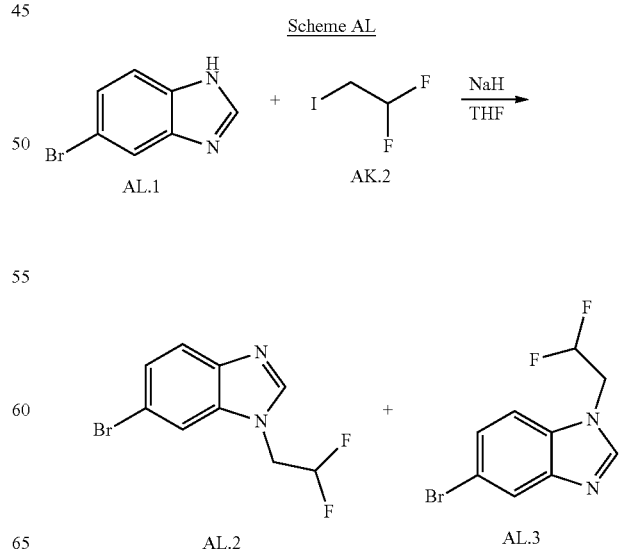

Intermediates AL.2 and AL.3 were also synthesized as a mixture according to the method shown in Scheme AP, but starting with AL.1. The mixture of 6-bromo-1-(2,2-difluoroethyl)-1H-benzo[d]imidazole and 5-bromo-1-(2,2-difluoroethyl)-1H-benzo[d]imidazole was purified by ACHIRAL-Prep-SFC [Column: IG, 21×250 mm; 15% [MeOH w/0.1% NaOH]/CO$_2$; Flow rate: 70 mL/min; 220 nm; First Eluting Peak (AL.2); Second Eluting Peak (AL.3)]. AL.2: MS (ESI) m/z calc'd for $C_9H_8BrF_2N_2[M+H]^+$ 261.0, found 261.0, 263.0. AL.3: MS (ESI) m/z calc'd for $C_9H_8BrF_2N_2[M+H]^+$ 261.0, found 261.0, 263.0.

Preparation of Intermediate AM.2, 1-(4-bromo-1H-benzo[d]imidazol-1-yl)-2-methylpropan-2-ol

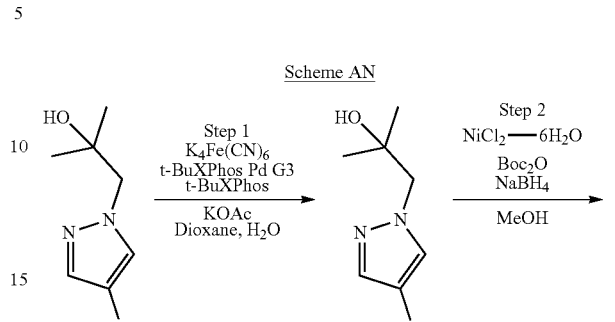

A 100 mL round bottom flask was charged with 4-bromo-1H-benzo[d]imidazole (500 mg, 2.54 mmol). DMF (36.3 mL) and cesium carbonate (2.48 g, 7.61 mmol) were added, and the reaction mixture was stirred at 25° C. for 30 min. 2,2-Dimethyloxirane (0.565 mL, 6.34 mmol) was then added and the mixture was heated to 80° C. and stirred overnight. After cooling, water (50 mL) and EtOAc (75 mL) were added and the layers were separated. The aq. layer was extracted with EtOAc (2×100 mL), and the combined organic layers were washed with water (2×50 mL) and brine (50 mL), dried over anhydrous MgSO$_4$, filtered, and concentrated. The resulting crude residue was purified by silica gel chromatography (gradient elution: 0-10% MeOH/DCM) to provide 1-(4-bromo-1H-benzo[d]imidazol-1-yl)-2-methylpropan-2-ol. MS (ESI) m/z calc'd for $C_{11}H_{14}BrN_2O$ $[M+H]^+$ 269.0, found 269.1, 271.1.

Preparation of Intermediate AN.4, 1-(4-(aminomethyl)-1H-pyrazol-1-yl)-2-methylpropan-2-ol hydrochloride

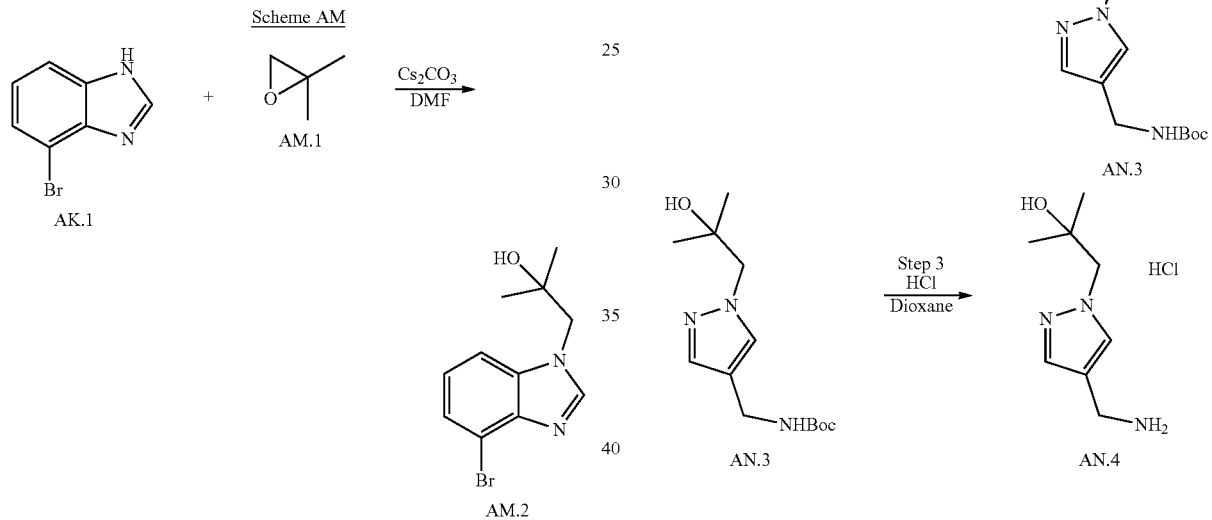

Step 1—Synthesis of Intermediate AN.2, 1-(2-hydroxy-2-methylpropyl)-1H-pyrazole-4-carbonitrile 1-(4-bromo-1H-pyrazol-1-yl)-2-methylpropan-2-ol (500 mg, 2.28 mmol), potassium ferrocyanide (420 mg, 1.14 mmol), potassium acetate (28 mg, 0.285 mmol), tBuXPhos (9.7 mg, 0.023 mmol), and 3$^{rd}$ Generation tBuXPhos Precatalyst (18.1 mg, 0.023 mmol) were combined. The reaction vessel was sealed and flushed with nitrogen for 5 min, evacuated for 1 min, and backfilled with nitrogen for 1 min. Dioxane (5.7 mL) and water (5.7 mL) were then added, and the reaction mixture was degassed by sparging with nitrogen for 15 min, then backfilled with nitrogen for 1 min. The reaction mixture was then stirred at 100° C. for 1 h under microwave irradiation. After cooling, the reaction was quenched with brine (25 mL) and extracted with EtOAc (3×25 mL). The combined organic layers were dried over anhydrous MgSO$_4$, filtered, and concentrated. The resulting crude residue was purified by silica gel chromatography (gradient elution: 0-10% MeOH/DCM) to provide 1-(2-hydroxy-2-methylpropyl)-1H-pyrazole-4-carbonitrile. MS (ESI) m/z calc'd for $C_8H_{12}N_3O$ $[M+H]^+$ 166.1, found 166.2.

Step 2—Synthesis of Intermediate AN.3, tert-butyl ((1-(2-hydroxy-2-methylpropyl)-1H-pyrazol-4-yl)methyl)carbamate Boc$_2$O (1.06 mL, 4.56 mmol) and nickel(II) chloride hexahydrate (54 mg, 0.228 mmol) were sequentially added to a stirred solution of 1-(2-hydroxy-2-methylpropyl)-1H-pyrazole-4-carbonitrile (377 mg, 2.28 mmol) in MeOH (18 mL). The reaction mixture was cooled to 0° C. and stirred for 5 min at that temperature. Sodium borohydride (604 mg, 16.0 mmol) was then added over a period of 30 min in 6 equal portions. The reaction mixture was stirred for 2 h while slowly warming the mixture from 0° C. to 25° C. The reaction was then quenched with diethylenetriamine (0.159 mL, 2.28 mmol) and stirred for an additional 30 min. The reaction mixture was then concentrated, diluted with sat. aq. NaHCO$_3$ (20 mL), and extracted with DCM (3×25 mL). The combined organic layers were dried over anhydrous MgSO$_4$, filtered, and concentrated to provide tert-butyl ((1-(2-hydroxy-2-methylpropyl)-1H-pyrazol-4-yl)methyl)carbamate, which was used in the subsequent reaction without additional purification. MS (ESI) m/z calc'd for C$_{13}$H$_{24}$N$_3$O$_3$ [M+H]$^+$ 270.2, found 270.2.

Step 3—Preparation of Intermediate AN.4, 1-(4-(aminomethyl)-1H-pyrazol-1-yl)-2-methylpropan-2-ol hydrochloride HCl (4 M in dioxane, 1.71 mL, 6.85 mmol) was added to a stirred solution of tert-butyl ((1-(2-hydroxy-2-methylpropyl)-1H-pyrazol-4-yl)methyl)carbamate (614 mg, 2.28 mmol) in DCM (4.6 mL). The resulting mixture was stirred vigorously at 25° C. for 18 h. The reaction mixture was then concentrated to provide 1-(4-(aminomethyl)-1H-pyrazol-1-yl)-2-methylpropan-2-ol hydrochloride, which was used in subsequent reactions without further purification. MS (ESI) m/z calc'd for C$_8$H$_{16}$N$_3$O [M+H]$^+$ 170.1, found 170.3.

Preparation of Intermediates AO.4 and AO.5, 1-cyclopentyl-4,5,6,7-tetrahydro-1H-imidazo[4,5-c]pyridine and 3-cyclopentyl-4,5,6, 7-tetrahydro-3H-imidazo[4,5-c]pyridine

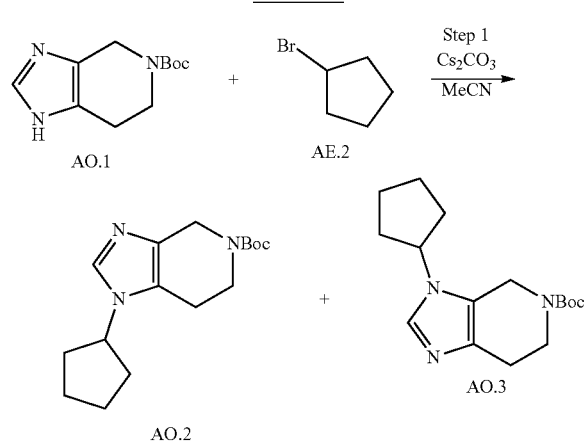

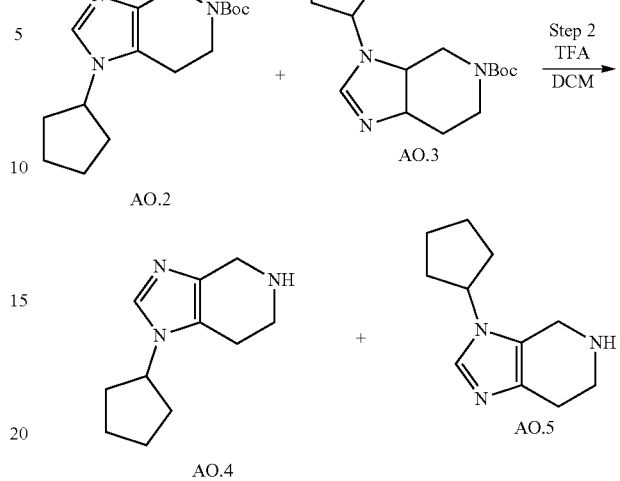

Step 1—Synthesis of Intermediates AO.2 and AO.3, tert-butyl 1-cyclopentyl-1,4,6,7-tetrahydro-5H-imidazo[4,5-c]pyridine-5-carboxylate and tert-butyl 3-cyclopentyl-3,4,6,7-tetrahydro-5H-imidazo[4,5-c]pyridine-5-carboxylate A 40 mL scintillation vial equipped with a stir bar was charged with tert-butyl 1,4,6,7-tetrahydro-5H-imidazo[4,5-c]pyridine-5-carboxylate (400 mg, 1.792 mmol), cesium carbonate (1.75 g, 5.37 mmol) and bromocyclopentane (534 mg, 3.58 mmol). The vial was evacuated and backfilled with nitrogen (3×). MeCN (18 mL) was added, and the reaction mixture was then stirred at 85° C. overnight. After completion of the reaction, DCM (50 mL) and water (50 mL), were added, and the layers were separated. The aq. layer was extracted with DCM (2×50 mL), and the combined organic layers were dried over anhydrous MgSO$_4$, filtered, and concentrated to provide a mixture of tert-butyl 1-cyclopentyl-1,4,6,7-tetrahydro-5H-imidazo[4,5-c]pyridine-5-carboxylate and tert-butyl 3-cyclopentyl-3,4,6,7-tetrahydro-5H-imidazo[4,5-c]pyridine-5-carboxylate, which was used in the subsequent reaction without further purification. MS (ESI) m/z calc'd for C$_{16}$H$_{26}$N$_3$O$_2$ [M+H]$^+$ 292.2, found 292.3.

Step 2—Preparation of Intermediates AO.4 and AO.5, 1-cyclopentyl-4,5,6,7-tetrahydro-1H-imidazo[4,5-c]pyridine and 3-cyclopentyl-4,5,6, 7-tetrahydro-3H-imidazo[4,5-c]pyridine A 40 mL scintillation vial equipped with a stir bar was charged with the mixture of tert-butyl 1-cyclopentyl-1,4,6,7-tetrahydro-5H-imidazo[4,5-c]pyridine-5-carboxylate and tert-butyl 3-cyclopentyl-3,4,6,7-tetrahydro-5H-imidazo[4,5-c]pyridine-5-carboxylate from step 1, then DCM (8.4 ml) and TFA (8.4 mL, 109 mmol) were added. The resulting reaction mixture was stirred at 25° C. for 2 h. After completion, the reaction mixture was concentrated to provide a mixture of 1-cyclopentyl-4,5,6,7-tetrahydro-1H-imidazo[4,5-c]pyridine and 3-cyclopentyl-4,5,6,7-tetrahydro-3H-imidazo[4,5-c]pyridine, which was used in the subsequent reaction without further purification. MS (ESI) m/z calc'd for C$_{11}$H$_{18}$N$_3$ [M+H]$^+$ 192, found 192.

Preparation of Intermediate AP.5, 5-bromo-1-(3,3-difluorocyclobutyl)-1H-benzo[d][1,2,3]triazole

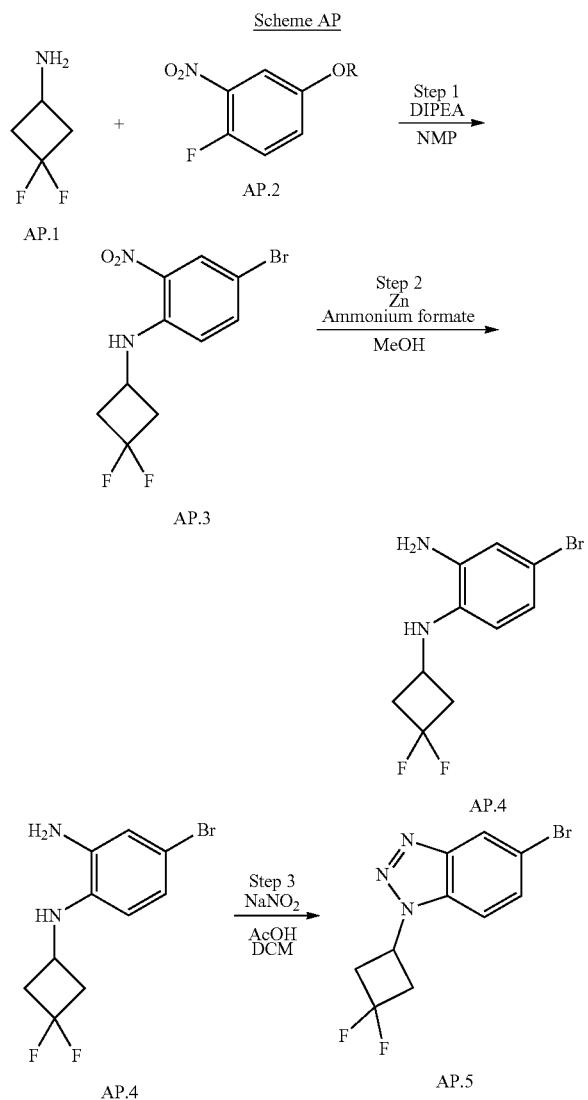

Step 1—Synthesis of Intermediate AP.3, 4-bromo-N-(3,3-difluorocyclobutyl)-2-nitroaniline DIPEA (3.65 ml, 20.9 mmol) was added dropwise to a stirring mixture of 3,3-difluorocyclobutan-1-amine hydrochloride (1 g, 6.97 mmol) and 4-bromo-1-fluoro-2-nitrobenzene (0.858 ml, 6.97 mmol) in NMP (10 mL) at 25° C. The resulting mixture was stirred at 60° C. for 48 h. The reaction mixture was partitioned with diethyl ether (200 mL) and sat. aq. NaHCO₃(200 mL)) and stirred for 2 h. The layers were separated, and the aq. layer was extracted with diethyl ether (50 mL). The combined organic layers were washed with brine (50 mL), dried over anhydrous Mg₂SO₄, filtered, and concentrated to provide 4-bromo-N-(3,3-difluorocyclobutyl)-2-nitroaniline, which was used directly in the subsequent reaction without further purification. MS (ESI) m/z calc'd for $C_{10}H_{10}BrF_2N_2O_2$ [M+H]⁺ 307.0, found 307.0, 309.0.

Step 2—Synthesis of Intermediate AP.4, 4-bromo-N-(3,3-difluorocyclobutyl)benzene-1,2-diamine A stirring suspension of 4-bromo-N-(3,3-difluorocyclobutyl)-2-nitroaniline (342 mg, 1.11 mmol) and ammonium formate (330 mg, 5.23 mmol) in MeOH (11 mL) was treated with zinc (160 mg, 2.46 mmol). The resulting mixture was stirred at 60° C. for 24 h. After cooling, the reaction mixture was partitioned with EtOAc (75 mL) and sat. aq. NaHCO₃(75 mL)) and stirred for 2 h. The layers were then separated, and the aq. layer was extracted with EtOAc (50 mL). The combined organic layers were dried over anhydrous Mg₂SO₄, filtered, and concentrated to provide 4-bromo-N¹-(3,3-difluorocyclobutyl)benzene-1,2-diamine, which was used directly in the subsequent reaction without further purification. MS (ESI) m/z calc'd for $C_{10}H_{12}BrF_2N_2$ [M+H]⁺ 277.0, found 277.0, 279.0.

Step 3—Preparation of Intermediate AP.5, 5-bromo-1-(3,3-difluorocyclobutyl)-1H-benzo[d][1,2,3]triazole A stirring mixture of 4-bromo-N¹-(3,3-difluorocyclobutyl)benzene-1,2-diamine (306 mg, 1.10 mmol) in DCM (2.8 mL) and AcOH (2.8 mL) was cooled to 0° C. and sodium nitrite (137 mg, 1.99 mmol) was added. The resulting reaction mixture was stirred for 5 h, slowly warming to 25° C. After completion, the reaction was diluted with DCM (50 mL) and sat. aq. NaHCO₃ was added until pH 8 was observed. The layers of the biphasic mixture were then separated, and the aq. layer was extracted with DCM (2×40 mL). The combined organic layers were washed with brine (20 mL), dried over anhydrous Mg₂SO₄, filtered, and concentrated. The resulting crude residue was purified by silica gel chromatography (gradient elution: 0-100% EtOAc/Hexanes), to provide 5-bromo-1-(3,3-difluorocyclobutyl)-1H-benzo[d][1,2,3]triazole. MS (ESI) m/z calc'd for $C_{10}H_{19}BrF_2N_3$[M+H]⁺ 288.0, found 288.0, 290.0.

Preparation of Example 1.2, 2-benzyl-6-(oxazol-2-yl)-[1,2,4]triazolo[1,5-a]pyrazin-8-amine, TFA Salt

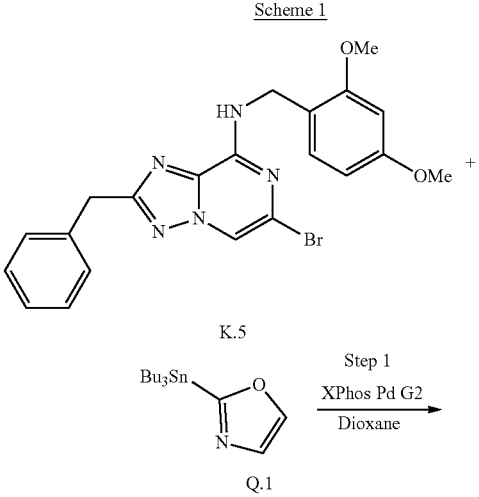

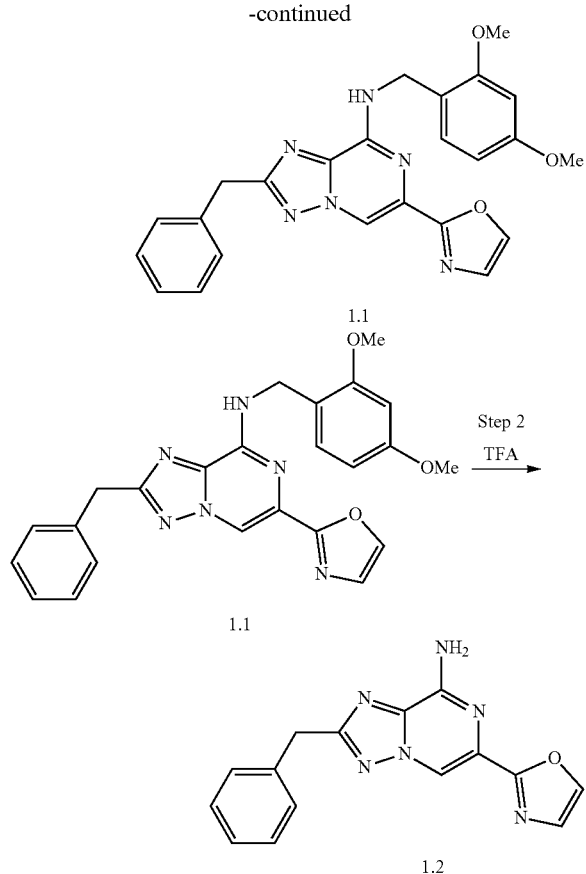

Step 1—Synthesis of Intermediate 1.1, 2-benzyl-N-(2,4-dimethoxybenzyl)-6-(oxazol-2-yl)-[1,2,4]triazolo[1,5-a]pyrazin-8-amine A 40 mL vial was charged with 2-benzyl-6-bromo-N-(2,4-dimethoxybenzyl)-[1,2,4]triazolo[1,5-a]pyrazin-8-amine (55 mg, 0.121 mmol) and XPhos Pd G2 (9.5 mg, 0.012 mmol), and the vial was evacuated and backfilled with nitrogen (3×). A degassed [Method C] solution of 2-(tributylstannyl)oxazole (51 µL, 0.242 mmol) in dioxane (1.2 mL) was added, and the reaction was heated to 80° C. overnight. The reaction was then cooled to 25° C. and concentrated. The resulting crude residue was then purified by silica gel chromatography (gradient elution: 0-100% EtOAc/Hexanes) to provide 2-benzyl-N-(2,4-dimethoxybenzyl)-6-(oxazol-2-yl)-[1,2,4]triazolo[1,5-a]pyrazin-8-amine. MS (ESI) m/z calc'd for $C_{24}H_{23}N_6O_3$ [M+H]$^+$ 443.2, found 443.2.

Step 2—Synthesis of Example 1.2, 2-benzyl-6-(oxazol-2-yl)-[1,2,4]triazolo[1,5-a]pyrazin-8-amine, TFA Salt A 40 mL scintillation vial was charged with 2-benzyl-N-(2,4-dimethoxybenzyl)-6-(oxazol-2-yl)-[1,2,4]triazolo[1,5-a]pyrazin-8-amine (49 mg, 0.111 mmol). TFA (1.1 mL) was added, and the reaction mixture was heated at 50° C. and stirred for 2 h. After cooling, the reaction mixture was concentrated and the residue was taken up in DMSO (2 mL), filtered, and purified via reversed-phase HPLC [Method A]. This provided 2-benzyl-6-(oxazol-2-yl)-[1,2,4]triazolo[1,5-a]pyrazin-8-amine, TFA salt (Example 1.2). MS (ESI) m/z calc'd for $C_{18}H_{13}N_6O$ [M+H]$^+$ 293.1, found 293.1. $^1$H NMR (600 MHz, DMSO-d$_6$) δ 8.66 (s, 1H), 8.24 (s, 1H), 7.68 (br s, 2H), 7.39 (s, 1H), 7.35-7.29 (m, 4H), 7.25-7.20 (m, 1H), 4.23 (s, 2H). A2a IC$_{50}$ 3.1 nM (A).

The following examples in Table 16 were prepared according to Scheme 1 and General Scheme 1 above, using intermediates K.4, K.6, AI.4, AI.5, AI.6, K.8, AI.2, AI.8, AI.9, AI.10, AI.11, AI.7, AI.12, AI.13, AI.14, or AI.2 and the appropriate commercial tributylstannane coupling partner. Asterisk (*) indicates that A2b data is not available.

TABLE 16

| | Examples Prepared According to General Scheme 1 and Scheme 1 | | |
|---|---|---|---|
| Example | Structure Name | Observed m/z [M + H]$^+$ | A2a IC$_{50}$ (nM) / A2b IC$_{50}$ (nM) |
| 1.3 | 2-benzyl-5-methyl-6-(thiazol-2-yl)-[1,2,4]-triazolo[1,5-a]pyrazin-8-amine | 323.2 | 1.3 (A) * |

TABLE 16-continued

Examples Prepared According to General Scheme 1 and Scheme 1

| Example | Structure / Name | Observed m/z [M + H]+ | A2a IC$_{50}$ (nM) / A2b IC$_{50}$ (nM) |
|---|---|---|---|
| 1.4 | 2-benzyl-5-methyl-6-(pyrimidin-2-yl)-[1,2,4]-triazolo[1,5-a]pyrazin-8-amine | 318.3 | 3.6 (A) * |
| 1.5 | 2-methyl-6-(oxazol-2-yl)-[1,2,4]-triazol[1,5-a]pyrazin-8-amine | 217.2 | 909.2 (A) * |
| 1.6 | 2-(2-(3-isopropyl-5,6-dihydroimidazo[1,5-a]pyrazin-7(8H)-yl)ethyl)-5-methyl-6-(oxazol-2-yl)-[1,2,4]triazolo[1,5a]pyrazin-8-amine | 408.2 | 16.4 (A) 88.7 |
| 1.7 | 8-methyl-2-(2-(2-methyl-4,6-dihydro-5H-pyrrolo[3,4-d]oxazol-5-yl)ethyl)-7-(oxazol-2-yl)-[1,2,4]triazolo[1,5-c]pyrimidin-5-amine | 367.2 | 7.4 (A) * |
| 1.8 | 8-methyl-2-(2-(2-methyl-6,7-dihydrothiazolo[5,4-c]pyridin-5(4H)-yl)ethyl)-7-(oxazol-2-yl)-[1,2,4]triazolo[1,5-c]pyrimidin-5-amine | 397.2 | 2.4 (B) * |

TABLE 16-continued

Examples Prepared According to General Scheme 1 and Scheme 1

| Example | Structure / Name | Observed m/z [M + H]+ | A2a IC$_{50}$ (nM) / A2b IC$_{50}$ (nM) |
|---|---|---|---|
| 1.9 | 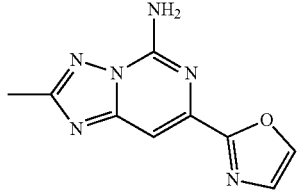 2-methyl-7-(oxazol-2-yl)-[1,2,4]-triazolo[1,5-c]pyrimidin-5-amine | 217.1 | 533.8 (A) * |
| 1.10 | 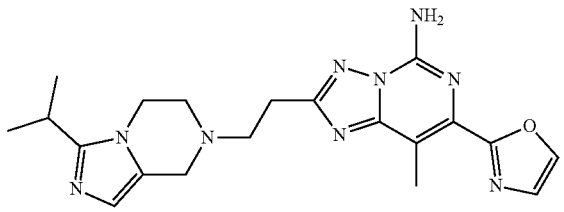 2-(2-(3-isopropyl-5,6-dihydroimidazo[1,5-a]pyrazin-7(8H)-yl)-ethyl)-8-methyl-7-(oxazol-2-yl)-[1,2,4]triazolo[1,5-c]pyrimidin-5-amine | 408.2 | 2.1 (A) 16.2 |
| 1.11 | 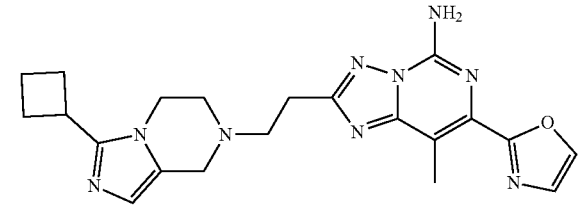 2-(2-(3-cyclobutyl-5,6-dihydroimidazo[1,5-a]pyrazin-7(8H)-yl)-ethyl)-8-methyl-7-(oxazol-2-yl)-[1,2,4]triazolo[1,5-c]pyrimidin-5-amine | 420.3 | 3.6 (A) 56.3 |
| 1.12 | 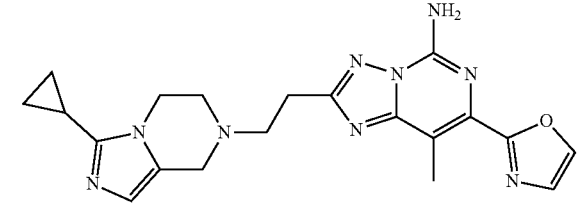 2-(2-(3-cyclopropyl-5,6-dihydroimidazo[1,5-a]pyrazin-7(8H)-yl)-ethyl)-8-methyl-7-(oxazol-2-yl)-[1,2,4]triazolo[1,5-c]pyrimidin-5-amine | 406.2 | 4.8 (A) 217.9 |
| 1.13 | 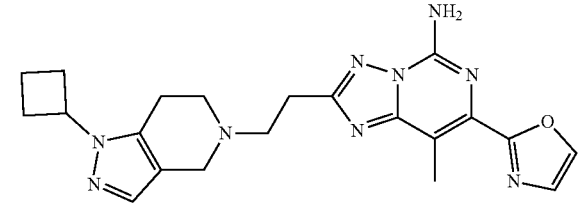 2-(2-(1-cyclobutyl-1,4,6,7-tetrahydro-5H-pyrazolo[4,3-c]pyridin-5-yl)ethyl)-8-methyl-7-(oxazol-2-yl)-[1,2,4]triazolo[1,5-c]pyrimidin-5-amine | 420.2 | 1.0 (A) 144.2 |

TABLE 16-continued

Examples Prepared According to General Scheme 1 and Scheme 1

| Example | Structure Name | Observed m/z [M + H]+ | A2a IC$_{50}$ (nM) A2b IC$_{50}$ (nM) |
|---|---|---|---|
| 1.14 | 2-(2-(2-cyclobutyl-2,4,6,7-tetrahydro-5H-pyrazolo[4,3-c]pyridin-5-yl)ethyl)-8-methyl-7-(oxazol-2-yl)-[1,2,4]triazolo[1,5-c]pyrimidin-5-amine | 420.2 | 6.7 (A)<br><br>399.0 |
| 1.15 | 2-(2-(1-isopropyl-1,4,6,7-tetrahydro-5H-[1,2,3]triazolo[4,5-c]-pyridin-5-yl)ethyl)-8-methyl-7-(oxazol-2-yl)-[1,2,4]triazolo-[1,5-c]pyrimidin-5-amine | 409.0 | 0.1 (A)<br><br>402.0 |
| 1.16 | 2-(2-(1-cyclopropyl-1,4,6,7-tetrahydro-5H-[1,2,3]triazolo[4,5-c]-pyridin-5-yl)ethyl)-8-methyl-7-(oxazol-2-yl)-[1,2,4]triazolo[1,5-c]pyrimidin-5-amine | 407.0 | 0.3 (A)<br><br>111.0 |
| 1.17 | 8-methyl-7-(oxazol-2-yl)-2-(2-(1-(2,2,2-trifluoroethyl)-1,4,6,7-tetrahydro-5H-[1,2,3]triazolo-[4,5-c]pyridin-5-yl)ethyl)-[1,2,4]-triazolo[1,5-c]pyrimidin-5-amine | 449.3 | 1.3 (A)<br><br>35.2 |

TABLE 16-continued

Examples Prepared According to General Scheme 1 and Scheme 1

| Example | Structure Name | Observed m/z [M + H]⁺ | A2a IC$_{50}$ (nM) A2b IC$_{50}$ (nM) |
|---|---|---|---|
| 1.18 | 1-(5-(2-(5-amino-8-methyl-7-(oxazol-2-yl)-[1,2,4]triazolo[1,5-c]-pyrimidin-2-yl)ethyl)-4,5,6,7-tetrahydro-1H-[1,2,3]triazolo[4,5-c]pyridin-1-yl)-2-methylpropan-2-ol | 439.4 | 18.1 (A) 694.5 |
| 1.19 | 2-(2-(3-isopropyl-5,6-dihydroimidazo[1,5-a]pyrazin-7(8H)-yl)ethyl)-7-(oxazol-2-yl)-[1,2,4]triazolo[1,5-c]pyrimidin-5-amine | 394.2 | 126.6 (A) 904.9 |

Preparation of Example 2.3, 2-benzyl-6-(4-fluorophenyl)-[1,2,4]triazolo[1,5-a]pyrazin-8-amine, TEA Salt Scheme 2

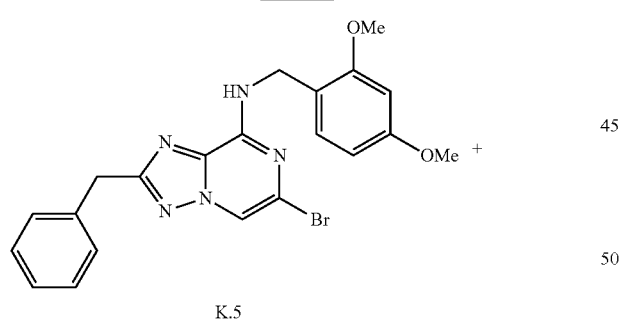

K.5

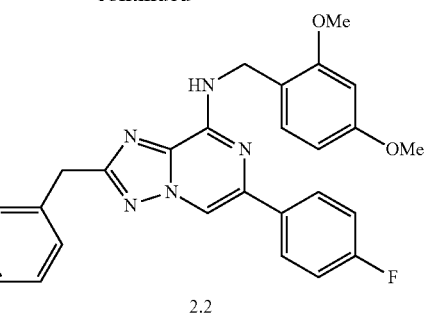

2.2

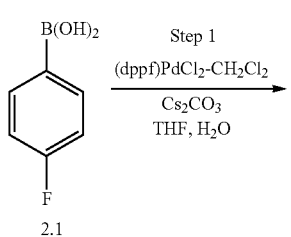

2.1

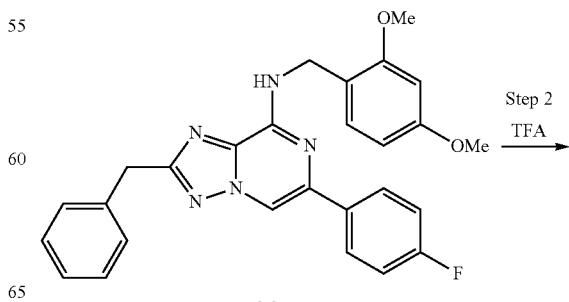

2.2

Step 1
(dppf)PdCl$_2$-CH$_2$Cl$_2$
Cs$_2$CO$_3$
THF, H$_2$O

Step 2
TFA

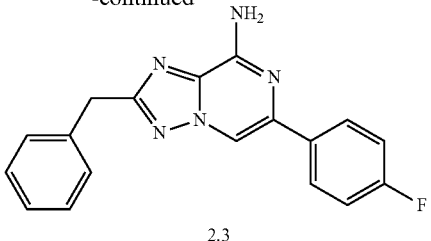

2.3

Step 1—Synthesis of Intermediate 2.2, 2-benzyl-N-(2,4-dimethoxybenzyl)-6-(4-fluorophenyl)-[1,2,4]triazolo[1,5-a]pyrazin-8-amine A 0.5 mL Biotage® microwave vial was charged with 2-benzyl-6-bromo-N-(2,4-dimethoxybenzyl)-[1,2,4]triazolo[1,5-a]pyrazin-8-amine (40 mg, 0.088 mmol), cesium carbonate (29 mg, 0.088 mmol), (4-fluorophenyl)boronic acid (13.6 mg, 0.097 mmol), and 1,1'-bis(diphenylphosphino)ferrocene-palladium(II)dichloride dichloromethane complex (7.2 mg, 8.80 μmol), and the vial was evacuated and backfilled with nitrogen (3×). A degassed [Method C] mixture of THF (0.4 mL) and water (0.1 mL) was added, and the vial was heated under microwave irradiation at 130° C. for 2.5 h. After completion of the reaction, water (5 mL) was added, and the reaction mixture was extracted with DCM (7 mL). The combined organic layers were dried over anhydrous $MgSO_4$, filtered, and concentrated. The resulting crude material was used without purification in the subsequent reaction. MS (ESI) m/z calc'd for $C_{27}H_{25}FN_5O_2$ $[M+H]^+$ 470.2, found 470.2.

Step 2—Synthesis of Example 2.3, 2-benzyl-6-(4-fluorophenyl)-[1,2,4]triazolo[1,5-a]pyrazin-8-amine, TFA Salt A 20 mL scintillation vial was charged with 2-benzyl-N-(2,4-dimethoxybenzyl)-6-(4-fluorophenyl)-[1,2,4]triazolo[1,5-a]pyrazin-8-amine (41 mg, 0.087 mmol). TFA (0.87 mL) was added, and the reaction mixture was heated at 50° C. and stirred for 2 h. After cooling, the reaction mixture was concentrated and the residue was taken up in DMSO (2 mL), filtered, and purified via reversed-phase HPLC [Method A]. This provided 2-benzyl-6-(4-fluorophenyl)-[1,2,4]triazolo[1,5-a]pyrazin-8-amine, TFA salt (Example 2.3). MS (ESI) m/z calc'd for $C_{18}H_{15}FN_5$ $[M+H]^+$ 320.1, found 320.2. $^1H$ NMR (600 MHz, DMSO-$d_6$) δ 8.71 (s, 1H), 8.05 (dd, J=8.9, 5.5 Hz, 2H), 7.47 (br s, 2H), 7.35-7.26 (m, 6H), 7.25-7.21 (m, 1H), 4.21 (s, 2H). A2a $IC_{50}$ 2.5 nM (A).

The following examples in Table 17 were prepared according to Scheme 2 and General Scheme 1 above, using intermediates K.5, K.6, or AI.4 and the appropriate commercial boronic acid coupling partner. Asterisk (*) indicates that A2b data is not available.

TABLE 17

Examples Prepared According to General Scheme 1 and Scheme 2

| Example | Structure / Name | Observed m/z [M + H]⁺ | A2a IC₅₀ (nM) / A2b IC₅₀ (nM) |
|---|---|---|---|
| 2.4 | 2-benzyl-6-phenyl-[1,2,4]triazolo[1,5-a]pyrazin-8-amine | 302.2 | 1.6 (A) * |
| 2.5 | 2-methyl-6-phenyl-[1,2,4]triazolo[1,5-a]pyrazin-8-amine | 226.1 | 112.0 (A) * |

TABLE 17-continued
Examples Prepared According to General Scheme 1 and Scheme 2
| Example | Structure Name | Observed m/z [M + H]⁺ | A2a IC$_{50}$ (nM) A2b IC$_{50}$ (nM) |
|---|---|---|---|
| 2.6 | 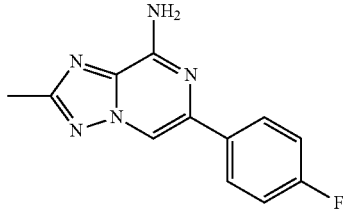 6-(4-fluorophenyl)-2-methyl-[1,2,4]triazolo-[1,5-a]pyrazin-8-amine | 244.1 | 523.2 (A) * |
| 2.7 | 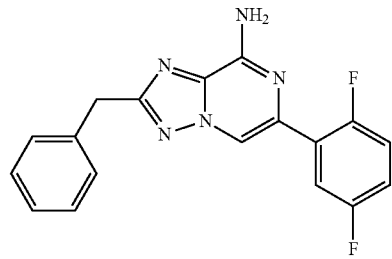 2-benzyl-6-(2,5-difluorophenyl)-[1,2,4]triazolo-[1,5-a]pyrazin-8-amine | 338.2 | 2.2 (A) * |
| 2.8 | 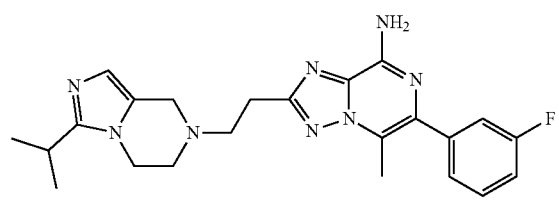 6-(3-fluorophenyl)-2-(2-(3-isopropyl-5,6-dihydroimidazo[1,5-a]-pyrazin-7(8H)-yl)ethyl)-5-methyl-[1,2,4]triazolo[1,5-a]pyrazin-8-amine | 435.2 | 160.3 (A) 48.1 |

The following examples in Table 18 were prepared using a similar procedure as above, but using dioxane in place of THF during Step 1 and running the reactions at 80° C. overnight. Intermediates AL.3, AL.2, AL.7, 0.7, or AI.16 were used, in conjunction with commercially available boronic acid coupling partners. Asterisk (*) indicates that A2b data is not available.

TABLE 18

Examples Prepared According to General Scheme 1 and Similarly to Scheme 2

| Example | Structure / Name | Observed m/z [M + H]+ | A2a IC$_{50}$ (nM) / A2b IC$_{50}$ (nM) |
|---|---|---|---|
| 2.9 | 7-(3,5-difluoro-2-methoxyphenyl)-2-(2-(3-isopropyl-5,6-dihydro-imidazo[1,5-a]pyrazin-7(8H)-yl)ethyl)-[1,2,4]triazolo[1,5-c]-pyrimidin-5-amine | 469.2 | 636.1 (A) / 248.2 |
| 2.10 | 2-(5-amino-2-(2-(3-isopropyl-5,6-dihydroimidazo[1,5-a]pyrazin-7(8H)-yl)ethyl)-[1,2,4]triazolo[1,5-c]pyrimidin-7-yl)-4-fluorophenol | 437.2 | 1000.0 (A) / 400.0 |
| 2.11 | 7-(2,5-difluorophenyl)-2-(2-(3-isopropyl-5,6-dihydroimidazo[1,5-a]pyrazin-7(8H)-yl)ethyl)-[1,2,4]triazolo[1,5-c]pyrimidin-5-amine | 439.2 | 246.5 (A) / 177.6 |
| 2.12 | 7-(2-chloro-5-fluorophenyl)-2-(2-(3-isopropyl-5,6-dihydroimidazo-[1,5-a]pyrazin-7(8H)-yl)ethyl)-[1,2,4]triazolo[1,5-c]pyrimidin-5-amine | 455.2 | 439.8 (A) / 214.6 |

TABLE 18-continued

Examples Prepared According to General Scheme 1 and Similarly to Scheme 2

| Example | Structure / Name | Observed m/z [M + H]+ | A2a IC$_{50}$ (nM) / A2b IC$_{50}$ (nM) |
|---|---|---|---|
| 2.13 | 7-(3-fluorophenyl)-2-(2-(3-isopropyl-5,6-dihydroimidazo[1,5-a]-pyrazin-7(8H)-yl)ethyl)-[1,2,4]triazolo[1,5-c]pyrimidin-5-amine | 421.3 | 35.4 (A) / 95.5 |
| 2.14 | 7-(3,5-difluorophenyl)-2-(2-(3-isopropyl-5,6-dihydroimidazo-[1,5-c]pyrazin-7(8H)-yl)ethyl)-[1,2,4]triazolo[1,5-c]pyrimidin-5-amine | 439.2 | 361.8 (A) / 222.8 |
| 2.15 | 7-(3-fluorophenyl)-2-(2-(3-isopropyl-5,6-dihydroimidazo[1,5-a]-pyrazin-7(8H)-yl)ethyl)-8-methyl-[1,2,4]triazolo[1,5-c]pyrimidin-5-amine | 435.2 | 16.4 (A) / 36.8 |
| 2.16 | 7-(3-fluorophenyl)-2-(2-(1-isopropyl-1,4,6,7-tetrahydro-5H-[1,2,3]triazolo[4,5-c]pyridin-5-yl)ethyl)-8-methyl-[1,2,4]-triazolo[1,5-c]pyrimidin-5-amine | 435.9 | 2.3 (A) / 73.4 |
| 2.17 | 7-(4-fluorophenyl)-2-(2-(3-isopropyl-5,6-dihydroimidazo[1,5-a]-pyrazin-7(8H)-yl)ethyl)-8-methyl-[1,2,4]triazolo[1,5-c]pyrimidin-5-amine | 435.2 | 123.9 (A) / * |

TABLE 18-continued

Examples Prepared According to General Scheme 1 and Similarly to Scheme 2

| Example | Structure Name | Observed m/z [M + H]⁺ | A2a IC$_{50}$ (nM) A2b IC$_{50}$ (nM) |
|---|---|---|---|
| 2.18 | 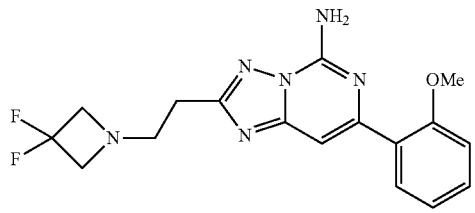<br>2-(2-(3,3-difluoroazetidin-1-yl)ethyl)-7-(2-methoxyphenyl)-[1,2,4]triazolo[1,5-c]pyrimidin-5-amine | 361 | 667.6 (C)<br>* |
| 2.19 | 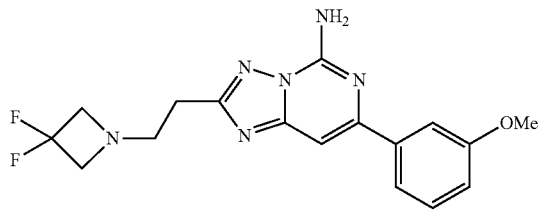<br>2-(2-(3,3-difluoroazetidin-1-yl)ethyl)-7-(3-methoxyphenyl)-[1,2,4]triazolo[1,5-c]pyrimidin-5-amine | 361 | 388.7 (C)<br>* |
| 2.20 | 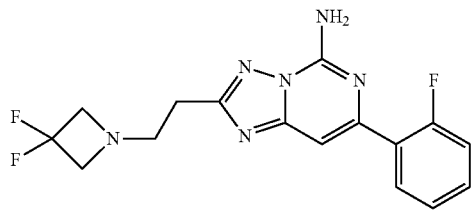<br>2-(2-(3,3-difluoroazetidin-1-yl)ethyl)-7-(2-fluorophenyl)-[1,2,4]triazolo[1,5-c]pyrimidin-5-amine | 349 | 240.7 (C)<br>* |
| 2.21 | 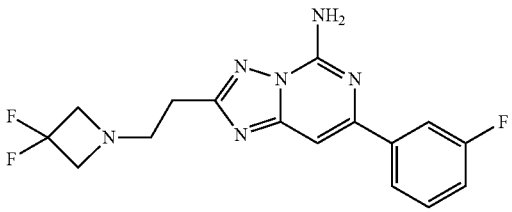<br>2-(2-(3,3-difluoroazetidin-1-yl)ethyl)-7-(3-fluorophenyl)-[1,2,4]triazolo[1,5-c]pyrimidin-5-amine | 349 | 91.7 (C)<br>* |
| 2.22 | 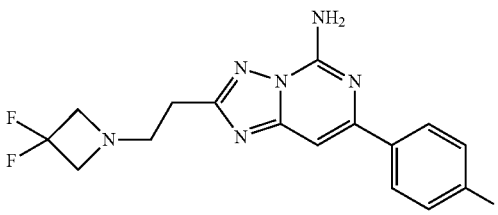<br>2-(2-(3,3-difluoroazetidin-1-yl)ethyl)-7-(4-fluorophenyl)-[1,2,4]-triazolo[1,5-c]pyrimidin-5-amine | 349 | 275.0 (C)<br>* |

TABLE 18-continued

Examples Prepared According to General Scheme 1 and Similarly to Scheme 2

| Example | Structure<br>Name | Observed m/z [M + H]⁺ | A2a IC$_{50}$ (nM)<br>A2b IC$_{50}$ (nM) |
|---|---|---|---|
| 2.23 | 2-(2-(3,3-difluoroazetidin-1-yl)ethyl)-7-phenyl-[1,2,4]-triazolo[1,5-c]pyrimidin-5-amine | 331 | 149.6 (C)<br>* |
| 2.24 | 3-(5-Amino-2-(2-(1-isopropyl-1,4,6,7-tetrahydro-5H-[1,2,3]-triazolo[4,5-c]pyridin-5-yl)ethyl)-[1,2,4]triazolo[1,5-c]-pyrimidin-7-yl)-2-fluorobenzonitrile | 447.3 | 0.9 (A)<br>73.6 |

The following examples in Table 19 were prepared using a similar procedure as for Table 18, but using (2-dicyclohexylphosphino-2',4',6'-triisopropyl-1,1'-biphenyl)[2-(2-aminoethyl)phenyl]palladium(II) chloride as the palladium catalyst in Step 1 and running the reactions at 100° C. overnight. Intermediates AI.5 or AI.6 were used, in conjunction with the corresponding oxazolyl pinacolate boronic ester. Asterisk (*) indicates that A2b data is not available.

TABLE 19

Examples Prepared According to General Scheme 1 and Similarly to Scheme 2

| Example | Structure<br>Name | Observed m/z [M + H]⁺ | A2a IC$_{50}$ (nM)<br>A2b IC$_{50}$ (nM) |
|---|---|---|---|
| 2.25 | 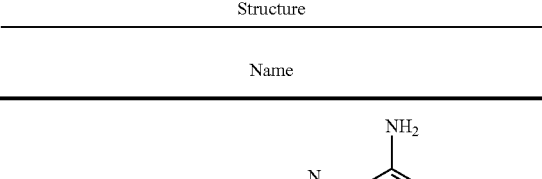<br>8-methyl-2-(2-(2-methyl-4,6-dihydro-5H-pyrrolo[3,4-d]oxazol-5-yl)ethyl)-7-(oxazol-5-yl)-[1,2,4]triazolo[1,5-c]pyrimidin-5-amine | 367 | 26.7 (A)<br>* |

141

TABLE 19-continued

Examples Prepared According to General Scheme 1 and Similarly to Scheme 2

| Example | Structure / Name | Observed m/z [M + H]+ | A2a IC$_{50}$ (nM) / A2b IC$_{50}$ (nM) |
|---|---|---|---|
| 2.26 | 8-methyl-2-(2-(2-methyl-6,7-dihydrothiazolo[5,4-c]pyridin-5(4H)-yl)ethyl)-7-(oxazol-5-yl)-[1,2,4]triazolo[1,5-c]pyrimidin-5-amine | 397 | 6.6 (B) * |

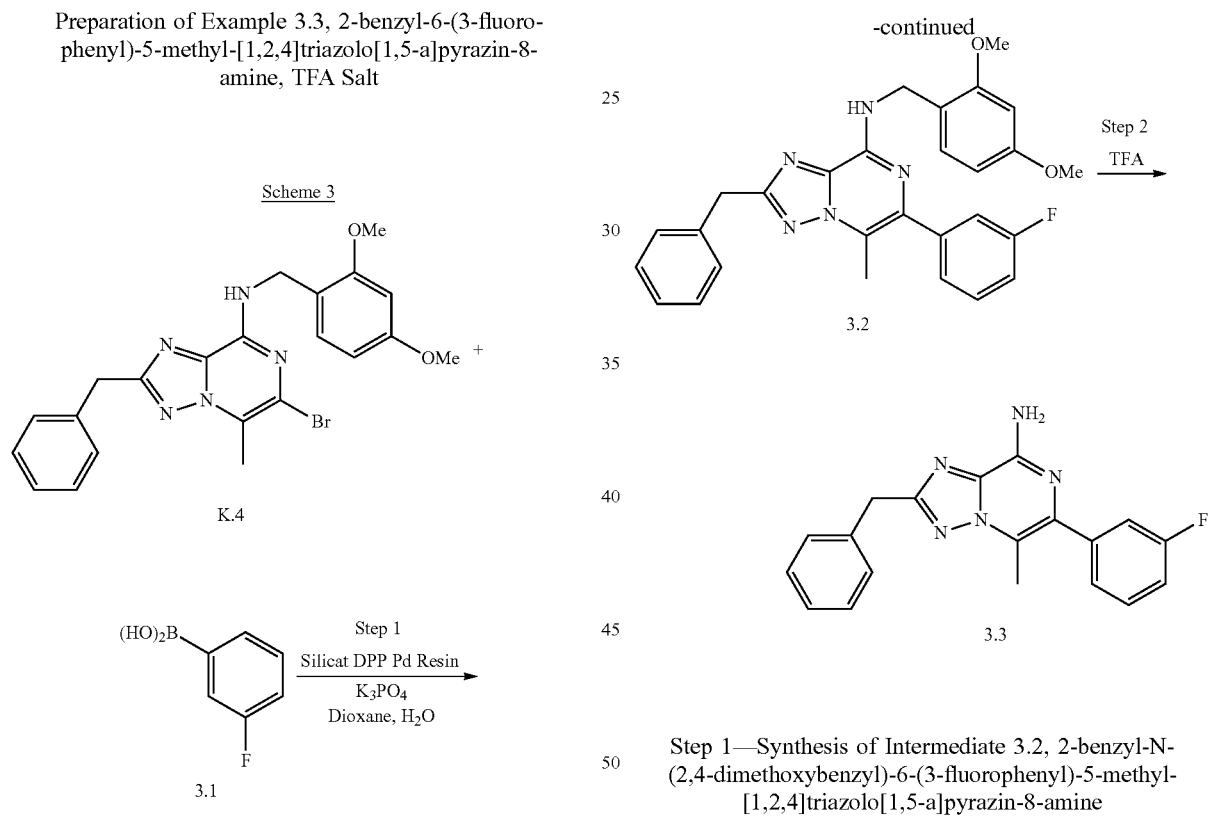

Preparation of Example 3.3, 2-benzyl-6-(3-fluoro-phenyl)-5-methyl-[1,2,4]triazolo[1,5-a]pyrazin-8-amine, TFA Salt Step 1—Synthesis of Intermediate 3.2, 2-benzyl-N-(2,4-dimethoxybenzyl)-6-(3-fluorophenyl)-5-methyl-[1,2,4]triazolo[1,5-a]pyrazin-8-amine A 0.5 mL Biotage® microwave vial equipped with 2 stir bars was charged with (3-fluorophenyl)boronic acid (14.34 mg, 0.102 mmol) and SiliaCat® DPP-Pd Resin (0.25 mmol/g, 102 mg, 0.026 mmol). A solution of 2-benzyl-6-bromo-N-(2,4-dimethoxybenzyl)-5-methyl-[1,2,4]triazolo[1,5-a]pyrazin-8-amine (40 mg, 0.085 mmol) in dioxane (850 µL) was then added, followed by a solution of tripotassium phosphate (18 mg, 0.085 mmol) in water (210 µL). The reaction vial was flushed with Argon for 30 sec, then capped and heated under microwave irradiation at 140° C. for 30 min. Upon completion of the reaction, the reaction mixture was diluted and filtered, then concentrated. The resulting crude material was used directly in the subsequent step. MS (ESI) m/z calc'd for $C_{28}H_{27}FN_5O_2$[M+H]+ 484.2, found 484.3.

Step 2—Synthesis of Example 3.3, 2-benzyl-6-(3-fluorophenyl)-5-methyl-[1,2,4]triazolo[1,5-a]pyrazin-8-amine, TFA Salt A 20 mL scintillation vial was charged with 2-benzyl-N-(2,4-dimethoxybenzyl)-6-(3-fluorophenyl)-5-methyl-[1,2,4]triazolo[1,5-a]pyrazin-8-amine (41 mg, 0.085 mmol). TFA (300 μL) was added, and the reaction mixture was heated at 50° C. and stirred for 2 h. After cooling, the reaction mixture was concentrated and the residue was taken up in DMSO (2 mL), filtered, and purified via reversed-phase HPLC [Method A]. This provided 2-benzyl-6-(3-fluorophenyl)-5-methyl-[1,2,4]triazolo[1,5-a]pyrazin-8-amine, TFA salt (Example 3.3). MS (ESI) m/z calc'd for $C_{19}H_{17}FN_5$ $[M+H]^+$ 334.1, found 334.3. $^1$H NMR (600 MHz, DMSO-$d_6$) δ 7.55-7.50 (m, 1H), 7.43-7.36 (m, 2H), 7.35-7.29 (m, 4H), 7.29-7.21 (m, 2H), 4.26 (s, 2H), 2.56 (s, 3H). A2a $IC_{50}$ 1.1 nM (A).

The following examples in Table 20 were prepared according to Scheme 3 and General Scheme 1 above, using Intermediate K.4 and the appropriate commercial boronic acid coupling partner. In cases where the boronic acid was not readily available (3.20, 3.44, 3.45, 3.46), the commercial pinacolate boronic ester was used instead. Asterisk (*) indicates that A2b data is not available.

TABLE 20

Examples Prepared According to General Scheme 1 and Scheme 3

| Example | Structure / Name | Observed m/z [M + H]+ | A2a IC$_{50}$ (nM) / A2b IC$_{50}$ (nM) |
|---|---|---|---|
| 3.4 | 2-benzyl-6-(2,5-difluorophenyl)-5-methyl-[1,2,4]-triazolo[1,5-a]pyrazin-8-amine | 352.1 | 1.1 (A) * |
| 3.5 | 2-benzyl-5-methyl-6-phenyl-[1,2,4]triazolo[1,5-a]pyrazin-8-amine | 316.3 | 2.2 (A) * |
| 3.6 | 2-benzyl-6-(2-fluorophenyl)-5-methyl-[1,2,4]-triazolo[1,5-a]pyrazin-8-amine | 334.1 | 6.4 (A) * |
| 3.7 | 2-benzyl-6-(3-chloro-4-methoxyphenyl)-5-methyl-[1,2,4]triazolo[1,5-a]pyrazin-8-amine | 380.1 | 11.0 (A) * |

TABLE 20-continued

Examples Prepared According to General Scheme 1 and Scheme 3

| Example | Structure / Name | Observed m/z [M + H]+ | A2a IC$_{50}$ (nM) / A2b IC$_{50}$ (nM) |
|---|---|---|---|
| 3.8 | 2-benzyl-6-(3-fluoro-4-methoxyphenyl)-5-methyl-[1,2,4]triazolo[1,5-a]pyrazin-8-amine | 364.2 | 20.6 (A) / * |
| 3.9 | 2-benzyl-6-(5-fluoropyridin-3-yl)-5-methyl-[1,2,4]-triazolo[1,5-a]pyrazin-8-amine | 335.1 | 24.5 (A) / * |
| 3.10 | 2-benzyl-6-(3,4-difluorophenyl)-5-methyl-[1,2,4]-triazolo[1,5-a]pyrazin-8-amine | 352.1 | 27.9 (A) / * |
| 3.11 | 2-benzyl-6-(2-fluoro-3-methoxyphenyl)-5-methyl-[1,2,4]triazolo[1,5-a]pyrazin-8-amine | 364.2 | 28.5 (A) / * |
| 3.12 | 2-benzyl-6-(3,4-dichlorophenyl)-5-methyl-[1,2,4]-triazolo[1,5-a]pyrazin-8-amine | 384.1 | 38.0 (A) / * |

TABLE 20-continued

Examples Prepared According to General Scheme 1 and Scheme 3

| Example | Structure / Name | Observed m/z [M + H]⁺ | A2a IC$_{50}$ (nM) / A2b IC$_{50}$ (nM) |
|---|---|---|---|
| 3.13 | 2-benzyl-6-(5-fluoro-6-methoxypyridin-3-yl)-5-methyl-[1,2,4]triazolo[1,5-a]pyrazin-8-amine | 365.1 | 40.0 (A) * |
| 3.14 | 2-benzyl-6-(2-fluoro-4-methoxyphenyl)-5-methyl-[1,2,4]triazolo[1,5-a]pyrazin-8-amine | 364.2 | 40.6 (A) * |
| 3.15 | 2-benzyl-5-methyl-6-(2-methylpyridin-4-yl)-[1,2,4]triazolo[1,5-a]pyrazin-8-amine | 331.2 | 54.8 (A) * |
| 3.16 | 2-benzyl-6-(4-chloro-3-fluorophenyl)-5-methyl-[1,2,4]triazolo[1,5-a]pyrazin-8-amine | 368.1 | 73.9 (A) * |
| 3.17 | 2-benzyl-6-(2,4-difluorophenyl)-5-methyl-[1,2,4]triazolo[1,5-a]pyrazin-8-amine | 352.1 | 82.2 (A) * |

TABLE 20-continued

Examples Prepared According to General Scheme 1 and Scheme 3

| Example | Structure / Name | Observed m/z [M + H]⁺ | A2a IC$_{50}$ (nM) / A2b IC$_{50}$ (nM) |
|---|---|---|---|
| 3.18 | 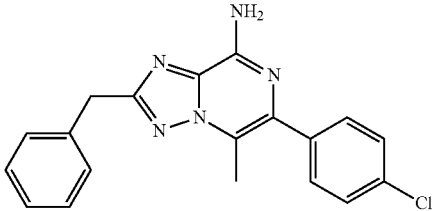 2-benzyl-6-(4-chlorophenyl)-5-methyl-[1,2,4]triazolo-[1,5-a]pyrazin-8-amine | 350.1 | 84.4 (A) * |
| 3.19 | 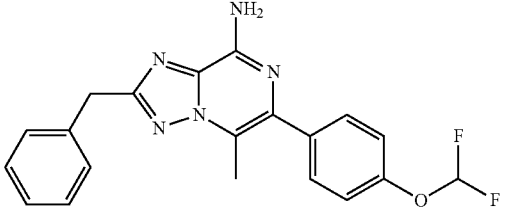 2-benzyl-6-(4-(difluoromethoxy)phenyl)-5-methyl-[1,2,4]triazol-[1,5-a]pyrazin-8-amine | 382.1 | 121.2 (A) * |
| 3.20 | 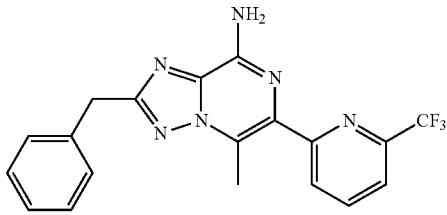 2-benzyl-5-methyl-6-(6-(trifluoromethyl)pyridin-2-yl)-[1,2,4]triazolo[1,5-a]pyrazin-8-amine | 385.2 | 157.3 (A) * |
| 3.21 | 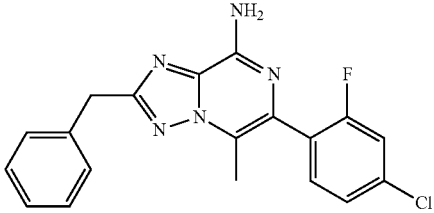 2-benzyl-6-(4-chloro-2-fluorophenyl)-5-methyl-[1,2,4]triazolo[1,5-a]pyrazin-8-amine | 368.2 | 168.0 (A) * |
| 3.22 | 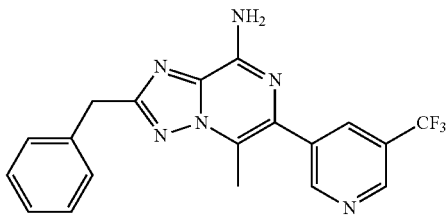 2-benzyl-5-methyl-6-(5-(trifluoromethyl)pyridin-3-yl)-[1,2,4]triazolo[1,5-a]pyrazin-8-amine | 385.1 | 835.7 (A) 8699 |

TABLE 20-continued

Examples Prepared According to General Scheme 1 and Scheme 3

| Example | Structure / Name | Observed m/z [M + H]⁺ | A2a IC$_{50}$ (nM) / A2b IC$_{50}$ (nM) |
|---|---|---|---|
| 3.23 | 2-benzyl-6-(3-chlorophenyl)-5-methyl-[1,2,4]triazolo-[1,5-a]pyrazin-8-amine | 349.9 | 2.7 (A) / 13.6 |
| 3.24 | 2-benzyl-6-(5-chloro-2-fluorophenyl)-5-methyl-[1,2,4]triazolo[1,5-a]pyrazin-8-amine | 367.9 | 0.7 (A) / 2.4 |
| 3.25 | 2-benzyl-6-(3,5-difluorophenyl)-5-methyl-[1,2,4]-triazolo[1,5-a]pyrazin-8-amine | 352.0 | 1.6 (A) / 19.8 |
| 3.26 | 2-benzyl-5-methyl-6-(2,3,5-trifluorophenyl)-[1,2,4]-triazolo[1,5-a]pyrazin-8-amine | 370.0 | 2.5 (A) / 2.7 |

TABLE 20-continued

Examples Prepared According to General Scheme 1 and Scheme 3

| Example | Structure / Name | Observed m/z [M + H]+ | A2a IC50 (nM) / A2b IC50 (nM) |
|---|---|---|---|
| 3.27 | 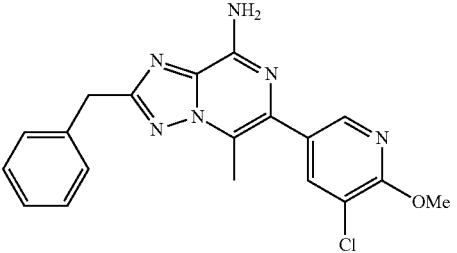<br>2-benzyl-6-(5-chloro-6-methoxypyridin-3-yl)-5-methyl-[1,2,4]triazolo[1,5-a]pyrazin-8-amine | 380.9 | 11.0 (A)<br>144.8 |
| 3.28 | 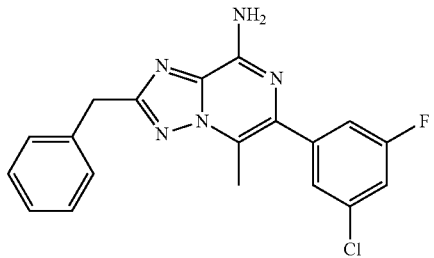<br>2-benzyl-6-(3-chloro-5-fluorophenyl)-5-methyl-[1,2,4]triazolo[1,5-a]pyrazin-8-amine | 368.0 | 2.9 (A)<br>34.4 |
| 3.29 | 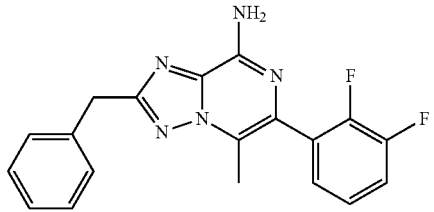<br>2-benzyl-6-(2,3-difluorophenyl)-5-methyl-[1,2,4]-triazolo[1,5-a]pyrazin-8-amine | 351.9 | 4.0 (A)<br>39.4 |
| 3.30 | 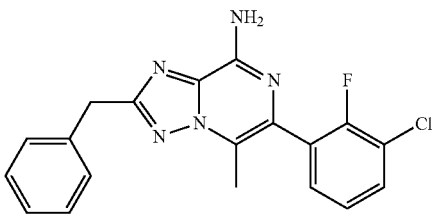<br>2-benzyl-6-(3-chloro-2-fluorophenyl)-5-methyl-[1,2,4]triazolo[1,5-a]pyrazin-8-amine | 367.9 | 7.6 (A)<br>46.2 |

TABLE 20-continued

Examples Prepared According to General Scheme 1 and Scheme 3

| Example | Structure / Name | Observed m/z [M + H]+ | A2a IC$_{50}$ (nM) / A2b IC$_{50}$ (nM) |
|---|---|---|---|
| 3.31 | 2-benzyl-6-(3-fluoro-5-methoxyphenyl)-5-methyl-[1,2,4]triazolo[1,5-a]pyrazin-8-amine | 364.0 | 6.2 (A) / 133.8 |
| 3.32 | 2-benzyl-6-(5-chloropyridin-3-yl)-5-methyl-[1,2,4]-triazolo[1,5-a]pyrazin-8-amine | 350.9 | 13.1 (A) / 147.1 |
| 3.33 | 2-benzyl-6-(3-chloro-4-fluorophenyl)-5-methyl-[1,2,4]-triazolo[1,5-a]pyrazin-8-amine | 367.9 | 27.2 (A) / 116.6 |
| 3.34 | 2-benzyl-5-methyl-6-(2,4,5-trifluorophenyl)-[1,2,4]-triazolo[1,5-a]pyrazin-8-amine | 369.9 | 32.2 (A) / 95.8 |
| 3.35 | 2-benzyl-6-(5-fluoro-2-methylphenyl)-5-methyl-[1,2,4]triazolo[1,5-a]pyrazin-8-amine | 348.0 | 65.6 (A) / 699.8 |

TABLE 20-continued

Examples Prepared According to General Scheme 1 and Scheme 3

| Example | Structure / Name | Observed m/z [M + H]⁺ | A2a IC$_{50}$ (nM) / A2b IC$_{50}$ (nM) |
|---|---|---|---|
| 3.36 | 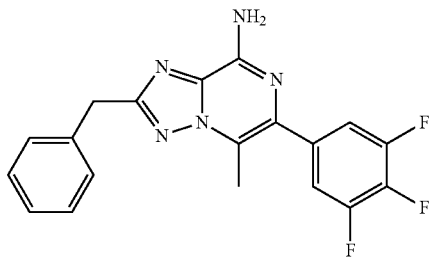 2-benzyl-5-methyl-6-(3,4,5-trifluorophenyl)-[1,2,4]-triazolo[1,5-a]pyrazin-8-amine | 370.0 | 76.5 (A) <br> 154.0 |
| 3.37 | 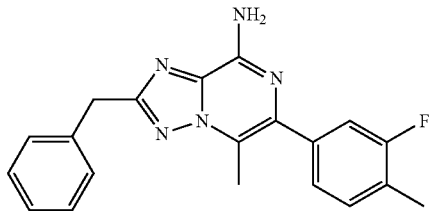 2-benzyl-6-(3-fluoro-4-methylphenyl)-5-methyl-[1,2,4]triazolo[1,5-a]pyrazin-8-amine | 348.0 | 1000 (A) <br> 3713 |
| 3.38 | 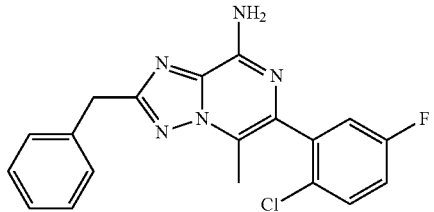 2-benzyl-6-(2-chloro-5-fluorophenyl)-5-methyl-[1,2,4]triazolo[1,5-a]pyrazin-8-amine | 367.9 | 97.6 (A) <br> 85.7 |
| 3.39 | 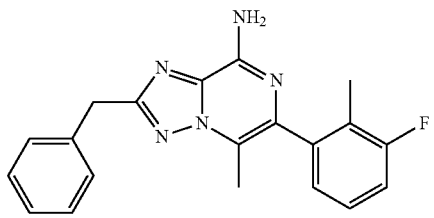 2-benzyl-6-(3-fluoro-2-methylphenyl)-5-methyl-[1,2,4]triazolo[1,5-a]pyrazin-8-amine | 348.0 | 98.5 (A) <br> 1021 |

TABLE 20-continued

Examples Prepared According to General Scheme 1 and Scheme 3

| Example | Structure / Name | Observed m/z [M + H]+ | A2a IC$_{50}$ (nM) / A2b IC$_{50}$ (nM) |
|---|---|---|---|
| 3.40 | 2-benzyl-5-methyl-6-(2,3,4-trifluorophenyl)-[1,2,4]-triazolo[1,5-a]pyrazin-8-amine | 370.0 | 280.0 (A) / 314.8 |
| 3.41 | 2-benzyl-6-(2-chloro-3-fluorophenyl)-5-methyl-[1,2,4]triazolo[1,5-a]pyrazin-8-amine | 367.9 | 288.6 (A) / 746.7 |
| 3.42 | 4-(8-amino-2-benzyl-5-methyl-[1,2,4]triazolo[1,5-a]-pyrazin-6-yl)-2-fluorobenzonitrile | 358.9 | 499.4 (A) / 1734 |
| 3.43 | 2-benzyl-6-(5-fluoro-2-methoxyphenyl)-5-methyl-[1,2,4]triazolo[1,5-a]pyrazin-8-amine | 364.0 | 611.3 (A) / 2521 |
| 3.44 | 2-benzyl-5-methyl-6-(1-(trifluoromethyl)-1H-pyrazol-4-yl)-[1,2,4]triazolo[1,5-a]pyrazin-8-amine | 374.3 | 490.3 (A) / * |

TABLE 20-continued

Examples Prepared According to General Scheme 1 and Scheme 3

| Example | Structure / Name | Observed m/z [M + H]⁺ | A2a IC$_{50}$ (nM) / A2b IC$_{50}$ (nM) |
|---|---|---|---|
| 3.45 | 2-benzyl-5-methyl-6-(1-methyl-3-(trifluoromethyl)-1H-pyrazol-5-yl)-[1,2,4]triazolo[1,5-a]pyrazin-8-amine | 388.1 | 17.8 (A) <br> * |
| 3.46 | 2-benzyl-5-methyl-6-(1-methyl-1H-pyrazol-3-yl)-[1,2,4]triazolo[1,5-a]pyrazin-8-amine | 320.3 | 4.4 (A) <br> 82.6 |

Preparation of Example 4.3, 6-(2,5-difluorophenyl)-5-methyl-2-((3-methylpyridin-2-yl)methyl)-[1,2,4]triazolo[1,5-a]pyrazin-8-amine, TFA Salt

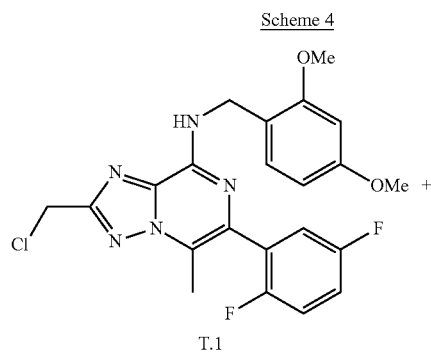

-continued

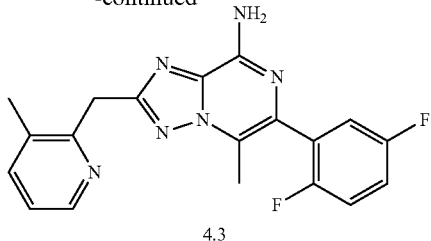

4.3

Step 1—Synthesis of Intermediate 4.2, 7-(2,5-difluorophenyl)-N-(2,4-dimethoxybenzyl)-8-methyl-2-((3-methylpyridin-2-yl)methyl)-[1,2,4]triazolo[1,5-c]pyrimidin-5-amine An oven-dried 20 mL scintillation vial was charged with 2-(chloromethyl)-7-(2,5-difluorophenyl)-N-(2,4-dimethoxybenzyl)-8-methyl-[1,2,4]triazolo[1,5-c]pyrimidin-5-amine (30 mg, 0.065 mmol), 2-bromo-3-methylpyridine (28 mg, 0.163 mmol), [Ni(dtbbpy)(H$_2$O)$_4$]Cl$_2$ (2.6 mg, 6.52 μmol), (Ir[dF(CF$_3$)ppy]$_2$(dtbbpy))PF$_6$ (0.3 mg, 0.33 μmol), lithium hydroxide (4.7 mg, 0.196 mmol), and 1,1,1,3,3,3-hexamethyl-2-(trimethylsilyl)trisilane (30 μL, 0.098 mmol), and the vial was evacuated and backfilled with nitrogen (3×). DME (2.6 mL) was added, and the reaction mixture was degassed for 15 min. The reaction mixture was then sealed and irradiated with blue LED lights for 8 h. DCM (5 mL) and water (5 mL) were then added, and the organic layer was separated. The aq. layer was extracted with DCM (2×10 mL), and then the combined organic layers were dried over anhydrous MgSO$_4$, filtered, and concentrated. The resulting crude material was used directly in the subsequent reaction. MS (ESI) m/z calc'd for $C_{28}H_{27}F_2N_6O_2$ [M+H]$^+$ 517.2, found 517.2.

Step 2—Synthesis of Example 4.3, 6-(2,5-difluorophenyl)-5-methyl-2-((3-methylpyridin-2-yl)methyl)-[1,2,4]triazolo[1,5-a]pyrazin-8-amine, TFA Salt A 20 mL scintillation vial was charged with 6-(2,5-difluorophenyl)-N-(2,4-dimethoxybenzyl)-5-methyl-2-((3-methylpyridin-2-yl)methyl)-[1,2,4]triazolo[1,5-a]pyrazin-8-amine (30 mg, 0.058 mmol). TFA (580.L) was added, and the reaction mixture was heated at 50° C. and stirred for 2 h. After cooling, the reaction was concentrated and the residue was taken up in DMSO (2 mL), filtered, and purified via reversed-phase HPLC [Method A]. This provided 6-(2,5-difluorophenyl)-5-methyl-2-((3-methylpyridin-2-yl)methyl)-[1,2,4]triazolo[1,5-a]pyrazin-8-amine, TFA salt (Example 4.3). MS (ESI) m/z calc'd for $C_{19}H_{17}F_2N_6$ [M+H]$^+$ 367.1, found 367.1. $^1$H NMR (600 MHz, DMSO-d$_6$) δ 8.59 (d, J=4.7 Hz, 1H), 8.18-8.09 (m, 1H), 7.70-7.61 (m, 1H), 7.43-7.32 (m, 3H), 7.26 (br s, 2H), 4.64 (s, 2H), 2.45 (s, 3H), 2.36 (d, J=1.4 Hz, 3H). A2a IC$_{50}$ 9.9 nM (A), A2b IC$_5$A 47.3 nM.

The following examples in Table 21 were prepared according to Scheme 4 and General Scheme 2 above, using intermediates T.1, T.3 or T.2, and the appropriate aryl bromide, either commercially available or among intermediates AK.3, AL.2, AL.3, AM.2, or AJ.2.

TABLE 21

Examples Prepared According to General Scheme 2 and Scheme 4

| Example | Structure Name | Observed m/z [M + H]$^+$ | A2a IC$_{50}$ (nM) A2b IC$_{50}$ (nM) |
|---|---|---|---|
| 4.4 | 6-(2,5-difluorophenyl)-2-((5-fluoropyridin-2-yl)methyl)-5-methyl-[1,2,4]triazolo[1,5-a]pyrazin-8-amine | 371.1 | 22.8 (A)<br>26.0 |

TABLE 21-continued

Examples Prepared According to General Scheme 2 and Scheme 4

| Example | Structure / Name | Observed m/z [M + H]+ | A2a IC$_{50}$ (nM) A2b IC$_{50}$ (nM) |
|---|---|---|---|
| 4.5 | 2-((1-(2,2-difluoroethyl)-1H-benzo[d]imidazol-4-yl)methyl)-6-(2,5-difluorophenyl)-5-methyl-[1,2,4]triazolo[1,5-a]-pyrazin-8-amine | 456.1 | 23.8 (A) <br> 31.8 |
| 4.6 | 2-((1-(2,2-difluoroethyl)-1H-benzo[d]imidazol-6-yl)methyl)-8-methyl-7-(oxazol-2-yl)-[1,2,4]triazolo[1,5-c]pyrimidin-5-amine | 411.2 | 22.8 (A) <br> 68.4 |
| 4.7 | 2-((1-(2,2-difluoroethyl)-1H-benzo[d]imidazol-5-yl)-methyl)-8-methyl-7-(oxazol-2-yl)-[1,2,4]triazolo-[1,5-c]pyrimidin-5-amine | 411.1 | 35.3 (A) <br> 7.6 |
| 4.8 | 6-(2,5-difluorophenyl)-2-((3-fluoropyridin-2-yl)-methyl)-5-methyl-[1,2,4]triazolo[1,5-a]pyrazin-8-amine | 371.1 | 18.7 (A) <br> 9.3 |

TABLE 21-continued

Examples Prepared According to General Scheme 2 and Scheme 4

| Example | Structure / Name | Observed m/z [M + H]⁺ | A2a IC$_{50}$ (nM) / A2b IC$_{50}$ (nM) |
|---|---|---|---|
| 4.9 | 1-(4-((8-amino-5-methyl-6-(oxazol-2-yl)-[1,2,4]triazolo[1,5-a]pyrazin-2-yl)methyl)-1H-benzo[d]imidazol-1-yl)-2-methylpropan-2-ol | 419.2 | 0.2 (A) <br> 1.2 |
| 4.10 | 2-((1-(2,2-difluoroethyl)-1H-benzo[d]imidazol-4-yl)methyl)-5-methyl-6-(oxazol-2-yl)-[1,2,4]triazolo[1,5-a]pyrazin-8-amine | 411.1 | 0.7 (A) <br> 6.5 |
| 4.11 | 2-(6-((8-amino-5-methyl-6-(oxazol-2-yl)-[1,2,4]-triazolo[1,5-a]pyrazin-2-yl)methyl)pyridin-3-yl)-propan-2-ol | 366.1 | 48.2 (A) <br> 66.5 |

Preparation of Examples 5.2 and 5.3, (1s,3s)-3-(4-((5-amino-8-methyl-7-(oxazol-2-yl)-[1,2,4]triazolo[1,5-c]pyrimidin-2-yl)methyl)phenyl)-1-methylcyclobutanol and (1r,3r)-3-(4-((5-amino-8-methyl-7-(oxazol-2-yl)-[1,2,4]triazolo[1,5-c]pyrimidin-2-yl)methyl)phenyl)-1-methylcyclobutanol

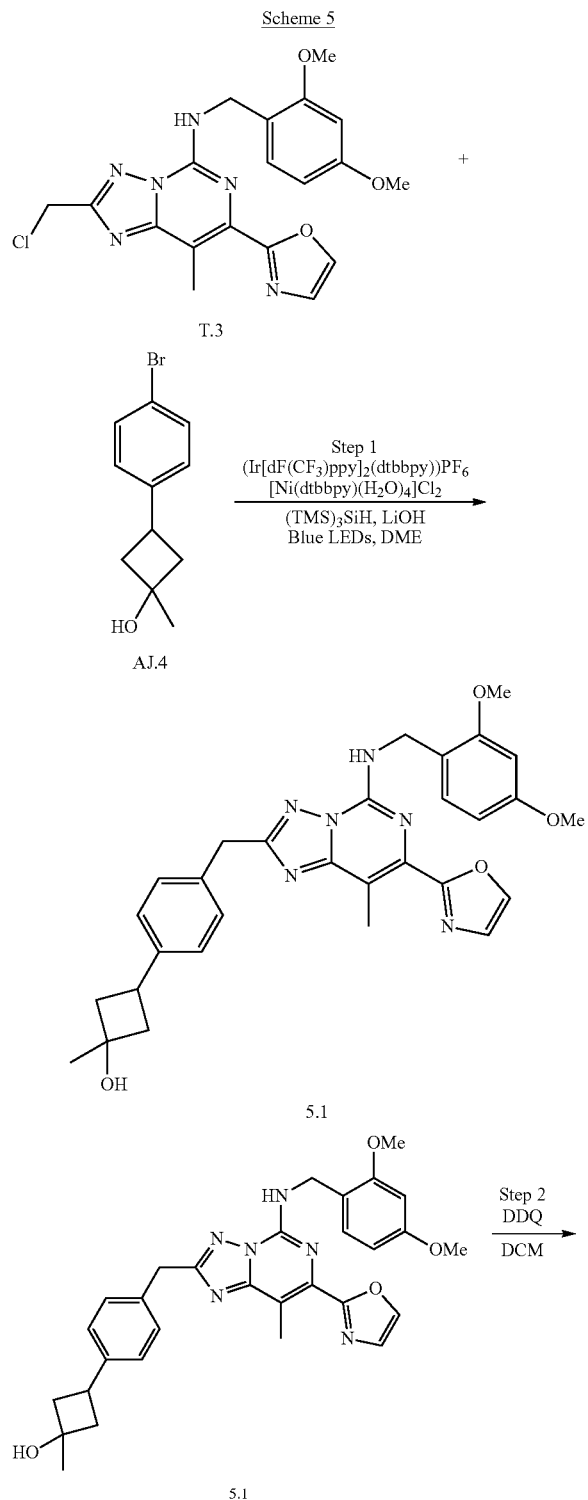

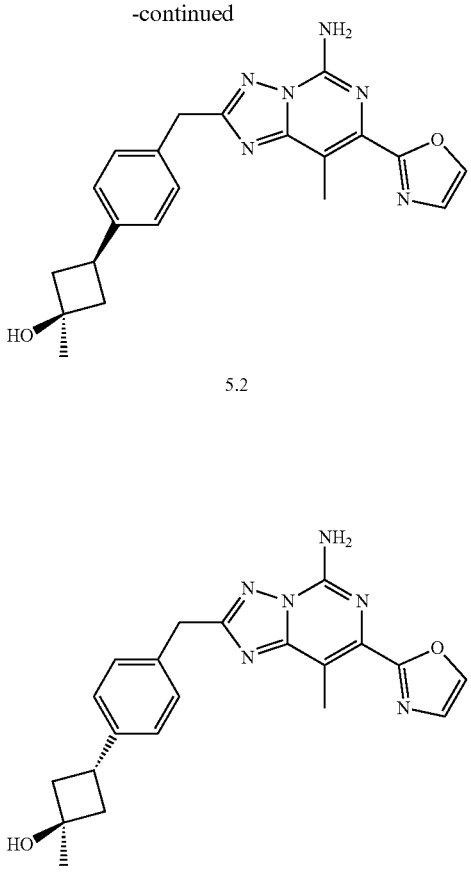

Step 1—Synthesis of Intermediate 5.1, 3-(4-((5-((2,4-dimethoxybenzyl)amino)-8-methyl-7-(oxazol-2-yl)-[1,2,4]triazolo[1,5-c]pyrimidin-2-yl)methyl)phenyl)-1-methylcyclobutanol An oven-dried 20 mL scintillation vial was charged with 2-(chloromethyl)-N-(2,4-dimethoxybenzyl)-8-methyl-7-(oxazol-2-yl)-[1,2,4]triazolo[1,5-c]pyrimidin-5-amine (100 mg, 0.241 mmol), 3-(4-bromophenyl)-1-methylcyclobutanol (145 mg, 0.603 mmol), [Ni(dtbbpy)(H$_2$O$_4$]Cl$_2$ (9.6 mg, 0.024 mmol), (Ir[dF(CF$_3$)ppy]2(dtbbpy))PF$_6$ (1.2 mg, 1.21 µmol), and lithium hydroxide (17 mg, 0.723 mmol), and the vial was evacuated and backfilled with nitrogen (3×). DME (480 µL) was added, and the reaction mixture was degassed for 15 min. The reaction mixture was then sealed and irradiated with blue LED lights for 8 h. DCM (10 mL) and water (10 mL) were then added, and the organic layer was separated. The aq. layer was extracted with DCM (2×15 mL), and then the combined organic layers were dried over anhydrous MgSO$_4$, filtered, and concentrated. The resulting crude residue was purified by silica gel chromatography (gradient elution: 0-10% MeOH/DCM) to provide 3-(4-((5-((2,4-dimethoxybenzyl)amino)-8-methyl-7-(oxazol-2-yl)-[1,2,4]triazolo[1,5-c]pyrimidin-2-yl)methyl)phenyl)-1-methylcyclobutanol as a mixture of diastereomers. These were taken forward without further separation at this stage. MS (ESI) m/z calc'd for C$_{30}$H$_{33}$N$_6$O$_4$ [M+H]$^+$ 541.3, found 541.2.

Step 2—Synthesis of Examples 5.2 and 5.3, (1s, 3s)-3-(4-((5-amino-8-methyl-7-(oxazol-2-yl)-[1,2,4]triazolo[1,5-c]pyrimidin-2-yl)methyl)phenyl)-1-methylcyclobutanol and (1r,3r)-3-(4-((5-amino-8-methyl-7-(oxazol-2-yl)-[1,2,4]triazolo[1,5-c]pyrimidin-2-yl)methyl)phenyl)-1-methylcyclobutanol A 25 mL round bottom flask was charged with 3-(4-((5-((2,4-dimethoxybenzyl)amino)-8-methyl-7-(oxazol-2-yl)-[1,2,4]triazolo[1,5-c]pyrimidin-2-yl)methyl)phenyl)-1-methylcyclobutanol (34 mg, 0.063 mmol). DCM (750 μL) and water (300 μL) were then added and the reaction mixture was cooled to 0° C. DDQ (21.4 mg, 0.094 mmol) was added, and the reaction mixture was stirred at 0° C. for 1 h. The reaction was quenched with sat. aq. sodium thiosulfate (10 mL) and DCM (10 mL), then stirred at 25° C. for 30 min. The layers were separated, and the aq. layer was extracted with DCM (2×10 mL). The combined organic layers were dried over anhydrous $MgSO_4$, filtered, and concentrated. The resulting crude residue was taken up in DMSO (2 mL), filtered and purified via reversed-phase HPLC [Method B]. This provided (1s,3s)-3-(4-((5-amino-8-methyl-7-(oxazol-2-yl)-[1,2,4]triazolo[1,5-c]pyrimidin-2-yl)methyl)phenyl)-1-methylcyclobutanol (Example 5.2) as the major product and the second-eluting peak. MS (ESI) m/z calc'd for $C_{21}H_{23}N_6O_2$ [M+H]$^+$ 391.2, found 391.1. $^1$H NMR (600 MHz, MeOD-$d_4$) δ 8.09 (s, 1H), 7.42 (s, 1H), 7.29 (d, J=8.1 Hz, 2H), 7.21 (d, J=8.1 Hz, 2H), 4.23 (s, 2H), 3.07-2.98 (m, 1H), 2.73 (s, 3H), 2.45-2.38 (m, 2H), 2.21-2.13 (m, 2H), 1.43 (s, 3H). A2a IC$_{50}$ 2.5 nM (A), A2b IC$_{50}$ 1.6 nM. It also provided (1r,3r)-3-(4-((5-amino-8-methyl-7-(oxazol-2-yl)-[1,2,4]triazolo[1,5-c]pyrimidin-2-yl)methyl)phenyl)-1-methylcyclobutanol (Example 5.3) as the minor product and the first-eluting peak. MS (ESI) m/z calc'd for $C_{21}H_{23}N_6O_2$ [M+H]$^+$ 391.2, found 391.2. $^1$H NMR (600 MHz, MeOD-$d_4$) δ 8.09 (s, 1H), 7.42 (s, 1H), 7.29 (d, J=8.1 Hz, 2H), 7.17 (d, J=8.0 Hz, 2H), 4.23 (s, 2H), 3.68-3.59 (m, 1H), 2.73 (s, 3H), 2.48-2.42 (m, 2H), 2.21-2.13 (m, 2H), 1.28 (s, 3H). A2a IC$_{50}$ 12.1 nM (A), A2b IC$_{50}$ 3.5 nM.

The following example in Table 22 was prepared according to Scheme 5 and General Scheme 2, using intermediates T.2 and AJ.3.

Preparation of Example 6.3, 1-(4-((5-amino-8-methyl-7-(oxazol-2-yl)-[1,2,4]triazolo[1,5-c]pyrimidin-2-yl)methyl)phenyl)cyclobutanol Scheme 6

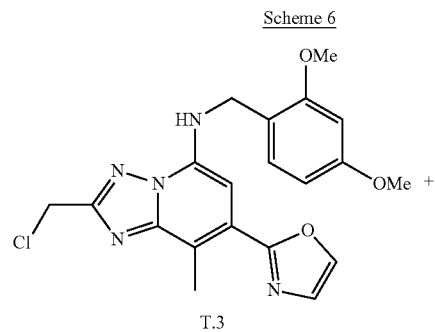

T.3

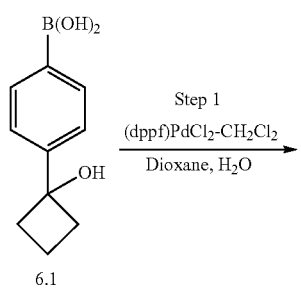

6.1

Step 1
(dppf)PdCl$_2$-CH$_2$Cl$_2$
Dioxane, H$_2$O

TABLE 22

Example Prepared According to General Scheme 2 and Scheme 5

| Example | Structure Name | Observed m/z [M + H]$^+$ | A2a IC$_{50}$ (nM) A2b IC$_{50}$ (nM) |
|---|---|---|---|
| 5.4 | 1-(4-((5-amino-8-methyl-7-(oxazol-2-yl)-[1,2,4]triazolo[1,5-c]pyrimidin-2-yl)methyl)phenyl)-2-methylpropan-2-ol | 379.1 | 37.2 (A) 11.0 |

-continued

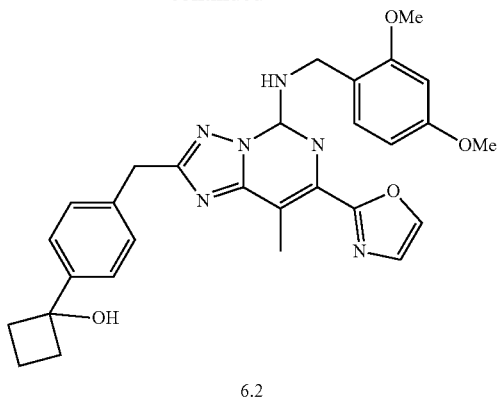

6.2

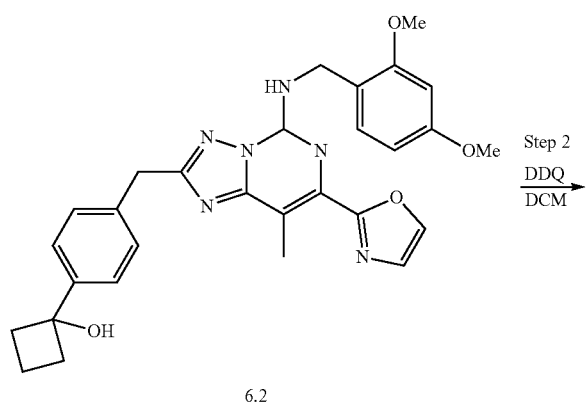

6.2

Step 2
DDQ
DCM

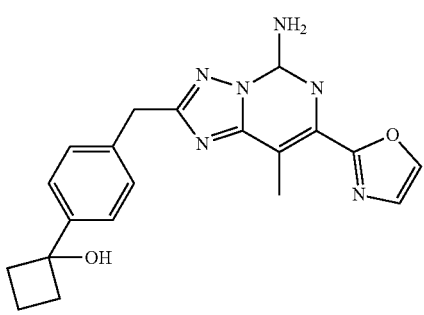

6.3

Step 1—Synthesis of Intermediate 6.2, 1-(4-((5-((2,4-dimethoxybenzyl)amino)-8-methyl-7-(oxazol-2-yl)-[1,2,4]triazolo[1,5-c]pyrimidin-2-yl)methyl)phenyl)cyclobutanol A 2 mL Biotage® microwave vial was charged with 2-(chloromethyl)-N-(2,4-dimethoxybenzyl)-8-methyl-7-(oxazol-2-yl)-[1,2,4]triazolo[1,5-c]pyrimidin-5-amine (91 mg, 0.219 mmol), 1-(4-(4,4,5,5-tetramethyl-1,3,2-dioxaborolan-2-yl)phenyl)cyclobutanol (120 mg, 0.438 mmol), tripotassium phosphate (93 mg, 0.438 mmol) and 1,1'-bis(diphenylphosphino)ferrocene-palladium(II)dichloride dichloromethane complex (53.7 mg, 0.066 mmol), and the vial was evacuated and backfilled with nitrogen (3×). A degassed [Method C] mixture of dioxane (1.7 mL) and water (0.44 mL) was added, and the reaction was heated at 110° C. overnight. After cooling, DCM (4 mL) and water (4 mL) were added, and the layers were separated. The aq. layer was extracted with DCM (2×4 mL), and the combined organic layers were dried over anhydrous MgSO$_4$, filtered, and concentrated. The resulting crude residue was then purified by silica gel chromatography (gradient elution: 0-10% MeOH/DCM) to provide 1-(4-((5-((2,4-dimethoxybenzyl)amino)-8-methyl-7-(oxazol-2-yl)-[1,2,4]triazolo[1,5-c]pyrimidin-2-yl)methyl)phenyl)cyclobutanol. MS (ESI) m/z calc'd for C$_{29}$H$_{31}$N$_6$O$_4$ [M+H]$^+$ 527.2, found 527.3.

Step 2—Synthesis of Example 6.3, 1-(4-((5-amino-8-methyl-7-(oxazol-2-yl)-[1,2,4]triazolo[1,5-c]pyrimidin-2-yl)methyl)phenyl)cyclobutanol A 25 mL round bottom flask was charged with 1-(4-((5-((2,4-dimethoxybenzyl)amino)-8-methyl-7-(oxazol-2-yl)-[1,2,4]triazolo[1,5-c]pyrimidin-2-yl)methyl)phenyl)cyclobutanol (89 mg, 0.169 mmol). DCM (2 mL) and water (0.8 mL) were then added and the reaction mixture was cooled to 0° C. DDQ (58 mg, 0.254 mmol) was added and the reaction was stirred for 1 h at 0° C. After completion, the reaction was poured into a 125 mL Erlenmeyer flask containing DCM (20 mL) and sat. aq. sodium thiosulfate (20 mL), and the mixture was stirred at 25° C. for 30 min. The layers were separated, and the aq. layer was extracted with DCM (2×30 mL). The combined organic layers were then dried over anhydrous MgSO$_4$, filtered, and concentrated. The resulting crude material was purified by silica gel chromatography (gradient elution: 5% MeOH/DCM to 15% (7 M NH$_3$ in MeOH)/DCM). The product obtained from this column was taken up in DMSO (2 mL), filtered and purified by reversed-phase HPLC [Method B]. This provided 1-(4-((5-amino-8-methyl-7-(oxazol-2-yl)-[1,2,4]triazolo[1,5-c]pyrimidin-2-yl)methyl)phenyl)cyclobutanol (Example 6.3). MS (ESI) m/z calc'd for C$_{20}$H$_{21}$N$_6$O$_2$ [M+H]$^+$ 377.2, found 377.1. $^1$H NMR (600 MHz, DMSO-d$_6$) δ 8.28 (s, 1H), 7.85 (br s, 2H), 7.49 (s, 1H), 7.42 (d, J=8.2 Hz, 2H), 7.31 (d, J=8.2 Hz, 2H), 4.19 (s, 2H), 2.66 (s, 3H), 2.39-2.31 (m, 2H), 2.30-2.20 (m, 2H), 1.92-1.83 (m, 1H), 1.66-1.54 (m, 1H). A2a IC$_{50}$ 17.1 nM (A), A2b IC$_{50}$ 10.7 nM.

The following examples in Table 23 were prepared according to Scheme 6 and General Scheme 2 above, using intermediates T.3 or T.2, and the appropriate commercial boronic acid coupling

TABLE 23

Examples Prepared According to General Scheme 2 and Scheme 6

| Example | Structure Name | Observed m/z [M + H]+ | A2a IC$_{50}$ (nM) A2b IC$_{50}$ (nM) |
|---|---|---|---|
| 6.4 | 2-(4-(1-methoxycyclobutyl)benzyl)-8-methyl-7-(oxazol-2-yl)-[1,2,4]triazolo[1,5-c]pyrimidin-5-amine | 391.2 | 4.9 (A) 5.7 |
| 6.5 | 2-(4-((5-amino-8-methyl-7-(oxazol-2-yl)-[1,2,4]triazolo[1,5-c]pyrimidin-2-yl)methyl)phenyl)propan-2-ol | 365.1 | 38.7 (A) 5.0 |
| 6.6 | 2-(3-((5-amino-8-methyl-7-(oxazol-2-yl)-[1,2,4]triazolo[1,5-c]pyrimidin-2-yl)methyl)phenyl)propan-2-ol | 365.1 | 1.9 (A) 243.4 |
| 6.7 | 2-(4-((8-amino-5-methyl-6-(oxazol-2-yl)-[1,2,4]triazolo[1,5-a]pyrazin-2-yl)methyl)phenyl)propan-2-ol | 365.2 | 15.7 (A) 30.1 |

TABLE 23-continued

Examples Prepared According to General Scheme 2 and Scheme 6

| Example | Structure Name | Observed m/z [M + H]+ | A2a IC50 (nM) A2b IC50 (nM) |
|---|---|---|---|
| 6.8 | 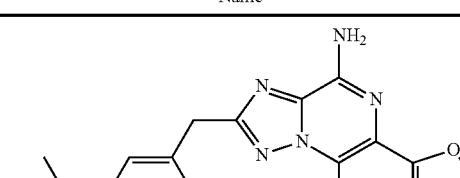<br>2-(3-((8-amino-5-methyl-6-(oxazol-2-yl)-[1,2,4]triazolo[1,5-a]pyrazin-2-yl)methyl)phenyl)propan-2-ol | 365.2<br><br>330.5 | 1.2 (A) |

Preparation of Example 7.3, N-2, 5-methyl-6-oxazol-2-yl)-2-(2-trifluoromethyl benzyl)-[1,2,4]triazolo[1,5-a]pyrazin-8-amine

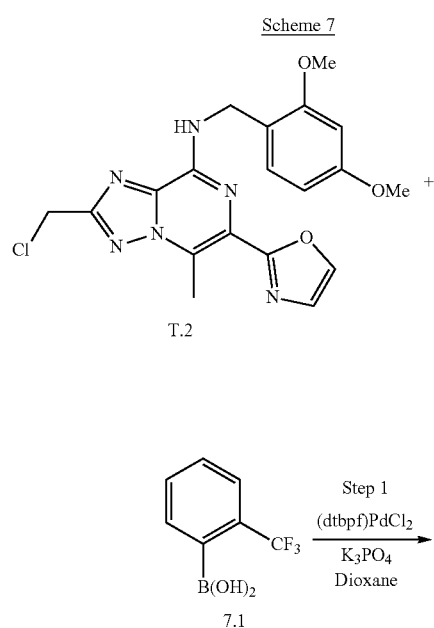

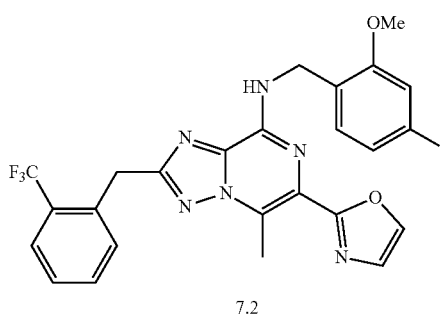

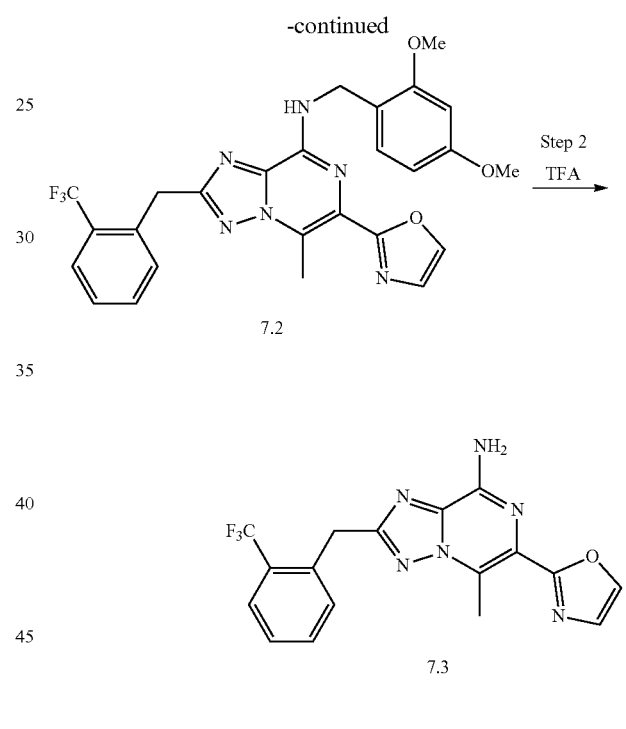

Step 1—Synthesis of intermediate 7.2, N-(2,4-dimethoxybenzyl)-5-methyl-6-(oxazol-2-yl)-2-(2-(trifluoromethyl)benzyl)-[1,2,4]triazolo[1,5-a]pyrazin-8-amine (dtbpf)PdCl$_2$ (6.3 mg, 9.64 µmol) was added to a stirred mixture of K$_3$PO$_4$ (41 mg, 0.193 mmol), 2-(chloromethyl)-N-(2,4-dimethoxybenzyl)-5-methyl-6-(oxazol-2-yl)-[1,2,4]triazolo[1,5-a]pyrazin-8-amine (40 mg, 0.096 mmol) and (2-(trifluoromethyl)phenyl)boronic acid (50 mg, 0.263 mmol) in dioxane (0.5 mL). The resulting mixture was heated to 80° C. and stirred for 16 h. After completion, the reaction mixture was filtered and concentrated. The resulting crude residue was purified by preparative TLC (silica gel, elution: 50% Et$_2$O/EtOAc) to provide N-(2,4-dimethoxybenzyl)-5-methyl-6-(oxazol-2-yl)-2-(2-(trifluoromethyl)benzyl)-[1,2,4]triazolo[1,5-a]pyrazin-8-amine. MS (ESI) m/z calc'd for C$_{26}$H$_{24}$F$_3$N$_6$O$_3$[M+H]$^+$ 525.2, found 525.3.

Step 2—Preparation of Example 7.3, N-(2, 5-methyl-6-(oxazol-2-yl)-2-(2-(trifluoromethyl)benzyl)-[1,2,4]triazolo[1,5-a]pyrazin-8-amine A solution of N-(2,4-dimethoxybenzyl)-5-methyl-6-(oxazol-2-yl)-2-(2-(trifluoromethyl)benzyl)-[1,2,4]triazolo[1,5-a]pyrazin-8-amine (20 mg, 0.038 mmol) in TFA (1 mL) was heated to 50° C. and stirred for 3 h. The reaction mixture was concentrated, and the resulting crude residue was purified by reversed-phase HPLC [Method A]. This provided 5-methyl-6-(oxazol-2-yl)-2-(2-(trifluoromethyl)benzyl)-[1,2,4]triazolo[1,5-a]pyrazin-8-amine (Example 7.3). MS (ESI) m/z calc'd for $C_{17}H_{14}F_3N_6O$ [M+H]$^+$ 375.1, found 375.1. $^1$H NMR (400 MHz, CDCl$_3$) δ 7.83 (s, 1H), 7.70 (d, J=7.45 Hz, 1H), 7.46-7.54 (m, 1H), 7.34-7.42 (m, 3H), 4.53 (s, 2H), 3.04 (s, 3H). A2a IC$_{50}$ 0.5 nM (A).

The following examples in Table 24 were prepared according to Scheme 7 and General Scheme 2, using intermediate T.2 or T.3 and the appropriate commercial boronic acid coupling partner. For the preparation of 7.6, a pinacolate boronic ester was used. Asterisk (*) indicates that A2b data is not available.

TABLE 24

Examples Prepared According to General Scheme 2 and Scheme 7

| Example | Structure Name | Observed m/z [M + H]$^+$ | A2a IC$_{50}$ (nM) A2b IC$_{50}$ (nM) |
|---|---|---|---|
| 7.4 | 6-(2,5-difluorophenyl)-5-methyl-2-(4-(trifluoromethyl)benzyl)-[1,2,4]triazolo[1,5-a]pyrazin-8-amine | 420.3 | 15.3 (A) * |
| 7.5 | 2-((1H-pyrazol-3-yl)methyl)-8-methyl-7-(oxazol-2-yl)-[1,2,4]triazolo[1,5-c]pyrimidin-5-amine | 297 | 4.7 (B) * |
| 7.6 | 8-methyl-2-((1-methyl-1H-pyrazol-3-yl)methyl)-7-(oxazol-2-yl)-[1,2,4]triazolo[1,5-c]pyrimidin-5-amine | 311.2 | 0.5 (A) 2.6 |

Preparation of Example 8.3, 5-methyl-2-((3-methylpyridin-2-yl)methy-(6-oxazol-2-yl)-[1,2,4]triazolo[1,5-a]pyrazin-8-amine Scheme 8

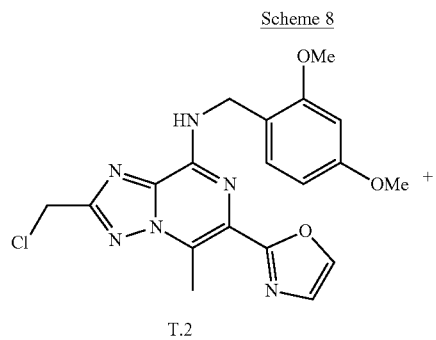

T.2

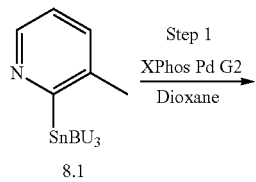

8.1

Step 1
XPhos Pd G2
Dioxane

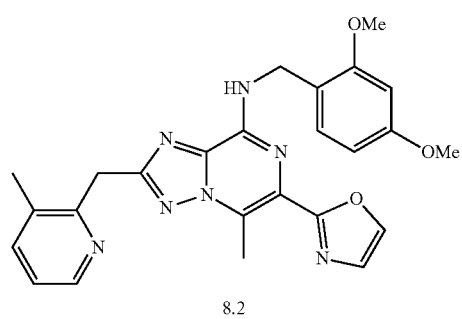

8.2

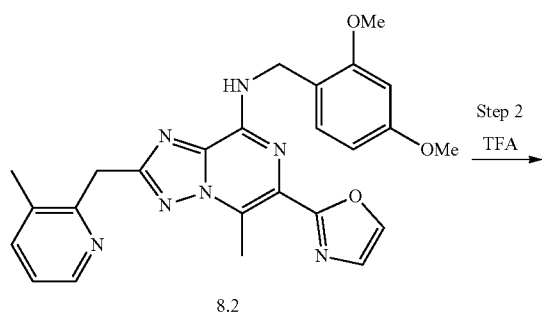

8.2

Step 2
TFA

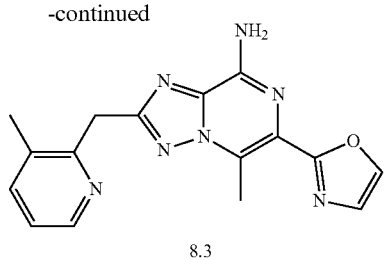

8.3

Step 1—Synthesis of intermediate 8.2, N-(2,4-dimethoxybenzyl)-5-methyl-2-((3-methylpyridin-2-yl)methyl)-6-(oxazol-2-yl)-[1,2,4]triazolo[1,5-a]pyrazin-8-amine XPhos Pd G2 (15.2 mg, 0.019 mmol) was added to a stirred mixture of 2-(chloromethyl)-N-(2,4-dimethoxybenzyl)-5-methyl-6-(oxazol-2-yl)-[1,2,4]triazolo[1,5-a]pyrazin-8-amine (40 mg, 0.096 mmol) and 3-methyl-2-(tributylstannyl)pyridine (147 mg, 0.386 mmol) in dioxane (1 mL). The resulting mixture was heated to 100° C. and stirred for 16 h. After cooling, the reaction was quenched with aq. KF (5 mL), and then extracted with EtOAc (2×5 mL). The combined organic layers were dried over anhydrous $Mg_2SO_4$, filtered, and concentrated. The resulting crude residue was purified by preparative TLC (silica gel, elution: 67% EtOAc/petroleum ether) to provide N-(2,4-dimethoxybenzyl)-5-methyl-2-((3-methylpyridin-2-yl)methyl)-6-(oxazol-2-yl)-[1,2,4]triazolo[1,5-a]pyrazin-8-amine. MS (ESI) m/z calc'd for $C_{25}H_{26}N_7O_3$ [M+H]$^+$ 472.2, found 472.0.

Step 2—Preparation of Example 8.3, 5-methyl-2-((3-methylpyridin-2-yl)methyl)-(6-(oxazol-2-yl)-[1,2,4]triazolo[1,5-a]pyrazin-8-amine A solution of N-(2,4-dimethoxybenzyl)-5-methyl-2-((3-methylpyridin-2-yl)methyl)-(6-(oxazol-2-yl)-[1,2,4]triazolo[1,5-a]pyrazin-8-amine (20 mg, 0.042 mmol) in TFA (2.00 mL, 26.0 mmol) was stirred at 20° C. for 20 min. The reaction mixture was concentrated, and the residue was purified by reversed-phase HPLC [Method A] This provided 5-methyl-2-((3-methylpyridin-2-yl)methyl)-(6-(oxazol-2-yl)-[1,2,4]triazolo[1,5-a]pyrazin-8-amine (Example 8.3). MS (ESI) m/z calc'd for $C_{16}H_{16}N_7O$ [M+H]$^+$ 322.1, found 322.0. $^1$H NMR (400 MHz, MeOD-d$_4$) δ 8.75 (d, J=5.2 Hz, 1H), 7.97 (d, J=7.6 Hz, 1H), 7.80 (s, 1H), 7.57-7.58 (m, 1H), 7.31 (s, 1H), 4.66-4.83 (m, 1H), 3.43-3.53 (m, 3H), 2.95-3.05 (m, 3H), 2.50 (s, 3H). A2a IC$_{50}$ 1.3 nM (A), A2b IC$_{50}$ 29.9 nM.

The following example in Table 25 was prepared by a similar procedure to Scheme 8 and General Scheme 2, using intermediate T.2 and the appropriate commercial stannane, and performing the reaction in Step 2 at 55° C.

TABLE 25

Example Prepared According to General Scheme 2 and Scheme 8

| Example | Structure Name | Observed m/z [M + H]+ | A2a IC50 (nM) A2b IC50 (nM) |
|---|---|---|---|
| 8.4 | 2-((3-fluoropyridin-2-yl)methyl)-5-methyl-6-(oxazol-2-yl)-[1,2,4]triazolo[1,5-a]pyrazin-8-amine | 326.2 | 1.3 (A) 18.6 |

Preparation of Example 9.6, 8-methyl-7-(oxazol-2-yl)-2-(pyridin-2-ylmethyl)-[1,2,4]triazolo[1,5-c]pyrimidin-5-amine

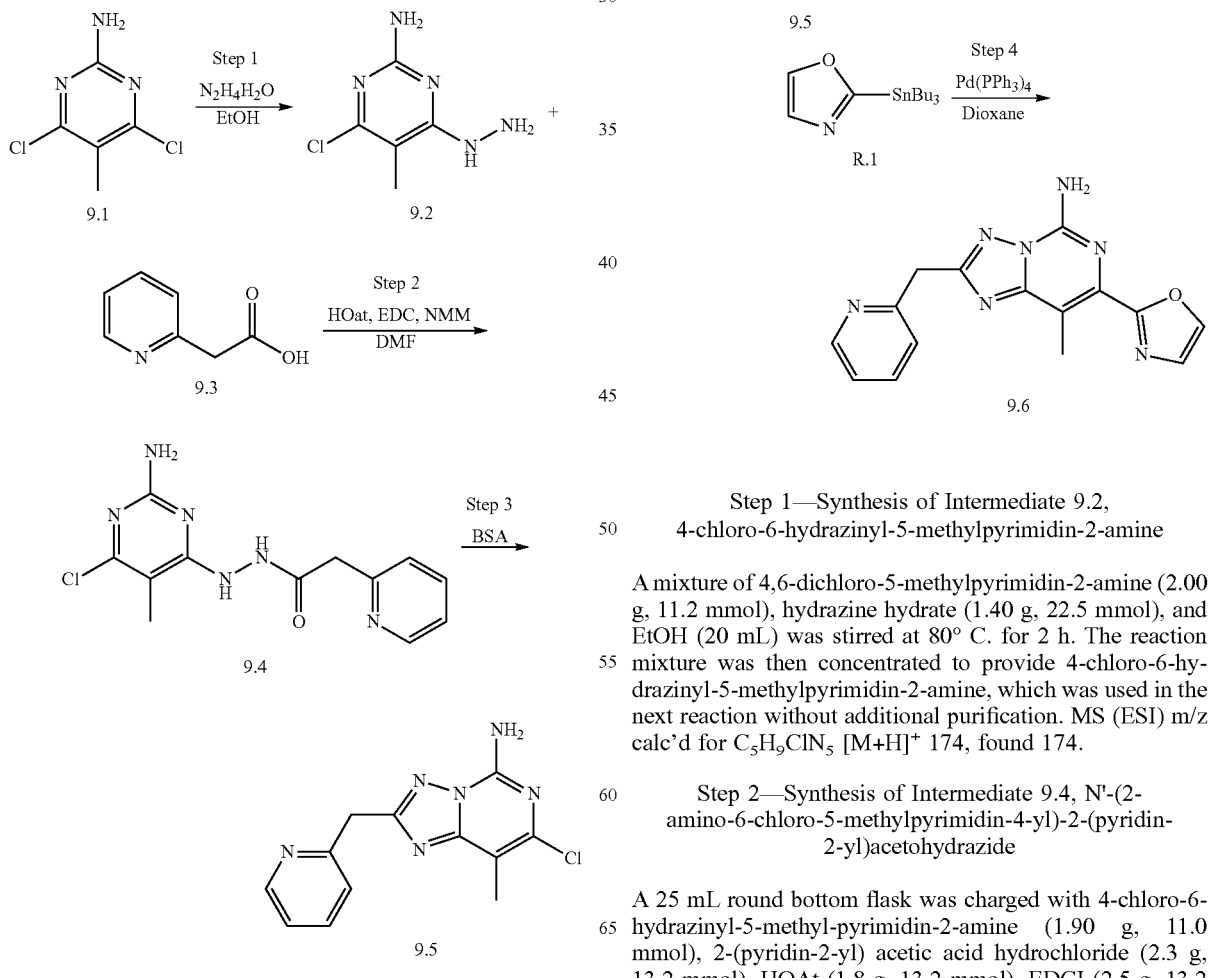

Step 1—Synthesis of Intermediate 9.2, 4-chloro-6-hydrazinyl-5-methylpyrimidin-2-amine A mixture of 4,6-dichloro-5-methylpyrimidin-2-amine (2.00 g, 11.2 mmol), hydrazine hydrate (1.40 g, 22.5 mmol), and EtOH (20 mL) was stirred at 80° C. for 2 h. The reaction mixture was then concentrated to provide 4-chloro-6-hydrazinyl-5-methylpyrimidin-2-amine, which was used in the next reaction without additional purification. MS (ESI) m/z calc'd for $C_5H_9ClN_5$ [M+H]+ 174, found 174.

Step 2—Synthesis of Intermediate 9.4, N'-(2-amino-6-chloro-5-methylpyrimidin-4-yl)-2-(pyridin-2-yl)acetohydrazide A 25 mL round bottom flask was charged with 4-chloro-6-hydrazinyl-5-methyl-pyrimidin-2-amine (1.90 g, 11.0 mmol), 2-(pyridin-2-yl) acetic acid hydrochloride (2.3 g, 13.2 mmol), HOAt (1.8 g, 13.2 mmol), EDCI (2.5 g, 13.2 mmol), and 4-methylmorpholine (3.4 g, 33.0 mmol). DMF (20 mL) was added and the mixture was stirred at 30° C. overnight. The reaction mixture was then treated with water (10 mL) and extracted with EtOAc (3×40 mL). The combined organic layers were concentrated to provide N-(2-amino-6-chloro-5-methylpyrimidin-4-yl)-2-(pyridin-2-yl)acetohydrazide, which was used in the next reaction without additional purification. MS (ESI) m/z calc'd for $C_{12}H_{14}ClN_6O$ [M+H]$^+$ 293, found 293.

Step 3—Synthesis of Intermediate 9.5, 7-chloro-2-(pyridin-2-ylmethyl)-[1,2,4]triazolo[1,5-c]pyrimidin-5-amine A 10 mL round-bottom flask was charged with N-(2-amino-6-chloro-5-methyl-pyrimidin-4-yl)-2-(pyridin-2-yl)acetohydrazide (3.20 g, 11.0 mmol). BSA (22.3 g, 110 mmol) was added and the resulting mixture was stirred at 140° C. overnight. After cooling, the reaction mixture was concentrated. The residue purified by reversed-phase HPLC [Method B]. This provided 7-chloro-2-(pyridin-2-ylmethyl)-[1,2,4]triazolo[1,5-c]pyrimidin-5-amine. MS (ESI) m/z calc'd for $C_{12}H_{12}ClN_6$ [M+H]$^+$ 275, found 289.

Step 4—Preparation of Example 9.6, 8-methyl-7-(oxazol-2-yl)-2-(pyridin-2-ylmethyl)-[1,2,4]triazolo[1,5-c]pyrimidin-5-amine A mixture of 7-chloro-2-(pyridin-2-ylmethyl)-[1,2,4]triazolo[1,5-c]pyrimidin-5-amine (70 mg, 0.26 mmol), Pd(PPh$_3$)$_4$ (30 mg, 0.026 mmol) and 2-(tributylstannyl)oxazole (140 mg, 0.40 mmol) in dioxane (2 mL) was stirred in a sealed tube under nitrogen at 130° C. for 18 h. After cooling, the reaction mixture was concentrated, and the residue was purified with preparative TLC (silica gel, elution: 1% MeOH/EtOAc) to provide 8-methyl-7-(oxazol-2-yl)-2-(pyridin-2-ylmethyl)-[1,2,4]triazolo[1,5-c]pyrimidin-5-amine (Example 9.6). MS (ESI) m/z calc'd for $C_{15}H_{14}N_7O$ [M+H]$^+$ 308, found 308. A2a IC$_{50}$ 0.7 nM (B). The following examples in Table 26 were prepared using the procedure of Scheme 9 and General Scheme 1 above, using the relevant commercially available carboxylic acids. Asterisk (*) indicates that A2b data is not available.

TABLE 26

| Example | Structure Name | Observed m/z [M + H]$^+$ | A2a IC$_{50}$ (nM) A2b IC$_{50}$ (nM) |
|---|---|---|---|
| 9.7 | 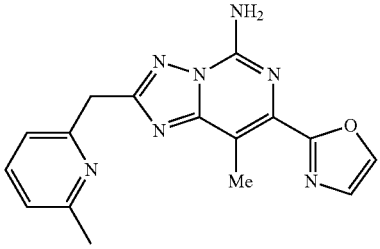 [SMILES: Cc1cccc(Cc2nc3c(C)c(-c4ncco4)nc(N)n3n2)n1]<br>8-methyl-2-((6-methylpyridin-2-yl)methyl)-7-(oxazol-2-yl)-[1,2,4]triazolo[1,5-c]pyrimidin-5-amine | 322 | 0.5 (B) * |
| 9.8 | 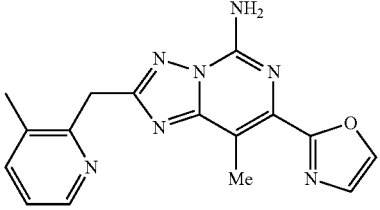 [SMILES: Cc1cccnc1Cc1nc2c(C)c(-c3ncco3)nc(N)n2n1]<br>8-methyl-2-((3-methylpyridin-2-yl)methyl)-7-(oxazol-2-yl)-[1,2,4]triazolo[1,5-c]pyrimidin-5-amine | 322 | 0.6 (B) * |

Preparation of Example 10.2, 8-methyl-7-(oxazol-2-yl)-2-(((4-(trifluoromethyl)benzyl)amino)methyl)-[1,2,4]triazolo[1,5-c]pyrimidin-5-amine, TFA Salt

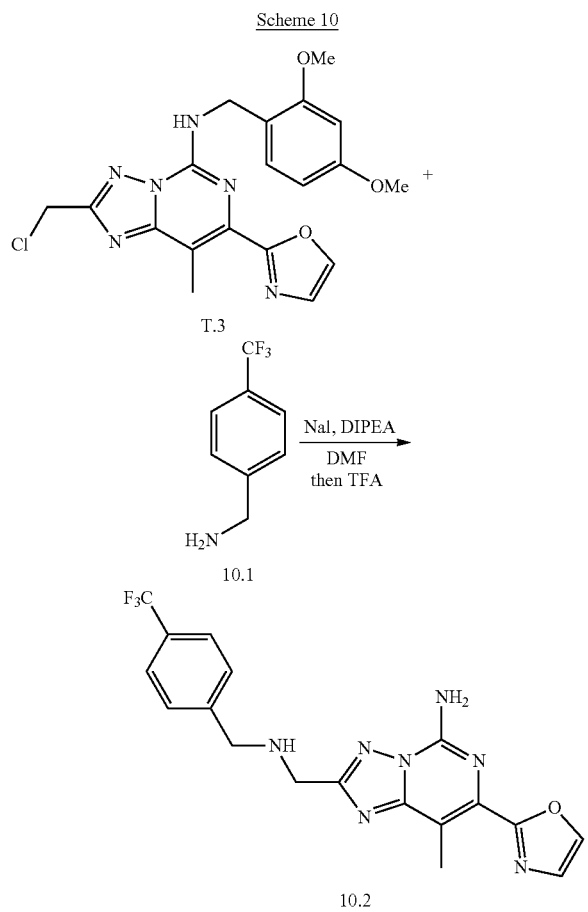

Scheme 10

2-(chloromethyl)-N-(2,4-dimethoxybenzyl)-8-methyl-7-(oxazol-2-yl)-[1,2,4]triazolo[1,5-c]pyrimidin-5-amine (150 mg, 0.362 mmol), sodium iodide (109 mg, 0.724 mmol), and cesium carbonate (295 mg, 0.904 mmol) were combined. DMF (0.89 mL), (4-(trifluoromethyl)phenyl)methanamine (64 µL, 0.452 mmol), and DIPEA (0.190 mL, 1.09 mmol) were sequentially added and reaction mixture was then heated to 80° C. and stirred overnight. The reaction was cooled to 25° C., quenched with water (10 mL), and extracted with EtOAc (3×10 mL). The combined organic layers were dried over anhydrous $MgSO_4$, filtered, and concentrated. The resulting crude material was dissolved in DCM (0.6 mL) and TFA (0.6 mL) was added. The resulting mixture was stirred for 4 h at 25° C. The reaction mixture was concentrated, and the crude residue was dissolved in DMSO (4 mL), filtered, and purified by reversed-phase HPLC [Method A]. This provided 8-methyl-7-(oxazol-2-yl)-2-(((4-(trifluoromethyl)benzyl)amino)methyl)-[1,2,4]triazolo[1,5-c]pyrimidin-5-amine, TFA Salt (Example 10.2). MS (ESI) m/z calc'd for $C_{18}H_{17}F_3N_7O$ [M+H]$^+$ 404.1, found 404.1. $^1$H NMR (500 MHz, DMSO-$d_6$): δ 9.87 (s, 2H), 8.34 (s, 1H), 8.05 (s, 2H), 7.85 (d, J=8.2 Hz, 2H), 7.78 (d, J=8.2 Hz, 2H), 7.54 (s, 1H), 4.50 (d, J=15.8 Hz, 4H), 2.75 (s, 3H). A2a IC$_{50}$ 4.5 nM (A), A2b IC$_{50}$ 48.4 nM.

The following examples in Table 27 were prepared according to Scheme 10 and General Scheme 3 above, using intermediates T.3 or T.4 and the appropriate amine coupling partner.

TABLE 27

Examples Prepared According to General Scheme 3 and Scheme 10

| Example | Structure Name | Observed m/z [M + H]$^+$ | A2a IC$_{50}$ (nM) A2b IC$_{50}$ (nM) |
|---|---|---|---|
| 10.3 | 2-((2,3-dihydro-1H-pyrrolo[2,3-b]pyridin-1-yl)methyl)-8-methyl-7-(oxazol-2-yl)-[1,2,4]triazolo[1,5-c]pyrimidin-5-amine | 349.2 | 0.4 (A) 14.5 |

TABLE 27-continued
Examples Prepared According to General Scheme 3 and Scheme 10
| Example | Structure Name | Observed m/z [M + H]+ | A2a IC$_{50}$ (nM) A2b IC$_{50}$ (nM) |
|---|---|---|---|
| 10.4 | 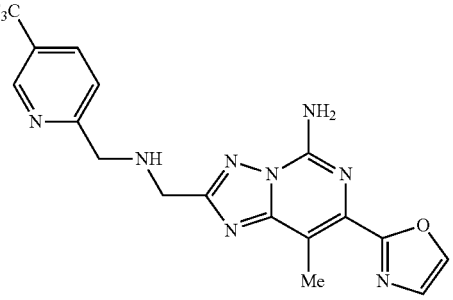 8-methyl-7-(oxazol-2-yl)-2-((((5-(trifluoromethyl)pyridin-2-yl)methyl)amino)methyl)-[1,2,4]triazolo[1,5-c]pyrimidin-5-amine | 405.2 | 155.9 (A) 330.4 |
| 10.5 | 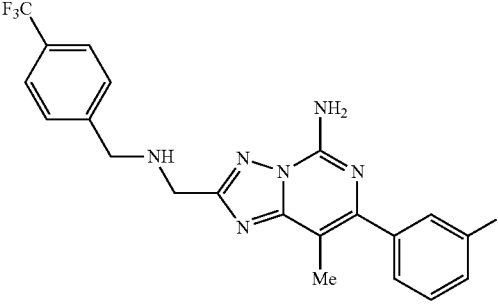 7-(3-fluorophenyl)-8-methyl-2-(((4-(trifluoromethyl)benzyl)amino)methyl)-[1,2,4]triazolo[1,5-c]pyrimidin-5-amine | 431.2 | 162.7 (A) 157.2 |

Preparation of Example 11.2, 2-(4-((((5-amino-8-methyl-7-(oxazol-2-yl)-[1,2,4]triazolo[1,5-c]pyrimidin-2-yl)methyl)amino)methyl)phenyl)propan-2-ol Scheme 11

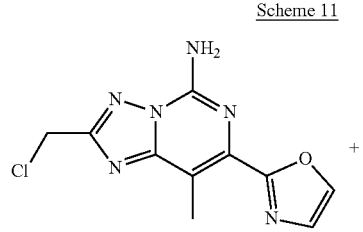

V.1

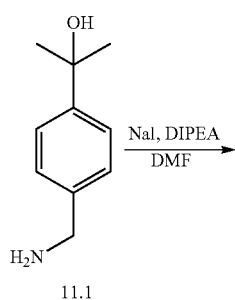

11.1

Nal, DIPEA
DMF

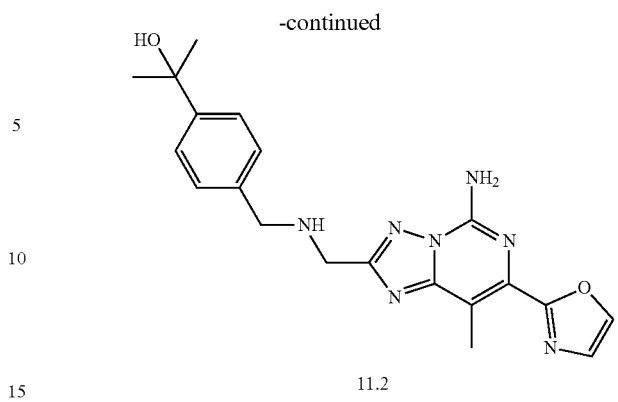

11.2

2-(chloromethyl)-8-methyl-7-(oxazol-2-yl)-[1,2,4]triazolo[1,5-c]pyrimidin-5-amine (25 mg, 0.094 mmol), sodium iodide (28 mg, 0.189 mmol), and 2-(4-(aminomethyl)phenyl)propan-2-ol (19.5 mg, 0.118 mmol) were combined. DMF (0.95 mL) and DIPEA (0.190 mL, 1.09 mmol) were sequentially added and the reaction mixture was then heated to 60° C. and stirred for 2 h. After cooling, the reaction mixture was concentrated. The resulting crude residue was dissolved in DMSO (4 mL), filtered, and purified by reversed-phase HPLC [Method B]. This provided 2-(4-((((5-amino-8-methyl-7-(oxazol-2-yl)-[1,2,4]triazolo[1,5-c]pyrimidin-2-yl)methyl)amino)methyl)phenyl)propan-2-ol (Example 11.2). MS (ESI) m/z calc'd for $C_{20}H_{24}N_7O_2$ [M+H]$^+$ 394.2, found 394.2. $^1$H NMR (500 MHz, DMSO-$d_6$): δ 8.30 (s, 1H), 7.87 (s, 2H), 7.51 (s, 1H), 7.41 (d, J=8.2 Hz, 2H), 7.30 (d, J=8.2 Hz, 2H), 4.95 (s, 1H), 3.93 (s, 2H), 3.80 (s, 2H), 2.70 (s, 3H), 1.41 (s, 6H). A2a IC$_{50}$ 1.1 nM (A), A2b IC$_{50}$ 62.6 nM.

The following examples in Table 28 were prepared according to Scheme 11 and General Scheme 3 above, using intermediate V.1 and the appropriate amine coupling partner, either commercially available or intermediate AN.4.

TABLE 28

Examples Prepared According to General Scheme 3 and Scheme 11

| Example | Structure Name | Observed m/z [M + H]$^+$ | A2a IC$_{50}$ (nM) A2b IC$_{50}$ (nM) |
|---|---|---|---|
| 11.3 | ![structure] 2-(6-((((5-amino-8-methyl-7-(oxazol-2-yl)-[1,2,4]triazolo[1,5-c]pyrimidin-2-yl)methyl)amino)methyl)pyridin-3-yl)propan-2-ol | 395.2 | 15.5 (A) 40.6 |

TABLE 28-continued

Examples Prepared According to General Scheme 3 and Scheme 11

| Example | Structure Name | Observed m/z [M + H]+ | A2a IC$_{50}$ (nM) A2b IC$_{50}$ (nM) |
|---|---|---|---|
| 11.4 | 2-(5-(((((5-amino-8-methyl-7-(oxazol-2-yl)-[1,2,4]triazolo[1,5-c]pyrimidin-2-yl)methyl)amino)methyl)pyridin-2-yl)propan-2-ol | 395.3 743.5 | 5.4 (A) |
| 11.5 | 1-(4-(((((5-amino-8-methyl-7-(oxazol-2-yl)-[1,2,4]triazolo[1,5-c]pyrimidin-2-yl)methyl)amino)methyl)-1H-pyrazol-1-yl)-2-methylpropan-2-ol | 398.3 1318 | 15.2 (A) |

Preparation of Example 12.3, 2-(((2,2-difluoroethyl)(4-(trifluoromethyl)benzyl)amino)methyl)-N-(2,4-dimethoxybenzyl)-8-methyl-7-(oxazol-2-yl)-[1,2,4]triazolo[1,5-c]pyrimidin-5-amine

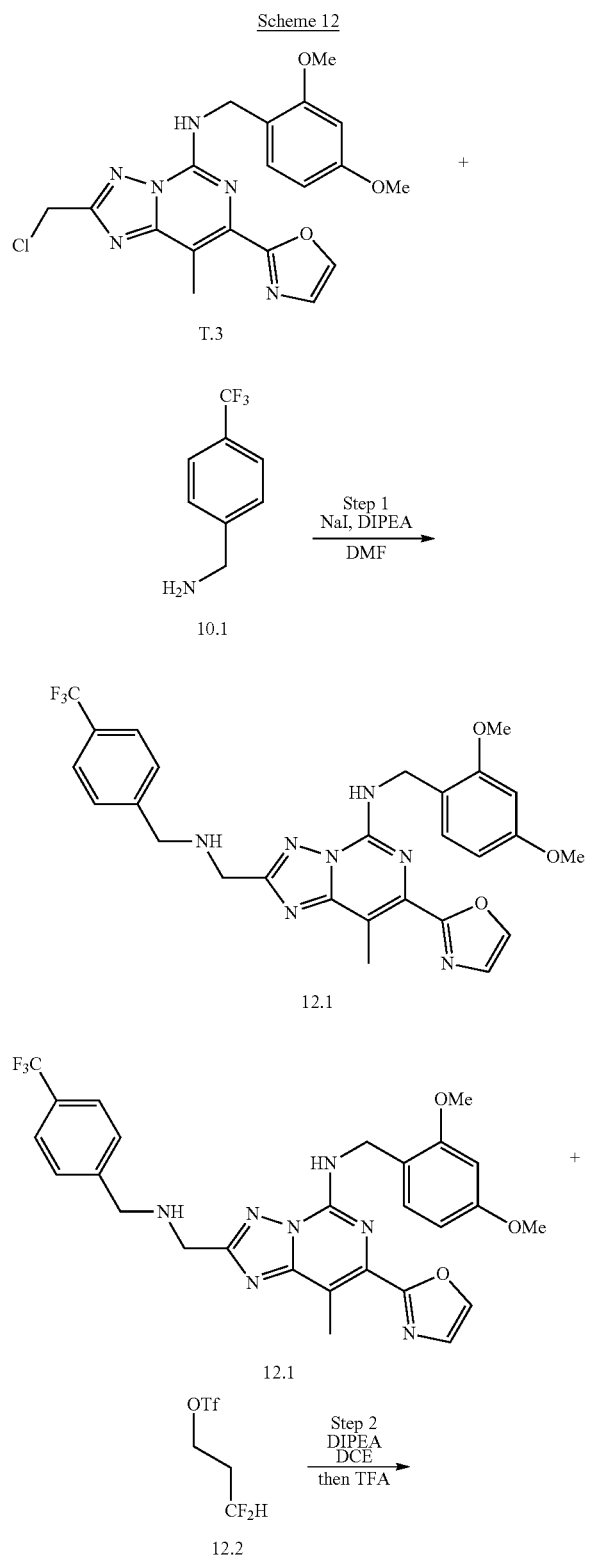

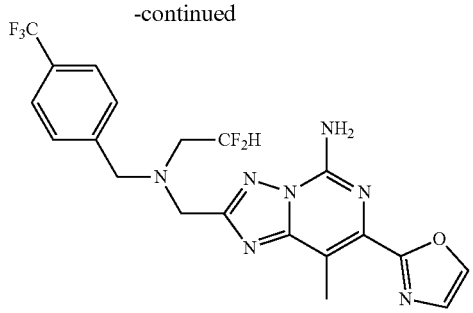

Step 1—Synthesis of Intermediate 12.1, N-(2,4-dimethoxybenzyl)-8-methyl-7-(oxazol-2-yl)-2-(((4-(trifluoromethyl)benzyl)amino)methyl)-[1,2,4]triazolo[1,5-c]pyrimidin-5-amine 2-(chloromethyl)-N-(2,4-dimethoxybenzyl)-8-methyl-7-(oxazol-2-yl)-[1,2,4]triazolo[1,5-c]pyrimidin-5-amine (150 mg, 0.362 mmol), sodium iodide (109 mg, 0.724 mmol), and cesium carbonate (295 mg, 0.904 mmol) were combined. DMF (0.89 mL), (4-(trifluoromethyl)phenyl)methanamine (64 µL, 0.452 mmol), and DIPEA (0.190 mL, 1.09 mmol) were sequentially added, and the reaction mixture was then heated to 80° C. and stirred overnight. The reaction mixture was cooled to 25° C., quenched with water (10 mL) and extracted with EtOAc (3×10 mL). The combined organic layers were dried over anhydrous MgSO$_4$, filtered, and concentrated. The resulting crude residue was purified by silica gel chromatography (gradient elution: 0-75% [3:1 EtOAc/EtOH]/DCM) to provide N-(2,4-dimethoxybenzyl)-8-methyl-7-(oxazol-2-yl)-2-(((4-(trifluoromethyl)benzyl)amino)methyl)-[1,2,4]triazolo[1,5-c]pyrimidin-5-amine. MS (ESI) m/z calc'd for $C_{27}H_{27}F_3N_7O_3$[M+H]$^+$ 554.2, found 554.2.

Step 2—Preparation of Example 12.3, 2-(((2,2-difluoroethyl)(4-(trifluoromethyl)benzyl)amino)methyl)-N-(2,4-dimethoxybenzyl)-8-methyl-7-(oxazol-2-yl)-[1,2,4]triazolo[1,5-c]pyrimidin-5-amine DIPEA (22 µL, 0.126 mmol) and 2,2-difluoroethyl trifluoromethanesulfonate (10 µL, 0.076 mmol) were added to a stirred solution of N-(2,4-dimethoxybenzyl)-8-methyl-7-(oxazol-2-yl)-2-(((4-(trifluoromethyl)benzyl)amino)methyl)-[1,2,4]triazolo[1,5-c]pyrimidin-5-amine (35 mg, 0.063 mmol) in DCE (0.6 mL). The reaction mixture was then heated to 60° C. overnight, after which point TFA (0.6 mL) was added. After stirring for an additional 30 min, the reaction mixture was cooled to 25° C. and concentrated under reduced pressure. The resulting crude residue was taken up in DMSO (2 mL), filtered, and purified by reversed-phase HPLC [Method B]. This provided 2-(((2,2-difluoroethyl)(4-(trifluoromethyl)benzyl)amino)methyl)-N-(2,4-dimethoxybenzyl)-8-methyl-7-(oxazol-2-yl)-[1,2,4]triazolo[1,5-c]pyrimidin-5-amine (Example 12.3). MS (ESI) m/z calc'd for $C_{20}H_{19}F_5N_7O$ [M+H]$^+$ 468.2, found 468.2. $^1$H NMR (500 MHz, DMSO-d$_6$) δ 8.31 (s, 1H), 7.91 (s, 2H), 7.51 (s, 1H), 3.70 (m, J=8.9, 7.0 Hz, 2H), 3.36-3.30 (m, 2H), 2.83-2.76 (m, 1H), 2.70 (s, 3H), 1.04-1.00 (m, 4H). A2a IC$_{50}$ 0.7 nM (A), A2b IC$_{50}$ 1993 nM.

Preparation of Example 13.1, 2-(4-((((5-amino-8-methyl-7-(oxazol-2-yl)-[1,2,4]triazolo[1,5-c]pyrimidin-2-yl)methyl)(2,2-difluoroethyl)amino)methyl)phenyl)propan-2-ol, TFA Salt

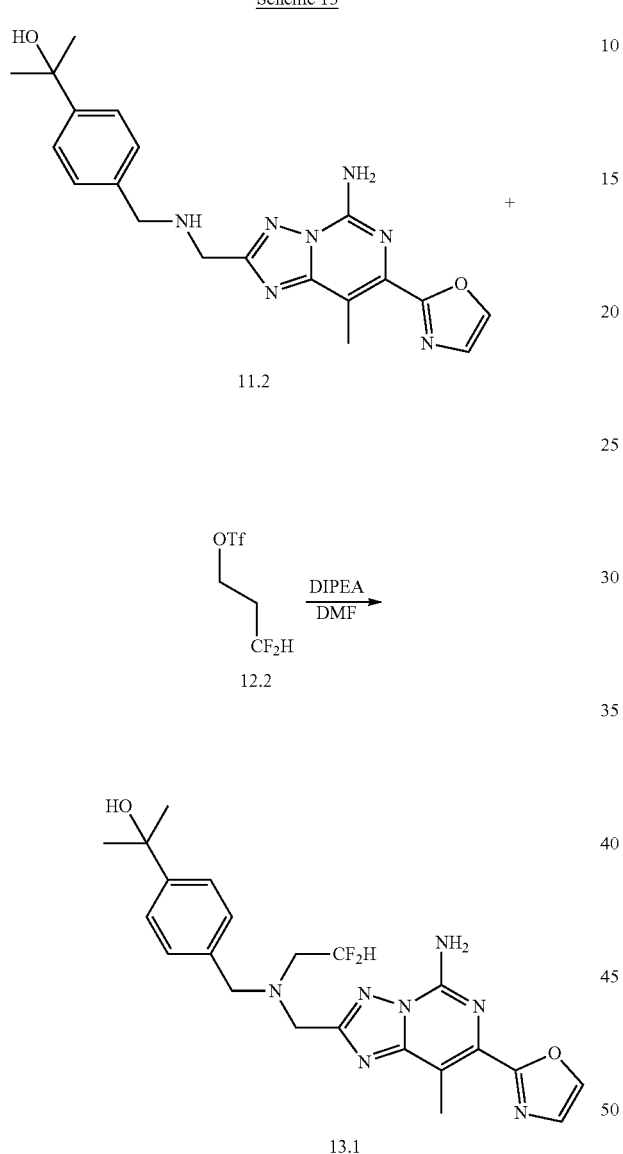

Preparation of Example 14.3, 2-(5-amino-7-phenyl-[1,2,4]triazolo[1,5-c]pyrimidin-2-yl)ethan-1-ol

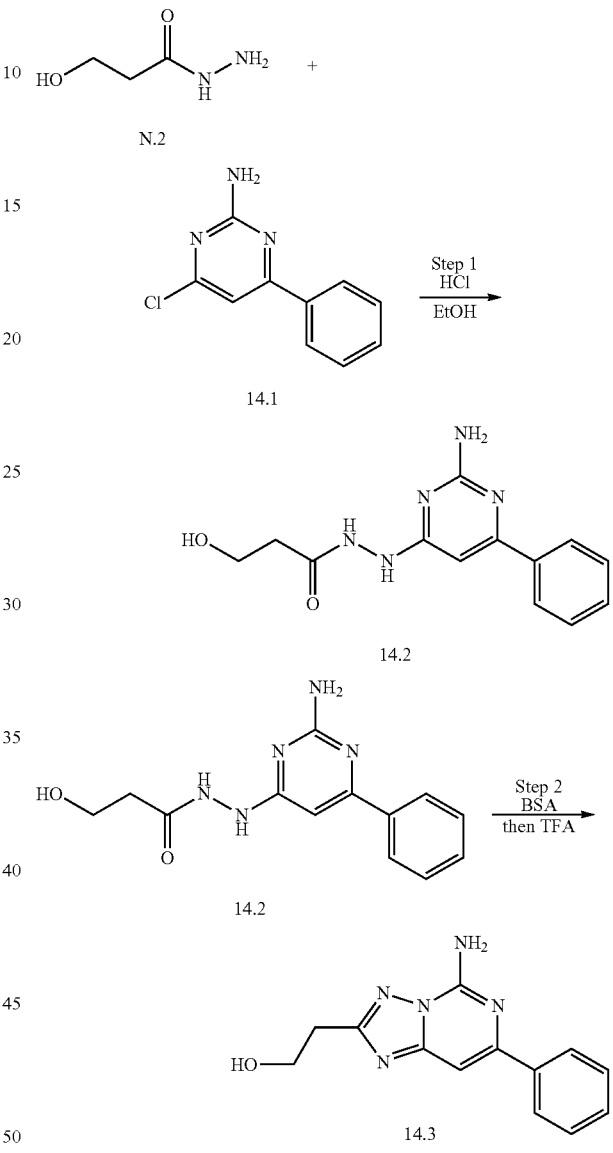

DIPEA (33 μL, 0.189 mmol) and 2,2-difluoroethyl trifluoromethanesulfonate (15 μL, 0.113 mmol) were added to a stirred solution of 2-(4-((((5-amino-8-methyl-7-(oxazol-2-yl)-[1,2,4]triazolo[1,5-c]pyrimidin-2-yl)methyl)amino)methyl)phenyl)propan-2-ol (37 mg, 0.095 mmol) in DMF (0.95 mL). The reaction mixture was then stirred at 25° C. overnight. The reaction mixture was directly purified by reversed-phase HPLC [Method A]. This provided 2-(4-((((5-amino-8-methyl-7-(oxazol-2-yl)-[1,2,4]triazolo[1,5-c]pyrimidin-2-yl)methyl)(2,2-difluoroethyl)amino)methyl)phenyl)propan-2-ol, TFA salt (Example 13.1). MS (ESI) m/z calc'd for $C_{22}H_{26}F_2N_7O_2$ [M+H]$^+$ 458.2, found 458.2. A2a $IC_{50}$ 0.4 nM (A), A2b $IC_{50}$ 489.3 nM.

Step 1—Synthesis of Intermediate 14.2, N'-(2-amino-6-phenylpyrimidin-4-yl)-3-hydroxypropanehydrazide To a solution of 4-chloro-6-phenylpyrimidin-2-amine (2.16 g, 10.5 mmol) and 3-hydroxypropanehydrazide (1.10 g, 10.5 mmol) in EtOH (30 mL), HCl (4 M in dioxane, 1.50 mL, 6.00 mmol) was added. The resulting mixture was stirred at 80° C. for 2 h. After completion, the reaction mixture was concentrated to provide N-(2-amino-6-phenylpyrimidin-4-yl)-3-hydroxypropanehydrazide, which was used in the subsequent reaction without further purification. MS (ESI) calc'd for $C_{13}H_{16}N_5O_2$ [M+H]$^+$ 274.1, found 274.1.

Step 2—Synthesis of Example 14.3, 2-(5-amino-7-phenyl-[1,2,4]triazolo[1,5-c]pyrimidin-2-yl)ethan-1-ol A mixture of N-(2-amino-6-phenylpyrimidin-4-yl)-3-hydroxypropanehydrazide (3.20 g, 11.90 mmol) and BSA (16 mL) was stirred at 140° C. for 3 h. After cooling, the reaction mixture was concentrated. The resulting crude residue was then diluted in DCM (10 mL) and TFA (2 mL) was added. The reaction mixture was stirred for 1 h at 25° C. Upon completion (deprotection of TMS groups), the reaction mixture was concentrated and the residue was purified by silica gel chromatography (gradient elution: 50-100% EtOAc/petroleum ether) to provide 2-(5-amino-7-phenyl-[1,2,4]triazolo[1,5-c]pyrimidin-2-yl)ethan-1-ol (Example 14.3). MS (ESI) calc'd for $C_{13}H_{14}N_5O$ $[M+H]^+$ 256.1, found 256.1. $^1H$ NMR (400 MHz, MeOD-$d_4$) δ 7.65-7.75 (m, 2H), 7.39-7.50 (m, 3H), 6.71 (s, 1H) 4.04 (t, J=6.58 Hz, 2H), 3.11 (t, J=6.58 Hz, 2H). A2a $IC_{50}$ 493.3 nM (A).

Preparation of Example 15.3, 2-(2-(cyclopropylsulfonyl)ethyl)-8-methyl-7-(oxazol-2-yl)-[1,2,4]triazolo[1,5-c]pyrimidin-5-amine, TFA Salt

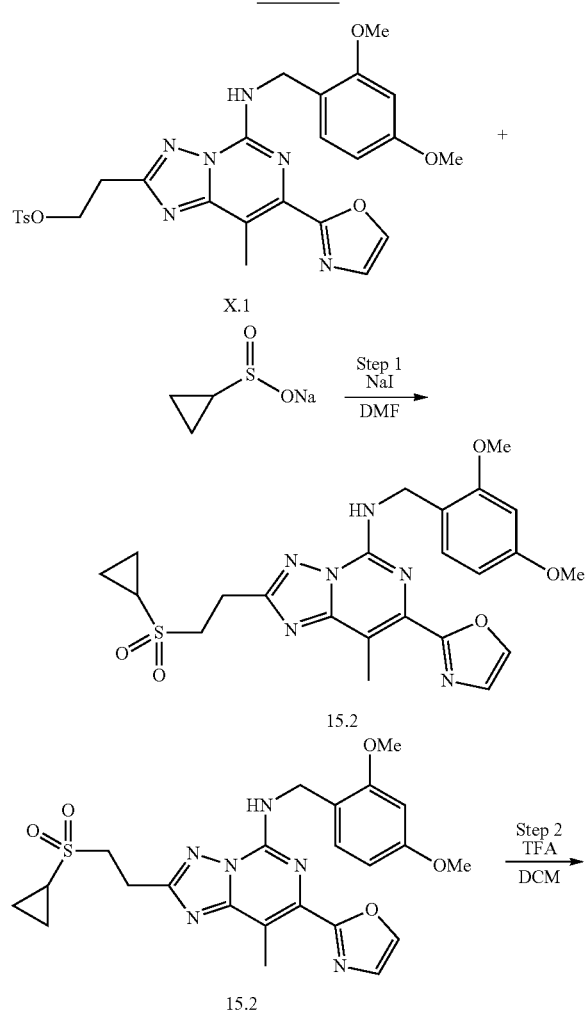

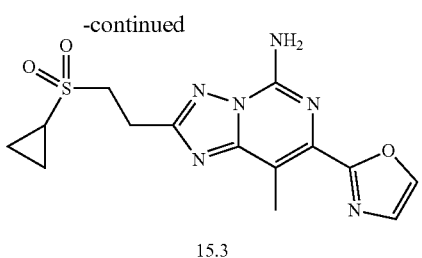

Step 1—Synthesis of Intermediate 15.2, 2-(2-(cyclopropylsulfonyl)ethyl)-N-(2,4-dimethoxybenzyl)-8-methyl-7-(oxazol-2-yl)-[1,2,4]triazolo[1,5-c]pyrimidin-5-amine 2-(5-((2,4-dimethoxybenzyl)amino)-8-methyl-7-(oxazol-2-yl)-[1,2,4]triazolo[1,5-c]pyrimidin-2-yl)ethyl 4-methylbenzenesulfonate (50 mg, 0.089 mmol), sodium iodide (26.5 mg, 0.177 mmol), and sodium cyclopropane sulfinate (34 mg, 0.266 mmol) were combined. DMF (0.9 mL) was added and the reaction mixture was then heated to 60° C. for 14 h. After cooling, the reaction mixture was concentrated under reduced pressure to provide 2-(2-(cyclopropylsulfonyl)ethyl)-N-(2,4-dimethoxybenzyl)-8-methyl-7-(oxazol-2-yl)-[1,2,4]triazolo[1,5-c]pyrimidin-5-amine. The resulting crude material was used in the subsequent reaction without further purification. MS (ESI) m/z calc'd for $C_{23}H_{27}N_6O_5S$ $[M+H]^+$ 499.2, found 499.1.

Step 2—Synthesis of Example 15.3, 2-(2-(cyclopropylsulfonyl)ethyl)-8-methyl-7-(oxazol-2-yl)-[1,2,4]triazolo[1,5-c]pyrimidin-5-amine, TFA Salt TFA (0.45 mL) was added to a stirred solution of 2-(2-(cyclopropylsulfonyl)ethyl)-N-(2,4-dimethoxybenzyl)-8-methyl-7-(oxazol-2-yl)-[1,2,4]triazolo[1,5-c]pyrimidin-5-amine (44 mg, 0.089 mmol) in DCM (0.45 mL). The reaction mixture was then heated to 40° C. and stirred for 2 h. After cooling, the reaction mixture was concentrated, and the resulting crude residue was taken up in DMSO (2 mL), filtered, and purified by reversed-phase HPLC [Method A]. This provided 2-(2-(cyclopropylsulfonyl)ethyl)-8-methyl-7-(oxazol-2-yl)-[1,2,4]triazolo[1,5-c]pyrimidin-5-amine, TFA salt (Example 15.3). MS (ESI) m/z calc'd for $C_{14}H_{17}N_6O_3S$ $[M+H]^+$ 349.1, found 349.1. $^1H$ NMR (500 MHz, DMSO-$d_6$) δ 8.31 (s, 1H), 7.89 (s, 2H), 7.69 (d, J=8.2 Hz, 2H), 7.64 (d, J=8.1 Hz, 2H), 7.51 (s, 1H), 6.37-6.09 (m, 1H), 4.01 (s, 2H), 3.98 (s, 2H), 3.17 (td, J=15.3, 4.2 Hz, 1H), 2.71 (s, 3H). A2a $IC_{50}$ 7.3 nM (A), A2b $IC_{50}$ 151.1 nM.

Preparation of Example 16.2, 2-(2-(cyclopropylsulfonyl)ethyl)-7-(3-fluorophenyl)-8-methyl-[1,2,4]triazolo[1,5-c]pyrimidin-5-amine, TFA Salt

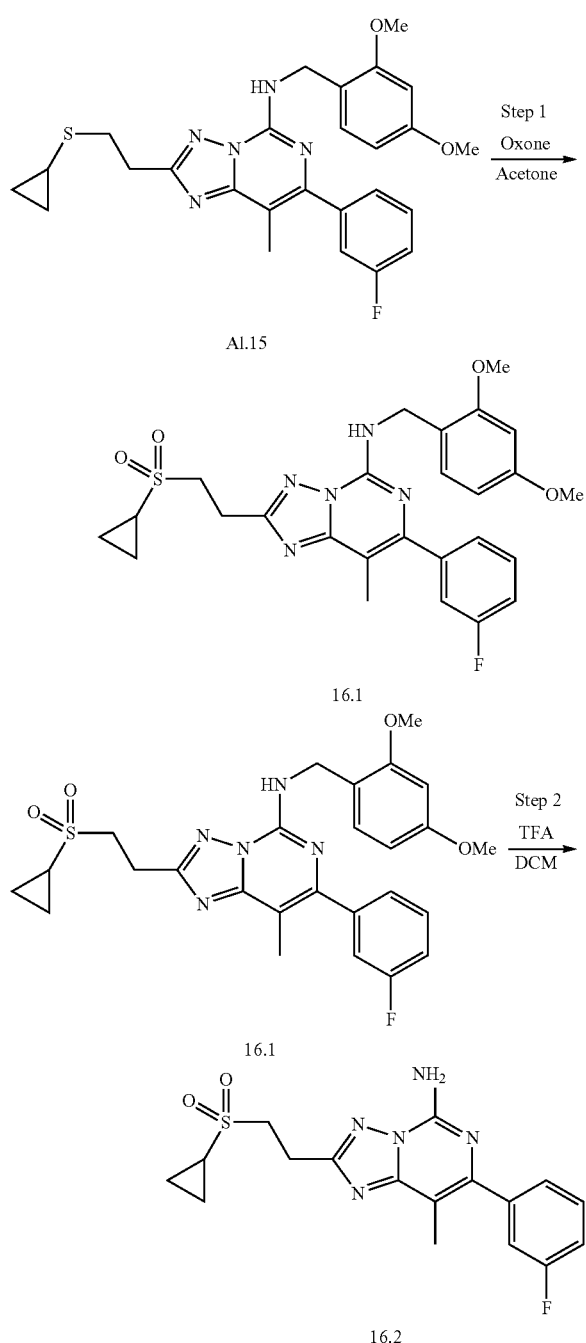

Step 1—Synthesis of Intermediate 16.1, 2-(2-(cyclopropylsulfonyl)ethyl)-N-(2,4-dimeth oxybenzyl)-7-(3-fluorophenyl)-8-methyl-[1,2,4]triazolo[1,5-c]pyrimidin-5-amine A solution of 2-(2-(cyclopropylthio)ethyl)-N-(2,4-dimethoxybenzyl)-7-(3-fluorophenyl)-8-methyl-[1,2,4] triazolo[1,5-c]pyrimidin-5-amine (35 mg, 0.071 mmol) in acetone (6 mL) was prepared and a solution of oxone (65 mg, 0.106 mmol) in water (3 mL) was added dropwise. The resulting mixture was stirred at 25° C. for 16 h. The reaction mixture was then poured into water (10 mL) and the aq. phase was extracted with EtOAc (20 mL). The combined organic layers were washed with sat. aq. NaHCO$_3$ (20 mL), dried over anhydrous Mg$_2$SO$_4$, filtered, and concentrated. The resulting crude material was purified by preparative TLC (silica gel, elution: 50% EtOAc/petroleum ether) to provide 2-(2-(cyclopropylsulfonyl)ethyl)-N-(2,4-dimethoxybenzyl)-7-(3-fluorophenyl)-8-methyl-[1,2,4]triazolo[1,5-c]pyrimidin-5-amine. MS (ESI) m/z calc'd for C$_{26}$H$_{29}$N$_5$O$_4$SF [M+H]$^+$ 526.2, found 526.4.

Step 2—Preparation of Example 16.2, 2-(2-(cyclopropylsulfonyl)ethyl)-7-(3-fluorophenyl)-8-methyl-[1,2,4]triazolo[1,5-c]pyrimidin-5-amine, TFA Salt A solution of 2-(2-(cyclopropylsulfonyl)ethyl)-N-(2,4-dimethoxybenzyl)-7-(3-fluorophenyl)-8-methyl-[1,2,4]triazolo[1,5-c]pyrimidin-5-amine (30 mg, 0.057 mmol) in DCM (2 mL) was treated with TFA (1 mL). The resulting mixture was stirred at 45° C. for 16 h. After cooling, the reaction mixture was concentrated, and the residue was purified by reversed-phase HPLC [Method A]. This provided 2-(2-(cyclopropylsulfonyl)ethyl)-7-(3-fluorophenyl)-8-methyl-[1,2,4]triazolo[1,5-c]pyrimidin-5-amine, TFA salt (Example 16.2). MS (ESI) m/z calc'd for C$_{17}$H$_{19}$N$_5$O$_2$SF [M+H]$^+$ 376.1, found 376.0. $^1$H NMR (500 MHz, DMSO-d$_6$) δ 7.74 (br s, 2H), 7.49-7.55 (m, 1H), 7.38-7.45 (m, 2H), 7.28 (dt, J=2.37, 8.51 Hz, 1H), 3.66-3.71 (m, 2H), 3.27-3.35 (m, 2H), 2.80 (quin, J=6.33 Hz, 1H), 2.34 (s, 3H), 1.02 (d, J=6.41 Hz, 4H). A2a IC$_{50}$ 19.3 nM (A), A2b IC$_{50}$ 453.1 nM.

Preparation of Example 17.2, 2-(2-(3-(3,3-difluorocyclobutyl)-5,6-dihydroimidazo[1,5-a]pyrazin-7(8H)-yl)ethyl)-8-methyl-7-(oxazol-2-yl)-[1,2,4]triazolo[1,5-c]pyrimidin-5-amine, TFA Salt

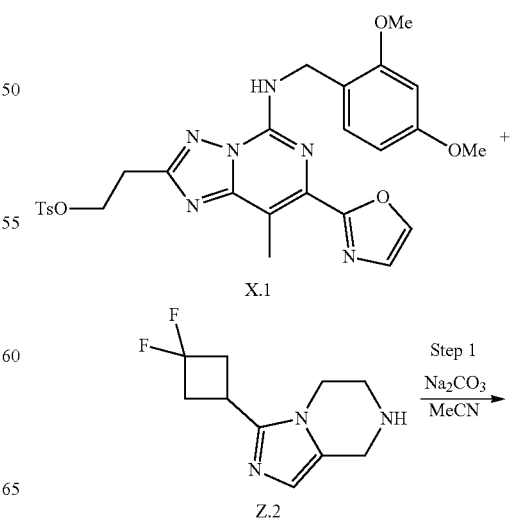

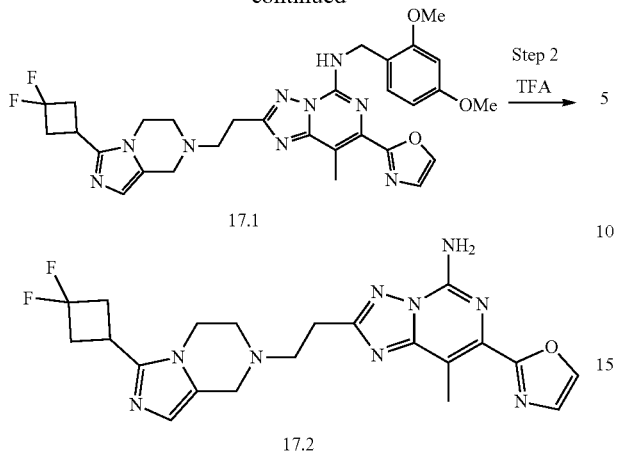

Step 1—Synthesis of Intermediate 17.1, 2-(2-(3-(3, 3-difluorocyclobutyl)-5,6-dihydroimidazo[1,5-a] pyrazin-7(8H)-yl)ethyl)-N-(2,4-dimethoxybenzyl)-8-methyl-7-(oxazol-2-yl)-[1,2,4]triazolo[1,5-c] pyrimidin-5-amine A 40 mL scintillation vial was charged with 3-(3,3-difluorocyclobutyl)-5,6,7,8-tetrahydroimidazo[1,5-a]pyrazine (31 mg, 0.145 mmol), 2-(5-((2,4-dimethoxybenzyl)amino)-8-methyl-7-(oxazol-2-yl)-[1,2,4]triazolo[1,5-c]pyrimidin-2-yl)ethyl 4-methylbenzenesulfonate (55 mg, 0.097 mmol) and sodium carbonate (25.7 mg, 0.243 mmol). MeCN (970 μL) was then added and the reaction mixture was stirred overnight at 85° C. After cooling to 25° C., DCM (4 mL) was added and the mixture was filtered through Celite™ (diatomaceous earth) and concentrated. The resulting crude residue was purified by silica gel chromatography (gradient elution: 0-10% MeOH/DCM) to provide 2-(2-(3-(3,3-difluorocyclobutyl)-5,6-dihydroimidazo[1,5-a]pyrazin-7(8H)-yl)ethyl)-N-(2,4-dimethoxybenzyl)-8-methyl-7-(oxazol-2-yl)-[1,2,4]triazolo[1,5-c]pyrimidin-5-amine. MS (ESI) m/z calc'd for $C_{30}H_{34}F_2N_9O_3$ $[M+H]^+$ 606.3, found 606.2.

Step 2—Synthesis of Example 17.2, 2-(2-(3-(3,3-difluorocyclobutyl)-5,6-dihydroimidazo[1,5-a] pyrazin-7(8H)-yl)ethyl)-8-methyl-7-(oxazol-2-yl)-[1, 2,4]triazolo[1,5-c]pyrimidin-5-amine, TFA Salt A 20 mL scintillation vial was charged with 2-(2-(3-(3,3-difluorocyclobutyl)-5,6-dihydroimidazo[1,5-a]pyrazin-7 (8H)-yl)ethyl)-N-(2,4-dimethoxybenzyl)-8-methyl-7-(oxazol-2-yl)-[1,2,4]triazolo[1,5-c]pyrimidin-5-amine (12 mg, 0.020 mmol). TFA (300 μL) was added, and the reaction mixture was heated at 50° C. and stirred for 2 h. After cooling, the reaction mixture was concentrated and the residue was taken up in DMSO (2 mL), filtered, and purified via reversed-phase HPLC [Method A]. This provided 2-(2-(3-(3,3-difluorocyclobutyl)-5,6-dihydroimidazo[1,5-a] pyrazin-7(8H)-yl)ethyl)-8-methyl-7-(oxazol-2-yl)-[1,2,4] triazolo[1,5-c]pyrimidin-5-amine, TFA salt (Example 17.2). MS (ESI) m/z calc'd for $C_{21}H_{24}F_2N_9O$ $[M+H]^+$ 456.2, found 456.2. $^1$H NMR (600 MHz, DMSO-$d_6$) δ 8.29 (s, 1H), 7.84 (br s, 2H), 7.50 (s, 1H), 7.44 (s, 1H), 4.12 (app t, J=5.5 Hz, 2H), 3.98 (s, 2H), 3.83-3.75 (m, 1H), 3.25-3.14 (m, 6H), 3.14-3.04 (m, 4H), 2.69 (s, 3H). A2a $IC_{50}$ 0.4 nM (A), A2b $IC_{50}$ 20.3 nM.

The following examples in Table 29 were prepared according to Scheme 17 and General Scheme 4 above, using intermediate X.1 and the appropriate amine coupling partner, either commercially available or intermediates Z.3, AA.1, AD.7, AH.2, AG.2, AE.6, AE.5, AC.10, AC.9, AC.8, AO.4 or AO.5. In the case of 17.17, the first step in Scheme 17 was run using $K_2CO_3$. The compounds were generally purified by silica gel chromatography, reversed-phase prep-HPLC and SFC. Where isomers were separated by SFC conditions are provided, following the table.

TABLE 29

Examples Prepared According to General Scheme 4 and Scheme 17

| Example | Structure Name | Observed m/z [M + H]⁺ | A2a IC₅₀ (nM) A2b IC₅₀ (nM) |
|---|---|---|---|
| 17.3 | ![structure] 2-(2-(3-cyclopentyl-5,6-dihydroimidazo[1,5-a]pyrazin-7(8H)-yl)ethyl)-8-methyl-7-(oxazol-2-yl)-[1,2,4]triazolo[1,5-c]pyrimidin-5-amine | 434.2 | 4.2 (A) 17.7 |
| 17.4 | ![structure] | 424.4 | 9.4 (A) |

TABLE 29-continued

Examples Prepared According to General Scheme 4 and Scheme 17

| Example | Structure Name | Observed m/z [M + H]⁺ | A2a IC$_{50}$ (nM) A2b IC$_{50}$ (nM) |
|---|---|---|---|
|  | 1-(5-(2-(5-amino-8-methyl-7-(oxazol-2-yl)-[1,2,4]triazolo[1,5-c]pyrimidin-2-yl)ethyl)-5,6-dihydropyrrolo[3,4-c]pyrazol-2(4H)-yl)-2-methylpropan-2-ol |  | 1426 |
| 17.5 |  | 366.2 | 43.6 (A) |
|  | 8-methyl-2-(2-(1-methyl-4,6-dihydropyrrolo[3,4-c]pyrazol-5(1H)-yl)ethyl)-7-(oxazol-2-yl)-[1,2,4]triazolo[1,5-c]pyrimidin-5-amine |  | 688.1 |
| 17.6 |  | 380.1 | 16.3 (A) |
|  | 8-methyl-2-(2-(2-methyl-6,7-dihydropyrazolo[1,5-a]pyrazin-5(4H)-yl)ethyl)-7-(oxazol-2-yl)-[1,2,4]triazolo[1,5-c]pyrimidin-5-amine |  | 677.3 |
| 17.7 |  | 432.2 | 0.6 (A) |
|  | 2-(2-(3-(bicyclo[1.1.1]pentan-1-yl)-5,6-dihydroimidazo[1,5-a]pyrazin-7(8H)-yl)ethyl)-8-methyl-7-(oxazol-2-yl)-[1,2,4]triazolo[1,5-c]pyrimidin-5-amine |  | 17.8 |
| 17.8-1 |  | 423.3 | 0.7 (A) |
|  | (R or S)-2-(2-(1-isopropyl-7-methyl-1,4,6,7-tetrahydro-5H-[1,2,3]triazolo[4,5-c]pyridin-5-yl)ethyl)-8-methyl-7-(oxazol-2-yl)-[1,2,4]triazolo[1,5-c]pyrimidin-5-amine |  | 1684 |

TABLE 29-continued

Examples Prepared According to General Scheme 4 and Scheme 17

| Example | Structure Name | Observed m/z [M + H]+ | A2a IC$_{50}$ (nM) A2b IC$_{50}$ (nM) |
|---|---|---|---|
| 17.8-2 | 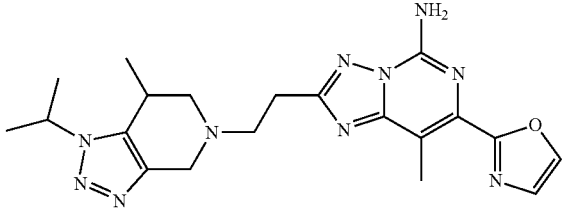 [SMILES: Cc1c(-c2ncco2)nc(N)n2nc(CCN3Cc4nnn(C(C)C)c4C(C)C3)nc12] (R or S)-2-(2-(1-isopropyl-7-methyl-1,4,6,7-tetrahydro-5H-[1,2,3]triazolo[4,5-c]pyridin-5-yl)ethyl)-8-methyl-7-(oxazol-2-yl)-[1,2,4]triazolo[1,5-c]pyrimidin-5-amine | 423.2 | 2.3 (A) 14.0 |
| 17.9 | 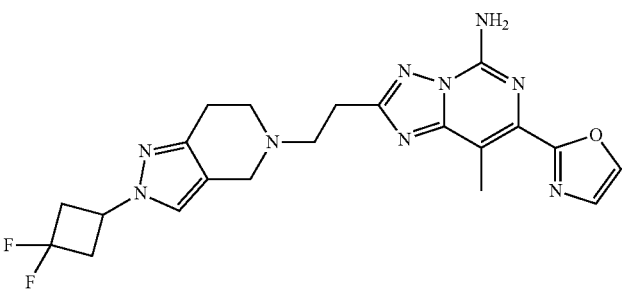 [SMILES: Cc1c(-c2ncco2)nc(N)n2nc(CCN3CCc4nn(C5CC(F)(F)C5)cc4C3)nc12] 2-(2-(2-(3,3-difluorocyclobutyl)-2,4,6,7-tetrahydro-5H-pyrazolo[4,3-c]pyridin-5-yl)ethyl)-8-methyl-7-(oxazol-2-yl)-[1,2,4]triazolo[1,5-c]pyrimidin-5-amine | 456.2 | 4.1 (A) 97.0 |
| 17.10 | 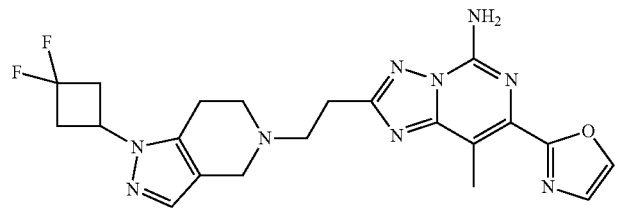 [SMILES: Cc1c(-c2ncco2)nc(N)n2nc(CCN3CCc4c(cnn4C4CC(F)(F)C4)C3)nc12] 2-(2-(1-(3,3-difluorocyclobutyl)-1,4,6,7-tetrahydro-5H-pyrazolo[4,3-c]pyridin-5-yl)ethyl)-8-methyl-7-(oxazol-2-yl)-[1,2,4]triazolo[1,5-c]pyrimidin-5-amine | 456.2 | 0.6 (A) 20.6 |
| 17.11 | 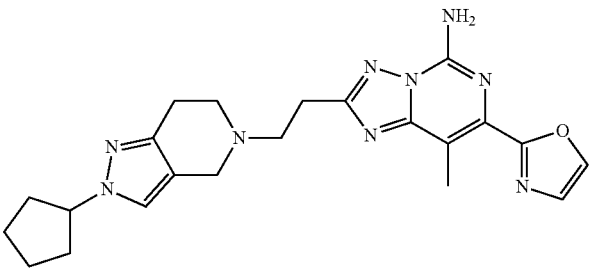 [SMILES: Cc1c(-c2ncco2)nc(N)n2nc(CCN3CCc4nn(C5CCCC5)cc4C3)nc12] 2-(2-(2-cyclopentyl-2,4,6,7-tetrahydro-5H-pyrazolo[4,3-c]pyridin-5-yl)ethyl)-8-methyl-7-(oxazol-2-yl)-[1,2,4]triazolo[1,5-c]pyrimidin-5-amine | 434.3 | 1.3 (A) 300.7 |

TABLE 29-continued

Examples Prepared According to General Scheme 4 and Scheme 17

| Example | Structure Name | Observed m/z [M + H]+ | A2a IC$_{50}$ (nM) A2b IC$_{50}$ (nM) |
|---|---|---|---|
| 17.12 | 2-(2-(1-cyclopentyl-1,4,6,7-tetrahydro-5H-pyrazolo[4,3-c]pyridin-5-yl)ethyl)-8-methyl-7-(oxazol-2-yl)-[1,2,4]triazolo[1,5-c]pyrimidin-5-amine | 434.3 | 1.2 (A) 45.0 |
| 17.13 | 2-(2-(1-cyclopentyl-1,4,6,7-tetrahydro-5H-[1,2,3]triazolo[4,5-c]pyridin-5-yl)ethyl)-8-methyl-7-(oxazol-2-yl)-[1,2,4]triazolo[1,5-c]pyrimidin-5-amine | 435.2 | 0.7 (A) 8.1 |
| 17.14 | 2-(2-(1-(3,3-difluorocyclobutyl)-1,4,6,7-tetrahydro-5H-[1,2,3]triazolo[4,5-c]pyridin-5-yl)ethyl)-8-methyl-7-(oxazol-2-yl)-[1,2,4]triazolo[1,5-c]pyrimidin-5-amine | 457.2 | 0.5 (A) 41.7 |
| 17.15 | 2-(2-(1-(bicyclo[1.1.1]pentan-1-yl)-1,4,6,7-tetrahydro-5H-[1,2,3]triazolo[4,5-c]pyridin-5-yl)ethyl)-8-methyl-7-(oxazol-2-yl)-[1,2,4]triazolo[1,5-c]pyrimidin-5-amine | 433.2 | 2.2 (A) 32.0 |
| 17.16 | | 364.2 | 1.2 (A) |

TABLE 29-continued

Examples Prepared According to General Scheme 4 and Scheme 17

| Example | Structure Name | Observed m/z [M + H]+ | A2a IC$_{50}$ (nM) A2b IC$_{50}$ (nM) |
|---|---|---|---|
| | 2-(2-(3,3-difluoropiperidin-1-yl)ethyl)-8-methyl-7-(oxazol-2-yl)-[1,2,4]triazolo[1,5-c]pyrimidin-5-amine | | 1105 |
| 17.17 | ethyl 1-(2-(5-amino-8-methyl-7-(oxazol-2-yl)-[1,2,4]triazolo[1,5-c]pyrimidin-2-yl)ethyl)-1H-pyrazole-4-carboxylate | 383.1 | 34.9 (A) 9666 |
| 17.18 | 2-(2-(1-cyclopentyl-1,4,6,7-tetrahydro-5H-imidazo[4,5-c]pyridin-5-yl)ethyl)-8-methyl-7-(oxazol-2-yl)-[1,2,4]triazolo[1,5-c]pyrimidin-5-amine | 434.3 | 0.6 (A) * |
| 17.19 | 2-(2-(3-cyclopentyl-3,4,6,7-tetrahydro-5H-imidazo[4,5-c]pyridin-5-yl)ethyl)-8-methyl-7-(oxazol-2-yl)-[1,2,4]triazolo[1,5-c]pyrimidin-5-amine | 434.3 | 3.0 (A) * |

Example 17.8-1/17.8-2

2-(2-(1-isopropyl-7-methyl-6,7-dihydro-1H-[1,2,3]triazolo[4,5-c]pyridin-5(4H)-yl)ethyl)-8-methyl-7-(oxazol-2-yl)-[1,2,4]triazolo[1,5-c]pyrimidin-5-amine was purified by CHIRAL-Prep SFC [Column: DAICEL CHIRALPAK AD-H, 250×30 mm: Gradient elution: 5-40% (0.1% Ethanolamine in EtOH)/CO$_2$ in for 5.5 min, followed by 40% (0.1% Ethanolamine in EtOH)/CO$_2$ for 3 min, then 5% (0.1% Ethanolamine in EtOH)/CO$_2$ for 1.5 min; Flow rate: 50 mL/min; Column temp: 40° C.; 220 nm; First Eluting Peak (17.8-1); Second Eluting Peak (17.8-2)].

Example 17.18/17.19

A mixture of 2-(2-(1-cyclopentyl-1,4,6,7-tetrahydro-5H-imidazo[4,5-c]pyridin-5-yl)ethyl)-8-methyl-7-(oxazol-2-yl)-[1,2,4]triazolo[1,5-c]pyrimidin-5-amine and 2-(2-(3-cyclopentyl-3,4,6,7-tetrahydro-5H-imidazo[4,5-c]pyridin-5-yl)ethyl)-8-methyl-7-(oxazol-2-yl)-[1,2,4]triazolo[1,5-c]pyrimidin-5-amine was purified by achiral Prep SFC [Column: CCA, 21×250 mm; 15% [MeOH w/0.1% NH$_4$OH]/CO$_2$; Flow rate: 70 mL/min; 220 nm; First Eluting Peak (17.19); Second Eluting Peak (17.18).

The following examples in Table 30 were prepared using the above procedure (Scheme 17) but using DIPEA as base in place of Na$_2$CO$_3$ in Step 1. Intermediates X.2, W.4, or X.3 were used in conjunction with the appropriate amine coupling partner, either commercially available or intermediate AD.1. Asterisk (*) indicates that A2b data is not available.

TABLE 30

Examples Prepared According to General Scheme 4 and Scheme 17 with a slightly modified procedure.

| Example | Structure Name | Observed m/z [M + H]$^+$ | A2a IC$_{50}$ (nM) A2b IC$_{50}$ (nM) |
|---|---|---|---|
| 17.20 | 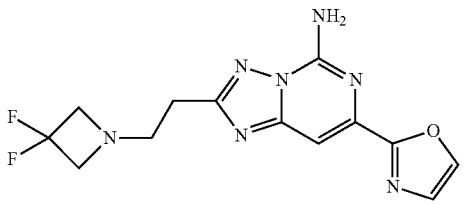 [SMILES: Nc1nc(-c2ncco2)cc2nc(CCN3CC(F)(F)C3)nn12]<br>2-(2-(3,3-difluoroazetidin-1-yl)ethyl)-7-(oxazol-2-yl)-[1,2,4]triazolo[1,5-c]pyrimidin-5-amine | 322.2 | 90.9 (A)<br>* |
| 17.21 | 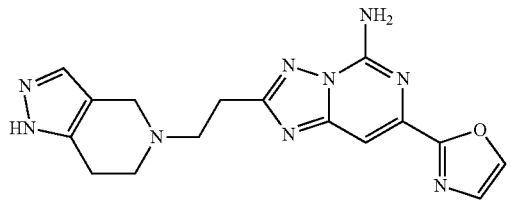 [SMILES: Nc1nc(-c2ncco2)cc2nc(CCN3CCc4[nH]ncc4C3)nn12]<br>7-(oxazol-2-yl)-2-(2-(1,4,6,7-tetrahydro-5H-pyrazolo[4,3-c]pyridin-5-yl)ethyl)-[1,2,4]triazolo[1,5-c]pyrimidin-5-amine | 352.1 | 449.6 (A)<br>* |
| 17.22 | 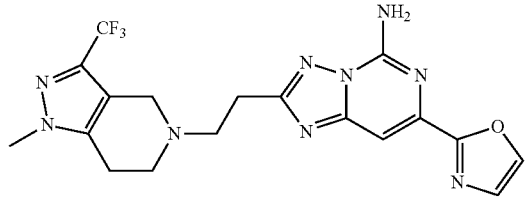 [SMILES: Cn1nc(C(F)(F)F)c2c1CCN(CCc1nc3cc(-c4ncco4)nc(N)n3n1)C2]<br>2-(2-(1-methyl-3-(trifluoromethyl)-1,4,6,7-tetrahydro-5H-pyrazolo[4,3-c]pyridin-5-yl)ethyl)-7-(oxazol-2-yl)-[1,2,4]triazolo[1,5-c]pyrimidin-5-amine | 434.1 | 78.9 (A)<br>* |
| 17.23 | 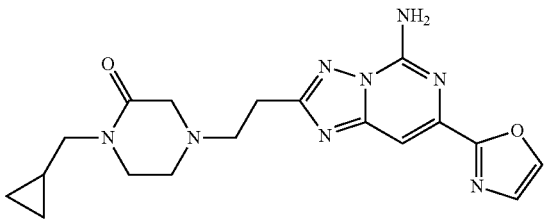 [SMILES: Nc1nc(-c2ncco2)cc2nc(CCN3CCN(CC4CC4)C(=O)C3)nn12]<br>4-(2-(5-amino-7-(oxazol-2-yl)-[1,2,4]triazolo[1,5-c]pyrimidin-2-yl)ethyl)-1-(cyclopropylmethyl)piperazin-2-one | 383.1 | 121.8 (A)<br>* |
| 17.24 | 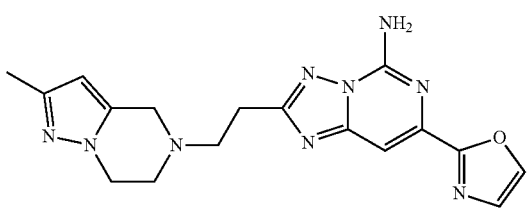 [SMILES: Cc1cc2n(n1)CCN(CCc1nc3cc(-c4ncco4)nc(N)n3n1)C2] | 366.1 | 319.0 (A) |

TABLE 30-continued

Examples Prepared According to General Scheme 4 and Scheme 17 with a slightly modified procedure.

| Example | Structure Name | Observed m/z [M + H]⁺ | A2a IC$_{50}$ (nM) A2b IC$_{50}$ (nM) |
|---|---|---|---|
| | 2-(2-(2-methyl-6,7-dihydropyrazolo[1,5-a]pyrazin-5(4H)-yl)ethyl)-7-(oxazol-2-yl)-[1,2,4]triazolo[1,5-c]pyrimidin-5-amine | | * |
| 17.25 | 2-(2-(7,8-dihydropyrido[3,4-b]pyrazin-6(5H)-yl)ethyl)-7-(oxazol-2-yl)-[1,2,4]triazolo[1,5-c]pyrimidin-5-amine | 364.1 | 402.3 (A) * |
| 17.26 | 2-(2-(3-isopropyl-5,6-dihydroimidazo[1,5-a]pyrazin-7(8H)-yl)ethyl)-6-(oxazol-2-yl)-[1,2,4]triazolo[1,5-a]pyrazin-8-amine | 394.2 | 628.7 (A) * |
| 17.27 | 2-(2-(3-cyclobutyl-5,6-dihydroimidazo[1,5-a]pyrazin-7(8H)-yl)ethyl)-7-phenyl-[1,2,4]triazolo[1,5-c]pyrimidin-5-amine | 415.0 | 39.9 (A) * |

217

Preparation of Example 18.6-6-4 fluorophenyl-2-(2-(3-isopropyl-5,6-dihydroimidazo[1,5-a]pyrazin-7(8H)-yl)ethyl)-5-methyl-[1,2,4] triazolo[1,5-a]pyrazin-8-amine, TEA Salt

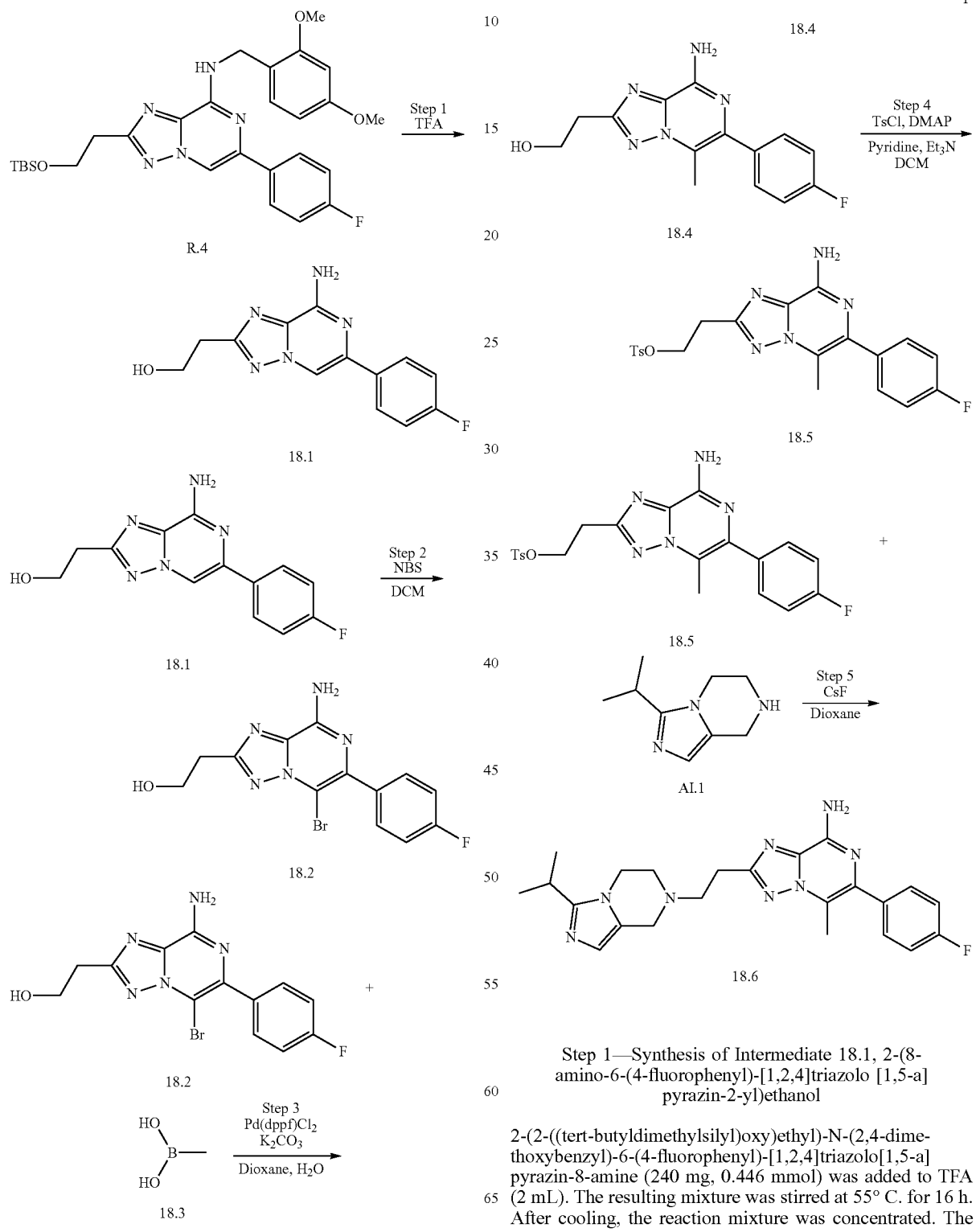

Step 1—Synthesis of Intermediate 18.1, 2-(8-amino-6-(4-fluorophenyl)-[1,2,4]triazolo [1,5-a]pyrazin-2-yl)ethanol 2-(2-((tert-butyldimethylsilyl)oxy)ethyl)-N-(2,4-dimethoxybenzyl)-6-(4-fluorophenyl)-[1,2,4]triazolo[1,5-a]pyrazin-8-amine (240 mg, 0.446 mmol) was added to TFA (2 mL). The resulting mixture was stirred at 55° C. for 16 h. After cooling, the reaction mixture was concentrated. The resulting crude residue was purified by preparative TLC (silica gel, elution: 9% MeOH/DCM) to provide 2-(8-amino-6-(4-fluorophenyl)-[1,2,4]triazolo [1,5-a]pyrazin-2-yl)ethanol. MS (ESI) calc'd for $C_{13}H_{13}FN_5O$ $[M+H]^+$ 274.1, found 274.1.

Step 2—Synthesis of Intermediate 18.2, 2-(8-amino-5-bromo-6-(4-fluorophenyl)-[1,2,4]triazolo[1,5-a]pyrazin-2-yl)ethanol NBS (56 mg, 0.315 mmol) was added to a stirred mixture of 2-(8-amino-6-(4-fluorophenyl)-[1,2,4] triazolo[1,5-a]pyrazin-2-yl)ethanol (85 mg, 0.311 mmol) in DCM (2 mL). The resulting mixture was stirred at 15° C. for 1 h. The reaction was quenched with sat. aq. $Na_2SO_3$ (5 mL) and the biphasic mixture was extracted with DCM (2×20 mL). The combined organic layers were washed with water (3×30 mL) and brine (10 mL), dried over anhydrous $Mg_2SO_4$, filtered, and concentrated. This provided 2-(8-amino-5-bromo-6-(4-fluorophenyl)-[1,2,4] triazolo[1,5-a]pyrazin-2-yl)ethanol, which was used in the next step without further purification. MS (ESI) calc'd for $C_{13}H_{12}BrFN_5O$ $[M+H]^+$ 352.0, found 352.0.

Step 3—Synthesis of Intermediate 18.4, 2-(8-amino-6-(4-fluorophenyl)-5-methyl-[1,2,4]triazolo [1,5-a]pyrazin-2-yl)ethanol $PdCl_2(dppf)$ (30 mg, 0.041 mmol) was added to a stirred mixture of methylboronic acid (70 mg, 1.169 mmol), 2-(8-amino-5-bromo-6-(4-fluorophenyl)-[1,2,4]triazolo[1,5-a]pyrazin-2-yl)ethanol (70 mg, 0.199 mmol), and potassium carbonate (82 mg, 0.596 mmol) in dioxane (1 mL). The resulting mixture was stirred at 125° C. under microwave irradiation for 1 h. After cooling, the mixture was extracted with EtOAc (10 mL). The organic layer was washed with brine (10 mL), dried over anhydrous $Mg_2SO_4$, filtered, and concentrated. The resulting crude residue was purified by preparative TLC (silica gel, elution: 10% MeOH/DCM) to provide 2-(8-amino-6-(4-fluorophenyl)-5-methyl-[1,2,4]triazolo[1,5-a]pyrazin-2-yl)ethanol. MS (ESI) calc'd for $C_{14}H_{15}FN_5O$ $[M+H]^+$ 288.1, found 288.2.

Step 4—Synthesis of Intermediate 18.5, 2-(8-amino-6-(4-fluorophenyl)-5-methyl-[1,2,4]triazolo [1,5-a]pyrazin-2-yl)ethyl 4-methylbenzenesulfonate TsCl (199 mg, 1.04 mmol) was added to a stirred mixture of 2-(8-amino-6-(4-fluorophenyl)-5-methyl-[1,2,4]triazolo[1,5-a]pyrazin-2-yl)ethanol (30 mg, 0.105 mmol), pyridine (0.026 mL, 0.316 mmol), DMAP (5 mg, 0.041 mmol)), and $Et_3N$ (0.22 mL, 1.57 mmol) in DCM (1.5 mL). The resulting mixture was stirred at 15° C. for 8 h. The reaction was quenched with HCl (1 M in $H_2O$, 5 mL) and the resulting biphasic mixture was extracted with DCM (20 mL). The organic layer was then washed with water (10 mL), dried over anhydrous $Mg_2SO_4$, filtered, and concentrated. The resulting crude residue was purified by preparative TLC (silica gel, elution: 9% MeOH/DCM) to provide 2-(8-amino-6-(4-fluorophenyl)-5-methyl-[1,2,4]triazolo[1,5-a]pyrazin-2-yl)ethyl 4-methylbenzenesulfonate. MS (ESI) calc'd for $C_{21}H_{21}FN_5O_3S$ $[M+H]^+$ 442.1, found 442.2.

Step 5—Synthesis of Example 18.6, 6-(4-fluorophenyl)-2-(2-(3-isopropyl-5,6-dihydroimidazo[1,5-a]pyrazin-7(8H)-yl)ethyl)-5-methyl-[1,2,4] triazolo[1,5-a]pyrazin-8-amine, TFA Salt Cesium fluoride (100 mg, 0.658 mmol) was added to a stirred mixture of 2-(8-amino-6-(4-fluorophenyl)-5-methyl-[1,2,4]triazolo[1,5-a]pyrazin-2-yl)ethyl 4-methylbenzenesulfonate (20 mg, 0.045 mmol) and 3-isopropyl-5,6,7,8-tetrahydroimidazo[1,5-a]pyrazine (30 mg, 0.182 mmol) in dioxane (1 mL). The resulting mixture was then stirred at 130° C. for 6 h. Upon cooling, the reaction mixture was purified by reversed-phase HPLC [Method A]. This provided 6-(4-fluorophenyl)-2-(2-(3-isopropyl-5,6-dihydroimidazo[1,5-a]pyrazin-7(8H)-yl)ethyl)-5-methyl-[1,2,4] triazolo[1,5-a]pyrazin-8-amine, TFA salt (Example 18.6). MS (ESI) calc'd for $C_{23}H_{28}FN_8$ $[M+H]^+$ 435.2, found 435.3. $^1H$ NMR (400 MHz, MeOD-$d_4$) δ 7.59 (dd, J=5.38, 8.80 Hz, 2H), 7.23-7.31 (m, 3H), 4.23 (t, J=5.62 Hz, 2H), 3.98 (s, 2H), 3.35-3.43 (m, 1H), 3.31-3.35 (m, 2H), 3.24 (br t, J=5.62 Hz, 2H), 2.55 (s, 3H), 1.38 (d, J=7.09 Hz, 6H). A2a $IC_{50}$ 345.9 nM.

Preparation of Example 19.3, 2-benzyl-8-methyl-7-(oxazol-2-yl)-[1,2,4]triazolo[1,5-c]pyrimidin-5-amine, TFA Salt

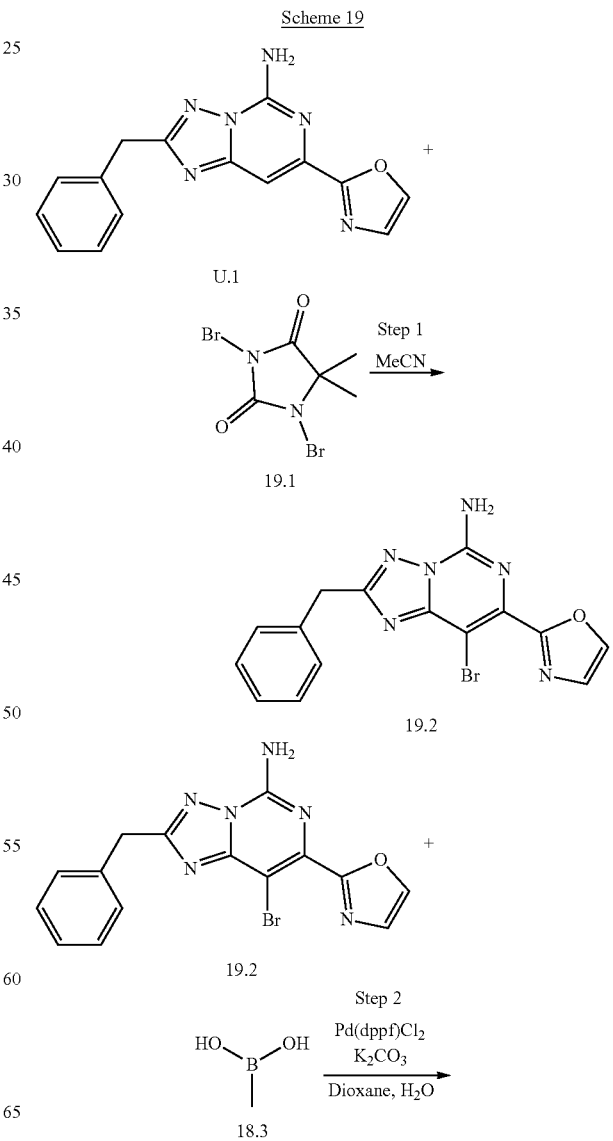

Scheme 19

-continued

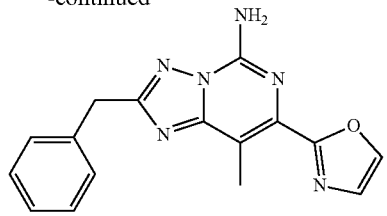

19.3

Step 1—Synthesis of Intermediate 19.2, 2-benzyl-8-bromo-7-(oxazol-2-yl)-[1,2,4]triazolo[1,5-c]pyrimidin-5-amine 1,3-dibromo-5,5-dimethylimidazolidine-2,4-dione (69.8 mg, 0.244 mmol) was added to a stirred solution of 2-benzyl-7-(oxazol-2-yl)-[1,2,4]triazolo[1,5-c]pyrimidin-5-amine (119 mg, 0.407 mmol) and TFA (0.06 mL, 0.814 mmol) in MeCN (1 mL). The resulting mixture was stirred at 25° C. for 4 h. The reaction was then concentrated and the resulting crude residue was purified by silica gel chromatography (elution: 100% EtOAc) to provide 2-benzyl-8-bromo-7-(oxazol-2-yl)-[1,2,4]triazolo[1,5-c]pyrimidin-5-amine. MS (ESI) m/z calc'd for $C_{15}H_{12}BrN_6O$ [M+H]$^+$ 371.0, found 371.0.

Step 2—Synthesis of Example 19.3, 2-benzyl-8-methyl-7-(oxazol-2-yl)-[1,2,4]triazolo[1,5-c]pyrimidin-5-amine, TFA Salt 2-benzyl-8-bromo-7-(oxazol-2-yl)-[1,2,4]triazolo[1,5-c]pyrimidin-5-amine (50 mg, 0.135 mmol), methylboronic acid (16 mg, 0.269 mmol), potassium carbonate (56 mg, 0.404 mmol), and Pd(dppf)Cl$_2$ (9.9 mg, 0.013 mmol) were combined. The reaction vessel was backfilled with nitrogen, and then dioxane (2.0 mL) and water (0.5 mL) were added. The reaction mixture was then stirred at 125° C. for 1 h under microwave irradiation. After cooling, the reaction mixture was filtered and concentrated, and the resulting crude residue was purified by reversed-phase HPLC [Method A]. This provided 2-benzyl-8-methyl-7-(oxazol-2-yl)-[1,2,4]triazolo[1,5-c]pyrimidin-5-amine, TFA salt (Example 19.3). MS (ESI) m/z calc'd for $C_{16}H_{15}N_6O$ [M+H]$^+$ 307.1, found 307.0. $^1$H NMR (400 MHz, CDCl$_3$): δ 7.83 (s, 1H), 7.45-7.28 (m, 4H), 7.27 (br s, 1H), 7.23 (br s, 1H), 4.29 (s, 2H), 2.85 (s, 3H). A2a IC$_{50}$ 0.5 nM (A).

Preparation of Example 20.2, 2-benzyl-5-methyl-6-(oxazol-2-yl)-[1,2,4]triazolo[1,5-a]pyrazin-8-amine, TFA Salt Scheme 20

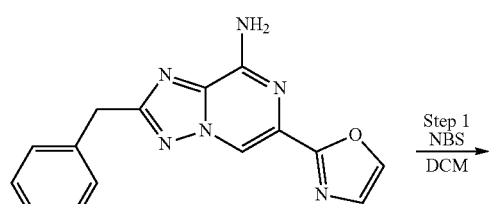

1.2

-continued

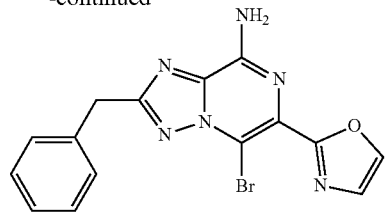

20.1

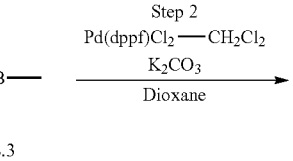

Step 2
Pd(dppf)Cl$_2$—CH$_2$Cl$_2$
K$_2$CO$_3$
Dioxane 20.2

Step 1—Synthesis of Intermediate 20.1, 2-benzyl-5-bromo-6-(oxazol-2-yl)-[1,2,4]triazolo[1,5-a]pyrazin-8-amine A 20 mL scintillation vial was charged with 2-benzyl-6-(oxazol-2-yl)-[1,2,4]triazolo[1,5-a]pyrazin-8-amine (105 mg, 0.359 mmol). DCM (4.8 mL) was added, followed by NBS (77 mg, 0.431 mmol), and the reaction mixture was stirred at 25° C. for 1 h. The reaction mixture was then concentrated and purified by silica gel chromatography (gradient elution: 0% to 10% MeOH/DCM) to provide 2-benzyl-5-bromo-6-(oxazol-2-yl)-[1,2,4]triazolo[1,5-a]pyrazin-8-amine. MS (ESI) m/z calc'd for $C_{18}H_{12}BrN_6O$ [M+H]$^+$ 371.0, found 371.0, 373.0.

Step 2—Synthesis of Example 20.2, 2-benzyl-5-methyl-6-(oxazol-2-yl)-[1,2,4]triazolo[1,5-a]pyrazin-8-amine, TFA Salt A 2 mL Biotage® microwave vial was charged with 2-benzyl-5-bromo-6-(oxazol-2-yl)-[1,2,4]triazolo[1,5-a]pyrazin-8-amine (40 mg, 0.108 mmol), methylboronic acid (12.9 mg, 0.216 mmol), potassium carbonate (45 mg, 0.323 mmol), and 1,1'-bis(diphenylphosphino)ferrocene-palladium(II)dichloride dichloromethane complex (17.6 mg, 0.022 mmol), and the vial was evacuated and backfilled with nitrogen (3×). A degassed [Method C] sample of dioxane (600 μL) was added and the reaction was heated to 125° C. overnight. The reaction was cooled to 25° C., and then DCM (5 mL) and water (5 mL) were added. The organic phase was separated, and the aq. phase was extracted with DCM (2×10 mL). The organic extracts were combined, dried over anhydrous $MgSO_4$, filtered, and concentrated. The resulting crude material was taken up in DMSO (2 mL), filtered, and purified via reversed-phase HPLC [Method A]. This provided 2-benzyl-5-methyl-6-(oxazol-2-yl)-[1,2,4]triazolo[1,5-a]pyrazin-8-amine, TFA salt (Example 20.2). MS (ESI) m/z calc'd for $C_{16}H_{15}N_6O$ $[M+H]^+$ 307.1, found 307.1. $^1H$ NMR (600 MHz, DMSO-$d_6$) δ 8.25 (s, 1H), 7.44 (s, 1H), 7.37-7.29 (m, 4H), 7.25-7.20 (m, 1H), 4.26 (s, 2H), 2.93 (s, 3H). A2a $IC_{50}$ 0.5 nM (A).

The following examples in Table 31 were prepared according to Scheme 20 and General Scheme 5 above, using Examples 2.3, 1.2, 2.7, or 2.23 and the appropriate commercial boronic acid coupling partner. Asterisk (*) indicates that A2b data is not available.

TABLE 31

Examples Prepared According to General Scheme 5 and Scheme 20

| Example | Structure Name | Observed m/z [M + H]$^+$ | A2a $IC_{50}$ (nM) A2b $IC_{50}$ (nM) |
|---|---|---|---|
| 20.3 | 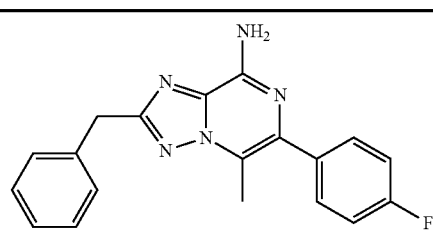<br>2-benzyl-6-(4-fluorophenyl)-5-methyl-[1,2,4]triazolo[1,5-a]pyrazin-8-amine | 334.1 | 40.0 (A) * |
| 20.4 | 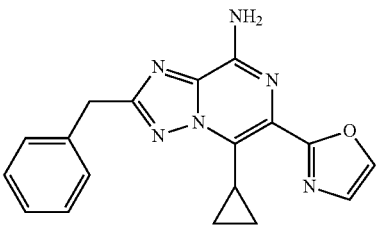 [SMILES: Nc1nc(-c2ncco2)c(C2CC2)n2nc(Cc3ccccc3)nc12]<br>2-benzyl-5-cyclopropyl-6-(oxazol-2-yl)-[1,2,4]triazolo[1,5-a]pyrazin-8-amine | 333.3 | 3.2 (A) * |
| 20.5 | 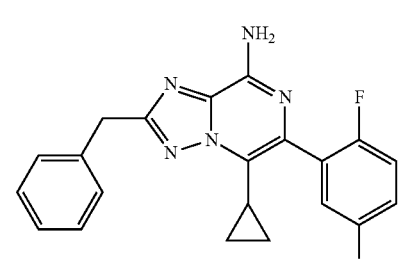<br>2-benzyl-5-cyclopropyl-6-(2,5-difluorophenyl)-[1,2,4]triazolo[1,5-a]pyrazin-8-amine | 378.3 | 13.5 (A) 117.0 |
| 20.6 | 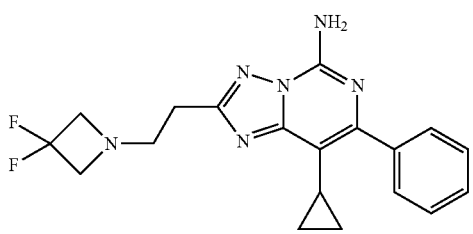 [SMILES: Nc1nc(-c2ccccc2)c(C2CC2)c2nc(CCN3CC(F)(F)C3)nn12]<br>8-cyclopropyl-2-(2-(3,3-difluoroazetidin-1-yl)ethyl)-7-phenyl-[1,2,4]triazolo[1,5-c]pyrimidin-5-amine | 370 | 121.8 (C) * |

225

Preparation of Example 21.3, 4-(1-((5-amino-8-methyl-7-(oxazol-2-yl)-[1,2,4]triazolo[1,5-c]pyrimidin-2-yl)methyl)-1H-pyrazol-4-yl)-2-methylbutan-2-ol

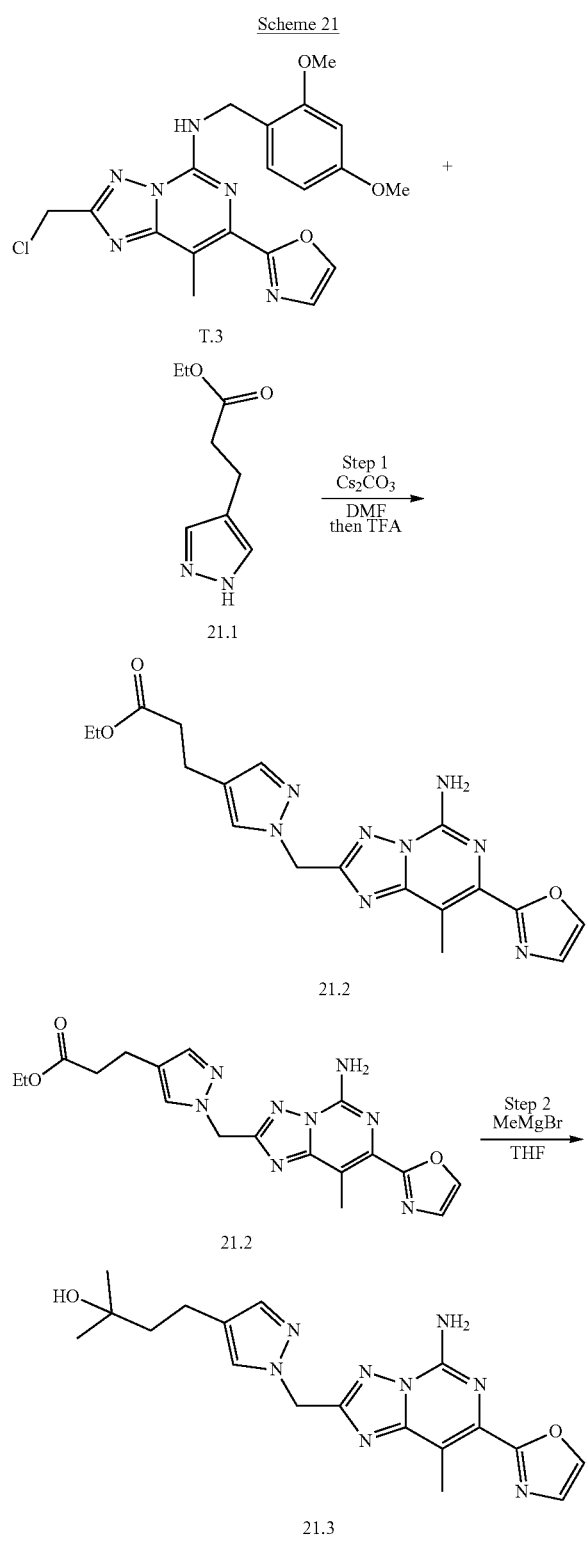

226

Step 1—Synthesis of Intermediate 21.2, ethyl 3-(1-((5-amino-8-methyl-7-(oxazol-2-yl)-[1,2,4]triazolo[1,5-c]pyrimidin-2-yl)methyl)-1H-pyrazol-4-yl)propanoate A stirring solution of 2-(chloromethyl)-N-(2,4-dimethoxybenzyl)-8-methyl-7-(oxazol-2-yl)-[1,2,4]triazolo[1,5-c]pyrimidin-5-amine (95 mg, 0.23 mmol) and ethyl 3-(1H-pyrazol-4-yl)propanoate (100 mg, 0.60 mmol) in DMF (1.5 mL) was treated with $Cs_2CO_3$ (224 mg, 0.69 mmol). The resulting mixture was stirred at 85° C. for 4 h. After cooling, the reaction mixture was diluted with water (10 mL) and extracted with EtOAc (3×20 mL). The combined organic layers were washed with 1% aq. LiCl (20 mL), dried over anhydrous $Mg_2SO_4$, filtered, and concentrated. The residue was then dissolved in TFA (2 mL), and the resulting mixture was stirred at 60° C. for 2 h. After cooling, the mixture was directly concentrated. The residue was taken up in DMSO (4 mL), filtered and purified via reversed-phase HPLC [Method B]. This provided ethyl 3-(1-((5-amino-8-methyl-7-(oxazol-2-yl)-[1,2,4]triazolo[1,5-c]pyrimidin-2-yl)methyl)-1H-pyrazol-4-yl)propanoate. MS (ESI) m/z calc'd for $C_{18}H_{21}N_8O_3$ [M+H]$^+$ 397.2, found 397.2.

Step 2—Preparation of Example 21.3, 4-(1-((5-amino-8-methyl-7-(oxazol-2-yl)-[1,2,4]triazolo[1,5-c]pyrimidin-2-yl)methyl)-1H-pyrazol-4-yl)-2-methylbutan-2-ol A solution of ethyl 3-(1-((5-amino-8-methyl-7-(oxazol-2-yl)-[1,2,4]triazolo[1,5-c]pyrimidin-2-yl)methyl)-1H-pyrazol-4-yl)propanoate (25 mg, 0.063 mmol) in THF (1.0 ml) was cooled to 0° C. and methylmagnesium bromide (3 M in $Et_2O$, 0.11 ml, 0.32 mmol) was slowly added. The resulting reaction mixture was stirred over 2 h while warming to 25° C. The reaction was then cooled to 0° C. and quenched with sat. aq. $NH_4Cl$ (0.25 ml), diluted with water and extracted with EtOAc (3×5 mL). The combined organic layers were dried over anhydrous $Mg_2SO_4$, filtered, and concentrated. The resulting crude residue was dissolved in a 1:1 mixture of DMSO and MeOH (3 mL), filtered and purified via reversed-phase HPLC [Method B]. This provided 4-(1-((5-amino-8-methyl-7-(oxazol-2-yl)-[1,2,4]triazolo[1,5-c]pyrimidin-2-yl)methyl)-1H-pyrazol-4-yl)-2-methylbutan-2-ol (Example 21.3). MS (ESI) m/z calc'd for $C_{18}H_{23}N_8O_2$ [M+H]$^+$ 383.2, found 383.2. $^1$H NMR (500 MHz, DMSO-$d_6$) δ 8.30 (s, 1H), 7.94 (s, 2H), 7.63 (s, 1H), 7.51 (s, 1H), 7.28 (s, 1H), 5.50 (s, 2H), 4.19 (s, 1H), 2.67 (s, 3H), 2.48-2.40 (m, 2H), 1.66-1.56 (m, 2H), 1.12 (s, 6H). A2a IC$_{50}$ 21.5 nM (A).

Preparation of Example 22.3, 2-(2-(1-(3,3-Difluorocyclobutyl)-1H-benzo[d][1,2,3]triazol-5-yl)ethyl)-8-methyl-7-(oxazol-2-yl)-[1,2,4]triazolo[1,5-c]pyrimidin-5-amine

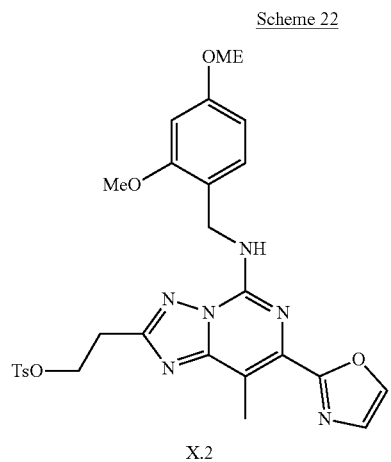

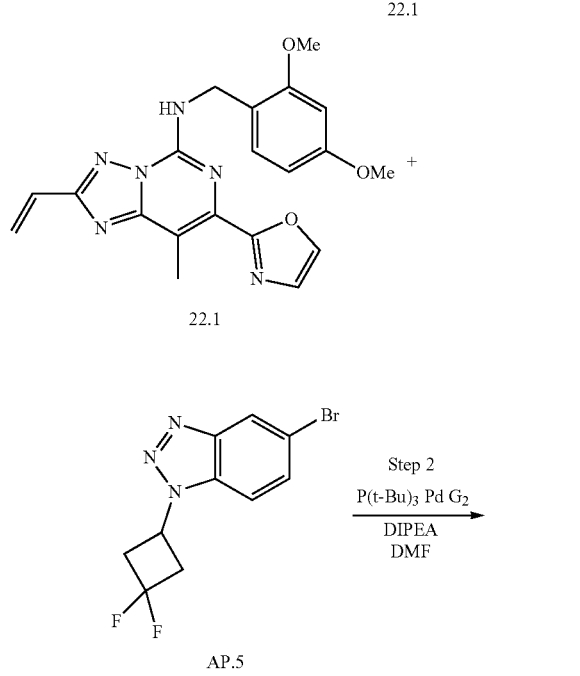

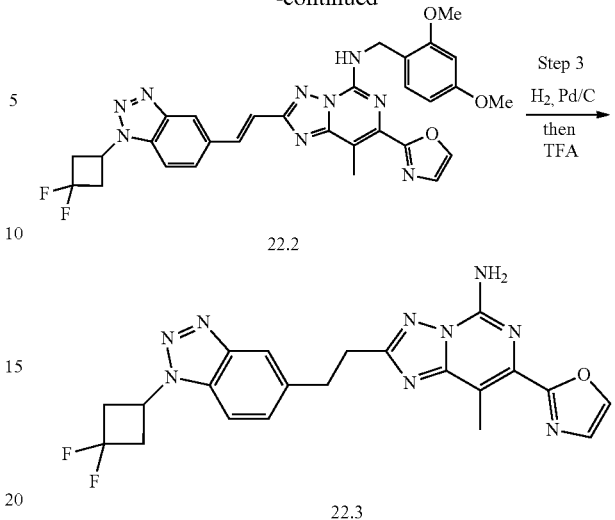

Step 1—Synthesis of Intermediate 22.1, N-(2,4-dimethoxybenzyl)-8-methyl-7-(oxazol-2-yl)-2-vinyl-[1,2,4]triazolo[1,5-c]pyrimidin-5-amine A 20 mL scintillation vial was charged with 2-(5-((2,4-dimethoxybenzyl)amino)-8-methyl-7-(oxazol-2-yl)-[1,2,4]triazolo[1,5-c]pyrimidin-2-yl)ethyl methanesulfonate (1.41 g, 2.89 mmol) and DCE (8.9 ml). DBU (0.87 ml, 5.77 mmol) was then added. The resulting grey slurry was stirred at 70° C. for 3 h. The reaction mixture was then cooled, diluted with DCM (20 mL), washed with aq. citric acid (1M, 2×15 mL), dried over anhydrous MgSO$_4$, filtered, and concentrated. The resulting crude residue was purified by silica gel chromatography (gradient elution: 5-50% [3:1 EtOAc; EtOH]/Hexanes) to provide N-(2,4-dimethoxybenzyl)-8-methyl-7-(oxazol-2-yl)-2-vinyl-[1,2,4]triazolo[1,5-c]pyrimidin-5-amine. MS (ESI) m/z calc'd for $C_{20}H_{21}N_6O_3$ [M+H]$^+$ 392.2, found 392.3.

Step 2—Synthesis of Intermediate 22.2, (E)-2-(2-(1-(3,3-difluorocyclobutyl)-1H-benzo[d][1,2,3]triazol-5-yl)vinyl)-N-(2,4-dimethoxybenzyl)-8-methyl-7-(oxazol-2-yl)-[1,2,4]triazolo[1,5-c]pyrimidin-5-amine An 8 mL vial with a stir bar was charged with N-(2,4-dimethoxybenzyl)-8-methyl-7-(oxazol-2-yl)-2-vinyl-[1,2,4]triazolo[1,5-c]pyrimidin-5-amine (120 mg, 0.306 mmol), 5-bromo-1-(3,3-difluorocyclobutyl)-1H-benzo[d][1,2,3]triazole (97 mg, 0.336 mmol), P(t-Bu)3 Pd G2 (15.67 mg, 0.031 mmol), and DIPEA (107 μl, 0.612 mmol). DMF (1.5 mL) was added, and nitrogen was bubbled through the reaction mixture for 5 min. The reaction was then stirred at 100° C. for 90 min. Upon completion, the mixture was concentrated, and the residue was taken up in EtOAc (30 mL), then washed with H$_2$O (2×20 mL) and brine (15 mL). The organic layer was then dried over anhydrous MgSO$_4$ concentrated. The resulting crude residue was purified via silica gel chromatography (gradient elution: 15-80% EtOAc/Hexanes) to provide (E)-2-(2-(1-(3,3-difluorocyclobutyl)-1H-benzo[d][1,2,3]triazol-5-yl)vinyl)-N-(2,4-dimethoxybenzyl)-8-methyl-7-(oxazol-2-yl)-[1,2,4]triazolo[1,5-c]pyrimidin-5-amine. MS (ESI) m/z calc'd for $C_{30}H_{28}F_2N_9O_3$ [M+H]$^+$ 600.2, found 600.3.

Step 3—Preparation of Example 22.3, 2-(2-(1-(3,3-Difluorocyclobutyl)-1H-benzo[d][1,2,3]triazol-5-yl)ethyl)-8-methyl-7-(oxazol-2-yl)-[1,2,4]triazolo[1,5-c]pyrimidin-5-amine A solution of (E)-2-(2-(1-(3,3-difluorocyclobutyl)-1H-benzo[d][1,2,3]triazol-5-yl)vinyl)-N-(2,4-dimethoxybenzyl)-8-methyl-7-(oxazol-2-yl)-[1,2,4]triazolo[1,5-c]pyrimidin-5-amine (220 mg, 0.367 mmol) in dioxane (9.2 mL) was recycled through a H-cube mini (1 mL/min flow rate) at 50° C. and 50 bar system pressure using a Pd/C cartridge for 30 min. After completion of the reaction, the mixture was concentrated, and the resulting crude residue was treated with TFA (0.5 mL). The resulting mixture was stirred at 70° C. for 1 h, then was cooled and concentrated. The residue was purified via reversed-phase HPLC [Method B]. This provided 2-(2-(1-(3,3-difluorocyclobutyl)-1H-benzo[d][1,2,3]triazol-5-yl)ethyl)-8-methyl-7-(oxazol-2-yl)-[1,2,4]triazolo[1,5-c]pyrimidin-5-amine (Example 22.3). MS (ESI) m/z calc'd for $C_{21}H_{20}F_2N_9O$ [M+H]$^+$ 452.2, found 452.3. A2a IC$_{50}$ 21.5 nM (A).

Preparation of Example 23.7, 7-(3-fluorophenyl)-2-(2-(1-isopropyl-1,4,6,7-tetrahydro-5H-[1,2,3]triazolo[4,5-c]pyridin-5-yl)ethyl)-8-(trifluoromethyl)-[1,2,4]triazolo[1,5-c]pyrimidin-5-amine

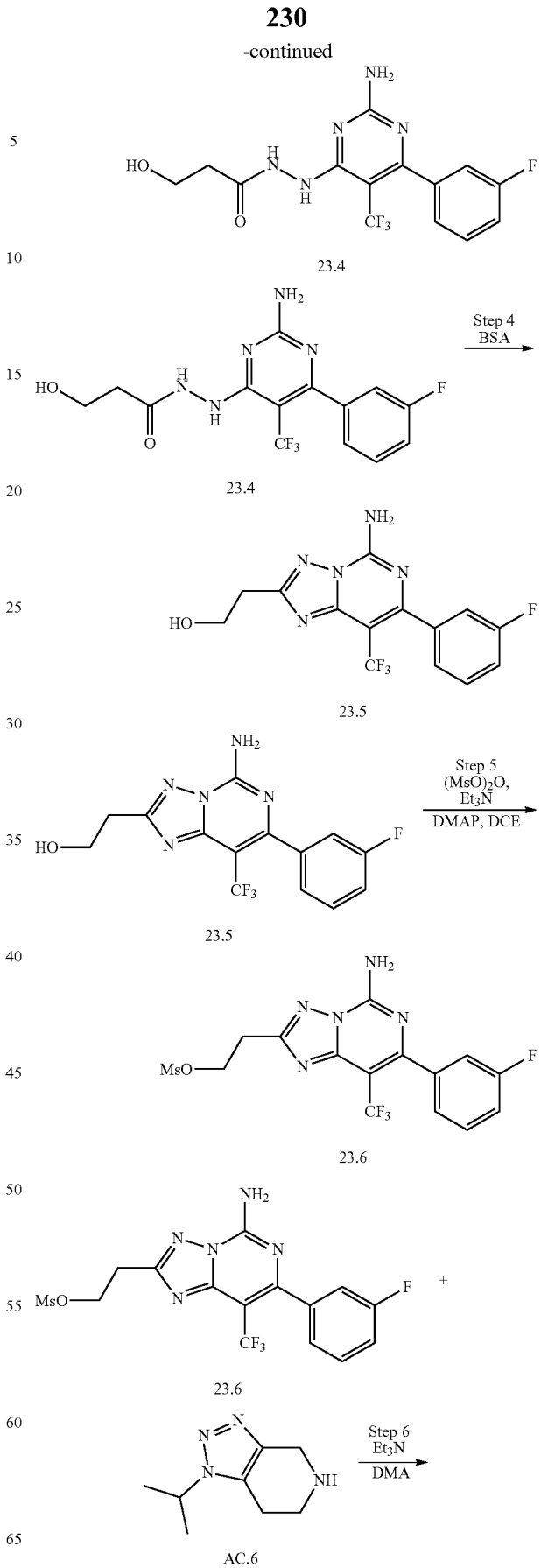
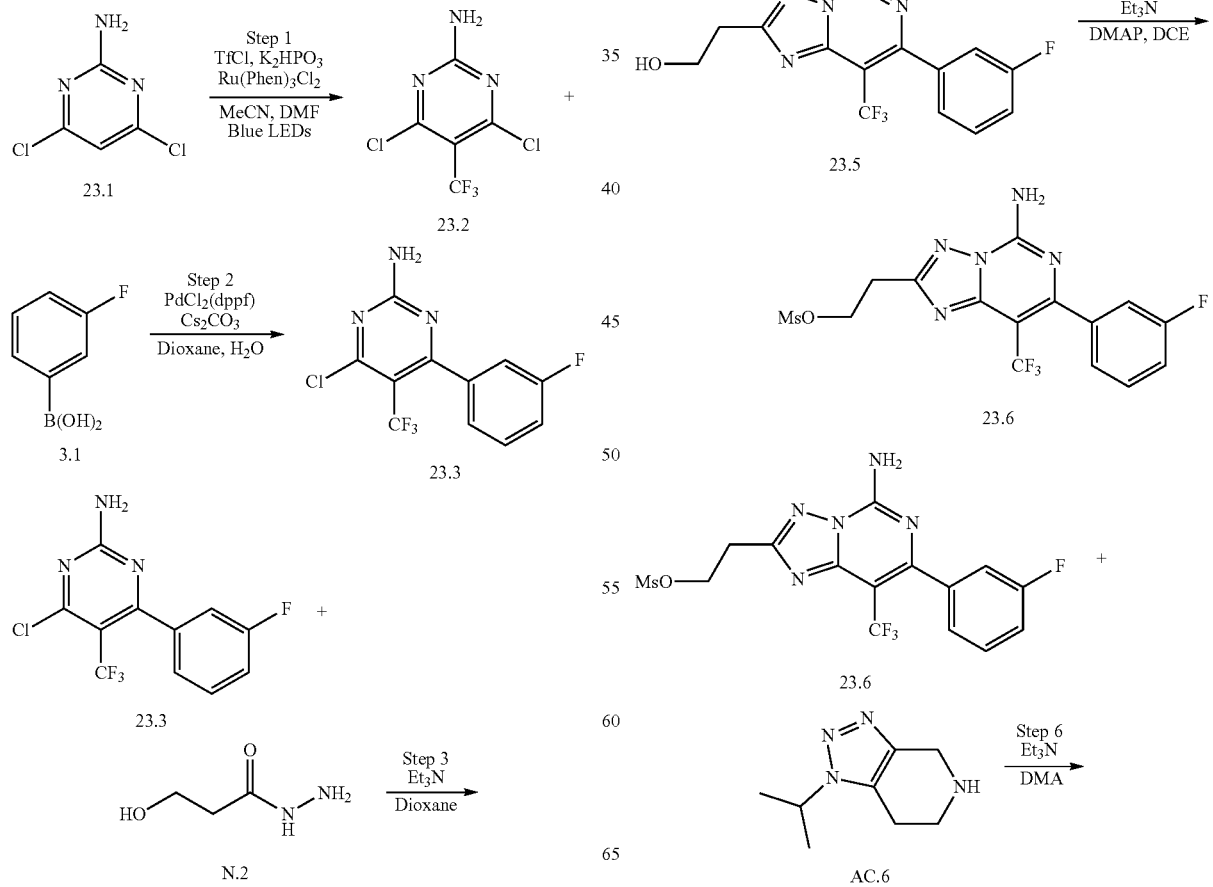

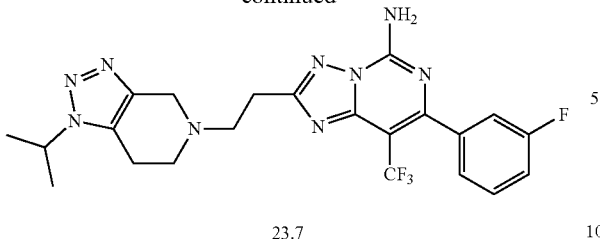

23.7

Step 1—Synthesis of Intermediate 23.2, 4,6-dichloro-5-(trifluoromethyl)pyrimidin-2-amine A 40 mL scintillation vial with a stir bar was charged with 4,6-dichloropyrimidin-2-amine (1.16 g, 7.07 mmol), Ru(Phen)$_3$Cl$_2$ (51 mg, 0.071 mmol) and potassium hydrogen phosphate (6.16 g, 35.4 mmol). The vial was evacuated and backfilled with nitrogen (3×). MeCN (27 mL) and DMF (1.1 mL) were added, and the mixture was degassed by bubbling nitrogen for 10 min. The reaction was then cooled to 0° C., and deoxygenated (flushed with nitrogen at 0° C.). Trifluoromethanesulfonyl chloride (3.01 ml, 28.3 mmol) was added. The reaction mixture was then sealed and irradiated with blue LED lights for 8 h at 30° C. After completion of the reaction, the mixture was filtered and concentrated. The resulting crude residue was purified by silica gel chromatography (gradient elution: 0-70% EtOAc/Hexanes) to provide 4,6-dichloro-5-(trifluoromethyl)pyrimidin-2-amine. MS (ESI) m/z calc'd for C$_5$H$_3$Cl$_2$F$_3$N$_3$ [M+H]$^+$ 233.0, found 233.1.

Step 2—Synthesis of Intermediate 23.3, 4-chloro-6-(3-fluorophenyl)-5-(trifluoromethyl)pyrimidin-2-amine A 20 mL scintillation vial equipped with a stir bar was charged with 4,6-dichloro-5-(trifluoromethyl)pyrimidin-2-amine (120 mg, 0.517 mmol), (3-fluorophenyl)boronic acid (76 mg, 0.543 mmol), PdCl$_2$(dppf)-CH$_2$Cl$_2$ (63.4 mg, 0.078 mmol) and Cs$_2$CO$_3$ (506 mg, 1.552 mmol). The vial was evacuated and backfilled with nitrogen (5×). Dioxane (4.3 mL) and water (0.86 mL) were added and the resulting mixture was stirred at 90° C. for 4 h. The reaction mixture was then cooled and concentrated, and the resulting crude residue was purified by silica gel chromatography (gradient elution: 5-40% [3:1 EtOAc:EtOH/Hexanes) to provide 4-chloro-6-(3-fluorophenyl)-5-(trifluoromethyl)pyrimidin-2-amine. MS (ESI) m/z calc'd for C$_{11}$H$_7$ClF$_4$N$_3$ [M+H]$^+$ 292.0, found 292.1.

Step 3—Synthesis of Intermediate 23.4, N'-(2-amino-6-(3-fluorophenyl)-5-(trifluoromethyl)pyrimidin-4-yl)-3-hydroxypropanehydrazide A 100 mL round bottom flask was charged with 4-chloro-6-(3-fluorophenyl)-5-(trifluoromethyl)pyrimidin-2-amine (210 mg, 0.720 mmol) and 3-hydroxypropanehydrazide (210 mg, 2.016 mmol). Dioxane (2.4 mL) and Et$_3$N (502 µL, 3.60 mmol) were then added. The reaction mixture was stirred at 80° C. for 20 h. The reaction mixture was then directly concentrated to provide N-(2-amino-6-(3-fluorophenyl)-5-(trifluoromethyl)pyrimidin-4-yl)-3-hydroxypropanehydrazide, which was used in the subsequent reaction without further purification. MS (ESI) m/z calc'd for C$_{14}$H$_{14}$F$_4$N$_5$O$_2$[M+H]$^+$ 360.0, found 360.1.

Step 4—Synthesis of Intermediate 23.5, 2-(5-amino-7-(3-fluorophenyl)-8-(trifluoromethyl)-[1,2,4]triazolo[1,5-c]pyrimidin-2-yl)ethan-1-ol A 20 mL scintillation vial equipped with a stir bar was charged with N-(2-amino-6-(3-fluorophenyl)-5-(trifluoromethyl)pyrimidin-4-yl)-3-hydroxypropanehydrazide (250 mg, 0.696 mmol). BSA (1.7 mL, 6.96 mmol) was added, and the resulting mixture was sealed and stirred at 120° C. overnight. Upon completion of the reaction, the mixture was cooled and concentrated. The resulting crude residue was taken up in DCM (10 mL) and washed with sat. aq. NaHCO$_3$ (10 mL). The organic layer was dried over anhydrous MgSO$_4$, filtered, and concentrated. The resulting crude residue was purified by silica gel chromatography (gradient elution: 5-40% [3:1 EtOAc:EtOH]/Hexanes) to provide 2-(5-amino-7-(3-fluorophenyl)-8-(trifluoromethyl)-[1,2,4]triazolo[1,5-c]pyrimidin-2-yl)ethan-1-ol. MS (ESI) m/z calc'd for C$_{14}$H$_{12}$F$_4$N$_5$O [M+H]$^+$ 342.0, found 342.1.

Step 5—Synthesis of Intermediate 23.6, 2-(5-amino-7-(3-fluorophenyl)-8-(trifluoromethyl)-[1,2,4]triazolo[1,5-c]pyrimidin-2-yl)ethyl methanesulfonate A 20 mL scintillation vial equipped with a stir bar was charged with 2-(5-amino-7-(3-fluorophenyl)-8-(trifluoromethyl)-[1,2,4]triazolo[1,5-c]pyrimidin-2-yl)ethan-1-ol (105 mg, 0.308 mmol), methanesulfonic anhydride (53.6 mg, 0.308 mmol), DMAP (18.8 mg, 0.154 mmol), and Et$_3$N (52 µL, 0.369 mmol). DCE (3 mL) was then added and the resulting mixture was sealed and stirred at 60° C. overnight. Upon completion, the reaction mixture was directly concentrated to provide 2-(5-amino-7-(3-fluorophenyl)-8-(trifluoromethyl)-[1,2,4]triazolo[1,5-c]pyrimidin-2-yl)ethyl methanesulfonate, which was used directly in the subsequent reaction without further purification. MS (ESI) m/z calc'd for C$_{15}$H$_{14}$F$_4$N$_5$O$_3$S [M+H]$^+$ 420.0, found 420.1.

Step 6—Preparation of Example 23.7, 7-(3-fluorophenyl)-2-(2-(1-isopropyl-1,4,6,7-tetrahydro-5H-[1,2,3]triazolo[4,5-c]pyridin-5-yl)ethyl)-8-(trifluoromethyl)-[1,2,4]triazolo[1,5-c]pyrimidin-5-amine An 8 mL scintillation vial equipped with a stir bar was charged with 2-(5-Amino-7-(3-fluorophenyl)-8-(trifluoromethyl)-[1,2,4]triazolo[1,5-c]pyrimidin-2-yl)ethyl methanesulfonate (22 mg, 0.052 mmol) and 1-isopropyl-4,5,6,7-tetrahydro-1H-[1,2,3]triazolo[4,5-c]pyridine (21.8 mg, 0.131 mmol). DMA (525 µL) was then added, followed by Et$_3$N (21.9 µL, 0.157 mmol), and the reaction mixture was then stirred at 70° C. overnight. Upon completion, the reaction was cooled and concentrated. The resulting crude residue was purified by silica gel chromatography (gradient elution: 10-75% [3:1 EtOAc:EtOH]/Hexanes) to provide 7-(3-fluorophenyl)-2-(2-(1-isopropyl-1,4,6,7-tetrahydro-5H-[1,2,3]triazolo[4,5-c]pyridin-5-yl)ethyl)-8-(trifluoromethyl)-[1,2,4]triazolo[1,5-c]pyrimidin-5-amine (Example 23.7). MS (ESI) m/z calc'd for C$_{22}$H$_{24}$F$_4$N$_9$ [M+H]$^+$ 490.1, found 490.2. $^1$H NMR (500 MHz, DMSO-d$_6$) δ 7.51 (td, J=8.0, 6.2 Hz, 1H), 7.34-7.27 (m, 3H), 4.68-4.57 (m, 1H), 3.64 (s, 2H), 3.16-3.10 (m, 2H), 3.08-3.01 (m, 2H), 2.85 (t, J=5.7 Hz, 2H), 2.75 (t, J=5.6 Hz, 2H), 1.46 (d, J=6.7 Hz, 6H). A2a IC$_{50}$ 0.9 nM (A), A2b IC$_{50}$ 52.8 nM.

Reverse Phase Prep-HPLC Methods:
Method A—TFA Modifier
C18 reversed-phase Prep-HPLC (gradient elution, MeCN/H$_2$O/0.1% TFA). Electrospray (ESI) Mass-triggered fraction collection was employed using positive ion polarity scanning to monitor for the target mass.
Method B—Basic Modifier
C18 reversed-phase Prep-HPLC (gradient elution, MeCN/H$_2$O/basic modifier—either 0.1% NH$_4$OH or 0.05% NH$_4$HCO$_3$). Electrospray (ESI) Mass-triggered fraction collection was employed using positive ion polarity scanning to monitor for the target mass.

What is claimed is:
1. A compound having a structural Formula (IA):

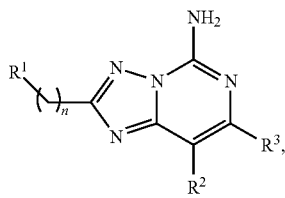

or a pharmaceutically acceptable salt thereof, wherein:
n is 1 or 2;
R$^1$ is selected from:
H,
OH,
S(O)$_2$R$^{1C}$, wherein R$^{1C}$ is selected from (C$_1$-C$_6$)alkyl and (C$_3$-C$_5$)cycloalkyl;
phenyl fused to a 5 or 6 membered partially or fully unsaturated ring comprising 1, 2, or 3 ring heteroatoms independently selected from N, O, and S, wherein said fused phenyl is unsubstituted or substituted with 1, 2, or 3 R$^{1AB}$ groups,
N(R$^{1A}$)(R$^{1B}$), and
C(O)N(R$^{1A}$)(R$^{1B}$), wherein:
R$^{1A}$ is selected from H, (C$_1$-C$_6$)alkyl, and (C$_1$-C$_6$)haloalkyl;
R$^{1B}$ is selected from —CH$_2$phenyl and —CH$_2$heteroaryl, wherein said —CH$_2$phenyl, and said —CH$_2$heteroaryl are unsubstituted or substituted with 1, 2 or 3 groups independently selected from (C$_1$-C$_6$)alkyl, (C$_1$-C$_6$)haloalkyl, and (C$_1$-C$_6$)alkyl-OH;
or, alternatively, R$^{1A}$ and R$^{1B}$ in each of said N(R$^{1A}$)(R$^{1B}$) and said C(O)N(R$^{1A}$)(R$^{1B}$) of R$^1$ are taken together with the nitrogen atom to which they are shown attached to form a 4, 5, or 6 membered monocyclic heterocycloalkyl ring comprising 1 or 2 ring nitrogen atoms (including the nitrogen atom of N(R$^{1A}$)(R$^{1B}$) and of C(O)N(R$^{1A}$)(R$^{1B}$)), wherein said monocyclic heterocycloalkyl ring is optionally fused to a 5 or 6 membered ring, which fused ring is partially or fully unsaturated and comprises 1, 2, or 3 additional ring heteroatoms independently selected from N, O, and S, and wherein said optionally fused heterocycloalkyl ring is unsubstituted or substituted with 1, 2, or 3 R$^{1AB}$ groups,
each R$^{1AB}$ group is independently selected from:
F, Cl, OH, CN, oxo, (C$_1$-C$_6$)alkyl, O(C$_1$-C$_6$)alkyl, (C$_1$-C$_6$)alkyl-OH, (C$_1$-C$_6$)haloalkyl, O(C$_1$-C$_6$)haloalkyl, C(O)O(C$_1$-C$_6$)alkyl, (C$_3$-C$_6$)cycloalkyl, (C$_1$-C$_4$)alkyl(C$_3$-C$_6$)cycloalkyl, C(O)(C$_3$-C$_6$)cycloalkyl, and heteroaryl, wherein said cycloalkyl and said heteroaryl portions of R$^{1AB}$ are unsubstituted or further substituted with 1, 2, or 3 R$^{ab}$ groups independently selected from F, OH, (C$_1$-C$_4$)alkyl, and O(C$_1$-C$_6$)alkyl;
R$^2$ is selected from H, (C$_1$-C$_6$)alkyl, and (C$_3$-C$_4$)cycloalkyl,
wherein each said (C$_1$-C$_6$)alkyl, and (C$_3$-C$_6$)cycloalkyl of R$^2$ is unsubstituted or substituted with 1, 2, or 3 R$^{2A}$ groups,
wherein each R$^{2A}$ group is independently selected from F, Cl, OH, oxo, (C$_1$-C$_6$)alkyl, O(C$_1$-C$_6$)alkyl, (C$_1$-C$_6$)alkyl-OH, and (C$_1$-C$_6$)haloalkyl, and
R$^3$ is selected from phenyl and heteroaryl, wherein said heteroaryl is a 4, 5 or 6 membered monocyclic ring comprising 1, 2, or 3 ring heteroatoms selected from N, O, and S,
wherein said phenyl and said heteroaryl of R$^3$ are each unsubstituted or substituted with 1, 2, or 3 R$^{3A}$ groups, and
wherein each R$^{3A}$ group is independently selected from the group consisting of F, Cl, OH, CN, (C$_1$-C$_6$)alkyl, (C$_1$-C$_6$)haloalkyl, O(C$_1$-C$_6$)alkyl, and O(C$_1$-C$_6$)haloalkyl;
provided that, in Formula (IA), when R$^1$ is:
OH,
then each R$^{3A}$ group is independently selected from the group consisting of F, Cl, OH, (C$_1$-C$_6$)alkyl, (C$_1$-C$_6$)haloalkyl, O(C$_1$-C$_6$)alkyl, and O(C$_1$-C$_6$)haloalkyl.
2. The compound of claim 1, or a pharmaceutically acceptable salt thereof, wherein
n is 2; and
R$^1$ is S(O)$_2$R$^{1C}$, wherein R$^{1C}$ is selected from (C$_1$-C$_6$)alkyl and (C$_3$C$_5$)cycloalkyl.
3. The compound of claim 1, or a pharmaceutically acceptable salt thereof, wherein
n is 1; and
R$^1$ is phenyl fused to a 5 or 6 membered partially or fully unsaturated ring comprising 1, 2, or 3 ring heteroatoms independently selected from N, O, and S, wherein said fused phenyl is unsubstituted or substituted with 1, 2, or 3 R$^{1AB}$ groups.
4. The compound of claim 1, or a pharmaceutically acceptable salt thereof, wherein
n is 1;
R$^1$ is selected from N(R$^{1A}$)(R$^{1B}$) and C(O)N(R$^{1A}$)(R$^{1B}$), wherein:
R$^{1A}$ is selected from H, (C$_1$-C$_6$)alkyl, and (C$_1$-C$_6$)haloalkyl;
R$^{1B}$ is selected from —CH$_2$-phenyl and —CH$_2$-heteroaryl, wherein said —CH$_2$-phenyl, and said —CH$_2$-heteroaryl are unsubstituted or substituted with 1 or 2 groups independently selected from (C$_1$-C$_6$)alkyl, (C$_1$-C$_6$)haloalkyl, and (C$_1$-C$_6$)alkyl-OH.
5. The compound of claim 1, or a pharmaceutically acceptable salt thereof, wherein
n is 1 or 2;
R$^1$ is selected from N(R$^{1A}$)(R$^{1B}$) and C(O)N(R$^{1A}$)(R$^{1B}$), wherein:
R$^{1A}$ and R$^{1B}$ in each of said N(R$^{1A}$)(R$^{1B}$) and said C(O)N(R$^{1A}$)(R$^{1B}$) of R$^1$ are taken together with the nitrogen atom to which they are shown attached to form a 4, 5, or 6 membered monocyclic heterocycloalkyl ring comprising 1 or 2 ring nitrogen atoms (including the nitrogen atom of N(R$^{1A}$)(R$^{1B}$) and of C(O)N(R$^{1A}$)(R$^{1B}$)), wherein said monocyclic heterocycloalkyl ring is optionally fused to a 5 or 6 membered ring, which fused ring is partially or fully unsaturated and comprises 1, 2, or 3 additional ring heteroatoms independently selected from N, O, and S, and wherein said optionally fused heterocycloalkyl ring is unsubstituted or substituted with 1, 2, or 3 $R^{1AB}$ groups.

6. The compound of claim 1, or a pharmaceutically acceptable salt thereof, wherein
$R^1$ is selected from H and OH.

7. The compound of claim 1, or a pharmaceutically acceptable salt thereof, wherein
in Formula (IA): $R^2$ is selected from H, methyl, and propyl, wherein said methyl, and propyl are unsubstituted or substituted with 1, 2, or 3 $R^{2A}$ groups.

8. The compound of claim 7, or a pharmaceutically acceptable salt thereof, wherein
$R^3$ is selected from phenyl, oxazolyl, pyrimidinyl, pyrazolyl, pyridinyl, and thiazoyl, wherein said phenyl, oxazolyl, pyrazolyl, pyridinyl, and thiazoyl are unsubstituted or substituted with 1, 2, or 3 $R^{3A}$ groups,
provided that, in Formula (IA), when $R^1$ is: OH,
each $R^{3A}$ group is independently selected from the group consisting of F, Cl, OH, $(C_1\text{-}C_6)$alkyl, $(C_1\text{-}C_6)$haloalkyl, $O(C_1\text{-}C_6)$alkyl, and $O(C_1\text{-}C_6)$haloalkyl.

9. The compound of claim 1, or a pharmaceutically acceptable salt thereof, wherein said compound is selected from:

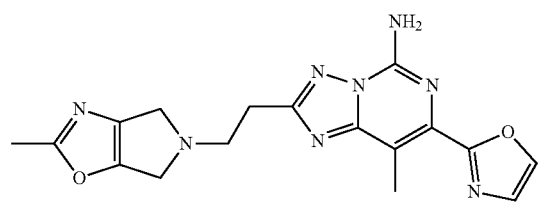

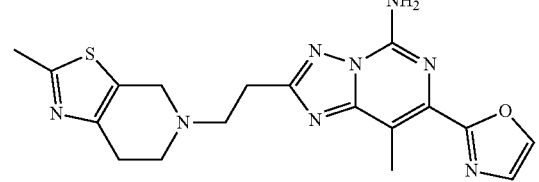

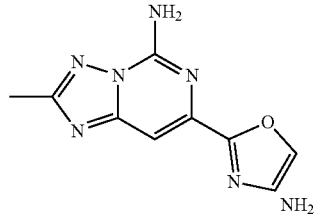

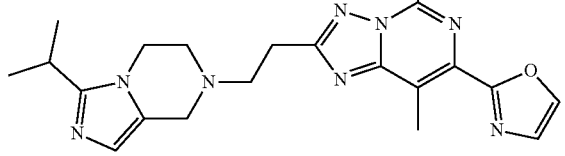

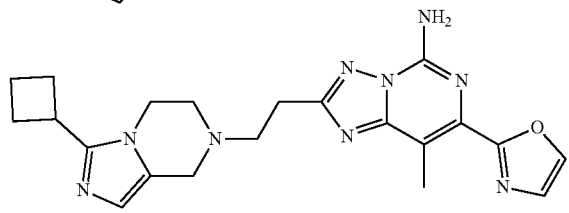

-continued

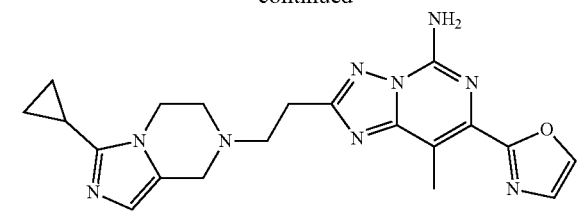

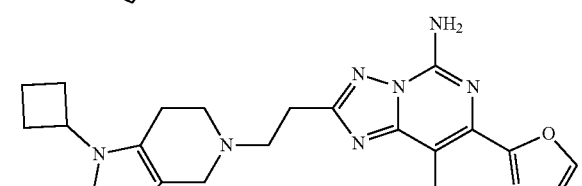

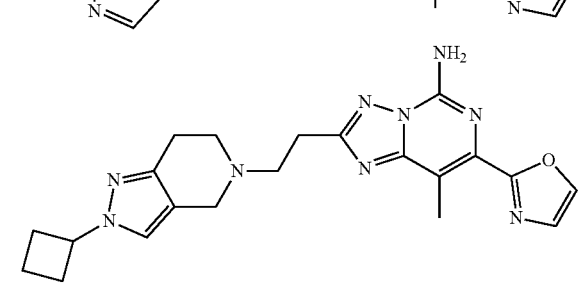

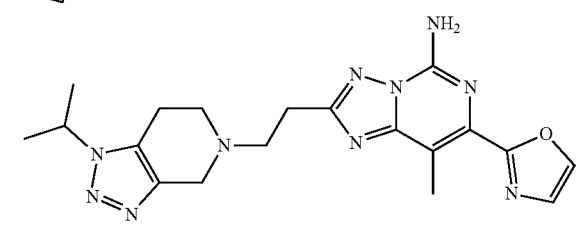

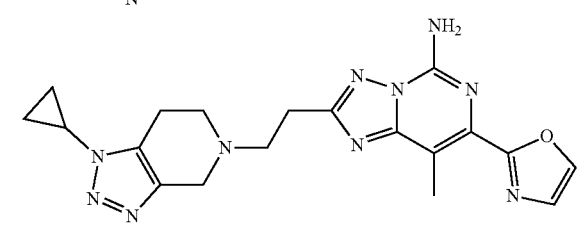

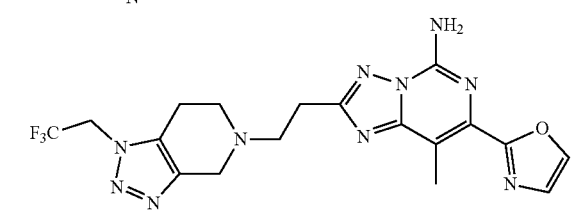

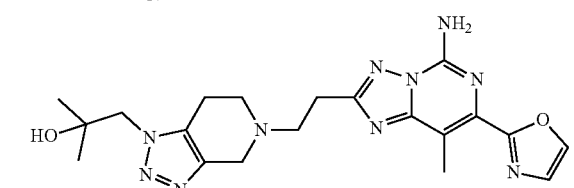

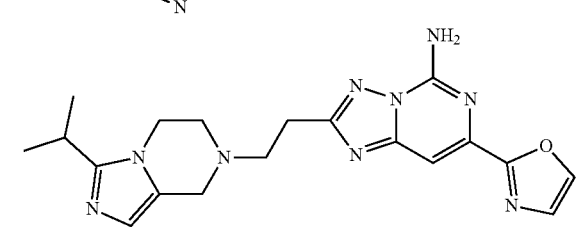

237
-continued
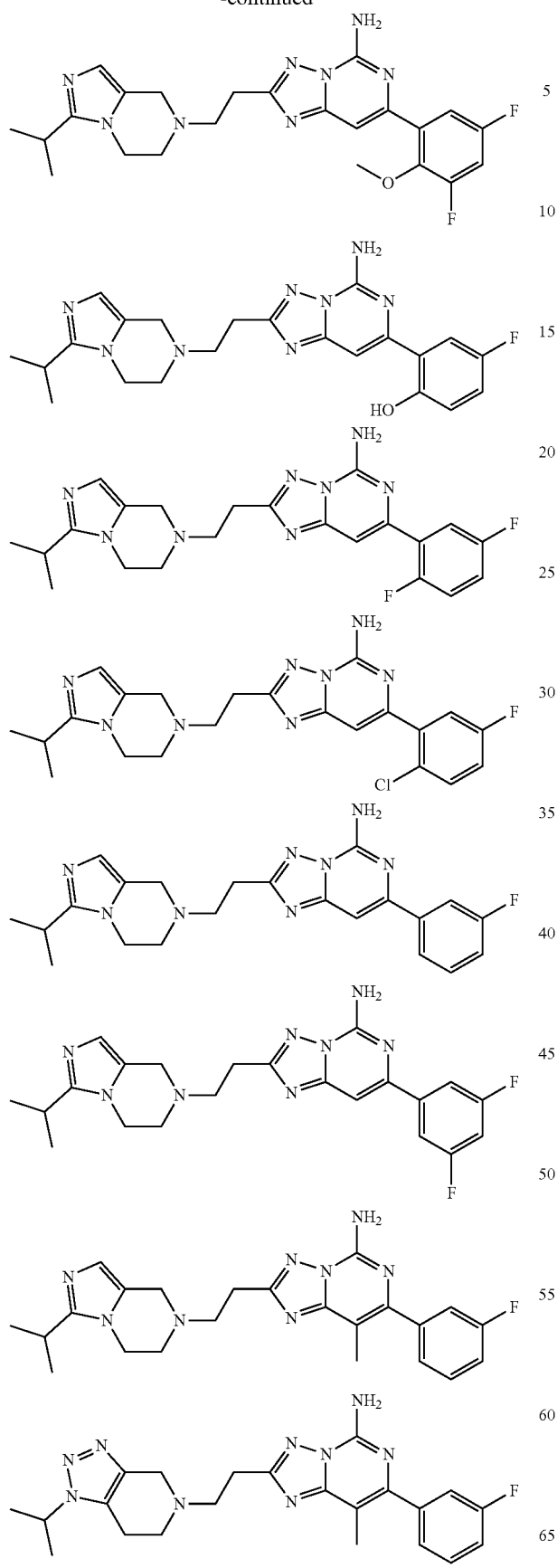
238
-continued
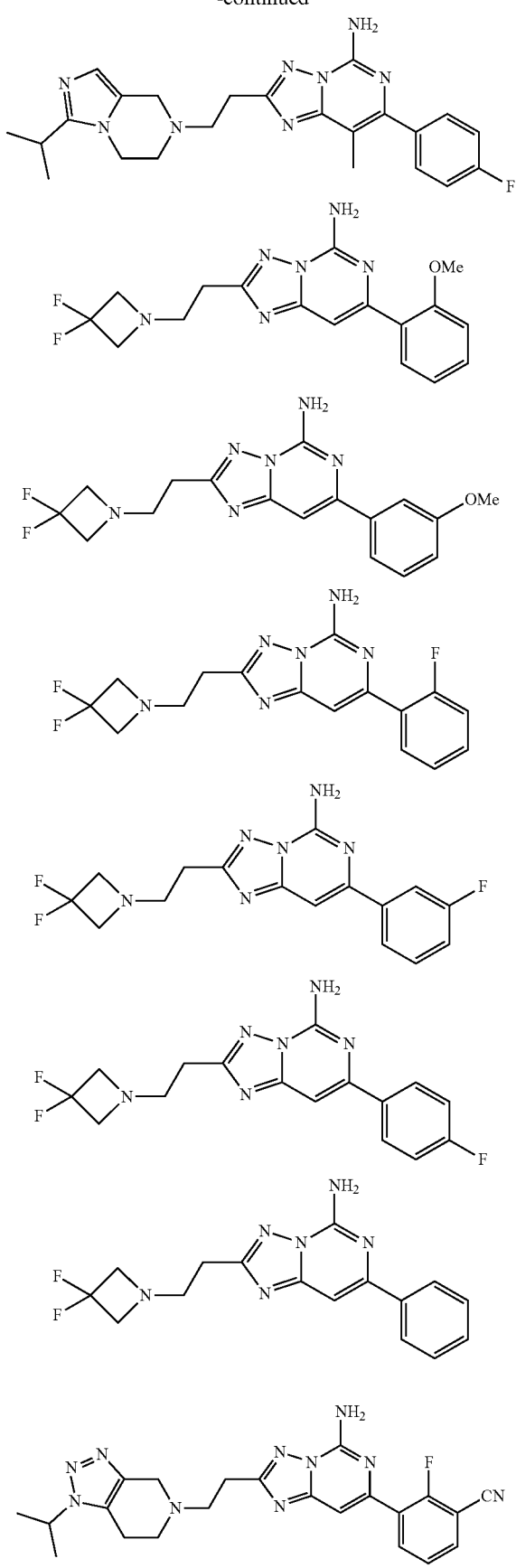

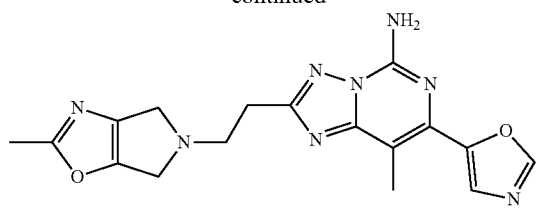
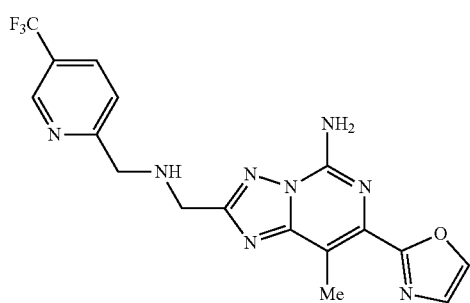
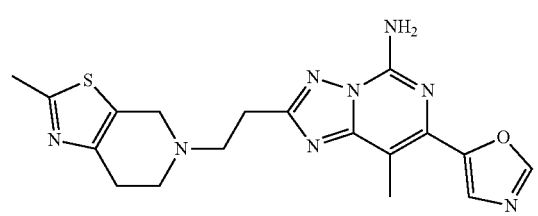
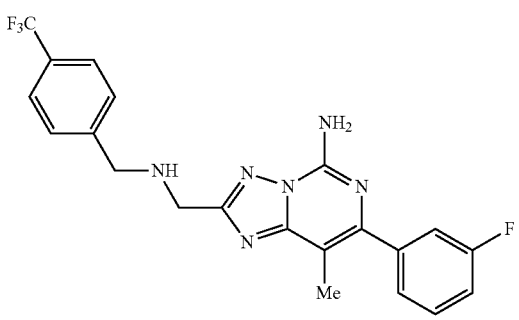
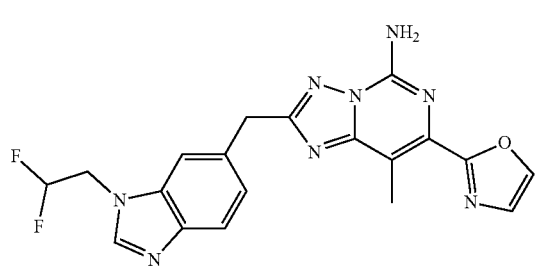
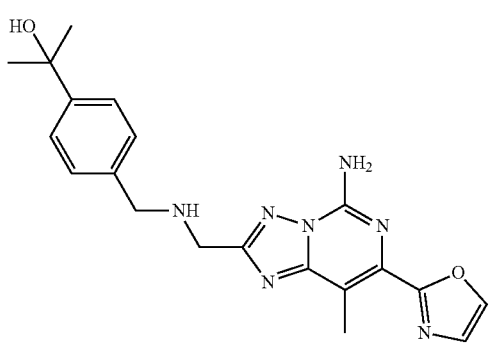
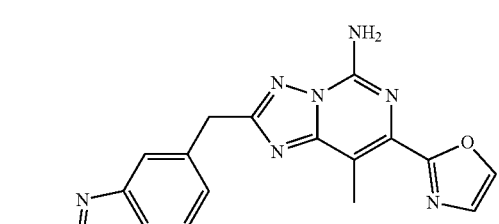
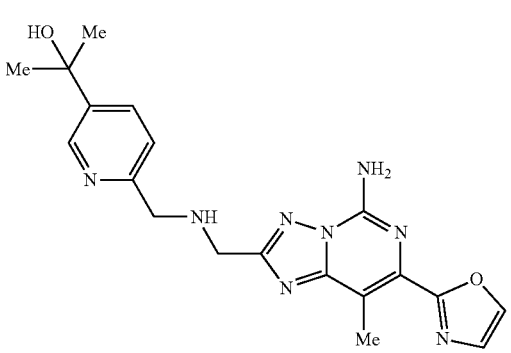
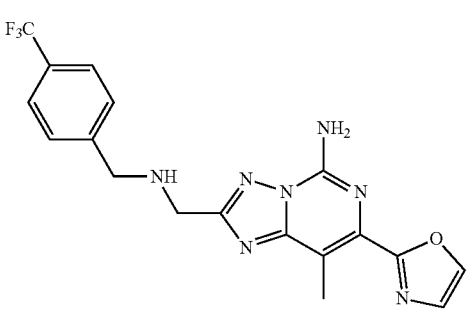
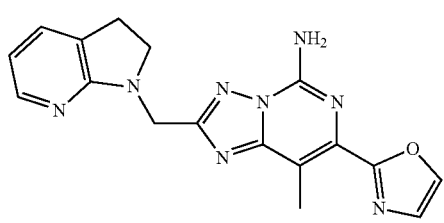 [SMILES: Cc1c(-c2ncco2)nc(N)n2nc(CN3CCc4cccnc43)nc12]
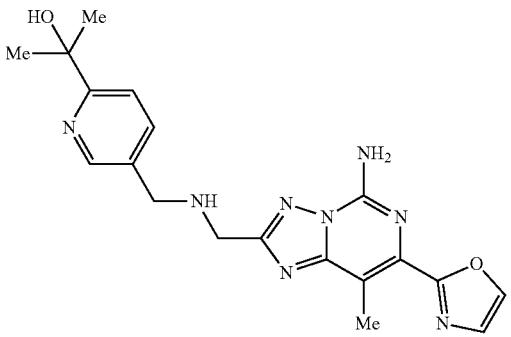

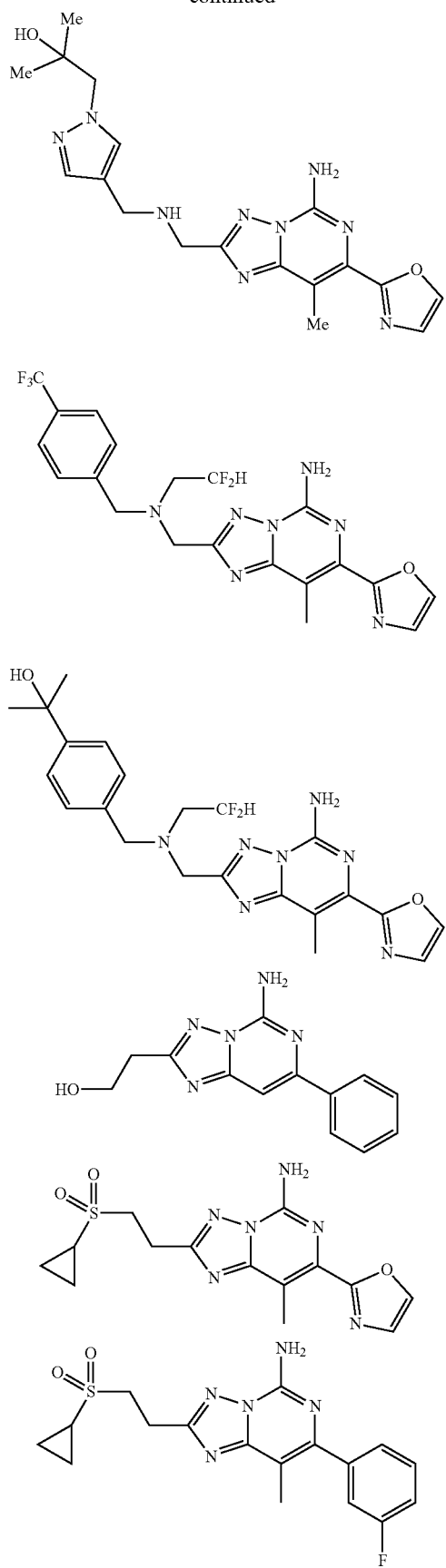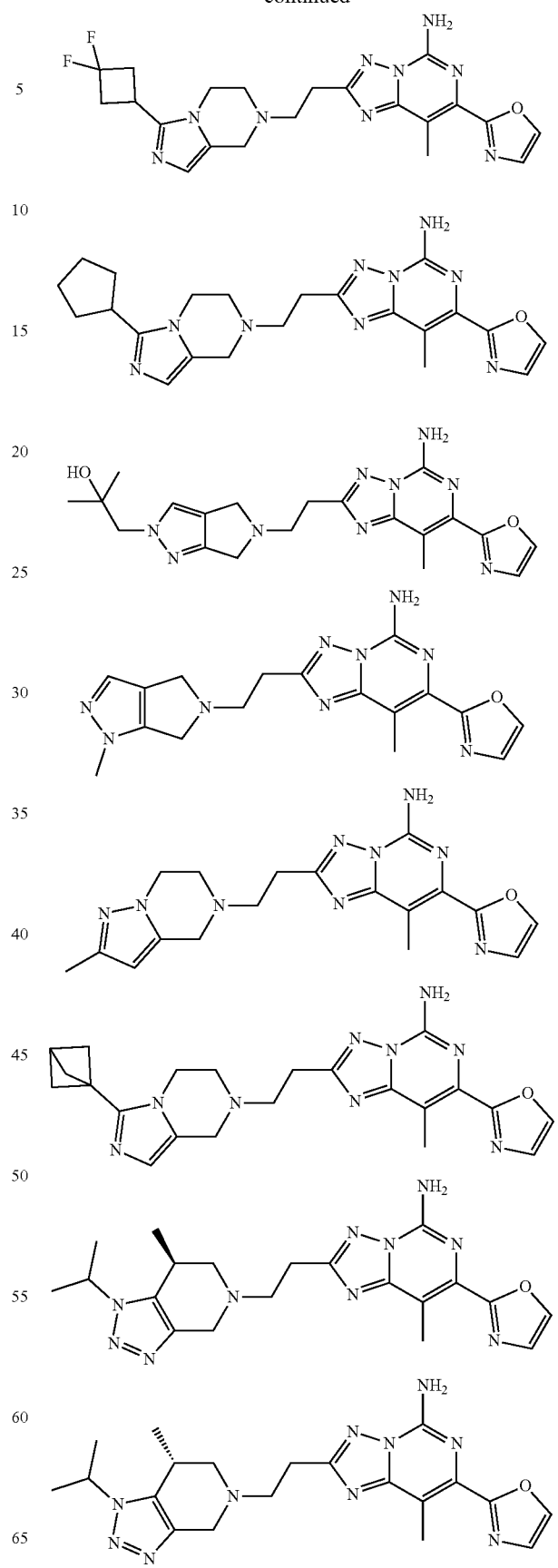

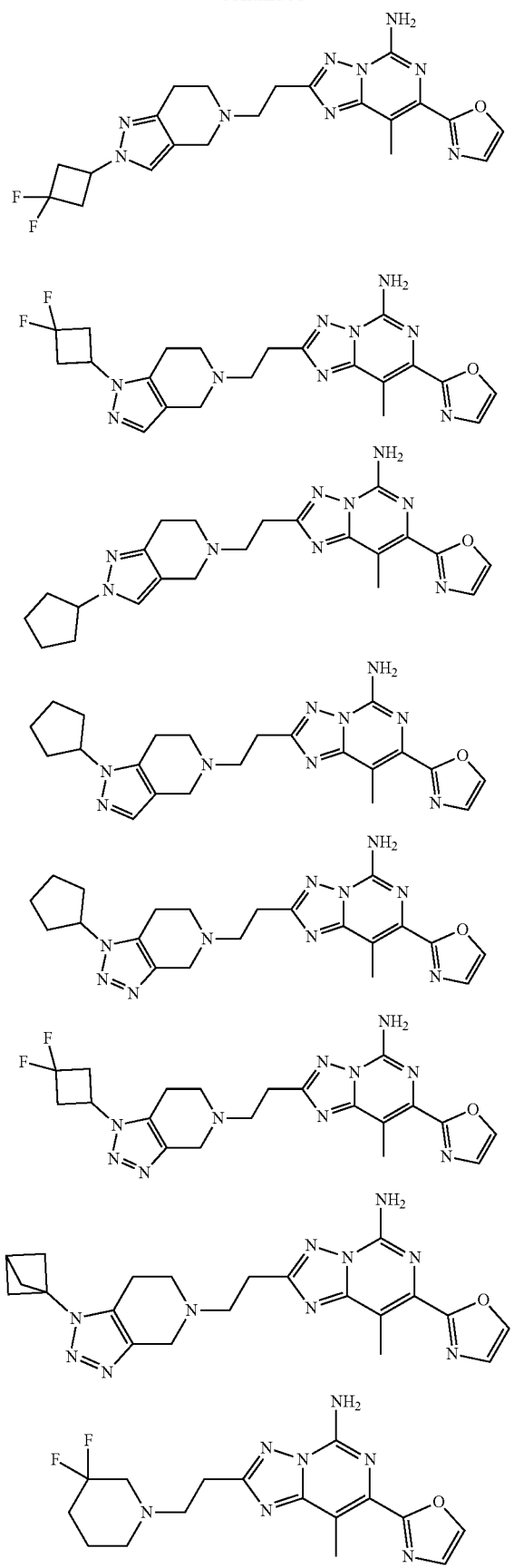
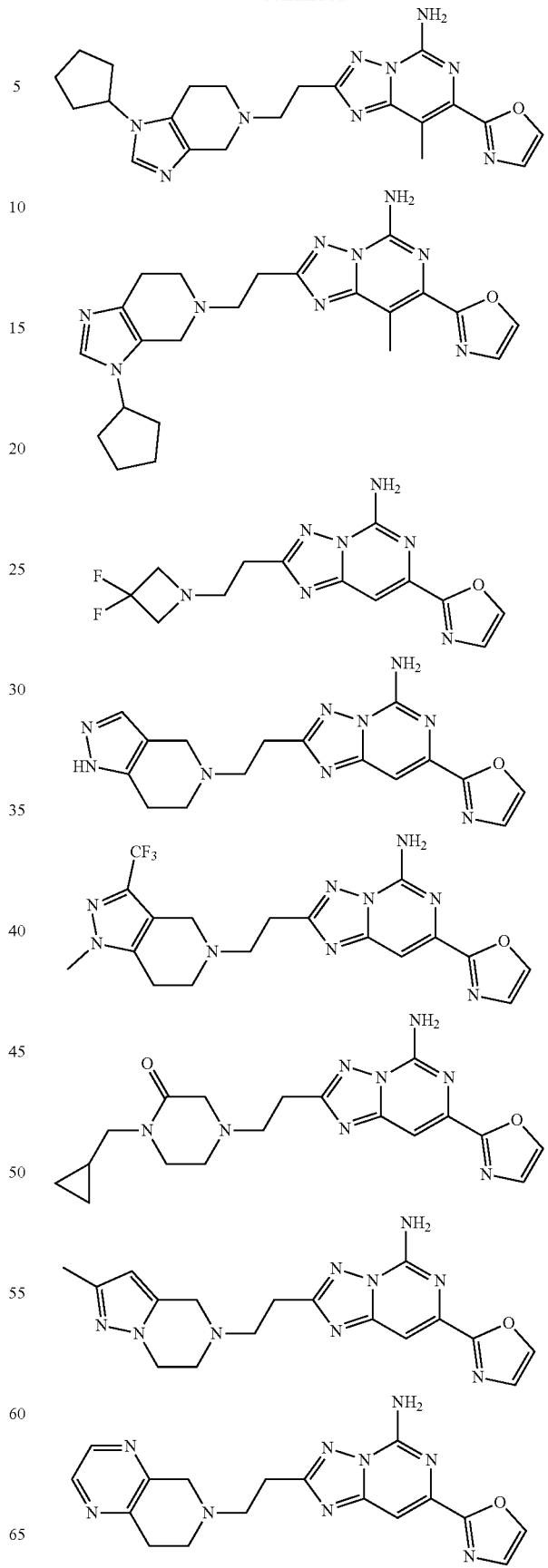

-continued
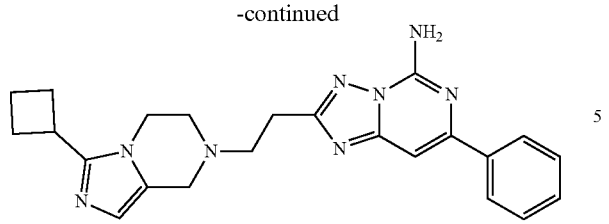
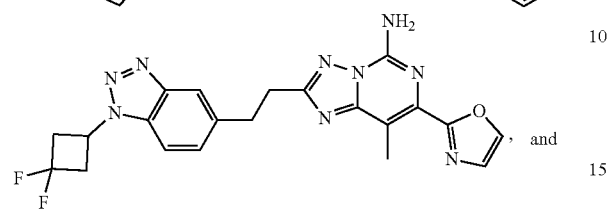
, and
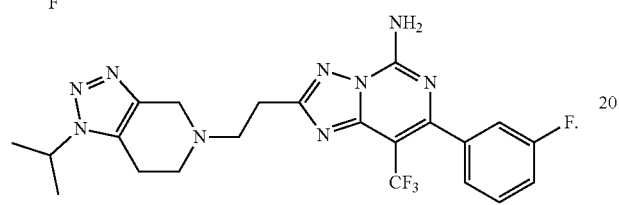
10. A pharmaceutical composition comprising a compound of claim 1, and a pharmaceutically acceptable carrier.
* * * * *